(12) United States Patent
Nicolai et al.

(10) Patent No.: US 10,993,999 B2
(45) Date of Patent: *May 4, 2021

(54) MATERIALS AND METHODS FOR PRODUCING IMPROVED LENTIVIRAL VECTOR PARTICLES

(71) Applicant: IMMUNE DESIGN CORP., Seattle, WA (US)

(72) Inventors: Christopher James Nicolai, Seattle, WA (US); Semih U. Tareen, Seattle, WA (US)

(73) Assignee: Immune DesignCorp., Seattle, WA (US)

( * ) Notice: Subject to any disclaimer, the term of this patent is extended or adjusted under 35 U.S.C. 154(b) by 77 days.

This patent is subject to a terminal disclaimer.

(21) Appl. No.: 16/513,263

(22) Filed: Jul. 16, 2019

(65) Prior Publication Data

US 2020/0030423 A1 Jan. 30, 2020

Related U.S. Application Data

(63) Continuation of application No. 15/612,192, filed on Jun. 2, 2017, now Pat. No. 10,391,157, which is a continuation of application No. 14/389,131, filed as application No. PCT/US2013/034640 on Mar. 29, 2013, now Pat. No. 9,713,635, which is a continuation of application No. 13/436,472, filed on Mar. 30, 2012, now Pat. No. 8,323,662.

(60) Provisional application No. 61/789,575, filed on Mar. 15, 2013, provisional application No. 61/732,756, filed on Dec. 3, 2012, provisional application No. 61/666,103, filed on Jun. 29, 2012.

(51) Int. Cl.
| | |
|---|---|
| *A61K 39/12* | (2006.01) |
| *C12N 7/00* | (2006.01) |
| *C12N 15/86* | (2006.01) |
| *A61K 39/00* | (2006.01) |
| *A61K 39/21* | (2006.01) |
| *A61K 47/42* | (2017.01) |

(52) U.S. Cl.
CPC .... *A61K 39/0011* (2013.01); *A61K 39/00115* (2018.08); *A61K 39/001106* (2018.08); *A61K 39/001151* (2018.08); *A61K 39/001156* (2018.08); *A61K 39/001157* (2018.08); *A61K 39/001164* (2018.08); *A61K 39/001168* (2018.08); *A61K 39/001181* (2018.08); *A61K 39/001182* (2018.08); *A61K 39/001184* (2018.08); *A61K 39/001186* (2018.08); *A61K 39/001188* (2018.08); *A61K 39/001191* (2018.08); *A61K 39/001192* (2018.08); *A61K 39/001194* (2018.08); *A61K 39/001195* (2018.08); *A61K 39/12* (2013.01); *A61K 39/21* (2013.01); *A61K 47/42* (2013.01); *C12N 7/00* (2013.01); *A61K 2039/5256* (2013.01); *A61K 2039/5258* (2013.01); *C12N 15/86* (2013.01); *C12N 2740/15034* (2013.01); *C12N 2740/16043* (2013.01); *C12N 2740/16051* (2013.01); *C12N 2740/16052* (2013.01); *C12N 2810/609* (2013.01); *Y02A 50/30* (2018.01)

(58) Field of Classification Search
None
See application file for complete search history.

(56) References Cited

U.S. PATENT DOCUMENTS

| | | |
|---|---|---|
| 5,168,062 A | 12/1992 | Stinski |
| 5,298,420 A | 3/1994 | Chang |
| 5,385,839 A | 1/1995 | Stinski |
| 6,013,516 A | 1/2000 | Verma et al. |
| 6,017,761 A | 1/2000 | Rigg et al. |
| 6,140,114 A | 10/2000 | Klatzmann et al. |
| 6,218,181 B1 | 4/2001 | Verma et al. |
| 6,297,004 B1 | 10/2001 | Russell et al. |
| 6,306,401 B1 | 10/2001 | Brown et al. |
| 6,416,997 B1 | 7/2002 | Mir-Shekari et al. |
| 6,432,699 B1 | 8/2002 | Meruelo et al. |
| 6,531,123 B1 | 3/2003 | Chang |
| 6,534,064 B1 | 3/2003 | O'Hagan et al. |
| 6,627,442 B1 | 9/2003 | Humeau et al. |
| 6,830,892 B2 | 12/2004 | Marasco et al. |
| 7,033,834 B2 | 4/2006 | Valerio et al. |
| 7,090,837 B2 | 8/2006 | Spencer et al. |
| 7,195,916 B2 | 3/2007 | Qin et al. |
| 7,285,642 B2 | 10/2007 | Figdor et al. |
| 7,323,619 B2 | 1/2008 | Baltimore et al. |
| 7,429,481 B2 | 9/2008 | Bergman et al. |
| 7,455,833 B2 | 11/2008 | Thorpe et al. |
| 7,604,802 B2 | 10/2009 | O'Hagan et al. |
| 7,611,712 B2 | 11/2009 | Karp |
| 7,612,173 B2 | 11/2009 | Abrecht et al. |
| 7,638,133 B2 | 12/2009 | Honda et al. |

(Continued)

FOREIGN PATENT DOCUMENTS

| | | |
|---|---|---|
| JP | 2008/503230 A | 2/2008 |
| WO | WO-1996/017072 A2 | 6/1996 |

(Continued)

OTHER PUBLICATIONS

U.S. Appl. No. 14/389,131, filed Sep. 29, 2014.

(Continued)

*Primary Examiner* — Stacy B Chen
(74) *Attorney, Agent, or Firm* — Andrew W. Custer; Anna L. Cocuzzo

(57) ABSTRACT

Materials and methods useful for generating highly mannosylated pseudotyped lentiviral vector particles comprising a Vpx protein are provided.

32 Claims, 34 Drawing Sheets

Figure 1A:
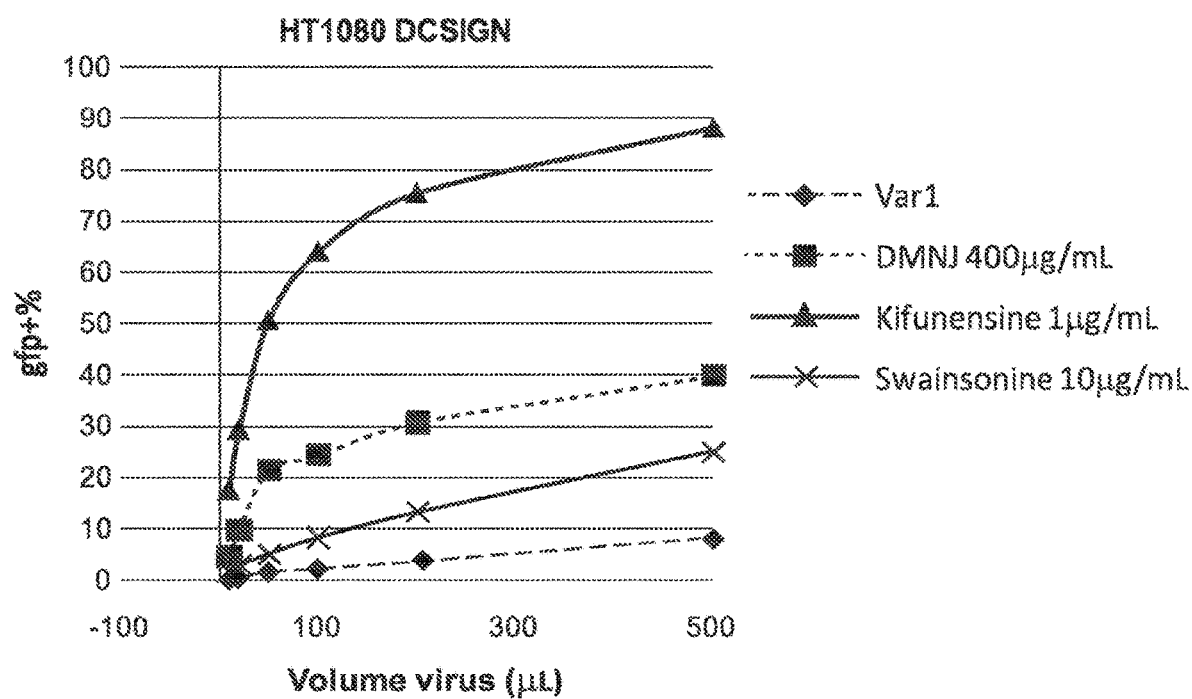
Figure 1B:
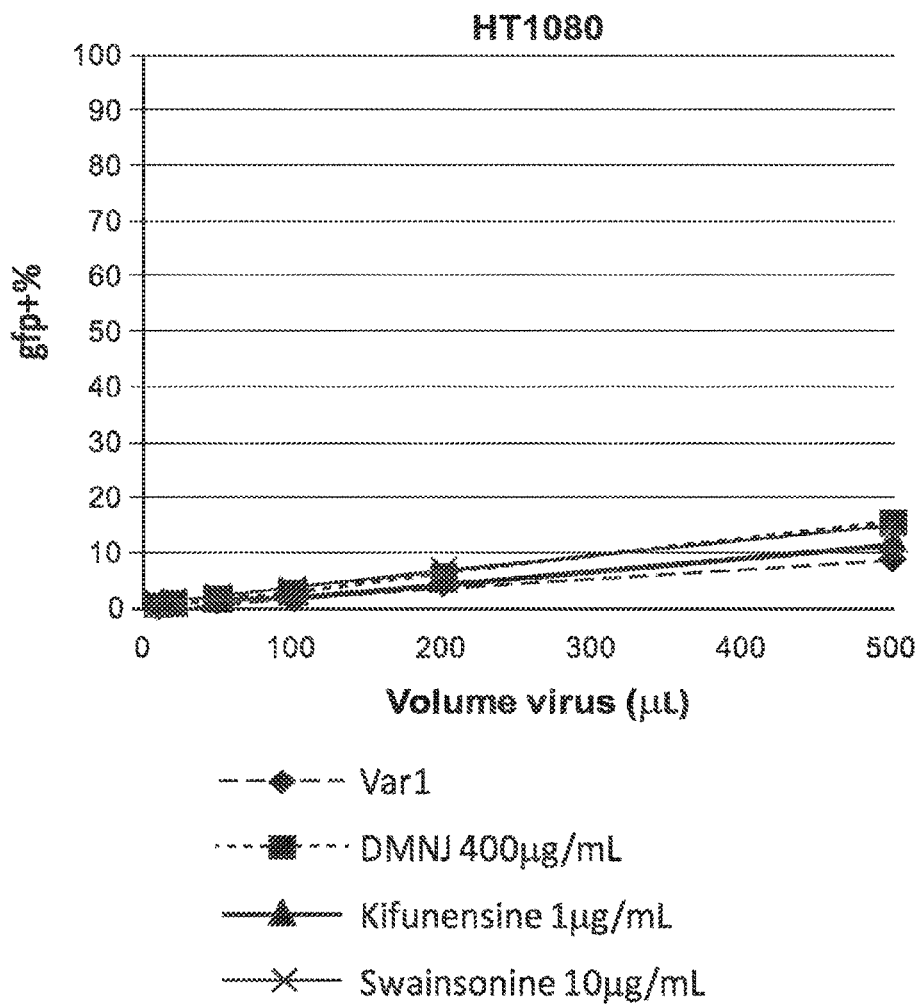
Figure 2A:
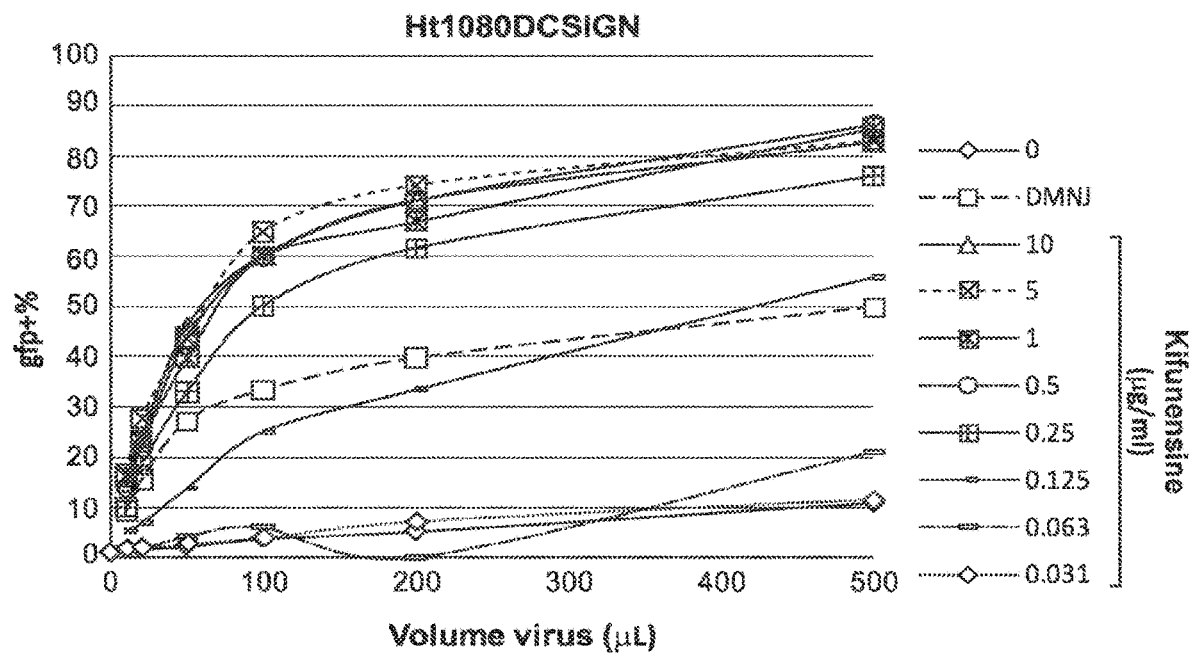
Figure 2B:
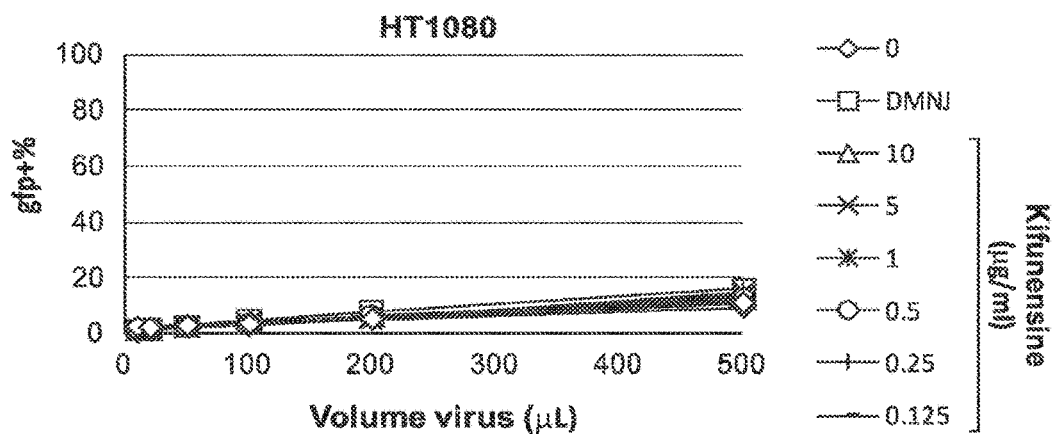

Specification includes a Sequence Listing.

(56) References Cited

U.S. PATENT DOCUMENTS

| | | |
|---|---|---|
| 7,771,979 B2 | 8/2010 | Polo et al. |
| 8,187,872 B2 | 5/2012 | Allen et al. |
| 8,323,662 B1 | 12/2012 | Nicolai et al. |
| 8,821,856 B2 | 9/2014 | Baltimore et al. |
| 9,713,635 B2 | 7/2017 | Nicolai et al. |
| 10,391,157 B2 | 8/2019 | Nicolai et al. |
| 2002/0155430 A1 | 10/2002 | Marsco et al. |
| 2003/0059944 A1 | 3/2003 | Lois-Caballe et al. |
| 2003/0068821 A1 | 4/2003 | Lois-Caballe et al. |
| 2003/0101471 A1 | 5/2003 | Baltimore et al. |
| 2003/0129163 A1 | 7/2003 | Hall et al. |
| 2003/0207438 A1 | 11/2003 | Schauber et al. |
| 2004/0071661 A1 | 4/2004 | Klatzmann et al. |
| 2004/0091853 A1 | 5/2004 | Hazuda et al. |
| 2004/0096823 A1 | 5/2004 | Greene et al. |
| 2005/0003547 A1 | 1/2005 | Spencer et al. |
| 2007/0275873 A1 | 11/2007 | Heidner et al. |
| 2008/0003682 A1 | 1/2008 | Lois-Caballe et al. |
| 2008/0019998 A1 | 1/2008 | Wang et al. |
| 2008/0089863 A1 | 4/2008 | Mallet et al. |
| 2008/0134352 A1 | 6/2008 | Baltimore et al. |
| 2008/0227736 A1 | 9/2008 | Chen et al. |
| 2010/0184206 A1 | 7/2010 | Chen et al. |
| 2011/0064763 A1 | 3/2011 | Allen et al. |
| 2012/0039932 A1 | 2/2012 | Allen et al. |

FOREIGN PATENT DOCUMENTS

| | | |
|---|---|---|
| WO | WO-2000/009730 A2 | 2/2000 |
| WO | WO-2000/061772 A2 | 10/2000 |
| WO | WO-2001/016324 A2 | 3/2001 |
| WO | WO-2001/016342 A1 | 3/2001 |
| WO | WO-2004/056966 A2 | 7/2004 |
| WO | WO-2004/067710 A2 | 8/2004 |
| WO | WO-2005/118802 A2 | 12/2005 |
| WO | WO-2006/130855 A2 | 12/2006 |
| WO | WO-2008/011636 A2 | 1/2008 |
| WO | WO-2009/019612 A2 | 2/2009 |
| WO | WO-2009/076524 A2 | 6/2009 |
| WO | WO-2010/105251 A2 | 9/2010 |
| WO | WO-2011/011584 A1 | 1/2011 |

OTHER PUBLICATIONS

U.S. Appl. No. 15/612,192, filed Jun. 2, 2017.
Kotsopoulou et al., A Rev Independent Human Immunodeficiency Virus Type 1 HIV 1 Based Vector that Exploits a Codon Optimized HIV 1 gag pol Gene, Journal of Virology, 2000, No. 10, vol. 74, pp. 4839-4852.
Yanez-Munoz, Effective Gene Therapy with Nonintegrating Lentviral Vectors, Letters—Nature Medicine, 2006, No. 3, vol. 12, pp. 348-353.
Ageichik et al., Lentivector trargeting to dendritic cells, Molec. Ther., 16(6): 1008-09 (2008).
Alignment for SEQ ID No. 11, cited in Non-Final Office Action for U.S. Appl. No. 13/301,545, dated Jan. 6, 2012.
Analyses of Merck's HIV vaccine Step' study. The Medical News, Nov. 12, 2008, Accessed at http://www.new-medical.net/news/2008/11/12/42892.aspx on Nov. 20, 2009.
Apolonia et al., Stable Gene Transfer to Muscle Using Non-integrating Lentiviral Vectors, Molecular Therapy, 15:1947-1954, 2007.
Avezov et al., Endoplasmic reticulum (ER) mannosidase I is compartmentalized and required for N-glycan trimming to Man5-6GlcNAc2 in glycoprotein ER-associated degradation. Molec. Biol. Cell, 19: 216-225 (2008).
Bailey et al., Transmission of human immunodeficiency virus type 1 from a patient who developed AIDS to an elite suppressor, J. Virol., 82(15): 7395-410 (2008).
Banchereau et al., Dendritic cells and the control of immunity, Nature, 392: 245-52 (1998).
Banchereau et al., Dendritic cells as therapeutic vaccines against cancer, Nat. Rev. Immunol., 5: 296-306 (2005).
Bangham et al., What is required of an HIV vaccine? Lancet, 350: 1617-21 (1997).
Barouch et al., Adenovirus vector-based vaccines for human immunodeficiency virus type 1, Hum. Gene. Ther., 16: 149-56 (2005).
Barouch et al., Challenges in the development of an HIV-1 vaccine, Nat. Rev., 455: 613-9 (2008).
Bayer et al., A Large U3 Deletion Causes Increased in Vivo Expression From a Nonintegrating Lentiviral Vector, Molecular Therapy, 16:1968-1976, 2008.
Bear et al., Heparin-binding and patterns of virulence for two recombinant strains of Sindbis virus, Virology, 347:183-190, 2006.
Belousova et al., Genetically targeted adenovirus vector directed to CD40-expressing cells, J. Virol., 77: 11367-77 (2003).
Berger et al., A simple, versatile and efficient method to genetically modify human monocyte-derived dendritic cells with HIV-1-derived lentiviral vectors, Nature Protocols, 6(6): 806-16 (2011).
Berger et al., SIVMAC Vpx improves the transduction of Dendritic cells with nonintegrative HIV-1-derived vectors. Gene Ther., 16: 159-63 (2009).
Betenbaugh et al., Biosynthesis of human-type N-glycans in heterologous systems, Curr. Opin. Struct. Biol., 14: 601-6 (2004).
Bhardwaj et al., Interactions of viruses with dendritic cells: A double-edged sword, J. Exp. Med., 186(6): 795-9 (1997).
Bonifaz et al., Efficient targeting of protein antigen to the dendritic cell receptor DEC-205 in the steady state leads to antigen presentation on major histocompatibility complex class I products and peripheral CD8+ T cell tolerance, J. Exp. Med., 196: 1627-38 (2002).
Bonifaz et al., In vivo targeting of antigens to maturing dendritic cells cia the DEC-205 receptor improves T cell vaccination, J. Exp. Med., 199(6): 815-24 (2004).
Branch, A good antisense molecule is hard to find, TIBS, 23: 45-50 (1998).
Breckpot et al., Lentiviral vectors for cancer immunotherapy: transforming infectious particles into therapeutics, Gene Therapy, 14:847-862, 2007.
Burgers et al., The challenges of HIV vaccine development and testing, Best Practice & Research: Clininal Obstetrics & Gynaecology, 19(1): 277-91 (2005).
Buschenfelde et al., Generation of tumor-reactive CTL against the tumor-associated antigen HER2 using retrovirally transduced dendritic cells derived from CD341 hemopoietic progenitor cells, J. Immunol., 165: 4133-40 (2000).
Butler et al., A quantitative assay for HIV DNA integration in vivo, Nat. Med., 7: 631-4 (2001).
Byrnes et al., Binding of Sindbis virus to cell surface heparan sulfate, J. Virol., 72: 7349-56 (1998).
Byrnes et al., Large-plaque mutants of Sindbis virus show reduced binding to heparan sulfate, heightened viremia, and slower clearance from the circulation, J. Virol., 74(2): 644-51 (2000).
Case et al., Stable transduction of quiescent CD34+CD38—human hematopoietic cells by HIV-1-based lentiviral vectors, Proc. Natl. Acad. Sci. USA, 96(6): 2988-93 (1999).
Chandrashekran et al., Targeted retroviral transduction of c-kit(+) hematopoietic cells using novel ligand display technology, Blood, 104: 2697-703 (2004).
Cheng et al., Mechanism of ad5 vaccine immunity and toxicity: Fiber shart targeting of dendritic cells, PLoS Pathog., 3:e25 (2007).
Cheong et al., Improved cellular and humoral immune responses in vivo following targeting of HIV Gag to dendritic cells within human anti-human DEC205 monoclonal antibody, Blood, 116: 3828-38 (2010).
Chinnasamy et al., Efficient gene transfer to human peripheral blood monocyte-derived dendritic cells using human immunodeficiency virus type 1-based lentiviral vectors, Hum. Gene Ther., 11(13): 1901-9 (2000).
Chirila et al., The use of synthetic polymers for delivery of therapeutic antisense oligodeoxynucleotides, Biomaterials, 23: 321-42 (2002).

(56) References Cited

OTHER PUBLICATIONS

Choi et al., Hybrid HIV/MSCV LTR enhances transgene expression of lentiviral vector in human CD34+ hematopoietic cells, Stem Cells, 19: 236-46 (2001).
Chou et al., Expression of chimeric monomer and dimer proteins on the plasma membrane of mammalian cells, Biotechnol. Bioengin., 65(2): 160-9 (1999).
Chu et al., Retroviral vector particles displaying the antigen-binding site of an antibody enable cell-type-specific gene transfer, J. Virol., 69(4): 2659-63 (1995).
Cockrell et al., Gene delivery by lentivirus vectors, Mol. Biotechnol., 36:184-204, 2007.
Cohen, Is an effective HIV vaccine feasible? Science, 309: 99 (2005).
Collins et al., Gene therapy meets vaccine development, TRENDS Biotech., 22(12): 623-6 (2004).
Cosset et al., Retroviral retargeting by envelopes expressing an N-terminal binding domain, J. Virol., 69(10): 6314-22 (1995).
Coutant et al., Protective Antiviral Immunity Conferred by a Nonintegrative Lentiviral Vector-Based Vaccine, Plos ONE, 3:e3973:1-6, 2008.
Cronin et al., Altering the tropism of lentiviral vectors through pseudotyping, Curr. Gene Ther., 5(4): 387-98 (2005).
Dai et al., HIV-I Gag-specific immunity induced by a lentivector-based vaccine directed to dendritic cells, Proc. Natl. Acad. Sci. U.S.A. 106:20382-20387, 2009.
Dakappagari et al., Internalizing antibodies to the C-type lectins, L-SIGN and DC-SIGN, inhibit viral glycoprotein binding and deliver antigen to human dendritic cells for the induction of T cell responses. J. Immunol., 176: 426-40 (2006).
De Felipe et al., Skipping the co-expression problem: The new 2A CHYSEL technology, Genet. Vaccines Ther.,2(13): 1-6 (2004).
De Filipe et al., Targeting of proteins derived from self-processing polyproteins containing multiple signal sequences, Traffic, 5: 616-26 (2004).
De Gruijl et al., Prolonged maturation and enhanced transduction of dendritic cells migrated from human skin explants after in situ delivery of CD40-targeted adenoviral, J. Immunol., 169: 5322-533 (2002).
De Ines et al., Apoptosis of a human melanoma cell line specifically induced by membrane-bound single-chain antibodies, J. Immunol., 163: 3948-56 (1999).
Declaration of Jan ter Meulen, M.D., Dr. Habil., DTM&H, cited as document D10 in Opposition against European Patent No. 2456786, dated Jul. 21, 2016.
Deonarain, Ligand-targeted receptor-mediated vectors for gene delivery, Exp. Opin. Therapeut. Pat., 8: 53-69 (1998).
Dimitrov et al., Quantitation of human immunodeficiency virus type 1 infection kinetics, J. Virol., 67(4): 2182-90 (1993).
Dimitrov et al., Virus entry: Molecular mechanisms and biomedical applications, Nat. Rev. Microbiol., 2: 109-22 (2004).
Dong et al., HIV-specific cytotoxic T cells from long-term survivors select a unique T cell receptor, J. Exp. Med., 200(12): 1547-57 (2004).
Drose et al., Bafilomycins and concanamycins as inhibitors of V-ATPases and P-ATPases, J. Exp. Biol., 200: 1-8 (1997).
Dullaers et al., Induction of effective therapeutic antitumor immunity by direct in vivo administration of lentiviral vectors, Gene Ther., 13: 630-40 (2006).
Elbien et al., Kifunensine, a potent inhibitor of the glycoprotein processing mannosidase I, J. Biol., Chem., 265(26): 15599-605 (1990).
Engelmayer et al., Vaccinia virus inhibits the maturation of human dendritic cells: A novel mechanism of immune evasion, J. Immunol., 163: 6762-8 (1999).
Engering et al., Subset of DC-SIGN dendritic cells in human blood transmits HIV-1 to T lymphocytes, Blood, 100(5)1 780-1786, 2002.
Esslinger et al., Efficient transduction of dendritic cells and induction of a T-cell response by third-generation lentivectors, Hum. Gene Ther., 13: 1091-100 (2002).
Esslinger et al., In vivo administration of a lentiviral vaccine targets DCs and induces efficient CD8(+) T cell responses, J. Clin. Invest., 111: 1673-81 (2003).
Evans et al., Human cord blood CD34+CD38—cell transduction via lentivirus-based gene transfer ventors, Hum. Gene Ther., 10(9): 1479-89 (1999).
Feinberg et al., Multiple modes of binding enhance the affinity of DC-SIGN for high-mannose N-linked glycans found on viral glycoproteins, J. Biol. Chem., 282(6): 4202-9 (2007).
Feinberg et al., Structural basis for selective recognition of oligosaccharides by DC-SIGN and DC-SIGNR, Science, 294: 2163-66 (2001).
Fielding et al., Inverse targeting of retroviral ventors: Selective gene transfer in a mixed population of hematopoietic and nonhematopoietic cells, Blood, 91(5): 1802-9 (1998).
Figdor et al., Dendritic cell immunotherapy: Mapping the way, Nat. Med., 10: 475-80 (2004).
Frolov et al., Translation of Sindbis virus mRNA: analysis of sequences downstream of the iniating AUG codon that enhances translation, J. Virol., 70(2): 1182-90 (1996).
Fuhrmann et al., Novel mannosidase inhibitor blocking conversion of high mannose to complex oligosaccharides, Nature, 307: 755-8 (1984).
Gardner et al., Infection of Human Dendritic Cells by a Sindbis Virus Replicon Vector Is Determined by a Single Amino Acid Substitution in the E2 Glycoprotein, J. Virol., 74:11849-11857, 2000.
Geijtenbeek et al., Self- and Nonself-Recognition by C-Type Lectins on Dendritic Cells, Annu. Rev. Immunol. 22:33-54, 2004.
Geijtenbeek et al., DC-SIGN, a dendritic cell-specific HIV-1-binding protein that enhances trans-infection of T cells, Cell, 100: 587-97 (2000).
Geijtenbeek et al., Identification of DC-SIGN, a novel dendritic cell-specific ICAM-3 receptor that supports primary immune responses, Cell, 100: 575-85 (2000).
Gollan et al., Redirecting retroviral tropism by insertion of short, nondisruptive peptide ligands into envelope, J. Virol., 76(7): 3558-63 (2002).
Gong et al., Induction of antigen-specific antitumor immunity with adenovirus-transduced dendritic cells, Gene Ther., 4: 1023-8 (1997).
Goujon et al., SIV SM/HIV-2 Vpx proteins promote retroviral escape from a proteasome-dependent restriction pathway present in human dendritic cells, Retrovirology, 4(1): 2 (2007).
Goujon et al., With a little help from a friend: Increasing HIV transduction of monocyte-derived Dendritic cells with virion-like particles of SIVMAC, Gene Ther., 13: 991-4 (2006).
Gramberg et al., Evidence for an activation domain at the amino terminus of simian immunodeficiency virus Vpx, J. Virol., 84(3): 1387-96 (2010).
Granelli-Piperno et al., Dendritic cells, infected with vesicular stromatitis virus-pseudotyped HIV-1, present viral antigens to CD4+ and CD8+ T cells from HIV-1-infected individuals, J. Immunol., 165: 6620-6 (2000).
Gunning et al., A human beta-actin expression vector system directs high-level accumulation of antisense transcripts, Proc. Natl. Acad. Sci. USA, 84: 4831-6 (1987).
Gupta et al., Antibody responses against HIV in rhesus macaques following combinations of mucosal and systemic immunizations with chimeric alphavirus-based replicon particles, AIDS Res., Hum. Retroviruses, 22(10): 993-7 (2006).
Han et al., Ligand-directed retroviral targeting of human breast cancer cells, Proc. Natl. Acad. Sci. USA, 92: 9747-51 (1995).
Hanke et al., Pre-clinical development of a multi-CTL epitope-based DNA prime MVA boost vaccine for AIDS, Immunol. Lett., 66: 177-81 (1999).
Hatziioannou et al., Incorporation of fowl plague virus hemagglutinin in murine leukemia virus particles and analysis of the infectivity of the pseudotyped retroviruses, J. Virol., 72: 5313 (1998).
Heidner et al., Lethality of PE2 incorporation into Sindbis virus can be suppressed by second-site mutation in E3 and E2, J. Virol., 68: 2683-92 (1994).

(56) References Cited

OTHER PUBLICATIONS

Heidner et al., The amino-terminal residue of Sindbus virus glycoprotein E2 influences virus maturation, specific infectivity for BHK cells, and virulence for mice, *J. Virol.*, 68: 8064-70 (1994).
Hernandez et al., Deletions in the transmembrane domain of a Sindbis virus glycoprotein alter virus infectivity, stability, and host range, *J. Virol.* 77(23): 12710-9 (2003).
Herscovics et al., Importance of glycosidases in mammalian glycoprotein biosynthesis, *Biochim. Biophys. Acta*, 1473: 96-107 (1999).
Herscovics et al., Structure and function of class I alpha-1,2-mannosidases involved in glycoprotein synthesis and endoplasmic reticulum quality control, *Biochimie*, 83: 757-62 (2001).
Hoffman et al., Functional and protein chemical characterization of the N-terminal domain of the rat corticotrophin-releasing factor receptor 1, *Protein Sci.*, 10: 2050-62 (2001).
International search reports from Application No. PCT/US2010/042870, dated Sep. 22, 2010.
Iwakuma et al., Self-activating lentiviral ventors with U3 and U5 modifications, *Virology*, 261: 120-32 (1999).
Iwasaki et al., Regulation of adaptive immunity by the innate immune system, *Science*, 327: 291-5 (2010).
Jahn et al., Analysing c-kit internalization using a functional c-kit-EGFP chimera containing the fluorochrome within the extracellular domain, *Oncogene*, 21: 4508-20 (2002).
Jiang et al., Cell-type-specific gene transfer into human cells with retroviral vectors that display single-chain antibodies, *J. Virol.*, 72(12): 10148-56 (1998).
Johnson-Saliba et al., Gene therapy: Optimising DNA delivery to the nucleus, *Curr. Drug Targets*, 2(4): 371-99 (2001).
Kahl et al., Human immunodeficiency virus type 1-derived lentivirus vectors pseudotyped with envelope glycoproteins derived from Ross River virus and Semliki Forest virus, *J. Virol.*, 79(3): 1421-30 (2004).
Kahl et al., Lentiviral vectors pseudotyped with glycoproteins from Ross River and vesicular stomatitis viruses: Variable transduction related to cell type and culture conditions, *Molec. Ther.*, 11(3): 470-82 (2005).
Kamrud et al., Analysys of Venezuelan equine encephalitis replicon particles packages in different coats, *PLoS ONE*, 3(7): e2709 (2008).
Kaplan et al., Induction of antitumor immunity with dendritic cells transduced with adenvirus vector-encoding edogenous tumor-associated antigens, *J. Immunol.*, 163: 699-707 (1999).
Karasuyama et al., Autocrine growth and tumorigenicity of interleukin 2-dependent helper T cells transfected with IL-2 gene, *J. Exp. Med.*, 169: 13-25 (1989).
Kaushik et al., A cellular restriction dictates the permissivity of nondividing monocytes/macrophages to lentivirus and gammaretrovirus infection, *Cell Host Microbe*, 6: 68-80 (2009).
Keller et al., Overexpression of HOX11 leads to the immortalization of embryonic presursors with both primitive and definitive hematopoietic potential, *Blood*, 92(3): 877-87 (1998).
Kielian et al., Alphavims Entry and Membrane Fusion, *Viruses*, 2:796-825, 2010.
Kim et al., Induction of therapeutic antitumor immunity by in vivo administration of a lentiviral vaccine, *Hum. Gene Ther.*, 16: 1255-66 (2005).
Kirk et al., Gene-modified dendritic cells for use in tumor vaccines, *Hum. Gene Ther.*, 11: 797-803 (2000).
Klimstra et al., Adaptation of Sindbis Virus to BHK Cells Selects for Use of Heparan Sulfate as an Attachment Receptor, *J. Virol.*, 72:7357-7366, 1998.
Klimstra et al., DC-SIGN and L-SIGN Can Act as Attachment Receptors for Alphaviruses and Distinguish between Mosquito Cell- and Mammalian Cell-Derived Viruses, *J. Virol.*, 77:12022-12032, 2003.
Klimstra et al., The Furin Protease Cleavage Recognition Sequence of Sindbis Virus PE2 Can Mediate Virion Attachment to Cell Surface Heparan Sulfate, *J. Virol.*, 73:6299-6306, 1999.
Klimstra et al., Infection of neonatal mice with Sindbis virus results in a systemic inflammatory response syndrome *J. Virol.*, 73(12): 10387-98 (1999).
Kolokoltsov et al., Efficient functional pseudotyping of oncoretroviral and lentiviral vectors by Venezuelan equine encephalitis virus envelope proteins, *J. Virol.*, 79(2): 756-63 (2005).
Korst et al., Active, specific immunotherapy for lung cancer: hurdles and strategies using genetic modification, *Annu. Thor. Surg.*, 76: 1319-26 (2003).
Korth et al., Interferon inhibits the replication of HIV-1, SIV, and SHIV chimeric viruses by distinct mechanisms, *Virology*, 247: 265-73 (1998).
Kumar et al., Cloning and expression of N-acetylglucosaminyltransferase I, the medial Golgi transferase that initiates complex N-linked carbohydrate formation, *Proc. Natl. Acad. Sci. USA*, 87: 9948-52 (1990).
Kung et al., A murine leukimia virus (MuLV) long terminal repeat derived from rhesus macaques in the context of a lentivirus vector and MuLV gag sequence results in high-level gene expression in human T lymphocytes, *J. Virol.*, 74(8): 3668-81 (2000).
Kutner et al., Production, concentration and titration of pseudotyped HIV-1-based lentiviral vectors, *Nature Protocols*, 4(4): 495-505 (2009).
Kwon et al., Determination of infectious retrovirus concentration from colony-forming assay with quantitative analysis, *J. Virol.*, 77(10): 5712-20 (2003).
Laguette et al., SAMHD1 is the dendritic- and myeloid-cell-specific HIV-1 restriction factor counteracted by Vpx, *Nat. Lett.*, 1-4 (2011).
Lahouassa et al., SAMHD1 restricts the replication of human immunodeficiency virus type 1 by depleting the intracellular pool of deoxynucleoside triphosphates, *Nat. Immuno.*, 13(3): 223-9 (2012).
Lavillette et al., Retargeting gene delivery using surface-engineered retroviral vetor particles, *Curr. Opin. Biotech.*, 12: 461-6 (2001).
Lee et al., A nonneutralizing anti-HIV-1 antibody turns into a neutralizing antibody when expressed on the surface of HIV-1-susceptible cells: A new way to fight HIV, *J. Immunol.*, 173: 4618-26 (2004).
Lei et al., Engineering fusogenic molecules to achieve targeted transduction of enveloped lentiviral vectors, *J. Biol. Engineering*, 3(8): doi: 10.1186/1754-1611-3-8 (2009).
Liao et al., Design of trangenes for efficient expression of active chimeric proteins on mammalian cells, *Biotechnol. Bioengin.* 73(4): 313-23 (2001).
Lim et al., The ability of primate lentiviruses to degrade the monocyte restriction factor SAMHD1 prededed the birth of the viral accessory protein Vpx, *Cell Host Microbe*, 11: 194-204 (2012).
Lin et al., Differential N-linked glycosylation of human immunodeficiency virus and ebola virus envelope glycoproteins modulates interactions with DC-SIGN and DC-SIGNR, *J. Virol.*, 77(5): 1337-46 (2003).
Lin et al., Receptor-specific targeting mediated by the coexpression of a targeted murine leukemia virus envelope protein and a binding-defective influenza hemagglutinin protein, *Hum. Gene Ther.*, 12(4): 323-32 (2001).
Liu et al., Immune control of an SIV challenge by a T-cell-based vaccine in rhesus monkeys, *Nat. Lett.*, 457: 87-91 (2009).
Lois et al., Germline transmission and tissue-specific expression of trangenes delivered by lentiviral vectors, *Science*, 295(5556): 868-72 (2002).
Lopes et al., Immunization with lentivector that targets tumor antigen expression to dendritic cells induces potent CD8+ and CD4+ T-cell responses, *J. Virol.*, 82(1): 86-95 (2008).
Lori et al., Cellular immunity and DNA vaccines for the treatment of HIV/AIDS, *Curr. Med. Chem. Anti-Infect. Agents*, 3: 31-41 (2004).
Lorimer et al., Targeting retrovirus to cancer cells expressing a mutant EGF receptor by insertion of a single chain antibody variable domain in the envelope glycoprotein receptor binding lobe, *J. Immunol. Meth.*, 237: 147-57 (2000).
Lu et al., Therapeutic dendritic-cell vaccine for chronic HIV-1 infection, *Nature Medicine*, 10(12):1359-1365, 2004).

(56) References Cited

OTHER PUBLICATIONS

Lubong Sabado et al., Directing dendritic cell immunotherapy towards successful cancer treatment, *Immunotherapy*, 2(1): 37-56 (2010).
Lutzko et al., Lentivirus ventors incorporating the immunoglobulin heavy chain enhancer and matrix attachment regions provide position-independent expression in B lymphocytes, *J. Virol.*, 77: 7341-51 (2003).
Manel et al., A cryptic sensor for HIV-1 activates antiviral innate immunity in dendritic cells. *Nat. Lett.*, 467: 214-19 (2010).
Mangeot et al., Development of minimal lentivirus vectors derived from simian immunodeficiency virus (SIVmac251) an their use for gene transfer into human dendritic cells, *J. Virol.*, 74: 8307-15 (2000).
Mangoet et al., High levels of transduction of human dendritic cells with optimized SIV vectors. *Molec. Ther.*, 5(3): 283-90 (2002).
Mariani et al., Species-specific exclusion of APOBEC3G from HIV-1 virions by VIF, *Cell*, 114: 21-31 (2003).
Marozsan et al., Relationships between infectious titer, capsid protein levels, and reverse transcriptase activities of diverse human immunodeficiency virus type 1 isolates, *J. Virol.*, 78(20): 11130-41 (2004).
Matano et al., Targeted infection of a retrovirus bearing a CD4-Env chimera into human cells expressing human immunodeficiency virus type 1, *J. Gen. Virol.*, 76: 3165-9 (1995).
Matsuno et al., A life stage of particle-laden rat dendritics in vivo: Their terminal division, active phagocytosis, and translocation from the liver to the draining lymph, *J. Exp. Med.*, 183: 1865-78 (1996).
Maurice et al., Efficient gene transfer into human primary blood lymphocytes by surface-engineered lentiviral vectors that display a T cell-activating polypeptide, *Blood*, 99(7): 2342-50 (2002).
McKnight et al., Deduced consensus sequence of Sindbis virus strain AR339: mutations contained in laboratory strains which affect cell culture and in vivo phenotypes, *J. Virol*, 70:1981-1989, 1996.
McMichael et al., Escape of human immunodeficiency virus from immune control, *Ann. Rev. Immunol.* . . 15: 271-96 (1997).
Meissner et al., Development of an inducible pol III transcription system essentially requiring a mutated form of the TATA-binding protein, *Nucl. Acids Res.*, 29(8): 1672-82 (2001).
Meyer zum Buschenfelde et al., Generation of tumor-reactive CTL against the tumor-associated antigen HER2 using retrovirally transduced dendritic cells derived from CD34+ hematopoietic profenitor cells, *J. Immunol.*, 165: 4311-40 (2000).
Miller et al., Targeted vectors for gene therapy, *FASEB J.*, 9(2): 190-9 (1995).
Miyoshi et al., Development of a self-inactivating lentivirus vector, *J. Virol.*, 72:8150-8157, 1998.
Miyoshi et al., Transduction of human CD34+ cells that mediate long-term engraftment of NOD/SCID mice by HIV vectors, *Science*, 283(5402): 682-6 (1999).
Morizono et al., Antibody-Directed Targeting of Retroviral Vectors via Cell Surface Antigens, *Viral*, 75:8016-8020 (2001).
Morizono et al., Lentiviral vector retargeting to P-glycoprotein on metastatic melanoma through intravenous injection, *Nature Medicine*, 11:346-352, 2005.
Morizono et al., Redirecting Lentiviral Vectors Pesudotyped with Sindbis Virus-Derived Envelope Proteins to DC-SIGN by Modification of N-Linked Glycans of Envelope Proteins, *Journal of Virology*, 84(14):6923-6934, 2010.
Morris et al., Induction of cytotoxic T-lymphocyte responses to enhance green and yellow fluorescent proteins after myeloablative conditioning, *Blood*, 103(2): 492-9 (2004).
Mukhopadhyay et al., A structural perspective of the flavivirus life cycle, *Nature Rev.*, 3:13-22, 2005.
Narayan et al., Biology and pathogenesis of lentiviruses. *J. Gen. Virol.*, 70: 1617-39 (1989).
Navaratnarajah et al., Functional characterization of the Sindbis virus E2 glycoprotein by transposon linker-insertion mutagenesis, *Virology*, 363:134-147, 2007.

Negri et al. Successful immunization with a single injection of non-integrating lentiviral vector, *Mol. Ther.*, 15:1716-1723, 2007.
Notice of Opposition against European Patent No. 2456786, dated Oct. 8, 2014.
Nussenzweig et al., Immune responses: Tails to teach a B cell, *Curr. Biol.*, 7: R355-7 (1997).
Nyberg-Hoffman et al., Sensitivity and reproducibility in adenoviral infectious titer determination, *Nat. Med.*, 3(7): 808-11 (1997).
Ohno et al., Cell-specific targeting of Sindbis virus vectors displaying IgG-binding domains of protein A, *Nature Biotechnology*, 15:763-767, 1997.
Op den Brouw et al., Branched oligosaccharide structures on HBV prevent interaction with both DC-SIGN and L-SIGN, *J. Viral Hepat.*, 15: 675-83 (2008).
Palmer et al., Gene therapy for colorectal cancer, *Brit. Med. Bull.*, 64: 201-25 (2002).
Palmowski et al., Intravenous injection of a lentiviral vector encoding NY-ESO-1 induces an effective CTL response, *J. Immunol.*, 172: 1582-7 (2004).
Papagatsias et al., Activity of different vaccine-associated promoter elements in human dendritic cells, *Immunol. Lett.*, 115:117-125, 2008.
Park et al., An essential role for Akt1 in dendritic cell function and tumor immunotherapy, *Nat. Biotechnol.*, 24(12): 1581-90 (2006).
Park et al., Five mouse homologues of the human dendritic cell C-type lectin, DC-SIGN, *Intl. Immunol.*, 13(10): 1283-90 (2001).
Paule et al., Transcription by RNA polymerase I and III, *Nucl. Acids Res.*, 28(6): 1283-98 (2000).
Pauwels, et al., State-of-the-Art Lentiviral Vectors for Research Use: Risk Assessment and Biosafety Recommendations, *Current Gene Therapy*, 9:459-474, 2009.
Perri et al., An alphavirus replicon particle chimera derived from venezuelan equine encephalitis and sindbis viruses is a potent gene-based vaccine delivery vector, *J. Virol.*, 77(19): 10394-403 (2003).
Pertel et al., Vpx rescues HIV-1 transduction of dendritic cells from the antiviral state establishes by type 1 interferon, *Retrovirology*, 8: 49-64 (2010).
Pfeifer et al., Gene therapy: promises and problems, *Annu. Rev. Genomics Hum. Genet.*, 2:177-211, 2001.
Philippe et al., Lentiviral vectors with a defective integrase allow efficient and sustained transgene expression in vitro and in vivo, *Proc. Natl. Acad. Sci. USA* 103:17684-17689, 2006.
Pitisuttithum et al., HIV-1 prophylactic vaccine trials in Thailand, *Curr. HIV Res.*, 3(1): 17-30 (2005).
Powlesland et al., Widely divergent biochemical properties of the complete set of mouse DC-SIGN-related proteins, *J. Biol. Chem.*, 281: 20440-9 (2006).
Racaniello, Are all virus particles infectious? Virology blog, http://www.virology.ws/2011/01/21are-all-virus-particles-infectious/, Jan. 21, 2011.
Racine et al., A short and convenient synthesis of 1-deoxymannojirimycin and N-oxy analogues from D-fructose, *J. Org. Chem.*, 74: 1766-9 (2009).
Ready et al., AIDSVAX flop leaves vaccine field unscathed, *Nat. Med.*, 9(4): 376 (2003).
Reed et al., New horizons in adjuvants for vaccine development, *Trends in Immunology*, 30:23-32, 2009.
Reeves et al., Structure and function in rhodopsin: High-level express of rhodopsin with restricted and homogeneous N-glycosylation by a tetracycline-inducible N-acetylglucosaminyltransferase I-negative HEK293S stable mammalian cell line, *Proc. Natl. Acad. Sci. USA*, 99(21): 13419-24 (2002).
Ribas et al., Cancer immunotherapy using gene-modified dendritic cells, *Curr. Gene Ther.*, 2: 57-78 (2000).
Rice et al., Mutations involved in Aicardi-Goutieres syndrome implicate SAMHD1 as regulator of the innate immune response, *Nat. Genet.*, 41(7): 829-33 (2009).
Rosenberg et al., Cancer immunotherapy moving beyong current vaccines, *Nat. Med.*, 10: 909-15 (2004).
Rowe et al., Immunication with a lentiviral vector stimulates both CD4 and CD8 T cell responses to an ovalbumin transgene, *Molec. Ther.*, 13(2): 310-9 (2006).

(56) References Cited

OTHER PUBLICATIONS

Russell et al., Sindbis Virus mutations which coordinately affect glycoprotein processing, penetration and virulence in mice, *J. Virol.*, 63(4): 1619-29 (1989).
Sanders, No false start for novel pseudotyped vectors, *Curr. Opin. Biotechol.*, 13(5): 437-42 (2002).
Sandrin et al., Targeting retroviral and lentiviral vectors, *Curr. Top. Microbiol. Immunol.*, 281: 137-78 (2003).
Sanz et al., Individual expression of sindbis virus glycoproteins, E1 alone promotes cell fusion, *Virology*, 305: 463-72 (2003).
Sastry et al., Titering lentiviral vectors: Comparison of DNA, RNA and marker expression methods, *Gene Ther.*, 9: 1155-62 (2002).
Schroers et al., Lentiviral transduction of human dendritic cells, *Meth. Mol. Biol.*, 246: 451-9 (2004).
Schuler et al., The use of dendritic cells in cancer immunotherapy, *Curr. Opin. Immunol.*, 15: 138-47 (2003).
Schwartz et al., Cloning and functional analysis of multiply spliced mRNA species of human immunodeficiency virus type 1, *J. Virol.*, 64(6): 2519-9 (1990).
SEQ ID No. 2 of WO-2005/118802 (D8), cited as document D11 by Opponent in Opposition against European Patent No. 245786, dated Jul. 21, 2016.
Sequence comparison of SEQ ID No. 1 of European Patent No. 2456786 and SEQ ID No. 2 of WO-2005/118802 (D8), cited as document D9 by Opponent in Opposition against European Patent No. 2456786, dated Jul. 21, 2016.
Sequence comparison of Sindbis E2 glycoprotein of ZZ SINDBIS and E2 glycoprotein of SEQ ID No. 1 of European Patent No. 2456786, cited as document D10 by Opponent in Opposition against European Patent No. 2456786, dated Jul. 21, 2016.
Sharkey et al., Ross River Virus Glycoprotein-Pseudotyped Retroviruses and Stable Cell Lines for Their Production, *J. Virol.*, 75:2653-2659, 2001.
Sharova et al., Primate lentiviral Vpx commandeers DDB1 to counteract a macrophage restriction, *PLoS*, 4(5): 1-12 (2008).
Shen et al., Silencing of SOCS1 enhances antigen presentation by dendritic cells and antigen-specific anti-tumor immunity, *Nat. Biotechnol.*, 22: 1546-53 (2004).
Shimizu et al., Internalization of kit together with stem cell factor on human fetal liver-derived mast cells: A new protein and RNA synthesis are required for reappearance of kit, *J. Immunol.*, 156: 3443-9 (1996).
Shiu eta l., Identification of ongoing human immunodeficiency virus type 1 (HIV-1) replication in residual viremia during recombinant HIV-1 poxvirus immunications in patients with clinically undetectable viral loads on durable suppressive highly active antiretroviral therapy, *J. Virol.*, 83(19): 9731-42 (2009).
Shiver et al., Recent Advances in the Development of HIV-1 Vaccines Using Replication—Incompetent Adenovirus Vectors, *Annu. Rev. Med.*, 55:355-372, 2004.
Shoji et al., Current status of delivery systems to improve target efficacy of oligonucleotides, *Curr. Pharm. Des.*, 10(7): 785-96 (2004).
Shortman et al., Improving vaccines by targeting antigens to dendritic cells, *Exp. Mol. Med.*, 41(2): 61-6 (2009).
Shresta et al., Critical Roles for Both STAT1-Dependent and STAT I-Independent Pathways in the Control of Primary Dengue Virus Infection in Mice, *The Journal of Immunology*,175:3946-3954, 2005.
Siemasko et al., IgA and IgB are required for efficient trafficking to late endosomes and to enhance antigen presentation, *J. Immunol.*, 162(11): 6518-25 (1999).
Singh et al., Targeting glycan modified OVA to murine DC-SIGN transgenic dendritic cells enhances MHC class I and II presentation, *Mol. Immunol.*, 47: 164-74 (2009).
Skehel et al., Receptor binding and membrane fusion in virus entry: The influenza hemagglutinin et al., *Annu. Rev. Biochem.*, 69: 531-69 (2000).

Sloan et al., MHC class I and class II presentation of tumor antigen in retrovirally and adenovirally trasnsduced dendritic cells, *Cancer Gene Ther.*, 9(11): 946-50 (2002).
Small et al., Immunotherapy of homone-refractory prostate cancer with antigen-loaded dendritic cells, *J. Clin. Oncol.*, 18(23): 2894-903 (2000).
Smit et al., PE2 Cleavage Mutants of Sindbis Virus: Correlation between Viral Infectivity and pH-Dependent Membrane Fusion Activation of the Spike Heterodimer, *J. Virol.*, 75:11196-11204, 2001.
Smit et al., Low-pH-dependent fusion of Sindbis virus with receptor-free cholesterol—an sphingolipid-containing liposomes, *J. Virol.*, 73(10): 8476-84 (1999).
Somia et al., Generation of targeted retroviral vectors by using single-chain variable fragment—An approach to in vivo gene delivery, *Proc. Natl. Acad. Sci. USA*, 92: 7570-4 (1995).
Song et al., Persistent, antigen-specific, therapeutic antitumor immunity by dendritic cells genetically modified with an adenviral vector to express a model tumor antigen, *Gene Ter.*, 7: 2080-6 (2000).
Stanley et al., Glycosylation mutants of animal cells, *Ann. Rev. Genet.*, 18: 525-52 (1984).
Steinmann et al., Tolerogenic dendritic cells, *Annu. Rev. Immunol.*, 21: 685-711 (2003).
Strang et at, Human Immunodeficiency Virus Type 1 Vectors with Alphavirus Envelope Glycoproteins Produced from Stable Packaging Cells, *J. Virol.*, 79:1765-1771, 2005.
Strauss et al., The alphaviruses: gene expression, replication, and evolution, *Microhiol. Rev.*, 58:491-562, 1994.
Strauss et al., Complete nucleotide sequence of the genomic RNA of Sindbis virus, *Virology*, 133: 92-110 (1984).
Strauss et al., GenBank Accession No. NC_001547.1, Sindbis virus, complete genome, dated Jun. 27, 2012.
Strauss et al., Host-cell receptors for Sindbis virus, *Arch. Virol.*, 9: 473-84 (1994).
Stricker et al., The maginot line and AIDS vaccines, *Medical Hypotheses*, 48: 527-9 (1997).
Su et al., DC-SIGN binds to HIV-1 glycoprotein 120 in a distinct but overlapping fashion compared with ICAM-2 and ICAM-3, *J. Biol. Chem.*, 279(18): 19122-32 (2004).
Sunseri et al., HIV-1 modified to package SIV Vpx efficiently infects macrophages and dendritic cells, *J. Virol.*, 1-44 (2011).
Sutton et al., Human immunodeficiency virus type 1 vectors efficiently transduce human hematopoietic stem cells, *J. Virol.*, 72(7): 5781-8 (1998).
Tacken eta I., Dendritic-cell immunotherapy: From ex vivo loading to in vivo targeting, *Nat. Rev. Immunol.*, 7: 790-802 (2007).
Tai et al., Production of lentiviral ventors with enhanced efficiency to target dendritic cells by attenuating mannosidase activity of mammalian cells, *J. Biol. Eng.*, 5(1): 1 (2011).
Takadera et al., Structure of the two promoters of the human Ick gene: Differential accumulation of two classes of Ick transcripts in T cells, *Mol. Cell. Biol.*, 9(5): 2173-80 (1989).
Takahara et al., Functional comparison of the mouse DC-SIGN, SIGNR1, SIGNR3 and Langerin, C-type lectins, *Int. Immunol.*, 16: 819-29 (2004).
Tang et al., Molecular links between the E2 envelope glycoprotein and nucleocapsid core in Sindbis virus, *J. Molec. Biol.*, 414: 442-59 (2011).
Tareen et al., DCVexTM: A novel integration-deficient lentiviral vector technology that incorporates genetic and post-translational elements to target dendritic cells (Immune Design)—cited in Opposition against European Patent No. 2456786 on Oct. 8, 2014.
Tarhini et al., Safety and immunogenicity of vaccination with MART-1 (26-35, 27L), gp100 (209-217, 210M), and tyrosinase (368-376, 370D) in adjuvant with PF-3512676 and GM-CSF in metastatic melanoma, *J. Immunother.* ,35(4): 359-66 (2012).
Tatsis et al., Adenoviruses as vaccine vectors, *Mol. Ther.*, 10: 616-29 (2004).
Temme et al., Efficient transduction and long-term retroviral expression of the melanoma-associated tumor antigen tyrosinase in CD34(+) cord blood-derived dendritic cells, *Gene Ther.*, 9: 1551-50 (2002).

(56) References Cited

OTHER PUBLICATIONS

Trumpfheller et al., Intensified and protective CD4+ T cell immunity in mice with anti-dendritic cell HIV gag fusion antibody vaccine, *J. Exp. Med.*, 1-11 (2006).
Tulsiani et al., Swainsonine inhibits the biosynthesis of complex glycoproteins by inhibition of Golgi mannosidase II, *J. Biol. Chem.*, 257(14): 7936-9 (1982).
Uchida et al., HIV, but not murine leukemia virus, vectors mediate high efficiency gene transfer into freshly isolated G0/G1 human hematopoietic stem cells, *Proc. Natl Acad. Sci. USA*, 95(20): 11939-44 (1998).
Valsesia-Wittmann et al., Modifications in the binding domain of avian retrovirus envelope protein to redirect the host range of retroviral vectors, *J. Virol.*, 68(7): 4609-19 (1994).
Van Brockhoven et al., Targeting dendritic cells with antigen-containing liposomes: A highly effective procedure for induction of antitumor immunity and for tumor immunotherapy, *Cancer Res.*, 64: 4357-65 (2004).
Veljkovic et al., AIDS epidemic at the beginning of the third millennium: Time for a new AIDS vaccine strategy, *Vaccine*, 19: 1855-62 (2001).
Verhoeyen et al., Surface—engineering of lentiviral vectors, *J. Gene Med.*, 6: S83-94 (2004).
Verma et al., Gene therapy—promises, problems and prospects, *Nature*, 389(6648): 239-42 (1997).
Vitale et al., Mannose analog 1-deoxymannojirimycin inhibits the Golgi-mediated processing of bean storage glycogproteins, *Plant Physiol.*, 89: 1079-84 (1989).
Waite et al., Inhibition of Sindbis virus release by media of low ionic strength: an electron microscope study, *J. Virol.*, 10(3): 537-44 (1972).
Wang et al., High-affinity laminin receptor is a receptor of Sindbis virus in mammalian cells, *J. Virol.*, 66: 4992-5001 (1992).
Wang et al., Phase I trial of MART-1 peptide vaccine with incomplete Freund's adjuvant for resected high-risk melanoma, *Clin. Cancer Res.*, 5(10): 2756-65 (1999).
Weber et al., Phase I clinical trial with HIV-1 gp160 plasmid vaccine in HIV-1-infected asymptomatic subjects. *Eur. J. Clin. Microbiol. Infect. Dis.*, 20: 800-3 (2001).
West et al., Mutations in the endodomain of Sindbis virus glycoprotein E2 define sequences critical for virus assembly, *J. Virol.*, 80:4458-4468, 2006.
Wigler et al., DNA-mediated transfer of the adenine phosphoribosyltransferase locus into mammalian cells, *Proc. Natl. Acad. Sci. USA*, 76(3): 1373-6 (1979).
Williamsburg BioProcessing Foundation, Reference Materials for Retroviruses and Lentiviruses—Final Report, pp. 1-13, Jun. 5, 2002.
Wu et al., Enhanced breadth of CD4 T-cell immunity by DNA prime adenovirus boost immunization to human immunodeficiency virus Env and Gag immunogens, *J. Virol.*, 79(13): 8024-31 (2005).
Wu et al., Multimerization of a chimeric anti-CD20 single-chain Fv-Fc fusion protein is mediated through variable domain exchange, *Protein Engin.*, 14(12): 1025-33 (2001).
Xiao et al., A TLR4 agonist synergizes with dendritic cell-directed lentiviral vectors for inducing antigen-specific immune response, *Vaccine*, 30: 2570-81 (2012).
Yang et al., Engineered lentivector targeting of dendritic cells for in vivo immunization, *Nature Biotechnology*, 26:326-334, 2008.
Yang et al., Long-term in vivo provision of antigen-specific T cell immunity by programming hematopoietic stem cells, *Proc. Natl. Acad. Sci. USA*, 102: 4518-23 (2005).
Yang et al., Targeted lentiviral vectors to specific cell types in vivo, *Proc. Natl. Acad. Sci. USA*, 103(31):11479-11484, 2006.
Yee et al., The regulation of myogenin gene expression during the embryonic development of the mouse, *Genes Dev.*, 7: 1277-89 (1993).
Yip et al., Organization of the human beta-1,2-N-acetylglucosaminyltransferase I gene (MGAT1), which controls complex and hybrid N-glycan synthesis, *Biochem. J.*, 321: 465-74 (1997).
You et al., Targeting dendritic cells to enhance DNA vaccine potency, *Cancer Res.*, 61: 3704-11 (2001).
Zarei et al., Transduction of dendritic cells by antigen-encoding lentiviral vectors permits antigen processing and MHC class I-dependent presentation, *J. Allergy Clin. Immunol.*, 109:988-994, 2002.
Zennou et al., HIV-1 Genome Nuclear Import is Mediated by a Central DNA Flap, *Cell*, 101:173-185, 2000.
Zhai et al., Antigen-specific tumor vaccines, *J. Immunol.*, 156(2): 700-10 (1996).
Zhang et al., Cell cycle inhibitory effects of HIV and SIV Vpr and Vpx in the yeast *Schizosaccharomyces pombe*, *Virology*, 230: 103-12 (1997).
Zhou et al., Current methods for loading dendritic cells with tumor antigen for the induction of antitumor immunity, *J. Immunol.*, 25(4): 289-303 (2002).
Zhou et al., DC-SIGN and immunoregulation. *Cell Mol. Immunol.*, 3: 279-83 (2006).
Zimmerman et al., Identification of a host protein essential for assembly of immature HIV-1 capsids, *Lett. Nat.*, 415: 88-92 (2002).
Zufferey et al., Self-Inactivating Lentivirus Vector for Safe and Efficient in Vivo Gene Delivery, *J. Viral.* 72:9873-9880, 1998.
Zufferey et al., Woodchuck hepatitis cirus posttranscriptional regulatory element enhances expression of trangenes delievered by retroviral vectors, *J. Virol.*, 74(4): 2886-92 (1999).
Goujon et al., Characterization of simian immunodeficiency virus SIVSM/human immunodeficiency virus type 2 Vpx function in human myeloid cells. J. Virol. 82(24): 12335-46 (2008).
Saeed et al., Role of the endoplasmic reticulum-associated degradation (ERAD) pathway in degradation of hepatitis C virus envelope proteins and production of virus particles. J. Biol. Chem. 286(43): 37264-73 (2011).
GenBank Accession No. CAA29688, X (AA 1-112) Human T-cell lymphotropic virus type 4, dated Apr. 18, 2005.
Laguette et al., Evolutionary and functional analyses of the interaction between the myeloid restriction factor SAMD1 and lentiviral Vpx protein. Cell Host Microbe.11(2): 205-17 (2012).
Nasir et al., Performance of coarse and fine timing synchronization in OFDM receivers. Future Compt. Commun. 2nd International Conference, 2: 412-6 (May 21-14, 2010).
Robbins et al., PS2-083 immunization with novel DC-targeting lentiviral vectors induces polyfunctional CD8 T cell responses and therapeutic anti-tumor immunity. Cytokine, 56(11): 86(2011).
Sunseri et al., Human immunodeficiency virus type 1 modified to package simian immunodeficiency virus Vpx efficiently infects macrophages and dendritic cells. J. Virol. 85(13): 6263-74 (2011).
Froelich et al., Virus-receptor Mediated Transduction of Dendritic Cells by Lentiviruses Enveloped with Glycoproteins Derived from Semliki Forest Virus, *pLOS One*, 6(6):e21491 (2011).
Laguette, SAMHD1 is the dendritic- and myeloid-cell-specific HIV-1 restriction factor counteracted by Vpx, *Nature*, 474:654-7 (2011).
Strauss et al., Accession No. NP_062890, Hyopthetical Protein [Sindbis Virus], (Aug. 2000).
Kestler et al., Accession No. AAB59908.1, VPX Protein [Simian Immunodeficiency Virus], (Nov. 2000).

Substrate Specificity:

PNGaseF:
Cleaves any N-linked glycosylation.
(Will target all 4 sites on SinVar1)

Substrate Specificity:

EndoH:
Cleaves only hi-mannose N-linked glycosylation.
(Will target 2/4 sites on SinVar1)

Man ○  GlcNAc ☐

FIGURE 3A

|  | Var1 | | | Var1 +DMNJ | | | Var1+ Kifunensine | | |
|---|---|---|---|---|---|---|---|---|---|
| PNGaseF: | − | + | − | − | + | − | − | + | − |
| EndoH: | − | − | + | − | − | + | − | − | + |

50kb →

FIGURE 3B

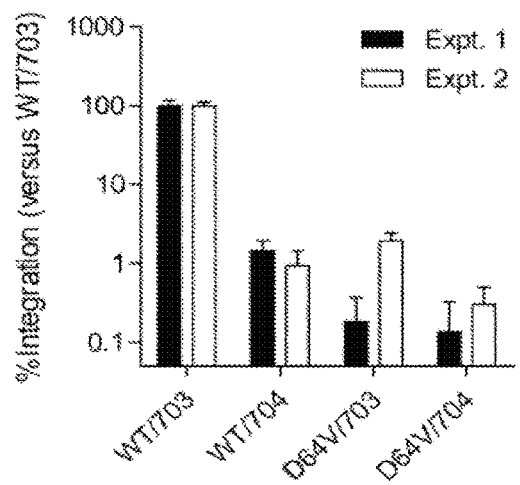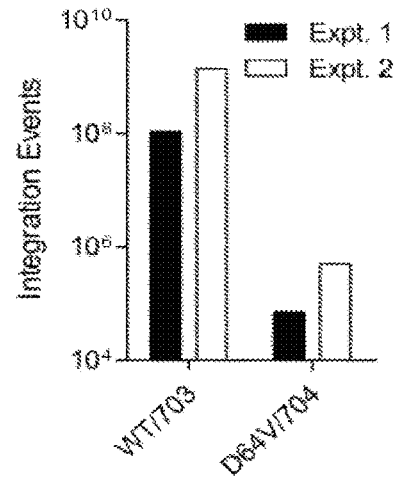
Figure 10A
Figure 10B
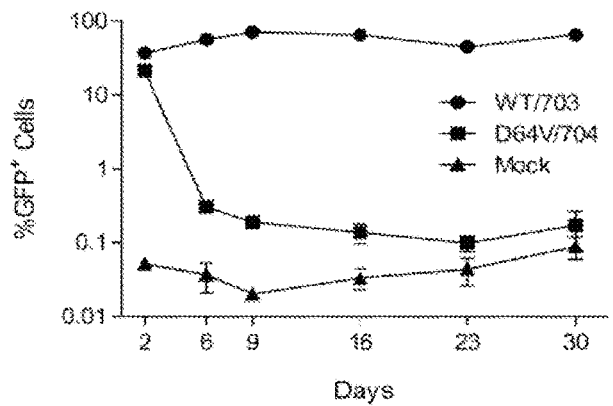
FIGURE 10C

|  | 6 µg gag/pol DNA | | 3 µg gag/pol DNA | |
| --- | --- | --- | --- | --- |
| | WT gag/pol | RI gag/pol | WT gag/pol | RI gag/pol |
| p24 (ng/mL) | 206+/- 21 | 235 +/- 6 | 84 +/- 3 | 100 +/- 6 |

Sequence of psi-gag recombinant amplicon

··· GAAGGAGAGAG ATGG···//··· AAGA AAAAAGCACAG··· positions: -1, -76, -414, -937

SEQ ID NO: 69

Vector Genome — WT gag/pol

Partial gag

Figure 17C

Sequence of RI-recombinant amplicon

··· AGGCCCGAAGGAATAGAAGAAGAAGGTG· TACAAGCGGTG··· positions: -1, -1253, -1254, -1329

SEQ ID NO: 70

Vector Genome — RI gag/pol

Figure 17D

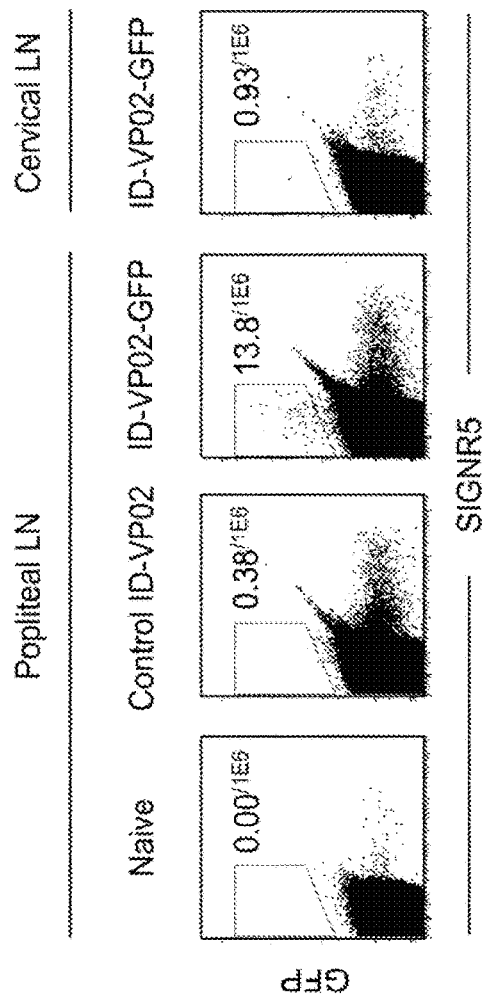
Figure 20A
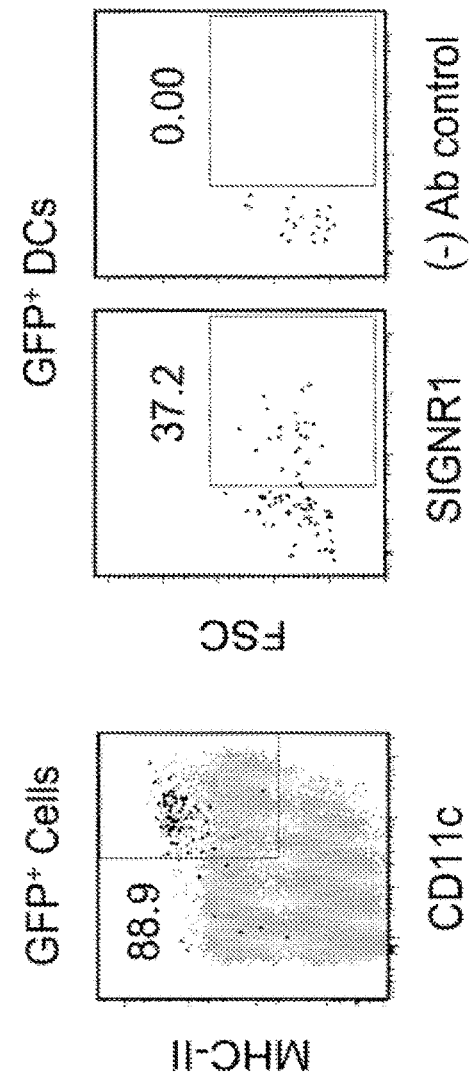
Figure 20B
Figure 20C

SEQUENCE LISTING

```
<160> NUMBER OF SEQ ID NOS: 70

<210> SEQ ID NO 1
<211> LENGTH: 423
<212> TYPE: PRT
<213> ORGANISM: Sindbis virus
<220> FEATURE:
<221> NAME/KEY: misc_feature
<222> LOCATION: (160)..(160)
<223> OTHER INFORMATION: Xaa can be any naturally occurring amino acid

<400> SEQUENCE: 1

Ser Val Ile Asp Asp Phe Thr Leu Thr Ser Pro Tyr Leu Gly Thr Cys
1               5                   10                  15

Ser Tyr Cys His His Thr Val Pro Cys Phe Ser Pro Val Lys Ile Glu
            20                  25                  30

Gln Val Trp Asp Glu Ala Asp Asp Asn Thr Ile Arg Ile Gln Thr Ser
        35                  40                  45

Ala Gln Phe Gly Tyr Asp Gln Ser Gly Ala Ala Ser Ala Asn Lys Tyr
    50                  55                  60

Arg Tyr Met Ser Leu Lys Gln Asp His Thr Val Lys Glu Gly Thr Met
65                  70                  75                  80

Asp Asp Ile Lys Ile Ser Thr Ser Gly Pro Cys Arg Arg Leu Ser Tyr
                85                  90                  95

Lys Gly Tyr Phe Leu Leu Ala Lys Cys Pro Pro Gly Asp Ser Val Thr
            100                 105                 110

Val Ser Ile Val Ser Ser Asn Ser Ala Thr Ser Cys Thr Leu Ala Arg
        115                 120                 125

Lys Ile Lys Pro Lys Phe Val Gly Arg Glu Lys Tyr Asp Leu Pro Pro
    130                 135                 140

Val His Gly Lys Lys Ile Pro Cys Thr Val Tyr Asp Arg Leu Lys Xaa
145                 150                 155                 160
```

Thr Thr Ala Gly Tyr Ile Thr Met His Arg Pro Arg Pro His Ala Tyr
            165                 170                 175

Thr Ser Tyr Leu Glu Glu Ser Ser Gly Lys Val Tyr Ala Lys Pro Pro
        180                 185                 190

Ser Gly Lys Asn Ile Thr Tyr Glu Cys Lys Cys Gly Asp Tyr Lys Thr
        195                 200                 205

Gly Thr Val Ser Thr Arg Thr Glu Ile Thr Gly Cys Thr Ala Ile Lys
        210                 215                 220

Gln Cys Val Ala Tyr Lys Ser Asp Gln Thr Lys Trp Val Phe Asn Ser
225                 230                 235                 240

Pro Asp Leu Ile Arg His Asp Asp His Thr Ala Gln Gly Lys Leu His
                245                 250                 255

Leu Pro Phe Lys Leu Ile Pro Ser Thr Cys Met Val Pro Val Ala His
                260                 265                 270

Ala Pro Asn Val Ile His Gly Phe Lys His Ile Ser Leu Gln Leu Asp
            275                 280                 285

Thr Asp His Leu Thr Leu Leu Thr Thr Arg Arg Leu Gly Ala Asn Pro
290                 295                 300

Glu Pro Thr Thr Glu Trp Ile Val Gly Lys Thr Val Arg Asn Phe Thr
305                 310                 315                 320

Val Asp Arg Asp Gly Leu Glu Tyr Ile Trp Gly Asn His Glu Pro Val
                325                 330                 335

Arg Val Tyr Ala Gln Glu Ser Ala Pro Gly Asp Pro His Gly Trp Pro
                340                 345                 350

His Glu Ile Val Gln His Tyr Tyr His Arg His Pro Val Tyr Thr Ile
                355                 360                 365

Leu Ala Val Ala Ser Ala Thr Val Ala Met Met Ile Gly Val Thr Val
        370                 375                 380

Ala Val Leu Cys Ala Cys Lys Ala Arg Arg Glu Cys Leu Thr Pro Tyr
385                 390                 395                 400

Ala Leu Ala Pro Asn Ala Val Ile Pro Thr Ser Leu Ala Leu Leu Cys
                405                 410                 415

Cys Val Arg Ser Ala Asn Ala
            420

<210> SEQ ID NO 2
<211> LENGTH: 986
<212> TYPE: PRT
<213> ORGANISM: Sindbis virus

<400> SEQUENCE: 2

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
            20                  25                  30

Arg Ala Leu Asp Ile Leu Glu Glu Asn Val Asn His Glu Ala Tyr Asp
        35                  40                  45

Thr Leu Leu Asn Ala Ile Leu Arg Cys Gly Ser Ser Gly Ser Val Ile
    50                  55                  60

Asp Asp Phe Thr Leu Thr Ser Pro Tyr Leu Gly Thr Cys Ser Tyr Cys
65                  70                  75                  80

His His Thr Val Pro Cys Phe Ser Pro Val Lys Ile Glu Gln Val Trp
                85                  90                  95

Asp Glu Ala Asp Asp Asn Thr Ile Arg Ile Gln Thr Ser Ala Gln Phe
            100                 105                 110

```
Gly Tyr Asp Gln Ser Gly Ala Ala Ser Ala Asn Lys Tyr Arg Tyr Met
            115                 120                 125

Ser Leu Lys Gln Met Tyr Pro Tyr Asp Val Pro Asp Tyr Ala Thr Val
        130                 135                 140

Lys Glu Gly Thr Met Asp Asp Ile Lys Ile Ser Thr Ser Gly Pro Cys
145                 150                 155                 160

Arg Arg Leu Ser Tyr Lys Gly Tyr Phe Leu Leu Ala Lys Cys Pro Pro
                165                 170                 175

Gly Asp Ser Val Thr Val Ser Ile Val Ser Ser Asn Ser Ala Thr Ser
            180                 185                 190

Cys Thr Leu Ala Arg Lys Ile Lys Pro Lys Phe Val Gly Arg Glu Lys
        195                 200                 205

Tyr Asp Leu Pro Pro Val His Gly Lys Lys Ile Pro Cys Thr Val Tyr
    210                 215                 220

Asp Arg Leu Ala Ala Thr Thr Ala Gly Tyr Ile Thr Met His Arg Pro
225                 230                 235                 240

Arg Pro His Ala Tyr Thr Ser Tyr Leu Glu Glu Ser Ser Gly Lys Val
                245                 250                 255

Tyr Ala Lys Pro Pro Ser Gly Lys Asn Ile Thr Tyr Glu Cys Lys Cys
            260                 265                 270

Gly Asp Tyr Lys Thr Gly Thr Val Ser Thr Arg Thr Glu Ile Thr Gly
        275                 280                 285

Cys Thr Ala Ile Lys Gln Cys Val Ala Tyr Lys Ser Asp Gln Thr Lys
    290                 295                 300

Trp Val Phe Asn Ser Pro Asp Leu Ile Arg His Asp Asp His Thr Ala
305                 310                 315                 320

Gln Gly Lys Leu His Leu Pro Phe Lys Leu Ile Pro Ser Thr Cys Met
                325                 330                 335

Val Pro Val Ala His Ala Pro Asn Val Ile His Gly Phe Lys His Ile
            340                 345                 350

Ser Leu Gln Leu Asp Thr Asp His Leu Thr Leu Leu Thr Thr Arg Arg
        355                 360                 365

Leu Gly Ala Asn Pro Glu Pro Thr Thr Glu Trp Ile Val Gly Lys Thr
    370                 375                 380

Val Arg Asn Phe Thr Val Asp Arg Asp Gly Leu Glu Tyr Ile Trp Gly
385                 390                 395                 400

Asn His Glu Pro Val Arg Val Tyr Ala Gln Glu Ser Ala Pro Gly Asp
                405                 410                 415

Pro His Gly Trp Pro His Glu Ile Val Gln His Tyr Tyr His Arg His
            420                 425                 430

Pro Val Tyr Thr Ile Leu Ala Val Ala Ser Ala Thr Val Ala Met Met
        435                 440                 445

Ile Gly Val Thr Val Ala Val Leu Cys Ala Cys Lys Ala Arg Arg Glu
    450                 455                 460

Cys Leu Thr Pro Tyr Ala Leu Ala Pro Asn Ala Val Ile Pro Thr Ser
465                 470                 475                 480

Leu Ala Leu Leu Cys Cys Val Arg Ser Ala Asn Ala Glu Thr Phe Thr
                485                 490                 495

Glu Thr Met Ser Tyr Leu Trp Ser Asn Ser Gln Pro Phe Phe Trp Val
            500                 505                 510

Gln Leu Cys Ile Pro Leu Ala Ala Phe Ile Val Leu Met Arg Cys Cys
        515                 520                 525
```

-continued

```
Ser Cys Cys Leu Pro Phe Leu Val Val Ala Gly Ala Tyr Leu Ala Lys
    530                 535                 540

Val Asp Ala Tyr Glu His Ala Thr Thr Val Pro Asn Val Pro Gln Ile
545                 550                 555                 560

Pro Tyr Lys Ala Leu Val Glu Arg Ala Gly Tyr Ala Pro Leu Asn Leu
                565                 570                 575

Glu Ile Thr Val Met Ser Ser Glu Val Leu Pro Ser Thr Asn Gln Glu
                580                 585                 590

Tyr Ile Thr Cys Lys Phe Thr Thr Val Val Pro Ser Pro Lys Ile Lys
                595                 600                 605

Cys Cys Gly Ser Leu Glu Cys Gln Pro Ala Ala His Ala Gly Tyr Thr
610                 615                 620

Cys Lys Val Phe Gly Gly Val Tyr Pro Phe Met Trp Gly Gly Ala Gln
625                 630                 635                 640

Cys Phe Cys Asp Ser Glu Asn Ser Gln Met Ser Glu Ala Tyr Val Glu
                645                 650                 655

Leu Ser Ala Asp Cys Ala Ser Asp His Ala Gln Ala Ile Lys Val His
                660                 665                 670

Thr Ala Ala Met Lys Val Gly Leu Arg Ile Val Tyr Gly Asn Thr Thr
                675                 680                 685

Ser Phe Leu Asp Val Tyr Val Asn Gly Val Thr Pro Gly Thr Ser Lys
                690                 695                 700

Asp Leu Lys Val Ile Ala Gly Pro Ile Ser Ala Ser Phe Thr Pro Phe
705                 710                 715                 720

Asp His Lys Val Val Ile His Arg Gly Leu Val Tyr Asn Tyr Asp Phe
                725                 730                 735

Pro Glu Tyr Gly Ala Met Lys Pro Gly Ala Phe Gly Asp Ile Gln Ala
                740                 745                 750

Thr Ser Leu Thr Ser Lys Asp Leu Ile Ala Ser Thr Asp Ile Arg Leu
                755                 760                 765

Leu Lys Pro Ser Ala Lys Asn Val His Val Pro Tyr Thr Gln Ala Ser
                770                 775                 780

Ser Gly Phe Glu Met Trp Lys Asn Asn Ser Gly Arg Pro Leu Gln Glu
785                 790                 795                 800

Thr Ala Pro Phe Gly Cys Lys Ile Ala Val Asn Pro Leu Arg Ala Val
                805                 810                 815

Asp Cys Ser Tyr Gly Asn Ile Pro Ile Ser Ile Asp Ile Pro Asn Ala
                820                 825                 830

Ala Phe Ile Arg Thr Ser Asp Ala Pro Leu Val Ser Thr Val Lys Cys
                835                 840                 845

Glu Val Ser Glu Cys Thr Tyr Ser Ala Asp Phe Gly Gly Met Ala Thr
850                 855                 860

Leu Gln Tyr Val Ser Asp Arg Glu Gly Gln Cys Pro Val His Ser His
865                 870                 875                 880

Ser Ser Thr Ala Thr Leu Gln Glu Ser Thr Val His Val Leu Glu Lys
                885                 890                 895

Gly Ala Val Thr Val His Phe Ser Thr Ala Ser Pro Gln Ala Asn Phe
                900                 905                 910

Ile Val Ser Leu Cys Gly Lys Lys Thr Thr Cys Asn Ala Glu Cys Lys
                915                 920                 925

Pro Pro Ala Asp His Ile Val Ser Thr Pro His Lys Asn Asp Gln Glu
930                 935                 940

Phe Gln Ala Ala Ile Ser Lys Thr Ser Trp Ser Trp Leu Phe Ala Leu
```

```
                    945                 950                 955                 960
                    Phe Gly Gly Ala Ser Ser Leu Leu Ile Ile Gly Leu Met Ile Phe Ala
                                    965                 970                 975
                    Cys Ser Met Met Leu Thr Ser Thr Arg Arg
                                    980                 985

<210> SEQ ID NO 3
<211> LENGTH: 982
<212> TYPE: PRT
<213> ORGANISM: Sindbis virus

<400> SEQUENCE: 3

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
            20                  25                  30

Arg Ala Leu Asp Ile Leu Glu Glu Asn Val Asn His Glu Ala Tyr Asp
        35                  40                  45

Thr Leu Leu Asn Ala Ile Leu Arg Cys Gly Ser Ser Gly Arg Ser Lys
    50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95

Glu Gln Val Trp Asp Glu Ala Asp Asp Asn Thr Ile Arg Ile Gln Thr
            100                 105                 110

Ser Ala Gln Phe Gly Tyr Asp Gln Ser Gly Ala Ala Ser Ala Asn Lys
        115                 120                 125

Tyr Arg Tyr Met Ser Leu Glu Gln Asp His Thr Val Lys Glu Gly Thr
    130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
        195                 200                 205

Pro Val His Gly Lys Lys Ile Pro Cys Thr Val Tyr Asp Arg Leu Glu
    210                 215                 220

Gly Thr Thr Ala Gly Tyr Ile Thr Met His Arg Pro Arg Pro His Ala
225                 230                 235                 240

Tyr Thr Ser Tyr Leu Glu Glu Ser Ser Gly Lys Val Tyr Ala Lys Pro
                245                 250                 255

Pro Ser Gly Lys Asn Ile Thr Tyr Glu Cys Lys Cys Gly Asp Tyr Lys
            260                 265                 270

Thr Gly Thr Val Ser Thr Arg Thr Glu Ile Thr Gly Cys Thr Ala Ile
        275                 280                 285

Lys Gln Cys Val Ala Tyr Lys Ser Asp Gln Thr Lys Trp Val Phe Asn
    290                 295                 300

Ser Pro Asp Leu Ile Arg His Asp Asp His Thr Ala Gln Gly Lys Leu
305                 310                 315                 320

His Leu Pro Phe Lys Leu Ile Pro Ser Thr Cys Met Val Pro Val Ala
                325                 330                 335
```

-continued

His Ala Pro Asn Val Ile His Gly Phe Lys His Ile Ser Leu Gln Leu
                340                 345                 350

Asp Thr Asp His Leu Thr Leu Leu Thr Thr Arg Arg Leu Gly Ala Asn
            355                 360                 365

Pro Glu Pro Thr Thr Glu Trp Ile Val Gly Lys Thr Val Arg Asn Phe
        370                 375                 380

Thr Val Asp Arg Asp Gly Leu Glu Tyr Ile Trp Gly Asn His Glu Pro
385                 390                 395                 400

Val Arg Val Tyr Ala Gln Glu Ser Ala Pro Gly Asp Pro His Gly Trp
                405                 410                 415

Pro His Glu Ile Val Gln His Tyr Tyr His Arg His Pro Val Tyr Thr
            420                 425                 430

Ile Leu Ala Val Ala Ser Ala Thr Val Ala Met Met Ile Gly Val Thr
        435                 440                 445

Val Ala Val Leu Cys Ala Cys Lys Ala Arg Arg Glu Cys Leu Thr Pro
450                 455                 460

Tyr Ala Leu Ala Pro Asn Ala Val Ile Pro Thr Ser Leu Ala Leu Leu
465                 470                 475                 480

Cys Cys Val Arg Ser Ala Asn Ala Glu Thr Phe Thr Glu Thr Met Ser
                485                 490                 495

Tyr Leu Trp Ser Asn Ser Gln Pro Phe Phe Trp Val Gln Leu Cys Ile
            500                 505                 510

Pro Leu Ala Ala Phe Ile Val Leu Met Arg Cys Cys Ser Cys Cys Leu
        515                 520                 525

Pro Phe Leu Val Val Ala Gly Ala Tyr Leu Ala Lys Val Asp Ala Tyr
    530                 535                 540

Glu His Ala Thr Thr Val Pro Asn Val Pro Gln Ile Pro Tyr Lys Ala
545                 550                 555                 560

Leu Val Glu Arg Ala Gly Tyr Ala Pro Leu Asn Leu Glu Ile Thr Val
                565                 570                 575

Met Ser Ser Glu Val Leu Pro Ser Thr Asn Gln Glu Tyr Ile Thr Cys
            580                 585                 590

Lys Phe Thr Thr Val Val Pro Ser Pro Lys Ile Lys Cys Cys Gly Ser
        595                 600                 605

Leu Glu Cys Gln Pro Ala Ala His Ala Asp Tyr Thr Cys Lys Val Phe
    610                 615                 620

Gly Gly Val Tyr Pro Phe Met Trp Gly Gly Ala Gln Cys Phe Cys Asp
625                 630                 635                 640

Ser Glu Asn Ser Gln Met Ser Glu Ala Tyr Val Glu Leu Ser Ala Asp
                645                 650                 655

Cys Ala Ser Asp His Ala Gln Ala Ile Lys Val His Thr Ala Ala Met
            660                 665                 670

Lys Val Gly Leu Arg Ile Val Tyr Gly Asn Thr Thr Ser Phe Leu Asp
        675                 680                 685

Val Tyr Val Asn Gly Val Thr Pro Gly Thr Ser Lys Asp Leu Lys Val
    690                 695                 700

Ile Ala Gly Pro Ile Ser Ala Ser Phe Thr Pro Phe Asp His Lys Val
705                 710                 715                 720

Val Ile His Arg Gly Leu Val Tyr Asn Tyr Asp Phe Pro Glu Tyr Gly
                725                 730                 735

Ala Met Lys Pro Gly Ala Phe Gly Asp Ile Gln Ala Thr Ser Leu Thr
            740                 745                 750

Ser Lys Asp Leu Ile Ala Ser Thr Asp Ile Arg Leu Leu Lys Pro Ser

```
            755                 760                 765
Ala Lys Asn Val His Val Pro Tyr Thr Gln Ala Ser Ser Gly Phe Glu
770                 775                 780

Met Trp Lys Asn Asn Ser Gly Arg Pro Leu Gln Glu Thr Ala Pro Phe
785                 790                 795                 800

Gly Cys Lys Ile Ala Val Asn Pro Leu Arg Ala Val Asp Cys Ser Tyr
                805                 810                 815

Gly Asn Ile Pro Ile Ser Ile Asp Ile Pro Asn Ala Ala Phe Ile Arg
                820                 825                 830

Thr Ser Asp Ala Pro Leu Val Ser Thr Val Lys Cys Glu Val Ser Glu
            835                 840                 845

Cys Thr Tyr Ser Ala Asp Phe Gly Gly Met Ala Thr Leu Gln Tyr Val
850                 855                 860

Ser Asp Arg Glu Gly Gln Cys Pro Val His Ser His Ser Ser Thr Ala
865                 870                 875                 880

Thr Leu Gln Glu Ser Thr Val His Val Leu Glu Lys Gly Ala Val Thr
                885                 890                 895

Val His Phe Ser Thr Ala Ser Pro Gln Ala Asn Phe Ile Val Ser Leu
                900                 905                 910

Cys Gly Lys Lys Thr Thr Cys Asn Ala Glu Cys Lys Pro Pro Ala Asp
            915                 920                 925

His Ile Val Ser Thr Pro His Lys Asn Asp Gln Glu Phe Gln Ala Ala
930                 935                 940

Ile Ser Lys Thr Ser Trp Ser Trp Leu Phe Ala Leu Phe Gly Gly Ala
945                 950                 955                 960

Ser Ser Leu Leu Ile Ile Gly Leu Met Ile Phe Ala Cys Ser Met Met
                965                 970                 975

Leu Thr Ser Thr Arg Arg
            980

<210> SEQ ID NO 4
<211> LENGTH: 982
<212> TYPE: PRT
<213> ORGANISM: Sindbis virus

<400> SEQUENCE: 4

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
                20                  25                  30

Arg Ala Leu Asp Ile Leu Glu Glu Asn Val Asn His Glu Ala Tyr Asp
            35                  40                  45

Thr Leu Leu Asn Ala Ile Leu Arg Cys Gly Ser Ser Gly Arg Ser Lys
        50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95

Glu Gln Val Trp Asp Glu Ala Asp Asp Asn Thr Ile Arg Ile Gln Thr
                100                 105                 110

Ser Ala Gln Phe Gly Tyr Asp Gln Ser Gly Ala Ala Ser Ala Asn Lys
            115                 120                 125

Tyr Arg Tyr Met Ser Leu Glu Gln Asp His Thr Val Glu Glu Gly Thr
        130                 135                 140
```

```
Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
            165                 170                 175

Thr Val Ser Ile Val Ser Ser Asn Ser Ala Thr Ser Cys Thr Leu Ala
                180                 185                 190

Arg Lys Ile Lys Pro Lys Phe Val Gly Arg Glu Lys Tyr Asp Leu Pro
        195                 200                 205

Pro Val His Gly Lys Lys Ile Pro Cys Thr Val Tyr Asp Arg Leu Glu
        210                 215                 220

Gly Thr Thr Ala Gly Tyr Ile Thr Met His Arg Pro Arg Pro His Ala
225                 230                 235                 240

Tyr Thr Ser Tyr Leu Glu Glu Ser Ser Gly Lys Val Tyr Ala Lys Pro
            245                 250                 255

Pro Ser Gly Lys Asn Ile Thr Tyr Glu Cys Lys Cys Gly Asp Tyr Lys
            260                 265                 270

Thr Gly Thr Val Ser Thr Arg Thr Glu Ile Thr Gly Cys Thr Ala Ile
        275                 280                 285

Lys Gln Cys Val Ala Tyr Lys Ser Asp Gln Thr Lys Trp Val Phe Asn
290                 295                 300

Ser Pro Asp Leu Ile Arg His Asp Asp His Thr Ala Gln Gly Lys Leu
305                 310                 315                 320

His Leu Pro Phe Lys Leu Ile Pro Ser Thr Cys Met Val Pro Val Ala
                325                 330                 335

His Ala Pro Asn Val Ile His Gly Phe Lys His Ile Ser Leu Gln Leu
            340                 345                 350

Asp Thr Asp His Leu Thr Leu Leu Thr Thr Arg Arg Leu Gly Ala Asn
        355                 360                 365

Pro Glu Pro Thr Thr Glu Trp Ile Val Gly Lys Thr Val Arg Asn Phe
370                 375                 380

Thr Val Asp Arg Asp Gly Leu Glu Tyr Ile Trp Gly Asn His Glu Pro
385                 390                 395                 400

Val Arg Val Tyr Ala Gln Glu Ser Ala Pro Gly Asp Pro His Gly Trp
            405                 410                 415

Pro His Glu Ile Val Gln His Tyr Tyr His Arg His Pro Val Tyr Thr
            420                 425                 430

Ile Leu Ala Val Ala Ser Ala Thr Val Ala Met Met Ile Gly Val Thr
        435                 440                 445

Val Ala Val Leu Cys Ala Cys Lys Ala Arg Arg Glu Cys Leu Thr Pro
450                 455                 460

Tyr Ala Leu Ala Pro Asn Ala Val Ile Pro Thr Ser Leu Ala Leu Leu
465                 470                 475                 480

Cys Cys Val Arg Ser Ala Asn Ala Glu Thr Phe Thr Glu Thr Met Ser
            485                 490                 495

Tyr Leu Trp Ser Asn Ser Gln Pro Phe Phe Trp Val Gln Leu Cys Ile
            500                 505                 510

Pro Leu Ala Ala Phe Ile Val Leu Met Arg Cys Cys Ser Cys Cys Leu
        515                 520                 525

Pro Phe Leu Val Val Ala Gly Ala Tyr Leu Ala Lys Val Asp Ala Tyr
        530                 535                 540

Glu His Ala Thr Thr Val Pro Asn Val Pro Gln Ile Pro Tyr Lys Ala
545                 550                 555                 560

Leu Val Glu Arg Ala Gly Tyr Ala Pro Leu Asn Leu Glu Ile Thr Val
```

```
            565                 570                 575
Met Ser Ser Glu Val Leu Pro Ser Thr Asn Gln Glu Tyr Ile Thr Cys
            580                 585                 590

Lys Phe Thr Thr Val Val Pro Ser Pro Lys Ile Lys Cys Cys Gly Ser
            595                 600                 605

Leu Glu Cys Gln Pro Ala Ala His Ala Asp Tyr Thr Cys Lys Val Phe
            610                 615                 620

Gly Gly Val Tyr Pro Phe Met Trp Gly Gly Ala Gln Cys Phe Cys Asp
625                 630                 635                 640

Ser Glu Asn Ser Gln Met Ser Glu Ala Tyr Val Glu Leu Ser Ala Asp
                    645                 650                 655

Cys Ala Ser Asp His Ala Gln Ala Ile Lys Val His Thr Ala Ala Met
                    660                 665                 670

Lys Val Gly Leu Arg Ile Val Tyr Gly Asn Thr Thr Ser Phe Leu Asp
                    675                 680                 685

Val Tyr Val Asn Gly Val Thr Pro Gly Thr Ser Lys Asp Leu Lys Val
                    690                 695                 700

Ile Ala Gly Pro Ile Ser Ala Ser Phe Thr Pro Phe Asp His Lys Val
705                 710                 715                 720

Val Ile His Arg Gly Leu Val Tyr Asn Tyr Asp Phe Pro Glu Tyr Gly
                    725                 730                 735

Ala Met Lys Pro Gly Ala Phe Gly Asp Ile Gln Ala Thr Ser Leu Thr
                    740                 745                 750

Ser Lys Asp Leu Ile Ala Ser Thr Asp Ile Arg Leu Leu Lys Pro Ser
                    755                 760                 765

Ala Lys Asn Val His Val Pro Tyr Thr Gln Ala Ser Ser Gly Phe Glu
                    770                 775                 780

Met Trp Lys Asn Asn Ser Gly Arg Pro Leu Gln Glu Thr Ala Pro Phe
785                 790                 795                 800

Gly Cys Lys Ile Ala Val Asn Pro Leu Arg Ala Val Asp Cys Ser Tyr
                    805                 810                 815

Gly Asn Ile Pro Ile Ser Ile Asp Ile Pro Asn Ala Ala Phe Ile Arg
                    820                 825                 830

Thr Ser Asp Ala Pro Leu Val Ser Thr Val Lys Cys Glu Val Ser Glu
                    835                 840                 845

Cys Thr Tyr Ser Ala Asp Phe Gly Gly Met Ala Thr Leu Gln Tyr Val
                    850                 855                 860

Ser Asp Arg Glu Gly Gln Cys Pro Val His Ser His Ser Ser Thr Ala
865                 870                 875                 880

Thr Leu Gln Glu Ser Thr Val His Val Leu Glu Lys Gly Ala Val Thr
                    885                 890                 895

Val His Phe Ser Thr Ala Ser Pro Gln Ala Asn Phe Ile Val Ser Leu
                    900                 905                 910

Cys Gly Lys Lys Thr Thr Cys Asn Ala Glu Cys Lys Pro Pro Ala Asp
                    915                 920                 925

His Ile Val Ser Thr Pro His Lys Asn Asp Gln Glu Phe Gln Ala Ala
                    930                 935                 940

Ile Ser Lys Thr Ser Trp Ser Trp Leu Phe Ala Leu Phe Gly Gly Ala
945                 950                 955                 960

Ser Ser Leu Leu Ile Ile Gly Leu Met Ile Phe Ala Cys Ser Met Met
                    965                 970                 975

Leu Thr Ser Thr Arg Arg
            980
```

<210> SEQ ID NO 5
<211> LENGTH: 980
<212> TYPE: PRT
<213> ORGANISM: Sindbis virus

<400> SEQUENCE: 5

Met Ser Ala Ala Pro Leu Val Thr Ala Met Cys Leu Leu Gly Asn Val
1 5 10 15

Ser Phe Pro Cys Asp Arg Pro Pro Thr Cys Tyr Thr Arg Glu Pro Ser
20 25 30

Arg Ala Leu Asp Ile Leu Glu Glu Asn Val Asn His Glu Ala Tyr Asp
35 40 45

Thr Leu Leu Asn Ala Ile Leu Arg Cys Gly Ser Ser Gly Arg Ser Lys
50 55 60

Arg Ser Val Ile Asp Asp Phe Thr Leu Thr Ser Pro Tyr Leu Gly Thr
65 70 75 80

Cys Ser Tyr Cys His His Thr Val Pro Cys Phe Ser Pro Val Lys Ile
85 90 95

Glu Gln Val Trp Asp Glu Ala Asp Asp Asn Thr Ile Arg Ile Gln Thr
100 105 110

Ser Ala Gln Phe Gly Tyr Asp Gln Ser Gly Ala Ala Ser Ala Asn Lys
115 120 125

Tyr Arg Tyr Met Ser Leu Glu Gln Asp His Thr Val Lys Glu Gly Thr
130 135 140

Met Asp Asp Ile Lys Ile Ser Thr Ser Gly Pro Cys Arg Arg Leu Ser
145 150 155 160

Tyr Lys Gly Tyr Phe Leu Leu Ala Lys Cys Pro Pro Gly Asp Ser Val
165 170 175

Thr Val Ser Ile Val Ser Ser Asn Ser Ala Thr Ser Cys Thr Leu Ala
180 185 190

Arg Lys Ile Lys Pro Lys Phe Val Gly Arg Glu Lys Tyr Asp Leu Pro
195 200 205

Pro Val His Gly Lys Lys Ile Pro Cys Thr Val Tyr Asp Arg Leu Thr
210 215 220

Thr Ala Gly Tyr Ile Thr Met His Arg Pro Arg Pro His Ala Tyr Thr
225 230 235 240

Ser Tyr Leu Glu Glu Ser Ser Gly Lys Val Tyr Ala Lys Pro Pro Ser
245 250 255

Gly Lys Asn Ile Thr Tyr Glu Cys Lys Cys Gly Asp Tyr Lys Thr Gly
260 265 270

Thr Val Ser Thr Arg Thr Glu Ile Thr Gly Cys Thr Ala Ile Lys Gln
275 280 285

Cys Val Ala Tyr Lys Ser Asp Gln Thr Lys Trp Val Phe Asn Ser Pro
290 295 300

Asp Leu Ile Arg His Asp Asp His Thr Ala Gln Gly Lys Leu His Leu
305 310 315 320

Pro Phe Lys Leu Ile Pro Ser Thr Cys Met Val Pro Val Ala His Ala
325 330 335

Pro Asn Val Ile His Gly Phe Lys His Ile Ser Leu Gln Leu Asp Thr
340 345 350

Asp His Leu Thr Leu Leu Thr Thr Arg Arg Leu Gly Ala Asn Pro Glu
355 360 365

Pro Thr Thr Glu Trp Ile Val Gly Lys Thr Val Arg Asn Phe Thr Val

```
             370                 375                 380
Asp Arg Asp Gly Leu Glu Tyr Ile Trp Gly Asn His Glu Pro Val Arg
385                 390                 395                 400

Val Tyr Ala Gln Glu Ser Ala Pro Gly Asp Pro His Gly Trp Pro His
                405                 410                 415

Glu Ile Val Gln His Tyr Tyr Arg His Pro Val Tyr Thr Ile Leu
                420                 425                 430

Ala Val Ala Ser Ala Thr Val Ala Met Met Ile Gly Val Thr Val Ala
                435                 440                 445

Val Leu Cys Ala Cys Lys Ala Arg Arg Glu Cys Leu Thr Pro Tyr Ala
            450                 455                 460

Leu Ala Pro Asn Ala Val Ile Pro Thr Ser Leu Ala Leu Leu Cys Cys
465                 470                 475                 480

Val Arg Ser Ala Asn Ala Glu Thr Phe Thr Glu Thr Met Ser Tyr Leu
                485                 490                 495

Trp Ser Asn Ser Gln Pro Phe Phe Trp Val Gln Leu Cys Ile Pro Leu
                500                 505                 510

Ala Ala Phe Ile Val Leu Met Arg Cys Cys Ser Cys Cys Leu Pro Phe
                515                 520                 525

Leu Val Val Ala Gly Ala Tyr Leu Ala Lys Val Asp Ala Tyr Glu His
            530                 535                 540

Ala Thr Thr Val Pro Asn Val Pro Gln Ile Pro Tyr Lys Ala Leu Val
545                 550                 555                 560

Glu Arg Ala Gly Tyr Ala Pro Leu Asn Leu Glu Ile Thr Val Met Ser
                565                 570                 575

Ser Glu Val Leu Pro Ser Thr Asn Gln Glu Tyr Ile Thr Cys Lys Phe
                580                 585                 590

Thr Thr Val Val Pro Ser Pro Lys Ile Lys Cys Cys Gly Ser Leu Glu
                595                 600                 605

Cys Gln Pro Ala Ala His Ala Asp Tyr Thr Cys Lys Val Phe Gly Gly
            610                 615                 620

Val Tyr Pro Phe Met Trp Gly Gly Ala Gln Cys Phe Cys Asp Ser Glu
625                 630                 635                 640

Asn Ser Gln Met Ser Glu Ala Tyr Val Glu Leu Ser Ala Asp Cys Ala
                645                 650                 655

Ser Asp His Ala Gln Ala Ile Lys Val His Thr Ala Ala Met Lys Val
            660                 665                 670

Gly Leu Arg Ile Val Tyr Gly Asn Thr Thr Ser Phe Leu Asp Val Tyr
                675                 680                 685

Val Asn Gly Val Thr Pro Gly Thr Ser Lys Asp Leu Lys Val Ile Ala
            690                 695                 700

Gly Pro Ile Ser Ala Ser Phe Thr Pro Phe Asp His Lys Val Val Ile
705                 710                 715                 720

His Arg Gly Leu Val Tyr Asn Tyr Asp Phe Pro Glu Tyr Gly Ala Met
                725                 730                 735

Lys Pro Gly Ala Phe Gly Asp Ile Gln Ala Thr Ser Leu Thr Ser Lys
                740                 745                 750

Asp Leu Ile Ala Ser Thr Asp Ile Arg Leu Leu Lys Pro Ser Ala Lys
            755                 760                 765

Asn Val His Val Pro Tyr Thr Gln Ala Ser Ser Gly Phe Glu Met Trp
            770                 775                 780

Lys Asn Asn Ser Gly Arg Pro Leu Gln Glu Thr Ala Pro Phe Gly Cys
785                 790                 795                 800
```

```
Lys Ile Ala Val Asn Pro Leu Arg Ala Val Asp Cys Ser Tyr Gly Asn
                805                 810                 815

Ile Pro Ile Ser Ile Asp Ile Pro Asn Ala Ala Phe Ile Arg Thr Ser
            820                 825                 830

Asp Ala Pro Leu Val Ser Thr Val Lys Cys Glu Val Ser Glu Cys Thr
        835                 840                 845

Tyr Ser Ala Asp Phe Gly Gly Met Ala Thr Leu Gln Tyr Val Ser Asp
    850                 855                 860

Arg Glu Gly Gln Cys Pro Val His Ser His Ser Ser Thr Ala Thr Leu
865                 870                 875                 880

Gln Glu Ser Thr Val His Val Leu Glu Lys Gly Ala Val Thr Val His
                885                 890                 895

Phe Ser Thr Ala Ser Pro Gln Ala Asn Phe Ile Val Ser Leu Cys Gly
            900                 905                 910

Lys Lys Thr Thr Cys Asn Ala Glu Cys Lys Pro Pro Ala Asp His Ile
        915                 920                 925

Val Ser Thr Pro His Lys Asn Asp Gln Glu Phe Gln Ala Ala Ile Ser
    930                 935                 940

Lys Thr Ser Trp Ser Trp Leu Phe Ala Leu Phe Gly Gly Ala Ser Ser
945                 950                 955                 960

Leu Leu Ile Ile Gly Leu Met Ile Phe Ala Cys Ser Met Met Leu Thr
                965                 970                 975

Ser Thr Arg Arg
            980

<210> SEQ ID NO 6
<211> LENGTH: 981
<212> TYPE: PRT
<213> ORGANISM: Sindbis virus

<400> SEQUENCE: 6

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
            20                  25                  30

Arg Ala Leu Asp Ile Leu Glu Glu Asn Val Asn His Glu Ala Tyr Asp
        35                  40                  45

Thr Leu Leu Asn Ala Ile Leu Arg Cys Gly Ser Ser Gly Arg Ser Lys
    50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95

Glu Gln Val Trp Asp Glu Ala Asp Asp Asn Thr Ile Arg Ile Gln Thr
            100                 105                 110

Ser Ala Gln Phe Gly Tyr Asp Gln Ser Gly Ala Ala Ser Ala Asn Lys
        115                 120                 125

Tyr Arg Tyr Met Ser Leu Glu Gln Asp His Thr Val Glu Glu Gly Thr
    130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
```

```
                180               185               190
Arg Lys Ile Lys Pro Lys Phe Val Gly Arg Glu Lys Tyr Asp Leu Pro
            195                 200                 205

Pro Val His Gly Lys Lys Ile Pro Cys Thr Val Tyr Asp Arg Leu Glu
        210                 215                 220

Thr Thr Ala Gly Tyr Ile Thr Met His Arg Pro Arg Pro His Ala Tyr
225                 230                 235                 240

Thr Ser Tyr Leu Glu Glu Ser Ser Gly Lys Val Tyr Ala Lys Pro Pro
                245                 250                 255

Ser Gly Lys Asn Ile Thr Tyr Glu Cys Lys Cys Gly Asp Tyr Lys Thr
            260                 265                 270

Gly Thr Val Ser Thr Arg Thr Glu Ile Thr Gly Cys Thr Ala Ile Lys
        275                 280                 285

Gln Cys Val Ala Tyr Lys Ser Asp Gln Thr Lys Trp Val Phe Asn Ser
    290                 295                 300

Pro Asp Leu Ile Arg His Asp Asp His Thr Ala Gln Gly Lys Leu His
305                 310                 315                 320

Leu Pro Phe Lys Leu Ile Pro Ser Thr Cys Met Val Pro Val Ala His
                325                 330                 335

Ala Pro Asn Val Ile His Gly Phe Lys His Ile Ser Leu Gln Leu Asp
            340                 345                 350

Thr Asp His Leu Thr Leu Leu Thr Thr Arg Arg Leu Gly Ala Asn Pro
        355                 360                 365

Glu Pro Thr Thr Glu Trp Ile Val Gly Lys Thr Val Arg Asn Phe Thr
    370                 375                 380

Val Asp Arg Asp Gly Leu Glu Tyr Ile Trp Gly Asn His Glu Pro Val
385                 390                 395                 400

Arg Val Tyr Ala Gln Glu Ser Ala Pro Gly Asp Pro His Gly Trp Pro
                405                 410                 415

His Glu Ile Val Gln His Tyr Tyr His Arg His Pro Val Tyr Thr Ile
            420                 425                 430

Leu Ala Val Ala Ser Ala Thr Val Ala Met Met Ile Gly Val Thr Val
        435                 440                 445

Ala Val Leu Cys Ala Cys Lys Ala Arg Arg Glu Cys Leu Thr Pro Tyr
    450                 455                 460

Ala Leu Ala Pro Asn Ala Val Ile Pro Thr Ser Leu Ala Leu Leu Cys
465                 470                 475                 480

Cys Val Arg Ser Ala Asn Ala Glu Thr Phe Thr Glu Thr Met Ser Tyr
                485                 490                 495

Leu Trp Ser Asn Ser Gln Pro Phe Phe Trp Val Gln Leu Cys Ile Pro
            500                 505                 510

Leu Ala Ala Phe Ile Val Leu Met Arg Cys Cys Ser Cys Cys Leu Pro
        515                 520                 525

Phe Leu Val Val Ala Gly Ala Tyr Leu Ala Lys Val Asp Ala Tyr Glu
    530                 535                 540

His Ala Thr Thr Val Pro Asn Val Pro Gln Ile Pro Tyr Lys Ala Leu
545                 550                 555                 560

Val Glu Arg Ala Gly Tyr Ala Pro Leu Asn Leu Glu Ile Thr Val Met
                565                 570                 575

Ser Ser Glu Val Leu Pro Ser Thr Asn Gln Glu Tyr Ile Thr Cys Lys
            580                 585                 590

Phe Thr Thr Val Val Pro Ser Pro Lys Ile Lys Cys Cys Gly Ser Leu
        595                 600                 605
```

Glu Cys Gln Pro Ala Ala His Ala Asp Tyr Thr Cys Lys Val Phe Gly
    610                 615                 620

Gly Val Tyr Pro Phe Met Trp Gly Gly Ala Gln Cys Phe Cys Asp Ser
625                 630                 635                 640

Glu Asn Ser Gln Met Ser Glu Ala Tyr Val Glu Leu Ser Ala Asp Cys
            645                 650                 655

Ala Ser Asp His Ala Gln Ala Ile Lys Val His Thr Ala Ala Met Lys
        660                 665                 670

Val Gly Leu Arg Ile Val Tyr Gly Asn Thr Thr Ser Phe Leu Asp Val
    675                 680                 685

Tyr Val Asn Gly Val Thr Pro Gly Thr Ser Lys Asp Leu Lys Val Ile
690                 695                 700

Ala Gly Pro Ile Ser Ala Ser Phe Thr Pro Phe Asp His Lys Val Val
705                 710                 715                 720

Ile His Arg Gly Leu Val Tyr Asn Tyr Asp Phe Pro Glu Tyr Gly Ala
            725                 730                 735

Met Lys Pro Gly Ala Phe Gly Asp Ile Gln Ala Thr Ser Leu Thr Ser
        740                 745                 750

Lys Asp Leu Ile Ala Ser Thr Asp Ile Arg Leu Leu Lys Pro Ser Ala
    755                 760                 765

Lys Asn Val His Val Pro Tyr Thr Gln Ala Ser Ser Gly Phe Glu Met
770                 775                 780

Trp Lys Asn Asn Ser Gly Arg Pro Leu Gln Glu Thr Ala Pro Phe Gly
785                 790                 795                 800

Cys Lys Ile Ala Val Asn Pro Leu Arg Ala Val Asp Cys Ser Tyr Gly
            805                 810                 815

Asn Ile Pro Ile Ser Ile Asp Ile Pro Asn Ala Ala Phe Ile Arg Thr
        820                 825                 830

Ser Asp Ala Pro Leu Val Ser Thr Val Lys Cys Glu Val Ser Glu Cys
    835                 840                 845

Thr Tyr Ser Ala Asp Phe Gly Gly Met Ala Thr Leu Gln Tyr Val Ser
850                 855                 860

Asp Arg Glu Gly Gln Cys Pro Val His Ser His Ser Ser Thr Ala Thr
865                 870                 875                 880

Leu Gln Glu Ser Thr Val His Val Leu Glu Lys Gly Ala Val Thr Val
            885                 890                 895

His Phe Ser Thr Ala Ser Pro Gln Ala Asn Phe Ile Val Ser Leu Cys
        900                 905                 910

Gly Lys Lys Thr Thr Cys Asn Ala Glu Cys Lys Pro Pro Ala Asp His
    915                 920                 925

Ile Val Ser Thr Pro His Lys Asn Asp Gln Glu Phe Gln Ala Ala Ile
930                 935                 940

Ser Lys Thr Ser Trp Ser Trp Leu Phe Ala Leu Phe Gly Gly Ala Ser
945                 950                 955                 960

Ser Leu Leu Ile Ile Gly Leu Met Ile Phe Ala Cys Ser Met Met Leu
            965                 970                 975

Thr Ser Thr Arg Arg
            980

<210> SEQ ID NO 7
<211> LENGTH: 982
<212> TYPE: PRT
<213> ORGANISM: Sindbis virus

```
<400> SEQUENCE: 7

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
            20                  25                  30

Arg Ala Leu Asp Ile Leu Glu Glu Asn Val Asn His Glu Ala Tyr Asp
        35                  40                  45

Thr Leu Leu Asn Ala Ile Leu Arg Cys Gly Ser Ser Gly Arg Ser Lys
    50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95

Glu Gln Val Trp Asp Glu Ala Asp Asn Thr Ile Arg Ile Gln Thr
            100                 105                 110

Ser Ala Gln Phe Gly Tyr Asp Gln Ser Gly Ala Ala Ser Ala Asn Lys
            115                 120                 125

Tyr Arg Tyr Met Ser Leu Lys Gln Asp His Thr Val Lys Glu Gly Thr
        130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
        195                 200                 205

Pro Val His Gly Lys Lys Ile Pro Cys Thr Val Tyr Asp Arg Leu Glu
    210                 215                 220

Gly Thr Thr Ala Gly Tyr Ile Thr Met His Arg Pro Arg Pro His Ala
225                 230                 235                 240

Tyr Thr Ser Tyr Leu Glu Glu Ser Ser Gly Lys Val Tyr Ala Lys Pro
                245                 250                 255

Pro Ser Gly Lys Asn Ile Thr Tyr Glu Cys Lys Cys Gly Asp Tyr Lys
            260                 265                 270

Thr Gly Thr Val Ser Thr Arg Thr Glu Ile Thr Gly Cys Thr Ala Ile
        275                 280                 285

Lys Gln Cys Val Ala Tyr Lys Ser Asp Gln Thr Lys Trp Val Phe Asn
290                 295                 300

Ser Pro Asp Leu Ile Arg His Asp Asp His Thr Ala Gln Gly Lys Leu
305                 310                 315                 320

His Leu Pro Phe Lys Leu Ile Pro Ser Thr Cys Met Val Pro Val Ala
                325                 330                 335

His Ala Pro Asn Val Ile His Gly Phe Lys His Ile Ser Leu Gln Leu
            340                 345                 350

Asp Thr Asp His Leu Thr Leu Leu Thr Thr Arg Arg Leu Gly Ala Asn
        355                 360                 365

Pro Glu Pro Thr Thr Glu Trp Ile Val Gly Lys Thr Val Arg Asn Phe
    370                 375                 380

Thr Val Asp Arg Asp Gly Leu Glu Tyr Ile Trp Gly Asn His Glu Pro
385                 390                 395                 400

Val Arg Val Tyr Ala Gln Glu Ser Ala Pro Gly Asp Pro His Gly Trp
                405                 410                 415
```

Pro His Glu Ile Val Gln His Tyr Tyr His Arg His Pro Val Tyr Thr
                420                 425                 430

Ile Leu Ala Val Ala Ser Ala Thr Val Ala Met Met Ile Gly Val Thr
                435                 440                 445

Val Ala Val Leu Cys Ala Cys Lys Ala Arg Arg Glu Cys Leu Thr Pro
            450                 455                 460

Tyr Ala Leu Ala Pro Asn Ala Val Ile Pro Thr Ser Leu Ala Leu Leu
465                 470                 475                 480

Cys Cys Val Arg Ser Ala Asn Ala Glu Thr Phe Thr Glu Thr Met Ser
                485                 490                 495

Tyr Leu Trp Ser Asn Ser Gln Pro Phe Phe Trp Val Gln Leu Cys Ile
                500                 505                 510

Pro Leu Ala Ala Phe Ile Val Leu Met Arg Cys Cys Ser Cys Cys Leu
            515                 520                 525

Pro Phe Leu Val Val Ala Gly Ala Tyr Leu Ala Lys Val Asp Ala Tyr
            530                 535                 540

Glu His Ala Thr Thr Val Pro Asn Val Pro Gln Ile Pro Tyr Lys Ala
545                 550                 555                 560

Leu Val Glu Arg Ala Gly Tyr Ala Pro Leu Asn Leu Glu Ile Thr Val
                565                 570                 575

Met Ser Ser Glu Val Leu Pro Ser Thr Asn Gln Glu Tyr Ile Thr Cys
            580                 585                 590

Lys Phe Thr Thr Val Val Pro Ser Pro Lys Ile Lys Cys Cys Gly Ser
                595                 600                 605

Leu Glu Cys Gln Pro Ala Ala His Ala Asp Tyr Thr Cys Lys Val Phe
            610                 615                 620

Gly Gly Val Tyr Pro Phe Met Trp Gly Gly Ala Gln Cys Phe Cys Asp
625                 630                 635                 640

Ser Glu Asn Ser Gln Met Ser Glu Ala Tyr Val Glu Leu Ser Ala Asp
                645                 650                 655

Cys Ala Ser Asp His Ala Gln Ala Ile Lys Val His Thr Ala Ala Met
            660                 665                 670

Lys Val Gly Leu Arg Ile Val Tyr Gly Asn Thr Thr Ser Phe Leu Asp
                675                 680                 685

Val Tyr Val Asn Gly Val Thr Pro Gly Thr Ser Lys Asp Leu Lys Val
            690                 695                 700

Ile Ala Gly Pro Ile Ser Ala Ser Phe Thr Pro Phe Asp His Lys Val
705                 710                 715                 720

Val Ile His Arg Gly Leu Val Tyr Asn Tyr Asp Phe Pro Glu Tyr Gly
                725                 730                 735

Ala Met Lys Pro Gly Ala Phe Gly Asp Ile Gln Ala Thr Ser Leu Thr
            740                 745                 750

Ser Lys Asp Leu Ile Ala Ser Thr Asp Ile Arg Leu Leu Lys Pro Ser
            755                 760                 765

Ala Lys Asn Val His Val Pro Tyr Thr Gln Ala Ser Ser Gly Phe Glu
            770                 775                 780

Met Trp Lys Asn Asn Ser Gly Arg Pro Leu Gln Glu Thr Ala Pro Phe
785                 790                 795                 800

Gly Cys Lys Ile Ala Val Asn Pro Leu Arg Ala Val Asp Cys Ser Tyr
                805                 810                 815

Gly Asn Ile Pro Ile Ser Ile Asp Ile Pro Asn Ala Ala Phe Ile Arg
                820                 825                 830

```
Thr Ser Asp Ala Pro Leu Val Ser Thr Val Lys Cys Glu Val Ser Glu
            835                 840                 845

Cys Thr Tyr Ser Ala Asp Phe Gly Gly Met Ala Thr Leu Gln Tyr Val
850                 855                 860

Ser Asp Arg Glu Gly Gln Cys Pro Val His Ser His Ser Ser Thr Ala
865                 870                 875                 880

Thr Leu Gln Glu Ser Thr Val His Val Leu Glu Lys Gly Ala Val Thr
            885                 890                 895

Val His Phe Ser Thr Ala Ser Pro Gln Ala Asn Phe Ile Val Ser Leu
            900                 905                 910

Cys Gly Lys Lys Thr Thr Cys Asn Ala Glu Cys Lys Pro Pro Ala Asp
            915                 920                 925

His Ile Val Ser Thr Pro His Lys Asn Asp Gln Glu Phe Gln Ala Ala
            930                 935                 940

Ile Ser Lys Thr Ser Trp Ser Trp Leu Phe Ala Leu Phe Gly Gly Ala
945                 950                 955                 960

Ser Ser Leu Leu Ile Ile Gly Leu Met Ile Phe Ala Cys Ser Met Met
            965                 970                 975

Leu Thr Ser Thr Arg Arg
            980

<210> SEQ ID NO 8
<211> LENGTH: 981
<212> TYPE: PRT
<213> ORGANISM: Sindbis virus

<400> SEQUENCE: 8

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
            20                  25                  30

Arg Ala Leu Asp Ile Leu Glu Glu Asn Val Asn His Glu Ala Tyr Asp
            35                  40                  45

Thr Leu Leu Asn Ala Ile Leu Arg Cys Gly Ser Ser Gly Arg Ser Lys
50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
            85                  90                  95

Glu Gln Val Trp Asp Glu Ala Asp Asp Asn Thr Ile Arg Ile Gln Thr
            100                 105                 110

Ser Ala Gln Phe Gly Tyr Asp Gln Ser Gly Ala Ala Ser Ala Asn Lys
            115                 120                 125

Tyr Arg Tyr Met Ser Leu Lys Gln Asp His Thr Val Lys Glu Gly Thr
            130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
            165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
            195                 200                 205

Pro Val His Gly Lys Lys Ile Pro Cys Thr Val Tyr Asp Arg Leu Glu
            210                 215                 220
```

-continued

Thr Thr Ala Gly Tyr Ile Thr Met His Arg Pro Arg Pro His Ala Tyr
225                 230                 235                 240

Thr Ser Tyr Leu Glu Glu Ser Ser Gly Lys Val Tyr Ala Lys Pro Pro
            245                 250                 255

Ser Gly Lys Asn Ile Thr Tyr Glu Cys Lys Cys Gly Asp Tyr Lys Thr
        260                 265                 270

Gly Thr Val Ser Thr Arg Thr Glu Ile Thr Gly Cys Thr Ala Ile Lys
    275                 280                 285

Gln Cys Val Ala Tyr Lys Ser Asp Gln Thr Lys Trp Val Phe Asn Ser
290                 295                 300

Pro Asp Leu Ile Arg His Asp Asp His Thr Ala Gln Gly Lys Leu His
305                 310                 315                 320

Leu Pro Phe Lys Leu Ile Pro Ser Thr Cys Met Val Pro Val Ala His
                325                 330                 335

Ala Pro Asn Val Ile His Gly Phe Lys His Ile Ser Leu Gln Leu Asp
            340                 345                 350

Thr Asp His Leu Thr Leu Leu Thr Arg Arg Leu Gly Ala Asn Pro
        355                 360                 365

Glu Pro Thr Thr Glu Trp Ile Val Gly Lys Thr Val Arg Asn Phe Thr
370                 375                 380

Val Asp Arg Asp Gly Leu Glu Tyr Ile Trp Gly Asn His Glu Pro Val
385                 390                 395                 400

Arg Val Tyr Ala Gln Glu Ser Ala Pro Gly Asp Pro His Gly Trp Pro
                405                 410                 415

His Glu Ile Val Gln His Tyr Tyr His Arg His Pro Val Tyr Thr Ile
            420                 425                 430

Leu Ala Val Ala Ser Ala Thr Val Ala Met Met Ile Gly Val Thr Val
        435                 440                 445

Ala Val Leu Cys Ala Cys Lys Ala Arg Arg Glu Cys Leu Thr Pro Tyr
450                 455                 460

Ala Leu Ala Pro Asn Ala Val Ile Pro Thr Ser Leu Ala Leu Leu Cys
465                 470                 475                 480

Cys Val Arg Ser Ala Asn Ala Glu Thr Phe Thr Glu Thr Met Ser Tyr
                485                 490                 495

Leu Trp Ser Asn Ser Gln Pro Phe Phe Trp Val Gln Leu Cys Ile Pro
            500                 505                 510

Leu Ala Ala Phe Ile Val Leu Met Arg Cys Cys Ser Cys Cys Leu Pro
        515                 520                 525

Phe Leu Val Val Ala Gly Ala Tyr Leu Ala Lys Val Asp Ala Tyr Glu
530                 535                 540

His Ala Thr Thr Val Pro Asn Val Pro Gln Ile Pro Tyr Lys Ala Leu
545                 550                 555                 560

Val Glu Arg Ala Gly Tyr Ala Pro Leu Asn Leu Glu Ile Thr Val Met
                565                 570                 575

Ser Ser Glu Val Leu Pro Ser Thr Asn Gln Glu Tyr Ile Thr Cys Lys
            580                 585                 590

Phe Thr Thr Val Val Pro Ser Pro Lys Ile Lys Cys Cys Gly Ser Leu
        595                 600                 605

Glu Cys Gln Pro Ala Ala His Ala Asp Tyr Thr Cys Lys Val Phe Gly
610                 615                 620

Gly Val Tyr Pro Phe Met Trp Gly Gly Ala Gln Cys Phe Cys Asp Ser
625                 630                 635                 640

```
Glu Asn Ser Gln Met Ser Glu Ala Tyr Val Glu Leu Ser Ala Asp Cys
                645                 650                 655

Ala Ser Asp His Ala Gln Ala Ile Lys Val His Thr Ala Ala Met Lys
            660                 665                 670

Val Gly Leu Arg Ile Val Tyr Gly Asn Thr Thr Ser Phe Leu Asp Val
        675                 680                 685

Tyr Val Asn Gly Val Thr Pro Gly Thr Ser Lys Asp Leu Lys Val Ile
690                 695                 700

Ala Gly Pro Ile Ser Ala Ser Phe Thr Pro Phe Asp His Lys Val Val
705                 710                 715                 720

Ile His Arg Gly Leu Val Tyr Asn Tyr Asp Phe Pro Glu Tyr Gly Ala
                725                 730                 735

Met Lys Pro Gly Ala Phe Gly Asp Ile Gln Ala Thr Ser Leu Thr Ser
            740                 745                 750

Lys Asp Leu Ile Ala Ser Thr Asp Ile Arg Leu Leu Lys Pro Ser Ala
        755                 760                 765

Lys Asn Val His Val Pro Tyr Thr Gln Ala Ser Ser Gly Phe Glu Met
770                 775                 780

Trp Lys Asn Asn Ser Gly Arg Pro Leu Gln Glu Thr Ala Pro Phe Gly
785                 790                 795                 800

Cys Lys Ile Ala Val Asn Pro Leu Arg Ala Val Asp Cys Ser Tyr Gly
                805                 810                 815

Asn Ile Pro Ile Ser Ile Asp Ile Pro Asn Ala Ala Phe Ile Arg Thr
            820                 825                 830

Ser Asp Ala Pro Leu Val Ser Thr Val Lys Cys Glu Val Ser Glu Cys
        835                 840                 845

Thr Tyr Ser Ala Asp Phe Gly Gly Met Ala Thr Leu Gln Tyr Val Ser
850                 855                 860

Asp Arg Glu Gly Gln Cys Pro Val His Ser His Ser Ser Thr Ala Thr
865                 870                 875                 880

Leu Gln Glu Ser Thr Val His Val Leu Glu Lys Gly Ala Val Thr Val
                885                 890                 895

His Phe Ser Thr Ala Ser Pro Gln Ala Asn Phe Ile Val Ser Leu Cys
            900                 905                 910

Gly Lys Lys Thr Thr Cys Asn Ala Glu Cys Lys Pro Pro Ala Asp His
        915                 920                 925

Ile Val Ser Thr Pro His Lys Asn Asp Gln Glu Phe Gln Ala Ala Ile
930                 935                 940

Ser Lys Thr Ser Trp Ser Trp Leu Phe Ala Leu Phe Gly Gly Ala Ser
945                 950                 955                 960

Ser Leu Leu Ile Ile Gly Leu Met Ile Phe Ala Cys Ser Met Met Leu
                965                 970                 975

Thr Ser Thr Arg Arg
            980

<210> SEQ ID NO 9
<211> LENGTH: 982
<212> TYPE: PRT
<213> ORGANISM: Sindbis virus

<400> SEQUENCE: 9

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
            20                  25                  30
```

```
Arg Ala Leu Asp Ile Leu Glu Glu Asn Val Asn His Glu Ala Tyr Asp
            35                  40                  45

Thr Leu Leu Asn Ala Ile Leu Arg Cys Gly Ser Ser Gly Arg Ser Lys
 50                  55                  60

Arg Ser Val Ile Asp Asp Phe Thr Leu Thr Ser Pro Tyr Leu Gly Thr
 65                  70                  75                  80

Cys Ser Tyr Cys His His Thr Val Pro Cys Phe Ser Pro Val Lys Ile
                    85                  90                  95

Glu Gln Val Trp Asp Glu Ala Asp Asn Thr Ile Arg Ile Gln Thr
                    100                 105                 110

Ser Ala Gln Phe Gly Tyr Asp Gln Ser Gly Ala Ala Ser Ala Asn Lys
            115                 120                 125

Tyr Arg Tyr Met Ser Leu Lys Gln Asp His Thr Val Glu Glu Gly Thr
            130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
            195                 200                 205

Pro Val His Gly Lys Lys Ile Pro Cys Thr Val Tyr Asp Arg Leu Glu
            210                 215                 220

Gly Thr Thr Ala Gly Tyr Ile Thr Met His Arg Pro Arg Pro His Ala
225                 230                 235                 240

Tyr Thr Ser Tyr Leu Glu Glu Ser Ser Gly Lys Val Tyr Ala Lys Pro
                245                 250                 255

Pro Ser Gly Lys Asn Ile Thr Tyr Glu Cys Lys Cys Gly Asp Tyr Lys
            260                 265                 270

Thr Gly Thr Val Ser Thr Arg Thr Glu Ile Thr Gly Cys Thr Ala Ile
            275                 280                 285

Lys Gln Cys Val Ala Tyr Lys Ser Asp Gln Thr Lys Trp Val Phe Asn
290                 295                 300

Ser Pro Asp Leu Ile Arg His Asp Asp His Thr Ala Gln Gly Lys Leu
305                 310                 315                 320

His Leu Pro Phe Lys Leu Ile Pro Ser Thr Cys Met Val Pro Val Ala
                325                 330                 335

His Ala Pro Asn Val Ile His Gly Phe Lys His Ile Ser Leu Gln Leu
            340                 345                 350

Asp Thr Asp His Leu Thr Leu Leu Thr Thr Arg Arg Leu Gly Ala Asn
            355                 360                 365

Pro Glu Pro Thr Thr Glu Trp Ile Val Gly Lys Thr Val Arg Asn Phe
            370                 375                 380

Thr Val Asp Arg Asp Gly Leu Glu Tyr Ile Trp Gly Asn His Glu Pro
385                 390                 395                 400

Val Arg Val Tyr Ala Gln Glu Ser Ala Pro Gly Asp Pro His Gly Trp
                405                 410                 415

Pro His Glu Ile Val Gln His Tyr Tyr His Arg His Pro Val Tyr Thr
            420                 425                 430

Ile Leu Ala Val Ala Ser Ala Thr Val Ala Met Met Ile Gly Val Thr
            435                 440                 445
```

```
Val Ala Val Leu Cys Ala Cys Lys Ala Arg Arg Glu Cys Leu Thr Pro
450                 455                 460
Tyr Ala Leu Ala Pro Asn Ala Val Ile Pro Thr Ser Leu Ala Leu Leu
465                 470                 475                 480
Cys Cys Val Arg Ser Ala Asn Ala Glu Thr Phe Thr Glu Thr Met Ser
                485                 490                 495
Tyr Leu Trp Ser Asn Ser Gln Pro Phe Phe Trp Val Gln Leu Cys Ile
            500                 505                 510
Pro Leu Ala Ala Phe Ile Val Leu Met Arg Cys Cys Ser Cys Cys Leu
            515                 520                 525
Pro Phe Leu Val Val Ala Gly Ala Tyr Leu Ala Lys Val Asp Ala Tyr
530                 535                 540
Glu His Ala Thr Thr Val Pro Asn Val Pro Gln Ile Pro Tyr Lys Ala
545                 550                 555                 560
Leu Val Glu Arg Ala Gly Tyr Ala Pro Leu Asn Leu Glu Ile Thr Val
                565                 570                 575
Met Ser Ser Glu Val Leu Pro Ser Thr Asn Gln Glu Tyr Ile Thr Cys
                580                 585                 590
Lys Phe Thr Thr Val Val Pro Ser Pro Lys Ile Lys Cys Cys Gly Ser
            595                 600                 605
Leu Glu Cys Gln Pro Ala Ala His Ala Asp Tyr Thr Cys Lys Val Phe
            610                 615                 620
Gly Gly Val Tyr Pro Phe Met Trp Gly Gly Ala Gln Cys Phe Cys Asp
625                 630                 635                 640
Ser Glu Asn Ser Gln Met Ser Glu Ala Tyr Val Glu Leu Ser Ala Asp
                645                 650                 655
Cys Ala Ser Asp His Ala Gln Ala Ile Lys Val His Thr Ala Ala Met
                660                 665                 670
Lys Val Gly Leu Arg Ile Val Tyr Gly Asn Thr Thr Ser Phe Leu Asp
            675                 680                 685
Val Tyr Val Asn Gly Val Thr Pro Gly Thr Ser Lys Asp Leu Lys Val
            690                 695                 700
Ile Ala Gly Pro Ile Ser Ala Ser Phe Thr Pro Phe Asp His Lys Val
705                 710                 715                 720
Val Ile His Arg Gly Leu Val Tyr Asn Tyr Asp Phe Pro Glu Tyr Gly
                725                 730                 735
Ala Met Lys Pro Gly Ala Phe Gly Asp Ile Gln Ala Thr Ser Leu Thr
                740                 745                 750
Ser Lys Asp Leu Ile Ala Ser Thr Asp Ile Arg Leu Leu Lys Pro Ser
            755                 760                 765
Ala Lys Asn Val His Val Pro Tyr Thr Gln Ala Ser Ser Gly Phe Glu
770                 775                 780
Met Trp Lys Asn Asn Ser Gly Arg Pro Leu Gln Glu Thr Ala Pro Phe
785                 790                 795                 800
Gly Cys Lys Ile Ala Val Asn Pro Leu Arg Ala Val Asp Cys Ser Tyr
                805                 810                 815
Gly Asn Ile Pro Ile Ser Ile Asp Ile Pro Asn Ala Ala Phe Ile Arg
                820                 825                 830
Thr Ser Asp Ala Pro Leu Val Ser Thr Val Lys Cys Glu Val Ser Glu
            835                 840                 845
Cys Thr Tyr Ser Ala Asp Phe Gly Gly Met Ala Thr Leu Gln Tyr Val
850                 855                 860
Ser Asp Arg Glu Gly Gln Cys Pro Val His Ser His Ser Ser Thr Ala
```

```
                   865                 870                 875                 880
Thr Leu Gln Glu Ser Thr Val His Val Leu Glu Lys Gly Ala Val Thr
                885                 890                 895

Val His Phe Ser Thr Ala Ser Pro Gln Ala Asn Phe Ile Val Ser Leu
                900                 905                 910

Cys Gly Lys Lys Thr Thr Cys Asn Ala Glu Cys Lys Pro Pro Ala Asp
                915                 920                 925

His Ile Val Ser Thr Pro His Lys Asn Asp Gln Glu Phe Gln Ala Ala
                930                 935                 940

Ile Ser Lys Thr Ser Trp Ser Trp Leu Phe Ala Leu Phe Gly Gly Ala
945                 950                 955                 960

Ser Ser Leu Leu Ile Ile Gly Leu Met Ile Phe Ala Cys Ser Met Met
                965                 970                 975

Leu Thr Ser Thr Arg Arg
                980

<210> SEQ ID NO 10
<211> LENGTH: 981
<212> TYPE: PRT
<213> ORGANISM: Sindbis virus

<400> SEQUENCE: 10

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
                20                  25                  30

Arg Ala Leu Asp Ile Leu Glu Glu Asn Val Asn His Glu Ala Tyr Asp
                35                  40                  45

Thr Leu Leu Asn Ala Ile Leu Arg Cys Gly Ser Ser Gly Arg Ser Lys
                50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95

Glu Gln Val Trp Asp Glu Ala Asp Asp Asn Thr Ile Arg Ile Gln Thr
                100                 105                 110

Ser Ala Gln Phe Gly Tyr Asp Gln Ser Gly Ala Ala Ser Ala Asn Lys
                115                 120                 125

Tyr Arg Tyr Met Ser Leu Lys Gln Asp His Thr Val Glu Glu Gly Thr
                130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
                180                 185                 190

Arg Lys Ile Lys Pro Lys Phe Val Gly Arg Glu Lys Tyr Asp Leu Pro
                195                 200                 205

Pro Val His Gly Lys Lys Ile Pro Cys Thr Val Tyr Asp Arg Leu Glu
                210                 215                 220

Thr Thr Ala Gly Tyr Ile Thr Met His Arg Pro Arg Pro His Ala Tyr
225                 230                 235                 240

Thr Ser Tyr Leu Glu Glu Ser Ser Gly Lys Val Tyr Ala Lys Pro Pro
                245                 250                 255
```

-continued

```
Ser Gly Lys Asn Ile Thr Tyr Glu Cys Lys Cys Gly Asp Tyr Lys Thr
            260                 265                 270

Gly Thr Val Ser Thr Arg Thr Glu Ile Thr Gly Cys Thr Ala Ile Lys
        275                 280                 285

Gln Cys Val Ala Tyr Lys Ser Asp Gln Thr Lys Trp Val Phe Asn Ser
    290                 295                 300

Pro Asp Leu Ile Arg His Asp Asp His Thr Ala Gln Gly Lys Leu His
305                 310                 315                 320

Leu Pro Phe Lys Leu Ile Pro Ser Thr Cys Met Val Pro Val Ala His
                325                 330                 335

Ala Pro Asn Val Ile His Gly Phe Lys His Ile Ser Leu Gln Leu Asp
            340                 345                 350

Thr Asp His Leu Thr Leu Leu Thr Thr Arg Arg Leu Gly Ala Asn Pro
        355                 360                 365

Glu Pro Thr Thr Glu Trp Ile Val Gly Lys Thr Val Arg Asn Phe Thr
    370                 375                 380

Val Asp Arg Asp Gly Leu Glu Tyr Ile Trp Gly Asn His Glu Pro Val
385                 390                 395                 400

Arg Val Tyr Ala Gln Glu Ser Ala Pro Gly Asp Pro His Gly Trp Pro
                405                 410                 415

His Glu Ile Val Gln His Tyr Tyr His Arg His Pro Val Tyr Thr Ile
            420                 425                 430

Leu Ala Val Ala Ser Ala Thr Val Ala Met Met Ile Gly Val Thr Val
        435                 440                 445

Ala Val Leu Cys Ala Cys Lys Ala Arg Arg Glu Cys Leu Thr Pro Tyr
    450                 455                 460

Ala Leu Ala Pro Asn Ala Val Ile Pro Thr Ser Leu Ala Leu Leu Cys
465                 470                 475                 480

Cys Val Arg Ser Ala Asn Ala Glu Thr Phe Thr Glu Thr Met Ser Tyr
                485                 490                 495

Leu Trp Ser Asn Ser Gln Pro Phe Phe Trp Val Gln Leu Cys Ile Pro
            500                 505                 510

Leu Ala Ala Phe Ile Val Leu Met Arg Cys Cys Ser Cys Cys Leu Pro
        515                 520                 525

Phe Leu Val Val Ala Gly Ala Tyr Leu Ala Lys Val Asp Ala Tyr Glu
    530                 535                 540

His Ala Thr Thr Val Pro Asn Val Pro Gln Ile Pro Tyr Lys Ala Leu
545                 550                 555                 560

Val Glu Arg Ala Gly Tyr Ala Pro Leu Asn Leu Glu Ile Thr Val Met
                565                 570                 575

Ser Ser Glu Val Leu Pro Ser Thr Asn Gln Glu Tyr Ile Thr Cys Lys
            580                 585                 590

Phe Thr Thr Val Val Pro Ser Pro Lys Ile Lys Cys Cys Gly Ser Leu
        595                 600                 605

Glu Cys Gln Pro Ala Ala His Ala Asp Tyr Thr Cys Lys Val Phe Gly
    610                 615                 620

Gly Val Tyr Pro Phe Met Trp Gly Gly Ala Gln Cys Phe Cys Asp Ser
625                 630                 635                 640

Glu Asn Ser Gln Met Ser Glu Ala Tyr Val Glu Leu Ser Ala Asp Cys
                645                 650                 655

Ala Ser Asp His Ala Gln Ala Ile Lys Val His Thr Ala Ala Met Lys
            660                 665                 670

Val Gly Leu Arg Ile Val Tyr Gly Asn Thr Thr Ser Phe Leu Asp Val
```

```
                675                 680                 685
Tyr Val Asn Gly Val Thr Pro Gly Thr Ser Lys Asp Leu Lys Val Ile
            690                 695                 700
Ala Gly Pro Ile Ser Ala Ser Phe Thr Pro Phe Asp His Lys Val Val
705                 710                 715                 720
Ile His Arg Gly Leu Val Tyr Asn Tyr Asp Phe Pro Glu Tyr Gly Ala
                725                 730                 735
Met Lys Pro Gly Ala Phe Gly Asp Ile Gln Ala Thr Ser Leu Thr Ser
            740                 745                 750
Lys Asp Leu Ile Ala Ser Thr Asp Ile Arg Leu Leu Lys Pro Ser Ala
                755                 760                 765
Lys Asn Val His Val Pro Tyr Thr Gln Ala Ser Ser Gly Phe Glu Met
770                 775                 780
Trp Lys Asn Asn Ser Gly Arg Pro Leu Gln Glu Thr Ala Pro Phe Gly
785                 790                 795                 800
Cys Lys Ile Ala Val Asn Pro Leu Arg Ala Val Asp Cys Ser Tyr Gly
                805                 810                 815
Asn Ile Pro Ile Ser Ile Asp Ile Pro Asn Ala Ala Phe Ile Arg Thr
            820                 825                 830
Ser Asp Ala Pro Leu Val Ser Thr Val Lys Cys Glu Val Ser Glu Cys
                835                 840                 845
Thr Tyr Ser Ala Asp Phe Gly Gly Met Ala Thr Leu Gln Tyr Val Ser
850                 855                 860
Asp Arg Glu Gly Gln Cys Pro Val His Ser His Ser Ser Thr Ala Thr
865                 870                 875                 880
Leu Gln Glu Ser Thr Val His Val Leu Glu Lys Gly Ala Val Thr Val
                885                 890                 895
His Phe Ser Thr Ala Ser Pro Gln Ala Asn Phe Ile Val Ser Leu Cys
            900                 905                 910
Gly Lys Lys Thr Thr Cys Asn Ala Glu Cys Lys Pro Pro Ala Asp His
                915                 920                 925
Ile Val Ser Thr Pro His Lys Asn Asp Gln Glu Phe Gln Ala Ala Ile
            930                 935                 940
Ser Lys Thr Ser Trp Ser Trp Leu Phe Ala Leu Phe Gly Gly Ala Ser
945                 950                 955                 960
Ser Leu Leu Ile Ile Gly Leu Met Ile Phe Ala Cys Ser Met Met Leu
                965                 970                 975
Thr Ser Thr Arg Arg
            980

<210> SEQ ID NO 11
<211> LENGTH: 982
<212> TYPE: PRT
<213> ORGANISM: Sindbis virus

<400> SEQUENCE: 11

Met Ser Ala Ala Pro Leu Val Thr Ala Met Cys Leu Leu Gly Asn Val
1               5                   10                  15
Ser Phe Pro Cys Asp Arg Pro Pro Thr Cys Tyr Thr Arg Glu Pro Ser
            20                  25                  30
Arg Ala Leu Asp Ile Leu Glu Glu Asn Val Asn His Glu Ala Tyr Asp
        35                  40                  45
Thr Leu Leu Asn Ala Ile Leu Arg Cys Gly Ser Ser Gly Arg Ser Lys
    50                  55                  60
```

-continued

```
Arg Ser Val Ile Asp Asp Phe Thr Leu Thr Ser Pro Tyr Leu Gly Thr
 65                  70                  75                  80

Cys Ser Tyr Cys His His Thr Val Pro Cys Phe Ser Pro Val Lys Ile
                 85                  90                  95

Glu Gln Val Trp Asp Glu Ala Asp Asn Thr Ile Arg Ile Gln Thr
            100                 105                 110

Ser Ala Gln Phe Gly Tyr Asp Gln Ser Gly Ala Ala Ser Ala Asn Lys
            115                 120                 125

Tyr Arg Tyr Met Ser Leu Lys Gln Asp His Thr Val Glu Glu Gly Thr
        130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
        195                 200                 205

Pro Val His Gly Lys Lys Ile Pro Cys Thr Val Tyr Asp Arg Leu Lys
    210                 215                 220

Gly Thr Thr Ala Gly Tyr Ile Thr Met His Arg Pro Arg Pro His Ala
225                 230                 235                 240

Tyr Thr Ser Tyr Leu Glu Glu Ser Ser Gly Lys Val Tyr Ala Lys Pro
                245                 250                 255

Pro Ser Gly Lys Asn Ile Thr Tyr Glu Cys Lys Cys Gly Asp Tyr Lys
            260                 265                 270

Thr Gly Thr Val Ser Thr Arg Thr Glu Ile Thr Gly Cys Thr Ala Ile
        275                 280                 285

Lys Gln Cys Val Ala Tyr Lys Ser Asp Gln Thr Lys Trp Val Phe Asn
    290                 295                 300

Ser Pro Asp Leu Ile Arg His Asp Asp His Thr Ala Gln Gly Lys Leu
305                 310                 315                 320

His Leu Pro Phe Lys Leu Ile Pro Ser Thr Cys Met Val Pro Val Ala
                325                 330                 335

His Ala Pro Asn Val Ile His Gly Phe Lys His Ile Ser Leu Gln Leu
            340                 345                 350

Asp Thr Asp His Leu Thr Leu Leu Thr Thr Arg Arg Leu Gly Ala Asn
        355                 360                 365

Pro Glu Pro Thr Thr Glu Trp Ile Val Gly Lys Thr Val Arg Asn Phe
    370                 375                 380

Thr Val Asp Arg Asp Gly Leu Glu Tyr Ile Trp Gly Asn His Glu Pro
385                 390                 395                 400

Val Arg Val Tyr Ala Gln Glu Ser Ala Pro Gly Asp Pro His Gly Trp
                405                 410                 415

Pro His Glu Ile Val Gln His Tyr Tyr His Arg His Pro Val Tyr Thr
            420                 425                 430

Ile Leu Ala Val Ala Ser Ala Thr Val Ala Met Met Ile Gly Val Thr
        435                 440                 445

Val Ala Val Leu Cys Ala Cys Lys Ala Arg Arg Glu Cys Leu Thr Pro
    450                 455                 460

Tyr Ala Leu Ala Pro Asn Ala Val Ile Pro Thr Ser Leu Ala Leu Leu
465                 470                 475                 480

Cys Cys Val Arg Ser Ala Asn Ala Glu Thr Phe Thr Glu Thr Met Ser
```

```
            485                 490                 495
Tyr Leu Trp Ser Asn Ser Gln Pro Phe Phe Trp Val Gln Leu Cys Ile
            500                 505                 510

Pro Leu Ala Ala Phe Ile Val Leu Met Arg Cys Cys Ser Cys Cys Leu
            515                 520                 525

Pro Phe Leu Val Val Ala Gly Ala Tyr Leu Ala Lys Val Asp Ala Tyr
            530                 535                 540

Glu His Ala Thr Thr Val Pro Asn Val Pro Gln Ile Pro Tyr Lys Ala
545                 550                 555                 560

Leu Val Glu Arg Ala Gly Tyr Ala Pro Leu Asn Leu Glu Ile Thr Val
                565                 570                 575

Met Ser Ser Glu Val Leu Pro Ser Thr Asn Gln Glu Tyr Ile Thr Cys
            580                 585                 590

Lys Phe Thr Thr Val Val Pro Ser Pro Lys Ile Lys Cys Cys Gly Ser
            595                 600                 605

Leu Glu Cys Gln Pro Ala Ala His Ala Asp Tyr Thr Cys Lys Val Phe
            610                 615                 620

Gly Gly Val Tyr Pro Phe Met Trp Gly Gly Ala Gln Cys Phe Cys Asp
625                 630                 635                 640

Ser Glu Asn Ser Gln Met Ser Glu Ala Tyr Val Glu Leu Ser Ala Asp
                645                 650                 655

Cys Ala Ser Asp His Ala Gln Ala Ile Lys Val His Thr Ala Ala Met
            660                 665                 670

Lys Val Gly Leu Arg Ile Val Tyr Gly Asn Thr Thr Ser Phe Leu Asp
            675                 680                 685

Val Tyr Val Asn Gly Val Thr Pro Gly Thr Ser Lys Asp Leu Lys Val
            690                 695                 700

Ile Ala Gly Pro Ile Ser Ala Ser Phe Thr Pro Phe Asp His Lys Val
705                 710                 715                 720

Val Ile His Arg Gly Leu Val Tyr Asn Tyr Asp Phe Pro Glu Tyr Gly
                725                 730                 735

Ala Met Lys Pro Gly Ala Phe Gly Asp Ile Gln Ala Thr Ser Leu Thr
            740                 745                 750

Ser Lys Asp Leu Ile Ala Ser Thr Asp Ile Arg Leu Leu Lys Pro Ser
            755                 760                 765

Ala Lys Asn Val His Val Pro Tyr Thr Gln Ala Ser Ser Gly Phe Glu
            770                 775                 780

Met Trp Lys Asn Asn Ser Gly Arg Pro Leu Gln Glu Thr Ala Pro Phe
785                 790                 795                 800

Gly Cys Lys Ile Ala Val Asn Pro Leu Arg Ala Val Asp Cys Ser Tyr
                805                 810                 815

Gly Asn Ile Pro Ile Ser Ile Asp Ile Pro Asn Ala Ala Phe Ile Arg
            820                 825                 830

Thr Ser Asp Ala Pro Leu Val Ser Thr Val Lys Cys Glu Val Ser Glu
            835                 840                 845

Cys Thr Tyr Ser Ala Asp Phe Gly Gly Met Ala Thr Leu Gln Tyr Val
850                 855                 860

Ser Asp Arg Glu Gly Gln Cys Pro Val His Ser His Ser Ser Thr Ala
865                 870                 875                 880

Thr Leu Gln Glu Ser Thr Val His Val Leu Glu Lys Gly Ala Val Thr
                885                 890                 895

Val His Phe Ser Thr Ala Ser Pro Gln Ala Asn Phe Ile Val Ser Leu
            900                 905                 910
```

```
Cys Gly Lys Lys Thr Thr Cys Asn Ala Glu Cys Lys Pro Pro Ala Asp
            915                 920                 925

His Ile Val Ser Thr Pro His Lys Asn Asp Gln Glu Phe Gln Ala Ala
            930                 935                 940

Ile Ser Lys Thr Ser Trp Ser Trp Leu Phe Ala Leu Phe Gly Gly Ala
945                 950                 955                 960

Ser Ser Leu Leu Ile Ile Gly Leu Met Ile Phe Ala Cys Ser Met Met
            965                 970                 975

Leu Thr Ser Thr Arg Arg
            980

<210> SEQ ID NO 12
<211> LENGTH: 981
<212> TYPE: PRT
<213> ORGANISM: Sindbis virus

<400> SEQUENCE: 12

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
            20                  25                  30

Arg Ala Leu Asp Ile Leu Glu Glu Asn Val Asn His Glu Ala Tyr Asp
            35                  40                  45

Thr Leu Leu Asn Ala Ile Leu Arg Cys Gly Ser Ser Gly Arg Ser Lys
        50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95

Glu Gln Val Trp Asp Glu Ala Asp Asp Asn Thr Ile Arg Ile Gln Thr
            100                 105                 110

Ser Ala Gln Phe Gly Tyr Asp Gln Ser Gly Ala Ala Ser Ala Asn Lys
        115                 120                 125

Tyr Arg Tyr Met Ser Leu Lys Gln Asp His Thr Val Glu Glu Gly Thr
130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
        195                 200                 205

Pro Val His Gly Lys Lys Ile Pro Cys Thr Val Tyr Asp Arg Leu Lys
210                 215                 220

Thr Thr Ala Gly Tyr Ile Thr Met His Arg Pro Arg Pro His Ala Tyr
225                 230                 235                 240

Thr Ser Tyr Leu Glu Glu Ser Ser Gly Lys Val Tyr Ala Lys Pro Pro
                245                 250                 255

Ser Gly Lys Asn Ile Thr Tyr Glu Cys Lys Cys Gly Asp Tyr Lys Thr
            260                 265                 270

Gly Thr Val Ser Thr Arg Thr Glu Ile Thr Gly Cys Thr Ala Ile Lys
        275                 280                 285

Gln Cys Val Ala Tyr Lys Ser Asp Gln Thr Lys Trp Val Phe Asn Ser
```

```
              290                 295                 300
Pro Asp Leu Ile Arg His Asp His Thr Ala Gln Gly Lys Leu His
305                 310                 315                 320

Leu Pro Phe Lys Leu Ile Pro Ser Thr Cys Met Val Pro Val Ala His
                325                 330                 335

Ala Pro Asn Val Ile His Gly Phe Lys His Ile Ser Leu Gln Leu Asp
                340                 345                 350

Thr Asp His Leu Thr Leu Leu Thr Thr Arg Arg Leu Gly Ala Asn Pro
                355                 360                 365

Glu Pro Thr Thr Glu Trp Ile Val Gly Lys Thr Val Arg Asn Phe Thr
370                 375                 380

Val Asp Arg Asp Gly Leu Glu Tyr Ile Trp Gly Asn His Glu Pro Val
385                 390                 395                 400

Arg Val Tyr Ala Gln Glu Ser Ala Pro Gly Asp Pro His Gly Trp Pro
                405                 410                 415

His Glu Ile Val Gln His Tyr Tyr His Arg His Pro Val Tyr Thr Ile
                420                 425                 430

Leu Ala Val Ala Ser Ala Thr Val Ala Met Met Ile Gly Val Thr Val
                435                 440                 445

Ala Val Leu Cys Ala Cys Lys Ala Arg Arg Glu Cys Leu Thr Pro Tyr
                450                 455                 460

Ala Leu Ala Pro Asn Ala Val Ile Pro Thr Ser Leu Ala Leu Leu Cys
465                 470                 475                 480

Cys Val Arg Ser Ala Asn Ala Glu Thr Phe Thr Glu Thr Met Ser Tyr
                485                 490                 495

Leu Trp Ser Asn Ser Gln Pro Phe Phe Trp Val Gln Leu Cys Ile Pro
                500                 505                 510

Leu Ala Ala Phe Ile Val Leu Met Arg Cys Cys Ser Cys Cys Leu Pro
                515                 520                 525

Phe Leu Val Val Ala Gly Ala Tyr Leu Ala Lys Val Asp Ala Tyr Glu
530                 535                 540

His Ala Thr Thr Val Pro Asn Val Pro Gln Ile Pro Tyr Lys Ala Leu
545                 550                 555                 560

Val Glu Arg Ala Gly Tyr Ala Pro Leu Asn Leu Glu Ile Thr Val Met
                565                 570                 575

Ser Ser Glu Val Leu Pro Ser Thr Asn Gln Glu Tyr Ile Thr Cys Lys
                580                 585                 590

Phe Thr Thr Val Val Pro Ser Pro Lys Ile Lys Cys Cys Gly Ser Leu
                595                 600                 605

Glu Cys Gln Pro Ala Ala His Ala Asp Tyr Thr Cys Lys Val Phe Gly
610                 615                 620

Gly Val Tyr Pro Phe Met Trp Gly Gly Ala Gln Cys Phe Cys Asp Ser
625                 630                 635                 640

Glu Asn Ser Gln Met Ser Glu Ala Tyr Val Glu Leu Ser Ala Asp Cys
                645                 650                 655

Ala Ser Asp His Ala Gln Ala Ile Lys Val His Thr Ala Ala Met Lys
                660                 665                 670

Val Gly Leu Arg Ile Val Tyr Gly Asn Thr Thr Ser Phe Leu Asp Val
                675                 680                 685

Tyr Val Asn Gly Val Thr Pro Gly Thr Ser Lys Asp Leu Lys Val Ile
690                 695                 700

Ala Gly Pro Ile Ser Ala Ser Phe Thr Pro Phe Asp His Lys Val Val
705                 710                 715                 720
```

Ile His Arg Gly Leu Val Tyr Asn Tyr Asp Phe Pro Glu Tyr Gly Ala
              725                 730                 735

Met Lys Pro Gly Ala Phe Gly Asp Ile Gln Ala Thr Ser Leu Thr Ser
              740                 745                 750

Lys Asp Leu Ile Ala Ser Thr Asp Ile Arg Leu Leu Lys Pro Ser Ala
              755                 760                 765

Lys Asn Val His Val Pro Tyr Thr Gln Ala Ser Ser Gly Phe Glu Met
              770                 775                 780

Trp Lys Asn Asn Ser Gly Arg Pro Leu Gln Glu Thr Ala Pro Phe Gly
785               790                 795                 800

Cys Lys Ile Ala Val Asn Pro Leu Arg Ala Val Asp Cys Ser Tyr Gly
              805                 810                 815

Asn Ile Pro Ile Ser Ile Asp Ile Pro Asn Ala Ala Phe Ile Arg Thr
              820                 825                 830

Ser Asp Ala Pro Leu Val Ser Thr Val Lys Cys Glu Val Ser Glu Cys
              835                 840                 845

Thr Tyr Ser Ala Asp Phe Gly Gly Met Ala Thr Leu Gln Tyr Val Ser
              850                 855                 860

Asp Arg Glu Gly Gln Cys Pro Val His Ser His Ser Ser Thr Ala Thr
865               870                 875                 880

Leu Gln Glu Ser Thr Val His Val Leu Glu Lys Gly Ala Val Thr Val
              885                 890                 895

His Phe Ser Thr Ala Ser Pro Gln Ala Asn Phe Ile Val Ser Leu Cys
              900                 905                 910

Gly Lys Lys Thr Thr Cys Asn Ala Glu Cys Lys Pro Pro Ala Asp His
              915                 920                 925

Ile Val Ser Thr Pro His Lys Asn Asp Gln Glu Phe Gln Ala Ala Ile
              930                 935                 940

Ser Lys Thr Ser Trp Ser Trp Leu Phe Ala Leu Phe Gly Gly Ala Ser
945               950                 955                 960

Ser Leu Leu Ile Ile Gly Leu Met Ile Phe Ala Cys Ser Met Met Leu
              965                 970                 975

Thr Ser Thr Arg Arg
              980

<210> SEQ ID NO 13
<211> LENGTH: 982
<212> TYPE: PRT
<213> ORGANISM: Sindbis virus

<400> SEQUENCE: 13

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
              20                  25                  30

Arg Ala Leu Asp Ile Leu Glu Glu Asn Val Asn His Glu Ala Tyr Asp
              35                  40                  45

Thr Leu Leu Asn Ala Ile Leu Arg Cys Gly Ser Ser Gly Arg Ser Lys
              50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
              85                  90                  95

Glu Gln Val Trp Asp Glu Ala Asp Asp Asn Thr Ile Arg Ile Gln Thr

```
                100             105             110
Ser Ala Gln Phe Gly Tyr Asp Gln Ser Gly Ala Ala Ser Ala Asn Lys
            115                 120             125

Tyr Arg Tyr Met Ser Leu Glu Gln Asp His Thr Val Lys Glu Gly Thr
    130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
        195                 200                 205

Pro Val His Gly Lys Lys Ile Pro Cys Thr Val Tyr Asp Arg Leu Lys
    210                 215                 220

Gly Thr Thr Ala Gly Tyr Ile Thr Met His Arg Pro Arg Pro His Ala
225                 230                 235                 240

Tyr Thr Ser Tyr Leu Glu Glu Ser Ser Gly Lys Val Tyr Ala Lys Pro
                245                 250                 255

Pro Ser Gly Lys Asn Ile Thr Tyr Glu Cys Lys Cys Gly Asp Tyr Lys
            260                 265                 270

Thr Gly Thr Val Ser Thr Arg Thr Glu Ile Thr Gly Cys Thr Ala Ile
        275                 280                 285

Lys Gln Cys Val Ala Tyr Lys Ser Asp Gln Thr Lys Trp Val Phe Asn
    290                 295                 300

Ser Pro Asp Leu Ile Arg His Asp His Thr Ala Gln Gly Lys Leu
305                 310                 315                 320

His Leu Pro Phe Lys Leu Ile Pro Ser Thr Cys Met Val Pro Val Ala
                325                 330                 335

His Ala Pro Asn Val Ile His Gly Phe Lys His Ile Ser Leu Gln Leu
            340                 345                 350

Asp Thr Asp His Leu Thr Leu Leu Thr Thr Arg Arg Leu Gly Ala Asn
        355                 360                 365

Pro Glu Pro Thr Thr Glu Trp Ile Val Gly Lys Thr Val Arg Asn Phe
    370                 375                 380

Thr Val Asp Arg Asp Gly Leu Glu Tyr Ile Trp Gly Asn His Glu Pro
385                 390                 395                 400

Val Arg Val Tyr Ala Gln Glu Ser Ala Pro Gly Asp Pro His Gly Trp
                405                 410                 415

Pro His Glu Ile Val Gln His Tyr Tyr His Arg His Pro Val Tyr Thr
            420                 425                 430

Ile Leu Ala Val Ala Ser Ala Thr Val Ala Met Met Ile Gly Val Thr
        435                 440                 445

Val Ala Val Leu Cys Ala Cys Lys Ala Arg Arg Glu Cys Leu Thr Pro
    450                 455                 460

Tyr Ala Leu Ala Pro Asn Ala Val Ile Pro Thr Ser Leu Ala Leu Leu
465                 470                 475                 480

Cys Cys Val Arg Ser Ala Asn Ala Glu Thr Phe Thr Glu Thr Met Ser
                485                 490                 495

Tyr Leu Trp Ser Asn Ser Gln Pro Phe Phe Trp Val Gln Leu Cys Ile
            500                 505                 510

Pro Leu Ala Ala Phe Ile Val Leu Met Arg Cys Cys Ser Cys Cys Leu
        515                 520                 525
```

```
Pro Phe Leu Val Val Ala Gly Ala Tyr Leu Ala Lys Val Asp Ala Tyr
    530                 535                 540

Glu His Ala Thr Thr Val Pro Asn Val Pro Gln Ile Pro Tyr Lys Ala
545                 550                 555                 560

Leu Val Glu Arg Ala Gly Tyr Ala Pro Leu Asn Leu Glu Ile Thr Val
                565                 570                 575

Met Ser Ser Glu Val Leu Pro Ser Thr Asn Gln Glu Tyr Ile Thr Cys
            580                 585                 590

Lys Phe Thr Thr Val Val Pro Ser Pro Lys Ile Lys Cys Cys Gly Ser
        595                 600                 605

Leu Glu Cys Gln Pro Ala Ala His Ala Asp Tyr Thr Cys Lys Val Phe
    610                 615                 620

Gly Gly Val Tyr Pro Phe Met Trp Gly Gly Ala Gln Cys Phe Cys Asp
625                 630                 635                 640

Ser Glu Asn Ser Gln Met Ser Glu Ala Tyr Val Glu Leu Ser Ala Asp
                645                 650                 655

Cys Ala Ser Asp His Ala Gln Ala Ile Lys Val His Thr Ala Ala Met
            660                 665                 670

Lys Val Gly Leu Arg Ile Val Tyr Gly Asn Thr Thr Ser Phe Leu Asp
        675                 680                 685

Val Tyr Val Asn Gly Val Thr Pro Gly Thr Ser Lys Asp Leu Lys Val
    690                 695                 700

Ile Ala Gly Pro Ile Ser Ala Ser Phe Thr Pro Phe Asp His Lys Val
705                 710                 715                 720

Val Ile His Arg Gly Leu Val Tyr Asn Tyr Asp Phe Pro Glu Tyr Gly
                725                 730                 735

Ala Met Lys Pro Gly Ala Phe Gly Asp Ile Gln Ala Thr Ser Leu Thr
            740                 745                 750

Ser Lys Asp Leu Ile Ala Ser Thr Asp Ile Arg Leu Leu Lys Pro Ser
        755                 760                 765

Ala Lys Asn Val His Val Pro Tyr Thr Gln Ala Ser Ser Gly Phe Glu
    770                 775                 780

Met Trp Lys Asn Asn Ser Gly Arg Pro Leu Gln Glu Thr Ala Pro Phe
785                 790                 795                 800

Gly Cys Lys Ile Ala Val Asn Pro Leu Arg Ala Val Asp Cys Ser Tyr
                805                 810                 815

Gly Asn Ile Pro Ile Ser Ile Asp Ile Pro Asn Ala Ala Phe Ile Arg
            820                 825                 830

Thr Ser Asp Ala Pro Leu Val Ser Thr Val Lys Cys Glu Val Ser Glu
        835                 840                 845

Cys Thr Tyr Ser Ala Asp Phe Gly Gly Met Ala Thr Leu Gln Tyr Val
    850                 855                 860

Ser Asp Arg Glu Gly Gln Cys Pro Val His Ser His Ser Ser Thr Ala
865                 870                 875                 880

Thr Leu Gln Glu Ser Thr Val His Val Leu Glu Lys Gly Ala Val Thr
                885                 890                 895

Val His Phe Ser Thr Ala Ser Pro Gln Ala Asn Phe Ile Val Ser Leu
            900                 905                 910

Cys Gly Lys Lys Thr Thr Cys Asn Ala Glu Cys Lys Pro Pro Ala Asp
        915                 920                 925

His Ile Val Ser Thr Pro His Lys Asn Asp Gln Glu Phe Gln Ala Ala
    930                 935                 940
```

```
Ile Ser Lys Thr Ser Trp Ser Trp Leu Phe Ala Leu Phe Gly Gly Ala
945                 950                 955                 960

Ser Ser Leu Leu Ile Ile Gly Leu Met Ile Phe Ala Cys Ser Met Met
                965                 970                 975

Leu Thr Ser Thr Arg Arg
            980

<210> SEQ ID NO 14
<211> LENGTH: 981
<212> TYPE: PRT
<213> ORGANISM: Sindbis virus

<400> SEQUENCE: 14

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
                20                  25                  30

Arg Ala Leu Asp Ile Leu Glu Glu Asn Val Asn His Glu Ala Tyr Asp
            35                  40                  45

Thr Leu Leu Asn Ala Ile Leu Arg Cys Gly Ser Ser Gly Arg Ser Lys
50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95

Glu Gln Val Trp Asp Glu Ala Asp Asp Asn Thr Ile Arg Ile Gln Thr
                100                 105                 110

Ser Ala Gln Phe Gly Tyr Asp Gln Ser Gly Ala Ala Ser Ala Asn Lys
            115                 120                 125

Tyr Arg Tyr Met Ser Leu Glu Gln Asp His Thr Val Lys Glu Gly Thr
130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
            195                 200                 205

Pro Val His Gly Lys Lys Ile Pro Cys Thr Val Tyr Asp Arg Leu Lys
210                 215                 220

Thr Thr Ala Gly Tyr Ile Thr Met His Arg Pro Arg Pro His Ala Tyr
225                 230                 235                 240

Thr Ser Tyr Leu Glu Glu Ser Ser Gly Lys Val Tyr Ala Lys Pro Pro
                245                 250                 255

Ser Gly Lys Asn Ile Thr Tyr Glu Cys Lys Cys Gly Asp Tyr Lys Thr
            260                 265                 270

Gly Thr Val Ser Thr Arg Thr Glu Ile Thr Gly Cys Thr Ala Ile Lys
            275                 280                 285

Gln Cys Val Ala Tyr Lys Ser Asp Gln Thr Lys Trp Val Phe Asn Ser
        290                 295                 300

Pro Asp Leu Ile Arg His Asp Asp His Thr Ala Gln Gly Lys Leu His
305                 310                 315                 320

Leu Pro Phe Lys Leu Ile Pro Ser Thr Cys Met Val Pro Val Ala His
                325                 330                 335
```

```
Ala Pro Asn Val Ile His Gly Phe Lys His Ile Ser Leu Gln Leu Asp
            340                 345                 350

Thr Asp His Leu Thr Leu Leu Thr Arg Arg Leu Gly Ala Asn Pro
        355                 360                 365

Glu Pro Thr Thr Glu Trp Ile Val Gly Lys Thr Val Arg Asn Phe Thr
    370                 375                 380

Val Asp Arg Asp Gly Leu Glu Tyr Ile Trp Gly Asn His Glu Pro Val
385                 390                 395                 400

Arg Val Tyr Ala Gln Glu Ser Ala Pro Gly Asp Pro His Gly Trp Pro
                405                 410                 415

His Glu Ile Val Gln His Tyr Tyr His Arg His Pro Val Tyr Thr Ile
            420                 425                 430

Leu Ala Val Ala Ser Ala Thr Val Ala Met Met Ile Gly Val Thr Val
        435                 440                 445

Ala Val Leu Cys Ala Cys Lys Ala Arg Arg Glu Cys Leu Thr Pro Tyr
    450                 455                 460

Ala Leu Ala Pro Asn Ala Val Ile Pro Thr Ser Leu Ala Leu Leu Cys
465                 470                 475                 480

Cys Val Arg Ser Ala Asn Ala Glu Thr Phe Thr Glu Thr Met Ser Tyr
                485                 490                 495

Leu Trp Ser Asn Ser Gln Pro Phe Phe Trp Val Gln Leu Cys Ile Pro
            500                 505                 510

Leu Ala Ala Phe Ile Val Leu Met Arg Cys Cys Ser Cys Cys Leu Pro
        515                 520                 525

Phe Leu Val Val Ala Gly Ala Tyr Leu Ala Lys Val Asp Ala Tyr Glu
    530                 535                 540

His Ala Thr Thr Val Pro Asn Val Pro Gln Ile Pro Tyr Lys Ala Leu
545                 550                 555                 560

Val Glu Arg Ala Gly Tyr Ala Pro Leu Asn Leu Glu Ile Thr Val Met
                565                 570                 575

Ser Ser Glu Val Leu Pro Ser Thr Asn Gln Glu Tyr Ile Thr Cys Lys
            580                 585                 590

Phe Thr Thr Val Val Pro Ser Pro Lys Ile Lys Cys Cys Gly Ser Leu
        595                 600                 605

Glu Cys Gln Pro Ala Ala His Ala Asp Tyr Thr Cys Lys Val Phe Gly
    610                 615                 620

Gly Val Tyr Pro Phe Met Trp Gly Gly Ala Gln Cys Phe Cys Asp Ser
625                 630                 635                 640

Glu Asn Ser Gln Met Ser Glu Ala Tyr Val Glu Leu Ser Ala Asp Cys
                645                 650                 655

Ala Ser Asp His Ala Gln Ala Ile Lys Val His Thr Ala Ala Met Lys
            660                 665                 670

Val Gly Leu Arg Ile Val Tyr Gly Asn Thr Thr Ser Phe Leu Asp Val
        675                 680                 685

Tyr Val Asn Gly Val Thr Pro Gly Thr Ser Lys Asp Leu Lys Val Ile
    690                 695                 700

Ala Gly Pro Ile Ser Ala Ser Phe Thr Pro Phe Asp His Lys Val Val
705                 710                 715                 720

Ile His Arg Gly Leu Val Tyr Asn Tyr Asp Phe Pro Glu Tyr Gly Ala
                725                 730                 735

Met Lys Pro Gly Ala Phe Gly Asp Ile Gln Ala Thr Ser Leu Thr Ser
            740                 745                 750
```

```
Lys Asp Leu Ile Ala Ser Thr Asp Ile Arg Leu Leu Lys Pro Ser Ala
            755                 760                 765
Lys Asn Val His Val Pro Tyr Thr Gln Ala Ser Ser Gly Phe Glu Met
770                 775                 780
Trp Lys Asn Asn Ser Gly Arg Pro Leu Gln Glu Thr Ala Pro Phe Gly
785                 790                 795                 800
Cys Lys Ile Ala Val Asn Pro Leu Arg Ala Val Asp Cys Ser Tyr Gly
            805                 810                 815
Asn Ile Pro Ile Ser Ile Asp Ile Pro Asn Ala Ala Phe Ile Arg Thr
            820                 825                 830
Ser Asp Ala Pro Leu Val Ser Thr Val Lys Cys Glu Val Ser Glu Cys
            835                 840                 845
Thr Tyr Ser Ala Asp Phe Gly Gly Met Ala Thr Leu Gln Tyr Val Ser
            850                 855                 860
Asp Arg Glu Gly Gln Cys Pro Val His Ser His Ser Ser Thr Ala Thr
865                 870                 875                 880
Leu Gln Glu Ser Thr Val His Val Leu Glu Lys Gly Ala Val Thr Val
            885                 890                 895
His Phe Ser Thr Ala Ser Pro Gln Ala Asn Phe Ile Val Ser Leu Cys
            900                 905                 910
Gly Lys Lys Thr Thr Cys Asn Ala Glu Cys Lys Pro Pro Ala Asp His
            915                 920                 925
Ile Val Ser Thr Pro His Lys Asn Asp Gln Glu Phe Gln Ala Ala Ile
            930                 935                 940
Ser Lys Thr Ser Trp Ser Trp Leu Phe Ala Leu Phe Gly Gly Ala Ser
945                 950                 955                 960
Ser Leu Leu Ile Ile Gly Leu Met Ile Phe Ala Cys Ser Met Met Leu
            965                 970                 975
Thr Ser Thr Arg Arg
            980

<210> SEQ ID NO 15
<211> LENGTH: 982
<212> TYPE: PRT
<213> ORGANISM: Sindbis virus

<400> SEQUENCE: 15

Met Ser Ala Ala Pro Leu Val Thr Ala Met Cys Leu Leu Gly Asn Val
1               5                   10                  15
Ser Phe Pro Cys Asp Arg Pro Pro Thr Cys Tyr Thr Arg Glu Pro Ser
            20                  25                  30
Arg Ala Leu Asp Ile Leu Glu Glu Asn Val Asn His Glu Ala Tyr Asp
            35                  40                  45
Thr Leu Leu Asn Ala Ile Leu Arg Cys Gly Ser Ser Gly Arg Ser Lys
        50                  55                  60
Arg Ser Val Ile Asp Asp Phe Thr Leu Thr Ser Pro Tyr Leu Gly Thr
65                  70                  75                  80
Cys Ser Tyr Cys His His Thr Val Pro Cys Phe Ser Pro Val Lys Ile
            85                  90                  95
Glu Gln Val Trp Asp Glu Ala Asp Asp Asn Thr Ile Arg Ile Gln Thr
            100                 105                 110
Ser Ala Gln Phe Gly Tyr Asp Gln Ser Gly Ala Ala Ser Ala Asn Lys
            115                 120                 125
Tyr Arg Tyr Met Ser Leu Glu Gln Asp His Thr Val Glu Glu Gly Thr
            130                 135                 140
```

```
Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
        195                 200                 205

Pro Val His Gly Lys Lys Ile Pro Cys Thr Val Tyr Asp Arg Leu Lys
    210                 215                 220

Gly Thr Thr Ala Gly Tyr Ile Thr Met His Arg Pro Arg Pro His Ala
225                 230                 235                 240

Tyr Thr Ser Tyr Leu Glu Glu Ser Ser Gly Lys Val Tyr Ala Lys Pro
                245                 250                 255

Pro Ser Gly Lys Asn Ile Thr Tyr Glu Cys Lys Cys Gly Asp Tyr Lys
            260                 265                 270

Thr Gly Thr Val Ser Thr Arg Thr Glu Ile Thr Gly Cys Thr Ala Ile
        275                 280                 285

Lys Gln Cys Val Ala Tyr Lys Ser Asp Gln Thr Lys Trp Val Phe Asn
    290                 295                 300

Ser Pro Asp Leu Ile Arg His Asp Asp His Thr Ala Gln Gly Lys Leu
305                 310                 315                 320

His Leu Pro Phe Lys Leu Ile Pro Ser Thr Cys Met Val Pro Val Ala
                325                 330                 335

His Ala Pro Asn Val Ile His Gly Phe Lys His Ile Ser Leu Gln Leu
            340                 345                 350

Asp Thr Asp His Leu Thr Leu Leu Thr Thr Arg Arg Leu Gly Ala Asn
        355                 360                 365

Pro Glu Pro Thr Thr Glu Trp Ile Val Gly Lys Thr Val Arg Asn Phe
    370                 375                 380

Thr Val Asp Arg Asp Gly Leu Glu Tyr Ile Trp Gly Asn His Glu Pro
385                 390                 395                 400

Val Arg Val Tyr Ala Gln Glu Ser Ala Pro Gly Asp Pro His Gly Trp
                405                 410                 415

Pro His Glu Ile Val Gln His Tyr Tyr His Arg His Pro Val Tyr Thr
            420                 425                 430

Ile Leu Ala Val Ala Ser Ala Thr Val Ala Met Met Ile Gly Val Thr
        435                 440                 445

Val Ala Val Leu Cys Ala Cys Lys Ala Arg Arg Glu Cys Leu Thr Pro
    450                 455                 460

Tyr Ala Leu Ala Pro Asn Ala Val Ile Pro Thr Ser Leu Ala Leu Leu
465                 470                 475                 480

Cys Cys Val Arg Ser Ala Asn Ala Glu Thr Phe Thr Glu Thr Met Ser
                485                 490                 495

Tyr Leu Trp Ser Asn Ser Gln Pro Phe Phe Trp Val Gln Leu Cys Ile
            500                 505                 510

Pro Leu Ala Ala Phe Ile Val Leu Met Arg Cys Cys Ser Cys Cys Leu
        515                 520                 525

Pro Phe Leu Val Val Ala Gly Ala Tyr Leu Ala Lys Val Asp Ala Tyr
    530                 535                 540

Glu His Ala Thr Thr Val Pro Asn Val Pro Gln Ile Pro Tyr Lys Ala
545                 550                 555                 560
```

```
Leu Val Glu Arg Ala Gly Tyr Ala Pro Leu Asn Leu Glu Ile Thr Val
                565                 570                 575
Met Ser Ser Glu Val Leu Pro Ser Thr Asn Gln Glu Tyr Ile Thr Cys
            580                 585                 590
Lys Phe Thr Thr Val Val Pro Ser Pro Lys Ile Lys Cys Cys Gly Ser
        595                 600                 605
Leu Glu Cys Gln Pro Ala Ala His Ala Asp Tyr Thr Cys Lys Val Phe
    610                 615                 620
Gly Gly Val Tyr Pro Phe Met Trp Gly Gly Ala Gln Cys Phe Cys Asp
625                 630                 635                 640
Ser Glu Asn Ser Gln Met Ser Glu Ala Tyr Val Glu Leu Ser Ala Asp
                645                 650                 655
Cys Ala Ser Asp His Ala Gln Ala Ile Lys Val His Thr Ala Ala Met
            660                 665                 670
Lys Val Gly Leu Arg Ile Val Tyr Gly Asn Thr Thr Ser Phe Leu Asp
        675                 680                 685
Val Tyr Val Asn Gly Val Thr Pro Gly Thr Ser Lys Asp Leu Lys Val
    690                 695                 700
Ile Ala Gly Pro Ile Ser Ala Ser Phe Thr Pro Phe Asp His Lys Val
705                 710                 715                 720
Val Ile His Arg Gly Leu Val Tyr Asn Tyr Asp Phe Pro Glu Tyr Gly
                725                 730                 735
Ala Met Lys Pro Gly Ala Phe Gly Asp Ile Gln Ala Thr Ser Leu Thr
            740                 745                 750
Ser Lys Asp Leu Ile Ala Ser Thr Asp Ile Arg Leu Leu Lys Pro Ser
        755                 760                 765
Ala Lys Asn Val His Val Pro Tyr Thr Gln Ala Ser Ser Gly Phe Glu
    770                 775                 780
Met Trp Lys Asn Asn Ser Gly Arg Pro Leu Gln Glu Thr Ala Pro Phe
785                 790                 795                 800
Gly Cys Lys Ile Ala Val Asn Pro Leu Arg Ala Val Asp Cys Ser Tyr
                805                 810                 815
Gly Asn Ile Pro Ile Ser Ile Asp Ile Pro Asn Ala Ala Phe Ile Arg
            820                 825                 830
Thr Ser Asp Ala Pro Leu Val Ser Thr Val Lys Cys Glu Val Ser Glu
        835                 840                 845
Cys Thr Tyr Ser Ala Asp Phe Gly Gly Met Ala Thr Leu Gln Tyr Val
    850                 855                 860
Ser Asp Arg Glu Gly Gln Cys Pro Val His Ser His Ser Ser Thr Ala
865                 870                 875                 880
Thr Leu Gln Glu Ser Thr Val His Val Leu Glu Lys Gly Ala Val Thr
                885                 890                 895
Val His Phe Ser Thr Ala Ser Pro Gln Ala Asn Phe Ile Val Ser Leu
            900                 905                 910
Cys Gly Lys Lys Thr Thr Cys Asn Ala Glu Cys Lys Pro Pro Ala Asp
        915                 920                 925
His Ile Val Ser Thr Pro His Lys Asn Asp Gln Glu Phe Gln Ala Ala
    930                 935                 940
Ile Ser Lys Thr Ser Trp Ser Trp Leu Phe Ala Leu Phe Gly Gly Ala
945                 950                 955                 960
Ser Ser Leu Leu Ile Ile Gly Leu Met Ile Phe Ala Cys Ser Met Met
                965                 970                 975
Leu Thr Ser Thr Arg Arg
```

-continued

<210> SEQ ID NO 16
<211> LENGTH: 981
<212> TYPE: PRT
<213> ORGANISM: Sindbis virus

<400> SEQUENCE: 16

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
            20                  25                  30

Arg Ala Leu Asp Ile Leu Glu Glu Asn Val Asn His Glu Ala Tyr Asp
        35                  40                  45

Thr Leu Leu Asn Ala Ile Leu Arg Cys Gly Ser Ser Gly Arg Ser Lys
    50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95

Glu Gln Val Trp Asp Glu Ala Asp Asp Asn Thr Ile Arg Ile Gln Thr
            100                 105                 110

Ser Ala Gln Phe Gly Tyr Asp Gln Ser Gly Ala Ala Ser Ala Asn Lys
        115                 120                 125

Tyr Arg Tyr Met Ser Leu Glu Gln Asp His Thr Val Glu Glu Gly Thr
    130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
        195                 200                 205

Pro Val His Gly Lys Lys Ile Pro Cys Thr Val Tyr Asp Arg Leu Lys
    210                 215                 220

Thr Thr Ala Gly Tyr Ile Thr Met His Arg Pro Arg Pro His Ala Tyr
225                 230                 235                 240

Thr Ser Tyr Leu Glu Glu Ser Ser Gly Lys Val Tyr Ala Lys Pro Pro
                245                 250                 255

Ser Gly Lys Asn Ile Thr Tyr Glu Cys Lys Cys Gly Asp Tyr Lys Thr
            260                 265                 270

Gly Thr Val Ser Thr Arg Thr Glu Ile Thr Gly Cys Thr Ala Ile Lys
        275                 280                 285

Gln Cys Val Ala Tyr Lys Ser Asp Gln Thr Lys Trp Val Phe Asn Ser
    290                 295                 300

Pro Asp Leu Ile Arg His Asp Asp His Thr Ala Gln Gly Lys Leu His
305                 310                 315                 320

Leu Pro Phe Lys Leu Ile Pro Ser Thr Cys Met Val Pro Val Ala His
                325                 330                 335

Ala Pro Asn Val Ile His Gly Phe Lys His Ile Ser Leu Gln Leu Asp
            340                 345                 350

Thr Asp His Leu Thr Leu Leu Thr Thr Arg Arg Leu Gly Ala Asn Pro
        355                 360                 365

-continued

Glu Pro Thr Thr Glu Trp Ile Val Gly Lys Thr Val Arg Asn Phe Thr
370                 375                 380

Val Asp Arg Asp Gly Leu Glu Tyr Ile Trp Gly Asn His Glu Pro Val
385                 390                 395                 400

Arg Val Tyr Ala Gln Glu Ser Ala Pro Gly Asp Pro His Gly Trp Pro
            405                 410                 415

His Glu Ile Val Gln His Tyr Tyr His Arg His Pro Val Tyr Thr Ile
            420                 425                 430

Leu Ala Val Ala Ser Ala Thr Val Ala Met Met Ile Gly Val Thr Val
            435                 440                 445

Ala Val Leu Cys Ala Cys Lys Ala Arg Arg Glu Cys Leu Thr Pro Tyr
450                 455                 460

Ala Leu Ala Pro Asn Ala Val Ile Pro Thr Ser Leu Ala Leu Leu Cys
465                 470                 475                 480

Cys Val Arg Ser Ala Asn Ala Glu Thr Phe Thr Glu Thr Met Ser Tyr
            485                 490                 495

Leu Trp Ser Asn Ser Gln Pro Phe Phe Trp Val Gln Leu Cys Ile Pro
            500                 505                 510

Leu Ala Ala Phe Ile Val Leu Met Arg Cys Cys Ser Cys Cys Leu Pro
            515                 520                 525

Phe Leu Val Val Ala Gly Ala Tyr Leu Ala Lys Val Asp Ala Tyr Glu
530                 535                 540

His Ala Thr Thr Val Pro Asn Val Pro Gln Ile Pro Tyr Lys Ala Leu
545                 550                 555                 560

Val Glu Arg Ala Gly Tyr Ala Pro Leu Asn Leu Glu Ile Thr Val Met
            565                 570                 575

Ser Ser Glu Val Leu Pro Ser Thr Asn Gln Glu Tyr Ile Thr Cys Lys
            580                 585                 590

Phe Thr Thr Val Val Pro Ser Pro Lys Ile Lys Cys Cys Gly Ser Leu
            595                 600                 605

Glu Cys Gln Pro Ala Ala His Ala Asp Tyr Thr Cys Lys Val Phe Gly
610                 615                 620

Gly Val Tyr Pro Phe Met Trp Gly Gly Ala Gln Cys Phe Cys Asp Ser
625                 630                 635                 640

Glu Asn Ser Gln Met Ser Glu Ala Tyr Val Glu Leu Ser Ala Asp Cys
            645                 650                 655

Ala Ser Asp His Ala Gln Ala Ile Lys Val His Thr Ala Ala Met Lys
            660                 665                 670

Val Gly Leu Arg Ile Val Tyr Gly Asn Thr Thr Ser Phe Leu Asp Val
            675                 680                 685

Tyr Val Asn Gly Val Thr Pro Gly Thr Ser Lys Asp Leu Lys Val Ile
690                 695                 700

Ala Gly Pro Ile Ser Ala Ser Phe Thr Pro Phe Asp His Lys Val Val
705                 710                 715                 720

Ile His Arg Gly Leu Val Tyr Asn Tyr Asp Phe Pro Glu Tyr Gly Ala
            725                 730                 735

Met Lys Pro Gly Ala Phe Gly Asp Ile Gln Ala Thr Ser Leu Thr Ser
            740                 745                 750

Lys Asp Leu Ile Ala Ser Thr Asp Ile Arg Leu Leu Lys Pro Ser Ala
            755                 760                 765

Lys Asn Val His Val Pro Tyr Thr Gln Ala Ser Ser Gly Phe Glu Met
770                 775                 780

Trp Lys Asn Asn Ser Gly Arg Pro Leu Gln Glu Thr Ala Pro Phe Gly

```
                785                 790                 795                 800
Cys Lys Ile Ala Val Asn Pro Leu Arg Ala Val Asp Cys Ser Tyr Gly
                805                 810                 815

Asn Ile Pro Ile Ser Ile Asp Ile Pro Asn Ala Ala Phe Ile Arg Thr
                820                 825                 830

Ser Asp Ala Pro Leu Val Ser Thr Val Lys Cys Glu Val Ser Glu Cys
                835                 840                 845

Thr Tyr Ser Ala Asp Phe Gly Gly Met Ala Thr Leu Gln Tyr Val Ser
    850                 855                 860

Asp Arg Glu Gly Gln Cys Pro Val His Ser His Ser Ser Thr Ala Thr
865                 870                 875                 880

Leu Gln Glu Ser Thr Val His Val Leu Glu Lys Gly Ala Val Thr Val
                885                 890                 895

His Phe Ser Thr Ala Ser Pro Gln Ala Asn Phe Ile Val Ser Leu Cys
                900                 905                 910

Gly Lys Lys Thr Thr Cys Asn Ala Glu Cys Lys Pro Pro Ala Asp His
                915                 920                 925

Ile Val Ser Thr Pro His Lys Asn Asp Gln Glu Phe Gln Ala Ala Ile
                930                 935                 940

Ser Lys Thr Ser Trp Ser Trp Leu Phe Ala Leu Phe Gly Gly Ala Ser
945                 950                 955                 960

Ser Leu Leu Ile Ile Gly Leu Met Ile Phe Ala Cys Ser Met Met Leu
                965                 970                 975

Thr Ser Thr Arg Arg
                980

<210> SEQ ID NO 17
<211> LENGTH: 982
<212> TYPE: PRT
<213> ORGANISM: Sindbis virus

<400> SEQUENCE: 17

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
                20                  25                  30

Arg Ala Leu Asp Ile Leu Glu Glu Asn Val Asn His Glu Ala Tyr Asp
            35                  40                  45

Thr Leu Leu Asn Ala Ile Leu Arg Cys Gly Ser Ser Gly Arg Ser Lys
        50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95

Glu Gln Val Trp Asp Glu Ala Asp Asp Asn Thr Ile Arg Ile Gln Thr
                100                 105                 110

Ser Ala Gln Phe Gly Tyr Asp Gln Ser Gly Ala Ala Ser Ala Asn Lys
            115                 120                 125

Tyr Arg Tyr Met Ser Leu Lys Gln Asp His Thr Val Lys Glu Gly Thr
        130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175
```

-continued

```
Thr Val Ser Ile Val Ser Ser Asn Ser Ala Thr Ser Cys Thr Leu Ala
                180                 185                 190

Arg Lys Ile Lys Pro Lys Phe Val Gly Arg Glu Lys Tyr Asp Leu Pro
            195                 200                 205

Pro Val His Gly Lys Lys Ile Pro Cys Thr Val Tyr Asp Arg Leu Lys
        210                 215                 220

Glu Thr Thr Ala Gly Tyr Ile Thr Met His Arg Pro Arg Pro His Ala
225                 230                 235                 240

Tyr Thr Ser Tyr Leu Glu Glu Ser Ser Gly Lys Val Tyr Ala Lys Pro
                245                 250                 255

Pro Ser Gly Lys Asn Ile Thr Tyr Glu Cys Lys Cys Gly Asp Tyr Lys
            260                 265                 270

Thr Gly Thr Val Ser Thr Arg Thr Glu Ile Thr Gly Cys Thr Ala Ile
        275                 280                 285

Lys Gln Cys Val Ala Tyr Lys Ser Asp Gln Thr Lys Trp Val Phe Asn
290                 295                 300

Ser Pro Asp Leu Ile Arg His Asp His Thr Ala Gln Gly Lys Leu
305                 310                 315                 320

His Leu Pro Phe Lys Leu Ile Pro Ser Thr Cys Met Val Pro Val Ala
                325                 330                 335

His Ala Pro Asn Val Ile His Gly Phe Lys His Ile Ser Leu Gln Leu
            340                 345                 350

Asp Thr Asp His Leu Thr Leu Leu Thr Thr Arg Arg Leu Gly Ala Asn
        355                 360                 365

Pro Glu Pro Thr Thr Glu Trp Ile Val Gly Lys Thr Val Arg Asn Phe
370                 375                 380

Thr Val Asp Arg Asp Gly Leu Glu Tyr Ile Trp Gly Asn His Glu Pro
385                 390                 395                 400

Val Arg Val Tyr Ala Gln Glu Ser Ala Pro Gly Asp Pro His Gly Trp
                405                 410                 415

Pro His Glu Ile Val Gln His Tyr Tyr His Arg His Pro Val Tyr Thr
            420                 425                 430

Ile Leu Ala Val Ala Ser Ala Thr Val Ala Met Met Ile Gly Val Thr
        435                 440                 445

Val Ala Val Leu Cys Ala Cys Lys Ala Arg Arg Glu Cys Leu Thr Pro
450                 455                 460

Tyr Ala Leu Ala Pro Asn Ala Val Ile Pro Thr Ser Leu Ala Leu Leu
465                 470                 475                 480

Cys Cys Val Arg Ser Ala Asn Ala Glu Thr Phe Thr Glu Thr Met Ser
                485                 490                 495

Tyr Leu Trp Ser Asn Ser Gln Pro Phe Phe Trp Val Gln Leu Cys Ile
            500                 505                 510

Pro Leu Ala Ala Phe Ile Val Leu Met Arg Cys Cys Ser Cys Cys Leu
        515                 520                 525

Pro Phe Leu Val Val Ala Gly Ala Tyr Leu Ala Lys Val Asp Ala Tyr
530                 535                 540

Glu His Ala Thr Thr Val Pro Asn Val Pro Gln Ile Pro Tyr Lys Ala
545                 550                 555                 560

Leu Val Glu Arg Ala Gly Tyr Ala Pro Leu Asn Leu Glu Ile Thr Val
                565                 570                 575

Met Ser Ser Glu Val Leu Pro Ser Thr Asn Gln Glu Tyr Ile Thr Cys
            580                 585                 590

Lys Phe Thr Thr Val Val Pro Ser Pro Lys Ile Lys Cys Cys Gly Ser
```

```
                595                 600                 605
Leu Glu Cys Gln Pro Ala Ala His Ala Asp Tyr Thr Cys Lys Val Phe
        610                 615                 620
Gly Gly Val Tyr Pro Phe Met Trp Gly Gly Ala Gln Cys Phe Cys Asp
625                 630                 635                 640
Ser Glu Asn Ser Gln Met Ser Glu Ala Tyr Val Glu Leu Ser Ala Asp
                645                 650                 655
Cys Ala Ser Asp His Ala Gln Ala Ile Lys Val His Thr Ala Ala Met
                660                 665                 670
Lys Val Gly Leu Arg Ile Val Tyr Gly Asn Thr Thr Ser Phe Leu Asp
            675                 680                 685
Val Tyr Val Asn Gly Val Thr Pro Gly Thr Ser Lys Asp Leu Lys Val
        690                 695                 700
Ile Ala Gly Pro Ile Ser Ala Ser Phe Thr Pro Phe Asp His Lys Val
705                 710                 715                 720
Val Ile His Arg Gly Leu Val Tyr Asn Tyr Asp Phe Pro Glu Tyr Gly
                725                 730                 735
Ala Met Lys Pro Gly Ala Phe Gly Asp Ile Gln Ala Thr Ser Leu Thr
                740                 745                 750
Ser Lys Asp Leu Ile Ala Ser Thr Asp Ile Arg Leu Leu Lys Pro Ser
            755                 760                 765
Ala Lys Asn Val His Val Pro Tyr Thr Gln Ala Ser Ser Gly Phe Glu
        770                 775                 780
Met Trp Lys Asn Asn Ser Gly Arg Pro Leu Gln Glu Thr Ala Pro Phe
785                 790                 795                 800
Gly Cys Lys Ile Ala Val Asn Pro Leu Arg Ala Val Asp Cys Ser Tyr
                805                 810                 815
Gly Asn Ile Pro Ile Ser Ile Asp Ile Pro Asn Ala Ala Phe Ile Arg
                820                 825                 830
Thr Ser Asp Ala Pro Leu Val Ser Thr Val Lys Cys Glu Val Ser Glu
            835                 840                 845
Cys Thr Tyr Ser Ala Asp Phe Gly Gly Met Ala Thr Leu Gln Tyr Val
        850                 855                 860
Ser Asp Arg Glu Gly Gln Cys Pro Val His Ser His Ser Ser Thr Ala
865                 870                 875                 880
Thr Leu Gln Glu Ser Thr Val His Val Leu Glu Lys Gly Ala Val Thr
                885                 890                 895
Val His Phe Ser Thr Ala Ser Pro Gln Ala Asn Phe Ile Val Ser Leu
                900                 905                 910
Cys Gly Lys Lys Thr Thr Cys Asn Ala Glu Cys Lys Pro Pro Ala Asp
            915                 920                 925
His Ile Val Ser Thr Pro His Lys Asn Asp Gln Glu Phe Gln Ala Ala
        930                 935                 940
Ile Ser Lys Thr Ser Trp Ser Trp Leu Phe Ala Leu Phe Gly Gly Ala
945                 950                 955                 960
Ser Ser Leu Leu Ile Ile Gly Leu Met Ile Phe Ala Cys Ser Met Met
                965                 970                 975
Leu Thr Ser Thr Arg Arg
            980

<210> SEQ ID NO 18
<211> LENGTH: 423
<212> TYPE: PRT
<213> ORGANISM: Sindbis virus
```

<400> SEQUENCE: 18

```
Ser Val Ile Asp Asp Phe Thr Leu Thr Ser Pro Tyr Leu Gly Thr Cys
1               5                   10                  15
Ser Tyr Cys His His Thr Val Pro Cys Phe Ser Pro Val Lys Ile Glu
            20                  25                  30
Gln Val Trp Asp Glu Ala Asp Asp Asn Thr Ile Arg Ile Gln Thr Ser
        35                  40                  45
Ala Gln Phe Gly Tyr Asp Gln Ser Gly Ala Ala Ser Ala Asn Lys Tyr
    50                  55                  60
Arg Tyr Met Ser Leu Lys Gln Asp His Thr Val Lys Glu Gly Thr Met
65                  70                  75                  80
Asp Asp Ile Lys Ile Ser Thr Ser Gly Pro Cys Arg Arg Leu Ser Tyr
                85                  90                  95
Lys Gly Tyr Phe Leu Leu Ala Lys Cys Pro Pro Gly Asp Ser Val Thr
            100                 105                 110
Val Ser Ile Val Ser Ser Asn Ser Ala Thr Ser Cys Thr Leu Ala Arg
        115                 120                 125
Lys Ile Lys Pro Lys Phe Val Gly Arg Glu Lys Tyr Asp Leu Pro Pro
    130                 135                 140
Val His Gly Lys Lys Ile Pro Cys Thr Val Tyr Asp Arg Leu Lys Glu
145                 150                 155                 160
Thr Thr Ala Gly Tyr Ile Thr Met His Arg Pro Arg Pro His Ala Tyr
                165                 170                 175
Thr Ser Tyr Leu Glu Glu Ser Ser Gly Lys Val Tyr Ala Lys Pro Pro
            180                 185                 190
Ser Gly Lys Asn Ile Thr Tyr Glu Cys Lys Cys Gly Asp Tyr Lys Thr
        195                 200                 205
Gly Thr Val Ser Thr Arg Thr Glu Ile Thr Gly Cys Thr Ala Ile Lys
    210                 215                 220
Gln Cys Val Ala Tyr Lys Ser Asp Gln Thr Lys Trp Val Phe Asn Ser
225                 230                 235                 240
Pro Asp Leu Ile Arg His Asp Asp His Thr Ala Gln Gly Lys Leu His
                245                 250                 255
Leu Pro Phe Lys Leu Ile Pro Ser Thr Cys Met Val Pro Val Ala His
            260                 265                 270
Ala Pro Asn Val Ile His Gly Phe Lys His Ile Ser Leu Gln Leu Asp
        275                 280                 285
Thr Asp His Leu Thr Leu Leu Thr Thr Arg Arg Leu Gly Ala Asn Pro
    290                 295                 300
Glu Pro Thr Thr Glu Trp Ile Val Gly Lys Thr Val Arg Asn Phe Thr
305                 310                 315                 320
Val Asp Arg Asp Gly Leu Glu Tyr Ile Trp Gly Asn His Glu Pro Val
                325                 330                 335
Arg Val Tyr Ala Gln Glu Ser Ala Pro Gly Asp Pro His Gly Trp Pro
            340                 345                 350
His Glu Ile Val Gln His Tyr Tyr His Arg His Pro Val Tyr Thr Ile
        355                 360                 365
Leu Ala Val Ala Ser Ala Thr Val Ala Met Met Ile Gly Val Thr Val
    370                 375                 380
Ala Val Leu Cys Ala Cys Lys Ala Arg Arg Glu Cys Leu Thr Pro Tyr
385                 390                 395                 400
Ala Leu Ala Pro Asn Ala Val Ile Pro Thr Ser Leu Ala Leu Leu Cys
```

```
                    405                 410                 415

Cys Val Arg Ser Ala Asn Ala
            420

<210> SEQ ID NO 19
<211> LENGTH: 65
<212> TYPE: PRT
<213> ORGANISM: Sindbis virus

<400> SEQUENCE: 19

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
            20                  25                  30

Arg Ala Leu Asp Ile Leu Glu Glu Asn Val Asn His Glu Ala Tyr Asp
        35                  40                  45

Thr Leu Leu Asn Ala Ile Leu Arg Cys Gly Ser Ser Gly Arg Ser Lys
    50                  55                  60

Arg
65

<210> SEQ ID NO 20
<211> LENGTH: 488
<212> TYPE: PRT
<213> ORGANISM: Sindbis virus

<400> SEQUENCE: 20

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
            20                  25                  30

Arg Ala Leu Asp Ile Leu Glu Glu Asn Val Asn His Glu Ala Tyr Asp
        35                  40                  45

Thr Leu Leu Asn Ala Ile Leu Arg Cys Gly Ser Ser Gly Arg Ser Lys
    50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95

Glu Gln Val Trp Asp Glu Ala Asp Asp Asn Thr Ile Arg Ile Gln Thr
            100                 105                 110

Ser Ala Gln Phe Gly Tyr Asp Gln Ser Gly Ala Ala Ser Ala Asn Lys
        115                 120                 125

Tyr Arg Tyr Met Ser Leu Lys Gln Asp His Thr Val Lys Glu Gly Thr
    130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
        195                 200                 205

Pro Val His Gly Lys Lys Ile Pro Cys Thr Val Tyr Asp Arg Leu Lys
    210                 215                 220

Glu Thr Thr Ala Gly Tyr Ile Thr Met His Arg Pro Arg Pro His Ala
```

```
                225                 230                 235                 240
Tyr Thr Ser Tyr Leu Glu Glu Ser Ser Gly Lys Val Tyr Ala Lys Pro
            245                 250                 255
Pro Ser Gly Lys Asn Ile Thr Tyr Glu Cys Lys Cys Gly Asp Tyr Lys
            260                 265                 270
Thr Gly Thr Val Ser Thr Arg Thr Glu Ile Thr Gly Cys Thr Ala Ile
            275                 280                 285
Lys Gln Cys Val Ala Tyr Lys Ser Asp Gln Thr Lys Trp Val Phe Asn
290                 295                 300
Ser Pro Asp Leu Ile Arg His Asp His Thr Ala Gln Gly Lys Leu
305                 310                 315                 320
His Leu Pro Phe Lys Leu Ile Pro Ser Thr Cys Met Val Pro Val Ala
            325                 330                 335
His Ala Pro Asn Val Ile His Gly Phe Lys His Ile Ser Leu Gln Leu
            340                 345                 350
Asp Thr Asp His Leu Thr Leu Leu Thr Thr Arg Arg Leu Gly Ala Asn
            355                 360                 365
Pro Glu Pro Thr Thr Glu Trp Ile Val Gly Lys Thr Val Arg Asn Phe
370                 375                 380
Thr Val Asp Arg Asp Gly Leu Glu Tyr Ile Trp Gly Asn His Glu Pro
385                 390                 395                 400
Val Arg Val Tyr Ala Gln Glu Ser Ala Pro Gly Asp Pro His Gly Trp
            405                 410                 415
Pro His Glu Ile Val Gln His Tyr Tyr His Arg His Pro Val Tyr Thr
            420                 425                 430
Ile Leu Ala Val Ala Ser Ala Thr Val Ala Met Met Ile Gly Val Thr
            435                 440                 445
Val Ala Val Leu Cys Ala Cys Lys Ala Arg Arg Glu Cys Leu Thr Pro
            450                 455                 460
Tyr Ala Leu Ala Pro Asn Ala Val Ile Pro Thr Ser Leu Ala Leu Leu
465                 470                 475                 480
Cys Cys Val Arg Ser Ala Asn Ala
            485

<210> SEQ ID NO 21
<211> LENGTH: 683
<212> TYPE: DNA
<213> ORGANISM: Human immunodeficiency virus type 1

<400> SEQUENCE: 21
cctagaaaaa catggagcaa tcacaagtag caatacagca gctaccaatg ctgattgtgc      60
ctggctagaa gcacaagagg aggaggaggt gggttttcca gtcacacctc aggtaccttt     120
aagaccaatg acttacaagg cagctgtaga tcttagccac tttttaaaag aaaaggggggg     180
actggaaggg ctaattcact cccaacgaag acaagatatc cttgatctgt ggatctacca     240
cacacaaggc tacttccctg attggcagaa ctacacacca gggccaggga tcagatatcc     300
actgaccttt ggatggtgct acaagctagt accagttgag caagagaagg tagaagaagc     360
caatgaagga gagaacaccc gcttgttaca ccctgtgagc ctgcatggga tggatgaccc     420
ggagagagaa gtattagagt ggaggtttga cagccgccta gcatttcatc acatggcccg     480
agagctgcat ccggactgta ctgggtctct ctggttagac cagatctgag cctgggagct     540
ctctggctaa ctagggaacc cactgcttaa gcctcaataa agcttgcctt gagtgcttca     600
agtagtgtgt gcccgtctgt tgtgtgactc tggtaactag agatccctca gacccttta     660
```

```
gtcagtgtgg aaaatctcta gca                                            683
```

<210> SEQ ID NO 22
<211> LENGTH: 416
<212> TYPE: DNA
<213> ORGANISM: Human immunodeficiency virus type 1

<400> SEQUENCE: 22

```
cctagaaaaa catggagcaa tcacaagtag caatacagca gctaccaatg ctgattgtgc     60
ctggctagaa gcacaagagg aggaggaggt gggttttcca gtcacacctc aggtaccttt    120
aagaccaatg acttacaagg cagctgtaga tcttagccac ttttttaaaag aaaaggggggg  180
actggaaggg ctaattcact cccaacgaag acaagatctg cttttttgcct gtactgggtc   240
tctctggtta gaccagatct gagcctggga gctctctggc taactaggga acccactgct   300
taagcctcaa taaagcttgc cttgagtgct tcaagtagtg tgtgcccgtc tgttgtgtga   360
ctctggtaac tagagatccc tcagacccctt ttagtcagtg tggaaaatct ctagca       416
```

<210> SEQ ID NO 23
<211> LENGTH: 401
<212> TYPE: DNA
<213> ORGANISM: Human immunodeficiency virus type 1

<400> SEQUENCE: 23

```
cctagaaaaa catggagcaa tcacaagtag caatacagca gctaccaatg ctgattgtgc     60
ctggctagaa gcacaagagg aggaggaggt gggttttcca gtcacacctc aggtaccttt    120
aagaccaatg acttacaagg cagctgtaga tcttagccac ttttttactgg aagggctaat   180
tcactcccaa cgaagacaag atctgctttt tgcctgtact gggtctctct ggttagacca    240
gatctgagcc tgggagctct ctggctaact agggaaccca ctgcttaagc ctcaataaag   300
cttgccttga gtgcttcaag tagtgtgtgc ccgtctgttg tgtgactctg gtaactagag   360
atccctcaga cccttttagt cagtgtggaa aatctctagc a                        401
```

<210> SEQ ID NO 24
<211> LENGTH: 8
<212> TYPE: PRT
<213> ORGANISM: Gallus gallus

<400> SEQUENCE: 24

```
Ser Ile Ile Asn Phe Glu Lys Leu
1               5
```

<210> SEQ ID NO 25
<211> LENGTH: 9
<212> TYPE: PRT
<213> ORGANISM: Mus musculus

<400> SEQUENCE: 25

```
Ser Pro Ser Tyr Ala Tyr His Gln Phe
1               5
```

<210> SEQ ID NO 26
<211> LENGTH: 5
<212> TYPE: PRT
<213> ORGANISM: Sindbis virus

<400> SEQUENCE: 26

```
Arg Ser Lys Arg Ser
1               5
```

<210> SEQ ID NO 27
<211> LENGTH: 4
<212> TYPE: PRT
<213> ORGANISM: Sindbis virus

<400> SEQUENCE: 27

Arg Ser Lys Arg
1

<210> SEQ ID NO 28
<211> LENGTH: 8
<212> TYPE: PRT
<213> ORGANISM: Artificial Sequence
<220> FEATURE:
<223> OTHER INFORMATION: Synthetic peptide

<400> SEQUENCE: 28

Asp Tyr Lys Asp Asp Asp Asp Lys
1               5

<210> SEQ ID NO 29
<211> LENGTH: 11
<212> TYPE: PRT
<213> ORGANISM: Artificial Sequence
<220> FEATURE:
<223> OTHER INFORMATION: Synthetic peptide

<400> SEQUENCE: 29

Ala Ala Val Lys Asn Trp Met Thr Gln Thr Leu
1               5                   10

<210> SEQ ID NO 30
<211> LENGTH: 423
<212> TYPE: PRT
<213> ORGANISM: Sindbis virus

<400> SEQUENCE: 30

Ser Val Ile Asp Asp Phe Thr Leu Thr Ser Pro Tyr Leu G

Thr Ser Tyr Leu Glu Glu Ser Ser Gly Lys Val Tyr Ala Lys Pro Pro
            180                 185                 190

Ser Gly Lys Asn Ile Thr Tyr Glu Cys Lys Cys Gly Asp Tyr Lys Thr
        195                 200                 205

Gly Thr Val Ser Thr Arg Thr Glu Ile Thr Gly Cys Thr Ala Ile Lys
    210                 215                 220

Gln Cys Val Ala Tyr Lys Ser Asp Gln Thr Lys Trp Val Phe Asn Ser
225                 230                 235                 240

Pro Asp Leu Ile Arg His Asp Asp His Thr Ala Gln Gly Lys Leu His
                245                 250                 255

Leu Pro Phe Lys Leu Ile Pro Ser Thr Cys Met Val Pro Val Ala His
            260                 265                 270

Ala Pro Asn Val Ile His Gly Phe Lys His Ile Ser Leu Gln Leu Asp
        275                 280                 285

Thr Asp His Leu Thr Leu Leu Thr Thr Arg Arg Leu Gly Ala Asn Pro
    290                 295                 300

Glu Pro Thr Thr Glu Trp Ile Val Gly Lys Thr Val Arg Asn Phe Thr
305                 310                 315                 320

Val Asp Arg Asp Gly Leu Glu Tyr Ile Trp Gly Asn His Glu Pro Val
                325                 330                 335

Arg Val Tyr Ala Gln Glu Ser Ala Pro Gly Asp Pro His Gly Trp Pro
            340                 345                 350

His Glu Ile Val Gln His Tyr Tyr His Arg His Pro Val Tyr Thr Ile
        355                 360                 365

Leu Ala Val Ala Ser Ala Thr Val Ala Met Met Ile Gly Val Thr Val
    370                 375                 380

Ala Val Leu Cys Ala Cys Lys Ala Arg Arg Glu Cys Leu Thr Pro Tyr
385                 390                 395                 400

Ala Leu Ala Pro Asn Ala Val Ile Pro Thr Ser Leu Ala Leu Leu Cys
                405                 410                 415

Cys Val Arg Ser Ala Asn Ala
            420

<210> SEQ ID NO 31
<211> LENGTH: 423
<212> TYPE: PRT
<213> ORGANISM: Sindbis virus

<400> SEQUENCE: 31

Ser Val Ile Asp Asp Phe Thr Leu Thr Ser Pro Tyr Leu Gly Thr Cys
1

Lys Ile Lys Pro Lys Phe Val Gly Arg Glu Lys Tyr Asp Leu Pro Pro
            130                 135                 140

Val His Gly Lys Lys Ile Pro Cys Thr Val Tyr Asp Arg Leu Glu Gly
145                 150                 155                 160

Thr Thr Ala Gly Tyr Ile Thr Met His Arg Pro Arg Pro His Ala Tyr
                165                 170                 175

Thr Ser Tyr Leu Glu Glu Ser Ser Gly Lys Val Tyr Ala Lys Pro Pro
            180                 185                 190

Ser Gly Lys Asn Ile Thr Tyr Glu Cys Lys Cys Gly Asp Tyr Lys Thr
        195                 200                 205

Gly Thr Val Ser Thr Arg Thr Glu Ile Thr Gly Cys Thr Ala Ile Lys
210                 215                 220

Gln Cys Val Ala Tyr Lys Ser Asp Gln Thr Lys Trp Val Phe Asn Ser
225                 230                 235                 240

Pro Asp Leu Ile Arg His Asp Asp His Thr Ala Gln Gly Lys Leu His
                245                 250                 255

Leu Pro Phe Lys Leu Ile Pro Ser Thr Cys Met Val Pro Val Ala His
            260                 265                 270

Ala Pro Asn Val Ile His Gly Phe Lys His Ile Ser Leu Gln Leu Asp
        275                 280                 285

Thr Asp His Leu Thr Leu Leu Thr Thr Arg Arg Leu Gly Ala Asn Pro
290                 295                 300

Glu Pro Thr Thr Glu Trp Ile Val Gly Lys Thr Val Arg Asn Phe Thr
305                 310                 315                 320

Val Asp Arg Asp Gly Leu Glu Tyr Ile Trp Gly Asn His Glu Pro Val
                325                 330                 335

Arg Val Tyr Ala Gln Glu Ser Ala Pro Gly Asp Pro His Gly Trp Pro
            340                 345                 350

His Glu Ile Val Gln His Tyr Tyr His Arg His Pro Val Tyr Thr Ile
        355                 360                 365

Leu Ala Val Ala Ser Ala Thr Val Ala Met Met Ile Gly Val Thr Val
370                 375                 380

Ala Val Leu Cys Ala Cys Lys Ala Arg Arg Glu Cys Leu Thr Pro Tyr
385                 390                 395                 400

Ala Leu Ala Pro Asn Ala Val Ile Pro Thr Ser Leu Ala Leu Leu Cys
                405                 410                 415

Cys Val Arg Ser Ala Asn Ala
            420

<210> SEQ ID NO 32
<211> LENGTH: 421
<212> TYPE: PRT
<213> ORGANISM: Sindbis virus

<400> SEQUENCE: 32

Ser Val Ile Asp Asp Phe Thr Leu Thr Ser Pro Tyr Leu Gly Thr Cys
1               5                   10                  15

Ser Tyr Cys His His Thr Val Pro Cys Phe Ser Pro Val Lys Ile Glu
            20                  25                  30

Gln Val Trp Asp Glu Ala Asp Asp Asn Thr Ile Arg Ile Gln Thr Ser
        35                  40                  45

Ala Gln Phe Gly Tyr Asp Gln Ser Gly Ala Ala Ser Ala Asn Lys Tyr
    50                  55                  60

Arg Tyr Met Ser Leu Glu Gln Asp His Thr Val Lys Glu Gly Thr Met

```
                65                  70                  75                  80
Asp Asp Ile Lys Ile Ser Thr Ser Gly Pro Cys Arg Arg Leu Ser Tyr
                    85                  90                  95
Lys Gly Tyr Phe Leu Leu Ala Lys Cys Pro Gly Asp Ser Val Thr
                100                 105                 110
Val Ser Ile Val Ser Ser Asn Ser Ala Thr Ser Cys Thr Leu Ala Arg
                115                 120                 125
Lys Ile Lys Pro Lys Phe Val Gly Arg Glu Lys Tyr Asp Leu Pro Pro
            130                 135                 140
Val His Gly Lys Lys Ile Pro Cys Thr Val Tyr Asp Arg Leu Thr Thr
145                 150                 155                 160
Ala Gly Tyr Ile Thr Met His Arg Pro Arg Pro His Ala Tyr Thr Ser
                    165                 170                 175
Tyr Leu Glu Glu Ser Ser Gly Lys Val Tyr Ala Lys Pro Pro Ser Gly
                180                 185                 190
Lys Asn Ile Thr Tyr Glu Cys Lys Cys Gly Asp Tyr Lys Thr Gly Thr
                195                 200                 205
Val Ser Thr Arg Thr Glu Ile Thr Gly Cys Thr Ala Ile Lys Gln Cys
            210                 215                 220
Val Ala Tyr Lys Ser Asp Gln Thr Lys Trp Val Phe Asn Ser Pro Asp
225                 230                 235                 240
Leu Ile Arg His Asp Asp His Thr Ala Gln Gly Lys Leu His Leu Pro
                245                 250                 255
Phe Lys Leu Ile Pro Ser Thr Cys Met Val Pro Val Ala His Ala Pro
                260                 265                 270
Asn Val Ile His Gly Phe Lys His Ile Ser Leu Gln Leu Asp Thr Asp
                275                 280                 285
His Leu Thr Leu Leu Thr Thr Arg Arg Leu Gly Ala Asn Pro Glu Pro
            290                 295                 300
Thr Thr Glu Trp Ile Val Gly Lys Thr Val Arg Asn Phe Thr Val Asp
305                 310                 315                 320
Arg Asp Gly Leu Glu Tyr Ile Trp Gly Asn His Glu Pro Val Arg Val
                    325                 330                 335
Tyr Ala Gln Glu Ser Ala Pro Gly Asp Pro His Gly Trp Pro His Glu
                340                 345                 350
Ile Val Gln His Tyr Tyr His Arg His Pro Val Tyr Thr Ile Leu Ala
                355                 360                 365
Val Ala Ser Ala Thr Val Ala Met Met Ile Gly Val Thr Val Ala Val
            370                 375                 380
Leu Cys Ala Cys Lys Ala Arg Arg Glu Cys Leu Thr Pro Tyr Ala Leu
385                 390                 395                 400
Ala Pro Asn Ala Val Ile Pro Thr Ser Leu Ala Leu Leu Cys Cys Val
                    405                 410                 415
Arg Ser Ala Asn Ala
            420

<210> SEQ ID NO 33
<211> LENGTH: 422
<212> TYPE: PRT
<213> ORGANISM: Sindbis virus

<400> SEQUENCE: 33

Ser Val Ile Asp Asp Phe Thr Leu Thr Ser Pro Tyr Leu Gly Thr Cys
1               5                   10                  15
```

-continued

Ser Tyr Cys His His Thr Val Pro Cys Phe Ser Pro Val Lys Ile Glu
            20              25              30

Gln Val Trp Asp Glu Ala Asp Asp Asn Thr Ile Arg Ile Gln Thr Ser
        35              40              45

Ala Gln Phe Gly Tyr Asp Gln Ser Gly Ala Ala Ser Ala Asn Lys Tyr
    50              55              60

Arg Tyr Met Ser Leu Glu Gln Asp His Thr Val Glu Glu Gly Thr Met
65              70              75              80

Asp Asp Ile Lys Ile Ser Thr Ser Gly Pro Cys Arg Arg Leu Ser Tyr
            85              90              95

Lys Gly Tyr Phe Leu Leu Ala Lys Cys Pro Pro Gly Asp Ser Val Thr
            100             105             110

Val Ser Ile Val Ser Ser Asn Ser Ala Thr Ser Cys Thr Leu Ala Arg
            115             120             125

Lys Ile Lys Pro Lys Phe Val Gly Arg Glu Lys Tyr Asp Leu Pro Pro
    130             135             140

Val His Gly Lys Lys Ile Pro Cys Thr Val Tyr Asp Arg Leu Glu Thr
145             150             155             160

Thr Ala Gly Tyr Ile Thr Met His Arg Pro Arg Pro His Ala Tyr Thr
                165             170             175

Ser Tyr Leu Glu Glu Ser Ser Gly Lys Val Tyr Ala Lys Pro Pro Ser
            180             185             190

Gly Lys Asn Ile Thr Tyr Glu Cys Lys Cys Gly Asp Tyr Lys Thr Gly
            195             200             205

Thr Val Ser Thr Arg Thr Glu Ile Thr Gly Cys Thr Ala Ile Lys Gln
210             215             220

Cys Val Ala Tyr Lys Ser Asp Gln Thr Lys Trp Val Phe Asn Ser Pro
225             230             235             240

Asp Leu Ile Arg His Asp Asp His Thr Ala Gln Gly Lys Leu His Leu
            245             250             255

Pro Phe Lys Leu Ile Pro Ser Thr Cys Met Val Pro Val Ala His Ala
            260             265             270

Pro Asn Val Ile His Gly Phe Lys His Ile Ser Leu Gln Leu Asp Thr
            275             280             285

Asp His Leu Thr Leu Leu Thr Thr Arg Arg Leu Gly Ala Asn Pro Glu
290             295             300

Pro Thr Thr Glu Trp Ile Val Gly Lys Thr Val Arg Asn Phe Thr Val
305             310             315             320

Asp Arg Asp Gly Leu Glu Tyr Ile Trp Gly Asn His Glu Pro Val Arg
            325             330             335

Val Tyr Ala Gln Glu Ser Ala Pro Gly Asp Pro His Gly Trp Pro His
            340             345             350

Glu Ile Val Gln His Tyr Tyr His Arg His Pro Val Tyr Thr Ile Leu
            355             360             365

Ala Val Ala Ser Ala Thr Val Ala Met Met Ile Gly Val Thr Val Ala
            370             375             380

Val Leu Cys Ala Cys Lys Ala Arg Arg Glu Cys Leu Thr Pro Tyr Ala
385             390             395             400

Leu Ala Pro Asn Ala Val Ile Pro Thr Ser Leu Ala Leu Leu Cys Cys
            405             410             415

Val Arg Ser Ala Asn Ala
            420

<210> SEQ ID NO 34
<211> LENGTH: 423
<212> TYPE: PRT
<213> ORGANISM: Sindbis virus

<400> SEQUENCE: 34

```
Ser Val Ile Asp Asp Phe Thr Leu Thr Ser Pro Tyr Leu Gly Thr Cys
1               5                   10                  15

Ser Tyr Cys His His Thr Val Pro Cys Phe Ser Pro Val Lys Ile Glu
            20                  25                  30

Gln Val Trp Asp Glu Ala Asp Asn Thr Ile Arg Ile Gln Thr Ser
        35                  40                  45

Ala Gln Phe Gly Tyr Asp Gln Ser Gly Ala Ala Ser Ala Asn Lys Tyr
    50                  55                  60

Arg Tyr Met Ser Leu Lys Gln Asp His Thr Val Lys Glu Gly Thr Met
65                  70                  75                  80

Asp Asp Ile Lys Ile Ser Thr Ser Gly Pro Cys Arg Arg Leu Ser Tyr
                85                  90                  95

Lys Gly Tyr Phe Leu Leu Ala Lys Cys Pro Pro Gly Asp Ser Val Thr
                100                 105                 110

Val Ser Ile Val Ser Ser Asn Ser Ala Thr Ser Cys Thr Leu Ala Arg
            115                 120                 125

Lys Ile Lys Pro Lys Phe Val Gly Arg Glu Lys Tyr Asp Leu Pro Pro
        130                 135                 140

Val His Gly Lys Lys Ile Pro Cys Thr Val Tyr Asp Arg Leu Glu Gly
145                 150                 155                 160

Thr Thr Ala Gly Tyr Ile Thr Met His Arg Pro Arg Pro His Ala Tyr
                165                 170                 175

Thr Ser Tyr Leu Glu Glu Ser Ser Gly Lys Val Tyr Ala Lys Pro Pro
            180                 185                 190

Ser Gly Lys Asn Ile Thr Tyr Glu Cys Lys Cys Gly Asp Tyr Lys Thr
        195                 200                 205

Gly Thr Val Ser Thr Arg Thr Glu Ile Thr Gly Cys Thr Ala Ile Lys
    210                 215                 220

Gln Cys Val Ala Tyr Lys Ser Asp Gln Thr Lys Trp Val Phe Asn Ser
225                 230                 235                 240

Pro Asp Leu Ile Arg His Asp Asp His Thr Ala Gln Gly Lys Leu His
                245                 250                 255

Leu Pro Phe Lys Leu Ile Pro Ser Thr Cys Met Val Pro Val Ala His
                260                 265                 270

Ala Pro Asn Val Ile His Gly Phe Lys His Ile Ser Leu Gln Leu Asp
            275                 280                 285

Thr Asp His Leu Thr Leu Leu Thr Thr Arg Arg Leu Gly Ala Asn Pro
        290                 295                 300

Glu Pro Thr Thr Glu Trp Ile Val Gly Lys Thr Val Arg Asn Phe Thr
305                 310                 315                 320

Val Asp Arg Asp Gly Leu Glu Tyr Ile Trp Gly Asn His Glu Pro Val
                325                 330                 335

Arg Val Tyr Ala Gln Glu Ser Ala Pro Gly Asp Pro His Gly Trp Pro
            340                 345                 350

His Glu Ile Val Gln His Tyr Tyr His Arg His Pro Val Tyr Thr Ile
        355                 360                 365

Leu Ala Val Ala Ser Ala Thr Val Ala Met Met Ile Gly Val Thr Val
    370                 375                 380
```

```
Ala Val Leu Cys Ala Cys Lys Ala Arg Arg Glu Cys Leu Thr Pro Tyr
385                 390                 395                 400

Ala Leu Ala Pro Asn Ala Val Ile Pro Thr Ser Leu Ala Leu Leu Cys
            405                 410                 415

Cys Val Arg Ser Ala Asn Ala
            420

<210> SEQ ID NO 35
<211> LENGTH: 422
<212> TYPE: PRT
<213> ORGANISM: Sindbis virus

<400> SEQUENCE: 35

Ser Val Ile Asp Asp Phe Thr Leu Thr Ser Pro Tyr Leu Gly Thr Cys
1               5                   10                  15

Ser Tyr Cys His His Thr Val Pro Cys Phe Ser Pro Val Lys Ile Glu
            20                  25                  30

Gln Val Trp Asp Glu Ala Asp Asp Asn Thr Ile Arg Ile Gln Thr Ser
        35                  40                  45

Ala Gln Phe Gly Tyr Asp Gln Ser Gly Ala Ala Ser Ala Asn Lys Tyr
    50                  55                  60

Arg Tyr Met Ser Leu Lys Gln Asp His Thr Val Lys Glu Gly Thr Met
65                  70                  75                  80

Asp Asp Ile Lys Ile Ser Thr Ser Gly Pro Cys Arg Arg Leu Ser Tyr
                85                  90                  95

Lys Gly Tyr Phe Leu Leu Ala Lys Cys Pro Pro Gly Asp Ser Val Thr
            100                 105                 110

Val Ser Ile Val Ser Ser Asn Ser Ala Thr Ser Cys Thr Leu Ala Arg
        115                 120                 125

Lys Ile Lys Pro Lys Phe Val Gly Arg Glu Lys Tyr Asp Leu Pro Pro
    130                 135                 140

Val His Gly Lys Lys Ile Pro Cys Thr Val Tyr Asp Arg Leu Glu Thr
145                 150                 155                 160

Thr Ala Gly Tyr Ile Thr Met His Arg Pro Arg Pro His Ala Tyr Thr
                165                 170                 175

Ser Tyr Leu Glu Glu Ser Ser Gly Lys Val Tyr Ala Lys Pro Pro Ser
            180                 185                 190

Gly Lys Asn Ile Thr Tyr Glu Cys Lys Cys Gly Asp Tyr Lys Thr Gly
        195                 200                 205

Thr Val Ser Thr Arg Thr Glu Ile Thr Gly Cys Thr Ala Ile Lys Gln
    210                 215                 220

Cys Val Ala Tyr Lys Ser Asp Gln Thr Lys Trp Val Phe Asn Ser Pro
225                 230                 235                 240

Asp Leu Ile Arg His Asp Asp His Thr Ala Gln Gly Lys Leu His Leu
                245                 250                 255

Pro Phe Lys Leu Ile Pro Ser Thr Cys Met Val Pro Val Ala His Ala
            260                 265                 270

Pro Asn Val Ile His Gly Phe Lys His Ile Ser Leu Gln Leu Asp Thr
        275                 280                 285

Asp His Leu Thr Leu Leu Thr Thr Arg Arg Leu Gly Ala Asn Pro Glu
    290                 295                 300

Pro Thr Thr Glu Trp Ile Val Gly Lys Thr Val Arg Asn Phe Thr Val
305                 310                 315                 320

Asp Arg Asp Gly Leu Glu Tyr Ile Trp Gly Asn His Glu Pro Val Arg
                325                 330                 335
```

```
Val Tyr Ala Gln Glu Ser Ala Pro Gly Asp Pro His Gly Trp Pro His
            340                 345                 350

Glu Ile Val Gln His Tyr Tyr His Arg His Pro Val Tyr Thr Ile Leu
            355                 360                 365

Ala Val Ala Ser Ala Thr Val Ala Met Met Ile Gly Val Thr Val Ala
            370                 375                 380

Val Leu Cys Ala Cys Lys Ala Arg Arg Glu Cys Leu Thr Pro Tyr Ala
385                 390                 395                 400

Leu Ala Pro Asn Ala Val Ile Pro Thr Ser Leu Ala Leu Leu Cys Cys
                405                 410                 415

Val Arg Ser Ala Asn Ala
            420

<210> SEQ ID NO 36
<211> LENGTH: 423
<212> TYPE: PRT
<213> ORGANISM: Sindbis virus

<400> SEQUENCE: 36

Ser Val Ile Asp Asp Phe Thr Leu Thr Ser Pro Tyr Leu Gly Thr Cys
1               5                   10                  15

Ser Tyr Cys His His Thr Val Pro Cys Phe Ser Pro Val Lys Ile Glu
            20                  25                  30

Gln Val Trp Asp Glu Ala Asp Asp Asn Thr Ile Arg Ile Gln Thr Ser
        35                  40                  45

Ala Gln Phe Gly Tyr Asp Gln Ser Gly Ala Ala Ser Ala Asn Lys Tyr
    50                  55                  60

Arg Tyr Met Ser Leu Lys Gln Asp His Thr Val Glu Glu Gly Thr Met
65                  70                  75                  80

Asp Asp Ile Lys Ile Ser Thr Ser Gly Pro Cys Arg Arg Leu Ser Tyr
                85                  90                  95

Lys Gly Tyr Phe Leu Leu Ala Lys Cys Pro Pro Gly Asp Ser Val Thr
            100                 105                 110

Val Ser Ile Val Ser Ser Asn Ser Ala Thr Ser Cys Thr Leu Ala Arg
        115                 120                 125

Lys Ile Lys Pro Lys Phe Val Gly Arg Glu Lys Tyr Asp Leu Pro Pro
    130                 135                 140

Val His Gly Lys Lys Ile Pro Cys Thr Val Tyr Asp Arg Leu Glu Gly
145                 150                 155                 160

Thr Thr Ala Gly Tyr Ile Thr Met His Arg Pro Arg Pro His Ala Tyr
                165                 170                 175

Thr Ser Tyr Leu Glu Glu Ser Ser Gly Lys Val Tyr Ala Lys Pro Pro
            180                 185                 190

Ser Gly Lys Asn Ile Thr Tyr Glu Cys Lys Cys Gly Asp Tyr Lys Thr
        195                 200                 205

Gly Thr Val Ser Thr Arg Thr Glu Ile Thr Gly Cys Thr Ala Ile Lys
    210                 215                 220

Gln Cys Val Ala Tyr Lys Ser Asp Gln Thr Lys Trp Val Phe Asn Ser
225                 230                 235                 240

Pro Asp Leu Ile Arg His Asp Asp His Thr Ala Gln Gly Lys Leu His
                245                 250                 255

Leu Pro Phe Lys Leu Ile Pro Ser Thr Cys Met Val Pro Val Ala His
            260                 265                 270

Ala Pro Asn Val Ile His Gly Phe Lys His Ile Ser Leu Gln Leu Asp
```

-continued

```
                275                 280                 285
Thr Asp His Leu Thr Leu Leu Thr Thr Arg Arg Leu Gly Ala Asn Pro
        290                 295                 300
Glu Pro Thr Thr Glu Trp Ile Val Gly Lys Thr Val Arg Asn Phe Thr
305                 310                 315                 320
Val Asp Arg Asp Gly Leu Glu Tyr Ile Trp Gly Asn His Glu Pro Val
                325                 330                 335
Arg Val Tyr Ala Gln Glu Ser Ala Pro Gly Asp Pro His Gly Trp Pro
                340                 345                 350
His Glu Ile Val Gln His Tyr Tyr His Arg His Pro Val Tyr Thr Ile
                355                 360                 365
Leu Ala Val Ala Ser Ala Thr Val Ala Met Met Ile Gly Val Thr Val
        370                 375                 380
Ala Val Leu Cys Ala Cys Lys Ala Arg Arg Glu Cys Leu Thr Pro Tyr
385                 390                 395                 400
Ala Leu Ala Pro Asn Ala Val Ile Pro Thr Ser Leu Ala Leu Leu Cys
                405                 410                 415
Cys Val Arg Ser Ala Asn Ala
                420

<210> SEQ ID NO 37
<211> LENGTH: 422
<212> TYPE: PRT
<213> ORGANISM: Sindbis virus

<400> SEQUENCE: 37

Ser Val Ile Asp Asp Phe Thr Leu Thr Ser Pro Tyr Leu Gly Thr Cys
1               5                   10                  15
Ser Tyr Cys His His Thr Val Pro Cys Phe Ser Pro Val Lys Ile Glu
                20                  25                  30
Gln Val Trp Asp Glu Ala Asp Asp Asn Thr Ile Arg Ile Gln Thr Ser
                35                  40                  45
Ala Gln Phe Gly Tyr Asp Gln Ser Gly Ala Ala Ser Ala Asn Lys Tyr
        50                  55                  60
Arg Tyr Met Ser Leu Lys Gln Asp His Thr Val Glu Glu Gly Thr Met
65                  70                  75                  80
Asp Asp Ile Lys Ile Ser Thr Ser Gly Pro Cys Arg Arg Leu Ser Tyr
                85                  90                  95
Lys Gly Tyr Phe Leu Leu Ala Lys Cys Pro Pro Gly Asp Ser Val Thr
                100                 105                 110
Val Ser Ile Val Ser Ser Asn Ser Ala Thr Ser Cys Thr Leu Ala Arg
        115                 120                 125
Lys Ile Lys Pro Lys Phe Val Gly Arg Glu Lys Tyr Asp Leu Pro Pro
130                 135                 140
Val His Gly Lys Lys Ile Pro Cys Thr Val Tyr Asp Arg Leu Glu Thr
145                 150                 155                 160
Thr Ala Gly Tyr Ile Thr Met His Arg Pro Arg Pro His Ala Tyr Thr
                165                 170                 175
Ser Tyr Leu Glu Glu Ser Ser Gly Lys Val Tyr Ala Lys Pro Pro Ser
                180                 185                 190
Gly Lys Asn Ile Thr Tyr Glu Cys Lys Cys Gly Asp Tyr Lys Thr Gly
                195                 200                 205
Thr Val Ser Thr Arg Thr Glu Ile Thr Gly Cys Thr Ala Ile Lys Gln
        210                 215                 220
```

-continued

Cys Val Ala Tyr Lys Ser Asp Gln Thr Lys Trp Val Phe Asn Ser Pro
225                 230                 235                 240

Asp Leu Ile Arg His Asp Asp His Thr Ala Gln Gly Lys Leu His Leu
            245                 250                 255

Pro Phe Lys Leu Ile Pro Ser Thr Cys Met Val Pro Val Ala His Ala
        260                 265                 270

Pro Asn Val Ile His Gly Phe Lys His Ile Ser Leu Gln Leu Asp Thr
    275                 280                 285

Asp His Leu Thr Leu Leu Thr Thr Arg Arg Leu Gly Ala Asn Pro Glu
290                 295                 300

Pro Thr Thr Glu Trp Ile Val Gly Lys Thr Val Arg Asn Phe Thr Val
305                 310                 315                 320

Asp Arg Asp Gly Leu Glu Tyr Ile Trp Gly Asn His Glu Pro Val Arg
            325                 330                 335

Val Tyr Ala Gln Glu Ser Ala Pro Gly Asp Pro His Gly Trp Pro His
        340                 345                 350

Glu Ile Val Gln His Tyr Tyr His Arg His Pro Val Tyr Thr Ile Leu
    355                 360                 365

Ala Val Ala Ser Ala Thr Val Ala Met Met Ile Gly Val Thr Val Ala
370                 375                 380

Val Leu Cys Ala Cys Lys Ala Arg Arg Glu Cys Leu Thr Pro Tyr Ala
385                 390                 395                 400

Leu Ala Pro Asn Ala Val Ile Pro Thr Ser Leu Ala Leu Leu Cys Cys
            405                 410                 415

Val Arg Ser Ala Asn Ala
            420

<210> SEQ ID NO 38
<211> LENGTH: 423
<212> TYPE: PRT
<213> ORGANISM: Sindbis virus

<400> SEQUENCE: 38

Ser Val Ile Asp Asp Phe Thr Leu Thr Ser Pro Tyr Leu Gly Thr Cys
1               5                   10                  15

Ser Tyr Cys His His Thr Val Pro Cys Phe Ser Pro Val Lys Ile Glu
            20                  25                  30

Gln Val Trp Asp Glu Ala Asp Asp Asn Thr Ile Arg Ile Gln Thr Ser
        35                  40                  45

Ala Gln Phe Gly Tyr Asp Gln Ser Gly Ala Ala Ser Ala Asn Lys Tyr
    50                  55                  60

Arg Tyr Met Ser Leu Lys Gln Asp His Thr Val Glu Glu Gly Thr Met
65                  70                  75                  80

Asp Asp Ile Lys Ile Ser Thr Ser Gly Pro Cys Arg Arg Leu Ser Tyr
            85                  90                  95

Lys Gly Tyr Phe Leu Leu Ala Lys Cys Pro Pro Gly Asp Ser Val Thr
        100                 105                 110

Val Ser Ile Val Ser Ser Asn Ser Ala Thr Ser Cys Thr Leu Ala Arg
    115                 120                 125

Lys Ile Lys Pro Lys Phe Val Gly Arg Glu Lys Tyr Asp Leu Pro Pro
130                 135                 140

Val His Gly Lys Lys Ile Pro Cys Thr Val Tyr Asp Arg Leu Lys Gly
145                 150                 155                 160

Thr Thr Ala Gly Tyr Ile Thr Met His Arg Pro Arg Pro His Ala Tyr
            165                 170                 175

Thr Ser Tyr Leu Glu Glu Ser Ser Gly Lys Val Tyr Ala Lys Pro Pro
            180                 185                 190

Ser Gly Lys Asn Ile Thr Tyr Glu Cys Lys Cys Gly Asp Tyr Lys Thr
        195                 200                 205

Gly Thr Val Ser Thr Arg Thr Glu Ile Thr Gly Cys Thr Ala Ile Lys
    210                 215                 220

Gln Cys Val Ala Tyr Lys Ser Asp Gln Thr Lys Trp Val Phe Asn Ser
225                 230                 235                 240

Pro Asp Leu Ile Arg His Asp His Thr Ala Gln Gly Lys Leu His
                245                 250                 255

Leu Pro Phe Lys Leu Ile Pro Ser Thr Cys Met Val Pro Val Ala His
            260                 265                 270

Ala Pro Asn Val Ile His Gly Phe Lys His Ile Ser Leu Gln Leu Asp
        275                 280                 285

Thr Asp His Leu Thr Leu Leu Thr Thr Arg Arg Leu Gly Ala Asn Pro
290                 295                 300

Glu Pro Thr Thr Glu Trp Ile Val Gly Lys Thr Val Arg Asn Phe Thr
305                 310                 315                 320

Val Asp Arg Asp Gly Leu Glu Tyr Ile Trp Gly Asn His Glu Pro Val
                325                 330                 335

Arg Val Tyr Ala Gln Glu Ser Ala Pro Gly Asp Pro His Gly Trp Pro
            340                 345                 350

His Glu Ile Val Gln His Tyr Tyr His Arg His Pro Val Tyr Thr Ile
        355                 360                 365

Leu Ala Val Ala Ser Ala Thr Val Ala Met Met Ile Gly Val Thr Val
    370                 375                 380

Ala Val Leu Cys Ala Cys Lys Ala Arg Arg Glu Cys Leu Thr Pro Tyr
385                 390                 395                 400

Ala Leu Ala Pro Asn Ala Val Ile Pro Thr Ser Leu Ala Leu Leu Cys
                405                 410                 415

Cys Val Arg Ser Ala Asn Ala
            420

<210> SEQ ID NO 39
<211> LENGTH: 422
<212> TYPE: PRT
<213> ORGANISM: Sindbis virus

<400> SEQUENCE: 39

Ser Val Ile Asp Asp Phe Thr Leu Thr Ser Pro Tyr Leu Gly Thr Cys
1               5                   10                  15

Ser Tyr Cys His His Thr Val Pro Cys Phe Ser Pro Val Lys Ile Glu
            20                  25                  30

Gln Val Trp Asp Glu Ala Asp Asp Asn Thr Ile Arg Ile Gln Thr Ser
        35                  40                  45

Ala Gln Phe Gly Tyr Asp Gln Ser Gly Ala Ala Ser Ala Asn Lys Tyr
    50                  55                  60

Arg Tyr Met Ser Leu Lys Gln Asp His Thr Val Glu Glu Gly Thr Met
65                  70                  75                  80

Asp Asp Ile Lys Ile Ser Thr Ser Gly Pro Cys Arg Arg Leu Ser Tyr
                85                  90                  95

Lys Gly Tyr Phe Leu Leu Ala Lys Cys Pro Pro Gly Asp Ser Val Thr
            100                 105                 110

Val Ser Ile Val Ser Ser Asn Ser Ala Thr Ser Cys Thr Leu Ala Arg

```
            115                 120                 125
Lys Ile Lys Pro Lys Phe Val Gly Arg Glu Lys Tyr Asp Leu Pro Pro
        130                 135                 140

Val His Gly Lys Lys Ile Pro Cys Thr Val Tyr Asp Arg Leu Lys Thr
145                 150                 155                 160

Thr Ala Gly Tyr Ile Thr Met His Arg Pro Arg Pro His Ala Tyr Thr
                165                 170                 175

Ser Tyr Leu Glu Glu Ser Ser Gly Lys Val Tyr Ala Lys Pro Pro Ser
            180                 185                 190

Gly Lys Asn Ile Thr Tyr Glu Cys Lys Cys Gly Asp Tyr Lys Thr Gly
        195                 200                 205

Thr Val Ser Thr Arg Thr Glu Ile Thr Gly Cys Thr Ala Ile Lys Gln
210                 215                 220

Cys Val Ala Tyr Lys Ser Asp Gln Thr Lys Trp Val Phe Asn Ser Pro
225                 230                 235                 240

Asp Leu Ile Arg His Asp Asp His Thr Ala Gln Gly Lys Leu His Leu
                245                 250                 255

Pro Phe Lys Leu Ile Pro Ser Thr Cys Met Val Pro Val Ala His Ala
            260                 265                 270

Pro Asn Val Ile His Gly Phe Lys His Ile Ser Leu Gln Leu Asp Thr
        275                 280                 285

Asp His Leu Thr Leu Leu Thr Thr Arg Arg Leu Gly Ala Asn Pro Glu
290                 295                 300

Pro Thr Thr Glu Trp Ile Val Gly Lys Thr Val Arg Asn Phe Thr Val
305                 310                 315                 320

Asp Arg Asp Gly Leu Glu Tyr Ile Trp Gly Asn His Glu Pro Val Arg
                325                 330                 335

Val Tyr Ala Gln Glu Ser Ala Pro Gly Asp Pro His Gly Trp Pro His
            340                 345                 350

Glu Ile Val Gln His Tyr Tyr His Arg His Pro Val Tyr Thr Ile Leu
        355                 360                 365

Ala Val Ala Ser Ala Thr Val Ala Met Met Ile Gly Val Thr Val Ala
370                 375                 380

Val Leu Cys Ala Cys Lys Ala Arg Arg Glu Cys Leu Thr Pro Tyr Ala
385                 390                 395                 400

Leu Ala Pro Asn Ala Val Ile Pro Thr Ser Leu Ala Leu Leu Cys Cys
                405                 410                 415

Val Arg Ser Ala Asn Ala
            420

<210> SEQ ID NO 40
<211> LENGTH: 423
<212> TYPE: PRT
<213> ORGANISM: Sindbis virus

<400> SEQUENCE: 40

Ser Val Ile Asp Asp Phe Thr Leu Thr Ser Pro Tyr Leu Gly Thr Cys
1               5                   10                  15

Ser Tyr Cys His His Thr Val Pro Cys Phe Ser Pro Val Lys Ile Glu
            20                  25                  30

Gln Val Trp Asp Glu Ala Asp Asp Asn Thr Ile Arg Ile Gln Thr Ser
        35                  40                  45

Ala Gln Phe Gly Tyr Asp Gln Ser Gly Ala Ala Ser Ala Asn Lys Tyr
    50                  55                  60
```

```
Arg Tyr Met Ser Leu Glu Gln Asp His Thr Val Lys Glu Gly Thr Met
 65                  70                  75                  80

Asp Asp Ile Lys Ile Ser Thr Ser Gly Pro Cys Arg Arg Leu Ser Tyr
                 85                  90                  95

Lys Gly Tyr Phe Leu Leu Ala Lys Cys Pro Pro Gly Asp Ser Val Thr
            100                 105                 110

Val Ser Ile Val Ser Ser Asn Ser Ala Thr Ser Cys Thr Leu Ala Arg
        115                 120                 125

Lys Ile Lys Pro Lys Phe Val Gly Arg Glu Lys Tyr Asp Leu Pro Pro
130                 135                 140

Val His Gly Lys Lys Ile Pro Cys Thr Val Tyr Asp Arg Leu Lys Gly
145                 150                 155                 160

Thr Thr Ala Gly Tyr Ile Thr Met His Arg Pro Arg Pro His Ala Tyr
                165                 170                 175

Thr Ser Tyr Leu Glu Glu Ser Ser Gly Lys Val Tyr Ala Lys Pro Pro
            180                 185                 190

Ser Gly Lys Asn Ile Thr Tyr Glu Cys Lys Cys Gly Asp Tyr Lys Thr
        195                 200                 205

Gly Thr Val Ser Thr Arg Thr Glu Ile Thr Gly Cys Thr Ala Ile Lys
210                 215                 220

Gln Cys Val Ala Tyr Lys Ser Asp Gln Thr Lys Trp Val Phe Asn Ser
225                 230                 235                 240

Pro Asp Leu Ile Arg His Asp Asp His Thr Ala Gln Gly Lys Leu His
                245                 250                 255

Leu Pro Phe Lys Leu Ile Pro Ser Thr Cys Met Val Pro Val Ala His
            260                 265                 270

Ala Pro Asn Val Ile His Gly Phe Lys His Ile Ser Leu Gln Leu Asp
        275                 280                 285

Thr Asp His Leu Thr Leu Leu Thr Thr Arg Arg Leu Gly Ala Asn Pro
290                 295                 300

Glu Pro Thr Thr Glu Trp Ile Val Gly Lys Thr Val Arg Asn Phe Thr
305                 310                 315                 320

Val Asp Arg Asp Gly Leu Glu Tyr Ile Trp Gly Asn His Glu Pro Val
                325                 330                 335

Arg Val Tyr Ala Gln Glu Ser Ala Pro Gly Asp Pro His Gly Trp Pro
            340                 345                 350

His Glu Ile Val Gln His Tyr Tyr His Arg His Pro Val Tyr Thr Ile
        355                 360                 365

Leu Ala Val Ala Ser Ala Thr Val Ala Met Met Ile Gly Val Thr Val
370                 375                 380

Ala Val Leu Cys Ala Cys Lys Ala Arg Arg Glu Cys Leu Thr Pro Tyr
385                 390                 395                 400

Ala Leu Ala Pro Asn Ala Val Ile Pro Thr Ser Leu Ala Leu Leu Cys
                405                 410                 415

Cys Val Arg Ser Ala Asn Ala
            420

<210> SEQ ID NO 41
<211> LENGTH: 422
<212> TYPE: PRT
<213> ORGANISM: Sindbis virus

<400> SEQUENCE: 41

Ser Val Ile Asp Asp Phe Thr Leu Thr Ser Pro Tyr Leu Gly Thr Cys
1               5                   10                  15
```

```
Ser Tyr Cys His His Thr Val Pro Cys Phe Ser Pro Val Lys Ile Glu
         20                  25                  30

Gln Val Trp Asp Glu Ala Asp Asp Asn Thr Ile Arg Ile Gln Thr Ser
         35                  40                  45

Ala Gln Phe Gly Tyr Asp Gln Ser Gly Ala Ala Ser Ala Asn Lys Tyr
 50                  55                  60

Arg Tyr Met Ser Leu Glu Gln Asp His Thr Val Lys Glu Gly Thr Met
 65                  70                  75                  80

Asp Asp Ile Lys Ile Ser Thr Ser Gly Pro Cys Arg Arg Leu Ser Tyr
             85                  90                  95

Lys Gly Tyr Phe Leu Leu Ala Lys Cys Pro Pro Gly Asp Ser Val Thr
            100                 105                 110

Val Ser Ile Val Ser Ser Asn Ser Ala Thr Ser Cys Thr Leu Ala Arg
            115                 120                 125

Lys Ile Lys Pro Lys Phe Val Gly Arg Glu Lys Tyr Asp Leu Pro Pro
130                 135                 140

Val His Gly Lys Lys Ile Pro Cys Thr Val Tyr Asp Arg Leu Lys Thr
145                 150                 155                 160

Thr Ala Gly Tyr Ile Thr Met His Arg Pro Arg Pro His Ala Tyr Thr
                165                 170                 175

Ser Tyr Leu Glu Glu Ser Ser Gly Lys Val Tyr Ala Lys Pro Pro Ser
                180                 185                 190

Gly Lys Asn Ile Thr Tyr Glu Cys Lys Cys Gly Asp Tyr Lys Thr Gly
            195                 200                 205

Thr Val Ser Thr Arg Thr Glu Ile Thr Gly Cys Thr Ala Ile Lys Gln
            210                 215                 220

Cys Val Ala Tyr Lys Ser Asp Gln Thr Lys Trp Val Phe Asn Ser Pro
225                 230                 235                 240

Asp Leu Ile Arg His Asp Asp His Thr Ala Gln Gly Lys Leu His Leu
                245                 250                 255

Pro Phe Lys Leu Ile Pro Ser Thr Cys Met Val Pro Val Ala His Ala
                260                 265                 270

Pro Asn Val Ile His Gly Phe Lys His Ile Ser Leu Gln Leu Asp Thr
            275                 280                 285

Asp His Leu Thr Leu Leu Thr Thr Arg Arg Leu Gly Ala Asn Pro Glu
290                 295                 300

Pro Thr Thr Glu Trp Ile Val Gly Lys Thr Val Arg Asn Phe Thr Val
305                 310                 315                 320

Asp Arg Asp Gly Leu Glu Tyr Ile Trp Gly Asn His Glu Pro Val Arg
                325                 330                 335

Val Tyr Ala Gln Glu Ser Ala Pro Gly Asp Pro His Gly Trp Pro His
                340                 345                 350

Glu Ile Val Gln His Tyr Tyr His Arg His Pro Val Tyr Thr Ile Leu
            355                 360                 365

Ala Val Ala Ser Ala Thr Val Ala Met Met Ile Gly Val Thr Val Ala
            370                 375                 380

Val Leu Cys Ala Cys Lys Ala Arg Arg Glu Cys Leu Thr Pro Tyr Ala
385                 390                 395                 400

Leu Ala Pro Asn Ala Val Ile Pro Thr Ser Leu Ala Leu Leu Cys Cys
                405                 410                 415

Val Arg Ser Ala Asn Ala
            420
```

```
<210> SEQ ID NO 42
<211> LENGTH: 423
<212> TYPE: PRT
<213> ORGANISM: Sindbis virus

<400> SEQUENCE: 42

Ser Val Ile Asp Asp Phe Thr Leu Thr Ser Pro Tyr Leu Gly Thr Cys
1               5                   10                  15

Ser Tyr Cys His His Thr Val Pro Cys Phe Ser Pro Val Lys Ile Glu
            20                  25                  30

Gln Val Trp Asp Glu Ala Asp Asp Asn Thr Ile Arg Ile Gln Thr Ser
        35                  40                  45

Ala Gln Phe Gly Tyr Asp Gln Ser Gly Ala Ala Ser Ala Asn Lys Tyr
    50                  55                  60

Arg Tyr Met Ser Leu Glu Gln Asp His Thr Val Glu Glu Gly Thr Met
65                  70                  75                  80

Asp Asp Ile Lys Ile Ser Thr Ser Gly Pro Cys Arg Arg Leu Ser Tyr
                85                  90                  95

Lys Gly Tyr Phe Leu Leu Ala Lys Cys Pro Pro Gly Asp Ser Val Thr
                100                 105                 110

Val Ser Ile Val Ser Ser Asn Ser Ala Thr Ser Cys Thr Leu Ala Arg
            115                 120                 125

Lys Ile Lys Pro Lys Phe Val Gly Arg Glu Lys Tyr Asp Leu Pro Pro
        130                 135                 140

Val His Gly Lys Lys Ile Pro Cys Thr Val Tyr Asp Arg Leu Lys Gly
145                 150                 155                 160

Thr Thr Ala Gly Tyr Ile Thr Met His Arg Pro Arg Pro His Ala Tyr
                165                 170                 175

Thr Ser Tyr Leu Glu Glu Ser Ser Gly Lys Val Tyr Ala Lys Pro Pro
            180                 185                 190

Ser Gly Lys Asn Ile Thr Tyr Glu Cys Lys Cys Gly Asp Tyr Lys Thr
        195                 200                 205

Gly Thr Val Ser Thr Arg Thr Glu Ile Thr Gly Cys Thr Ala Ile Lys
    210                 215                 220

Gln Cys Val Ala Tyr Lys Ser Asp Gln Thr Lys Trp Val Phe Asn Ser
225                 230                 235                 240

Pro Asp Leu Ile Arg His Asp Asp His Thr Ala Gln Gly Lys Leu His
                245                 250                 255

Leu Pro Phe Lys Leu Ile Pro Ser Thr Cys Met Val Pro Val Ala His
                260                 265                 270

Ala Pro Asn Val Ile His Gly Phe Lys His Ile Ser Leu Gln Leu Asp
            275                 280                 285

Thr Asp His Leu Thr Leu Leu Thr Thr Arg Arg Leu Gly Ala Asn Pro
        290                 295                 300

Glu Pro Thr Thr Glu Trp Ile Val Gly Lys Thr Val Arg Asn Phe Thr
305                 310                 315                 320

Val Asp Arg Asp Gly Leu Glu Tyr Ile Trp Gly Asn His Glu Pro Val
                325                 330                 335

Arg Val Tyr Ala Gln Glu Ser Ala Pro Gly Asp Pro His Gly Trp Pro
                340                 345                 350

His Glu Ile Val Gln His Tyr Tyr His Arg His Pro Val Tyr Thr Ile
            355                 360                 365

Leu Ala Val Ala Ser Ala Thr Val Ala Met Met Ile Gly Val Thr Val
        370                 375                 380
```

```
Ala Val Leu Cys Ala Cys Lys Ala Arg Arg Glu Cys Leu Thr Pro Tyr
385                 390                 395                 400

Ala Leu Ala Pro Asn Ala Val Ile Pro Thr Ser Leu Ala Leu Leu Cys
                405                 410                 415

Cys Val Arg Ser Ala Asn Ala
            420

<210> SEQ ID NO 43
<211> LENGTH: 422
<212> TYPE: PRT
<213> ORGANISM: Sindbis virus

<400> SEQUENCE: 43

Ser Val Ile Asp Asp Phe Thr Leu Thr Ser Pro Tyr Leu Gly Thr Cys
1               5                   10                  15

Ser Tyr Cys His His Thr Val Pro Cys Phe Ser Pro Val Lys Ile Glu
                20                  25                  30

Gln Val Trp Asp Glu Ala Asp Asp Asn Thr Ile Arg Ile Gln Thr Ser
            35                  40                  45

Ala Gln Phe Gly Tyr Asp Gln Ser Gly Ala Ala Ser Ala Asn Lys Tyr
50                  55                  60

Arg Tyr Met Ser Leu Glu Gln Asp His Thr Val Glu Glu Gly Thr Met
65                  70                  75                  80

Asp Asp Ile Lys Ile Ser Thr Ser Gly Pro Cys Arg Arg Leu Ser Tyr
                85                  90                  95

Lys Gly Tyr Phe Leu Leu Ala Lys Cys Pro Pro Gly Asp Ser Val Thr
            100                 105                 110

Val Ser Ile Val Ser Ser Asn Ser Ala Thr Ser Cys Thr Leu Ala Arg
        115                 120                 125

Lys Ile Lys Pro Lys Phe Val Gly Arg Glu Lys Tyr Asp Leu Pro Pro
130                 135                 140

Val His Gly Lys Lys Ile Pro Cys Thr Val Tyr Asp Arg Leu Lys Thr
145                 150                 155                 160

Thr Ala Gly Tyr Ile Thr Met His Arg Pro Arg Pro His Ala Tyr Thr
                165                 170                 175

Ser Tyr Leu Glu Glu Ser Ser Gly Lys Val Tyr Ala Lys Pro Pro Ser
            180                 185                 190

Gly Lys Asn Ile Thr Tyr Glu Cys Lys Cys Gly Asp Tyr Lys Thr Gly
        195                 200                 205

Thr Val Ser Thr Arg Thr Glu Ile Thr Gly Cys Thr Ala Ile Lys Gln
210                 215                 220

Cys Val Ala Tyr Lys Ser Asp Gln Thr Lys Trp Val Phe Asn Ser Pro
225                 230                 235                 240

Asp Leu Ile Arg His Asp Asp His Thr Ala Gln Gly Lys Leu His Leu
                245                 250                 255

Pro Phe Lys Leu Ile Pro Ser Thr Cys Met Val Pro Val Ala His Ala
            260                 265                 270

Pro Asn Val Ile His Gly Phe Lys His Ile Ser Leu Gln Leu Asp Thr
        275                 280                 285

Asp His Leu Thr Leu Leu Thr Thr Arg Arg Leu Gly Ala Asn Pro Glu
290                 295                 300

Pro Thr Thr Glu Trp Ile Val Gly Lys Thr Val Arg Asn Phe Thr Val
305                 310                 315                 320

Asp Arg Asp Gly Leu Glu Tyr Ile Trp Gly Asn His Glu Pro Val Arg
```

```
                    325                 330                 335
Val Tyr Ala Gln Glu Ser Ala Pro Gly Asp Pro His Gly Trp Pro His
                340                 345                 350

Glu Ile Val Gln His Tyr Tyr His Arg His Pro Val Tyr Thr Ile Leu
            355                 360                 365

Ala Val Ala Ser Ala Thr Val Ala Met Met Ile Gly Val Thr Val Ala
        370                 375                 380

Val Leu Cys Ala Cys Lys Ala Arg Arg Glu Cys Leu Thr Pro Tyr Ala
385                 390                 395                 400

Leu Ala Pro Asn Ala Val Ile Pro Thr Ser Leu Ala Leu Leu Cys Cys
                405                 410                 415

Val Arg Ser Ala Asn Ala
            420

<210> SEQ ID NO 44
<211> LENGTH: 112
<212> TYPE: PRT
<213> ORGANISM: Simian immunodeficiency virus

<400> SEQUENCE: 44

Met Ser Asp Pro Arg Glu Arg Ile Pro Pro Gly Asn Ser Gly Glu Glu
1               5                   10                  15

Thr Ile Gly Glu Ala Phe Glu Trp Leu Asn Arg Thr Val Glu Glu Ile
            20                  25                  30

Asn Arg Glu Ala Val Asn His Leu Pro Arg Glu Leu Ile Phe Gln Val
        35                  40                  45

Trp Gln Arg Ser Trp Glu Tyr Trp His Asp Glu Gly Met Ser Gln
    50                  55                  60

Ser Tyr Val Lys Tyr Arg Tyr Leu Cys Leu Met Gln Lys Ala Leu Phe
65                  70                  75                  80

Met His Cys Lys Lys Gly Cys Arg Cys Leu Gly Glu Gly His Gly Ala
                85                  90                  95

Gly Gly Trp Arg Pro Gly Pro Pro Pro Pro Pro Gly Leu Ala
            100                 105                 110

<210> SEQ ID NO 45
<211> LENGTH: 112
<212> TYPE: PRT
<213> ORGANISM: Simian immunodeficiency virus

<400> SEQUENCE: 45

Met Thr Asp Pro Arg Glu Arg Ile Pro Pro Gly Asn Ser Gly Glu Glu
1               5                   10                  15

Thr Ile Gly Glu Ala Phe Glu Trp Leu His Asn Thr Val Glu Ala Leu
            20                  25                  30

Asn Gln Thr Ala Val Gln His Leu Pro Arg Glu Leu Ile Phe Gln Val
        35                  40                  45

Trp Arg Arg Cys Trp Glu Tyr Trp Val Asp Glu Gln Gly Tyr Ser Pro
    50                  55                  60

Ser Tyr Ala Lys Tyr Arg Tyr Val Gln Leu Met Gln Lys Ala Met Phe
65                  70                  75                  80

Gln His Phe Arg Lys Gly Cys Thr Cys Arg Gly Glu Gly His Ser Gln
                85                  90                  95

Gly Gly Trp Arg Thr Gly Pro Pro Pro Pro Pro Gly Leu Ala
            100                 105                 110
```

-continued

```
<210> SEQ ID NO 46
<211> LENGTH: 112
<212> TYPE: PRT
<213> ORGANISM: Simian immunodeficiency virus

<400> SEQUENCE: 46

Met Ser Asp Pro Arg Glu Arg Ile Pro Pro Gly Asn Ser Gly Glu Glu
1               5                   10                  15

Thr Ile Gly Glu Ala Phe Asp Trp Leu Asp Arg Thr Val Glu Glu Ile
            20                  25                  30

Asn Arg Ala Ala Val Asn His Leu Pro Arg Glu Leu Ile Phe Gln Val
        35                  40                  45

Trp Arg Arg Ser Trp Glu Tyr Trp His Asp Glu Met Gly Met Ser Val
    50                  55                  60

Ser Tyr Thr Lys Tyr Arg Tyr Leu Cys Leu Ile Gln Lys Ala Met Phe
65                  70                  75                  80

Met His Cys Lys Lys Gly Cys Arg Cys Leu Gly Gly Glu His Gly Ala
                85                  90                  95

Gly Gly Trp Arg Pro Gly Pro Pro Pro Pro Pro Gly Leu Ala
            100                 105                 110

<210> SEQ ID NO 47
<211> LENGTH: 112
<212> TYPE: PRT
<213> ORGANISM: Human immunodeficiency virus type 2

<400> SEQUENCE: 47

Met Ala Asp Pro Arg Glu Arg Val Pro Pro Gly Asn Ser Gly Glu Glu
1               5                   10                  15

Thr Ile Gly Glu Ala Phe Glu Trp Leu Asp Arg Thr Ile Glu Ala Leu
            20                  25                  30

Asn Arg Glu Ala Val Asn His Leu Pro Arg Glu Leu Ile Phe Gln Val
        35                  40                  45

Trp Gln Arg Ser Trp Ala Tyr Trp His Asp Glu Gln Gly Met Ser Thr
    50                  55                  60

Ser Tyr Thr Lys Tyr Arg Tyr Leu Cys Ile Met Gln Lys Ala Val Tyr
65                  70                  75                  80

Ile His Phe Lys Lys Gly Cys Thr Cys Leu Gly Arg Gly His Gly Pro
                85                  90                  95

Gly Gly Trp Arg Pro Gly Pro Pro Pro Pro Pro Gly Leu Val
            100                 105                 110

<210> SEQ ID NO 48
<211> LENGTH: 117
<212> TYPE: PRT
<213> ORGANISM: Simian immunodeficiency virus

<400> SEQUENCE: 48

Met Glu Arg Tyr Pro Pro Ser His Pro Pro His Phe Thr Ser Arg Thr
1               5                   10                  15

Val Pro Met Thr Arg Leu Ala Leu Gln Gln Ala Met Gln Asp Leu Asn
            20                  25                  30

Glu Glu Ala Leu Lys His Phe Thr Arg Glu Glu Leu Trp Gly Val Trp
        35                  40                  45

Asn His Cys Val Asp Leu Pro Ala Gln Pro Asp Trp Thr Gly Glu Gln
    50                  55                  60

Ala Trp Ala Ala Ser Val Ile Asp Tyr Ile Lys Ile Val Gln Arg Met
65                  70                  75                  80
```

Leu Trp Leu His Leu Arg Glu Ala Cys Phe His Arg Glu Arg Glu Ala
                85                  90                  95

Thr Arg Arg Tyr Pro Asn Ile Arg Pro Leu Thr Gly Arg Asn Arg Glu
            100                 105                 110

Val Arg Asp Gly Glu
        115

<210> SEQ ID NO 49
<211> LENGTH: 135
<212> TYPE: PRT
<213> ORGANISM: Simian immunodeficiency virus

<400> SEQUENCE: 49

Met Glu Arg Val Pro Pro Ser His Arg Pro Pro Trp His Ser Arg Val
1               5                   10                  15

Val Pro Thr Thr Met Gln Gln Ala Gln Gln Ala Met Trp Asp Leu Asn
            20                  25                  30

Glu Glu Ala Glu Lys His Phe Ser Arg Glu Glu Leu Arg Gly Ile Trp
        35                  40                  45

Asn Asp Val Thr Glu Leu Pro Ala Asp Pro Asn Trp Thr Val Asp Gln
50                  55                  60

Ala Ala Ile Ala Cys Ala Ile Asp Tyr Ile Arg Arg Thr Gln Thr Leu
65                  70                  75                  80

Leu Phe Arg His Tyr Arg Glu Gly Cys Tyr His Arg Tyr Ser Asn Thr
                85                  90                  95

Ile Arg Arg Tyr Pro Asn Ile Arg Pro Leu Arg Gly Thr Gln Ala Pro
            100                 105                 110

Pro Ser Asn Ser Met Pro Asn Ala Asp Pro Thr Pro Pro Leu Arg Pro
        115                 120                 125

Ser Arg Tyr Arg Met Asp Glu
        130                 135

<210> SEQ ID NO 50
<211> LENGTH: 942
<212> TYPE: DNA
<213> ORGANISM: Homo sapiens

<400> SEQUENCE: 50
atgcctcttg agcagaggag tcagcactgc aagcctgaag aaggccttga ggcccgagga      60
gaggccctgg gcctggtggg tgcgcaggct cctgctactg aggagcagga ggctgcctcc     120
tcctcttcta ctctagttga agtcaccctg ggggaggtgc ctgctgccga gtcaccagat     180
cctccccaga gtcctcaggg agcctccagc ctccccacta ccatgaacta ccctctctgg     240
agccaatcct atgaggactc cagcaaccaa gaagaggagg gccaagcac cttccctgac      300 ctggagtccg agttccaagc agcactcagt aggaaggtgg ccgagttggt tcattttctg     360
ctcctcaagt atcgagccag ggagccggtc acaaaggcag aaatgctggg gagtgtcgtc     420
ggaaattggc agtatttctt tcctgtgatc ttcagcaagg cttccagttc cttgcagctg     480
gtctttggca tcgagctgat ggaagtggac cccatcggcc acttgtacat ctttgccacc     540
tgcctgggcc tctcctacga tggcctgctg ggtgacaatc agatcatgcc caaggcaggc     600
ctcctgataa tcgtcctggc cataatcgca agagagggcg actgtgcccc tgaggagaaa     660
atctgggagg agctgagtgt gttagaggtg tttgagggga gggaagacag tatcttgggc     720
gatcccaaga agctgctcac ccaacatttc gtgcaggaaa actacctgga gtaccggcag     780

| | |
|---|---|
| gtccccggca gtgatcctgc atgttatgag ttcctgtggg gtccaagggc cctcgttgaa | 840 |
| accagctatg tgaaagtcct gcaccacatg gtaaagatca gtggaggacc tcacatttcc | 900 |
| tacccacccc tgcatgagtg ggttttgaga gagggggaag ag | 942 |

<210> SEQ ID NO 51
<211> LENGTH: 540
<212> TYPE: DNA
<213> ORGANISM: Homo sapiens

<400> SEQUENCE: 51

| | |
|---|---|
| atgcaggccg aaggccgggg cacagggggt tcgacgggcg atgctgatgg cccaggaggc | 60 |
| cctggcattc ctgatggccc aggggggcaat gctggcggcc caggagaggc gggtgccacg | 120 |
| ggcggcagag gtccccgggg cgcaggggca gcaagggcct cggggccggg aggaggcgcc | 180 |
| ccgcggggtc cgcatggcgg cgcggcttca gggctgaatg gatgctgcag atgcggggcc | 240 |
| aggggggccgg agagccgcct gcttgagttc tacctcgcca tgccttccgc gacacccatg | 300 |
| gaagcagagc tggcccgcag gagcctggcc caggatgccc accgcttcc cgtgccaggg | 360 |
| gtgcttctga aggagttcac tgtgtccggc aacatactga ctatccgact gactgctgca | 420 |
| gaccaccgcc aactgcagct ctccatcagc tcctgtctcc agcagctttc cctgttgatg | 480 |
| tggatcacgc agtgctttct gcccgtgttt ttggctcagc ctcccctcagg gcagaggcgc | 540 |

<210> SEQ ID NO 52
<211> LENGTH: 54
<212> TYPE: DNA
<213> ORGANISM: Thosea asigna virus

<400> SEQUENCE: 52

| | |
|---|---|
| gagggcagag gcagtcttct gacatgtgga gatgtggaag aaaaccctgg cccc | 54 |

<210> SEQ ID NO 53
<211> LENGTH: 9020
<212> TYPE: DNA
<213> ORGANISM: Artificial Sequence
<220> FEATURE:
<223> OTHER INFORMATION: Synthetic polynucleotide

<400> SEQUENCE: 53

| | |
|---|---|
| atgcattagt tattaatagt aatcaattac ggggtcatta gttcatagcc catatatgga | 60 |
| gttccgcgtt acataactta cggtaaatgg cccgcctggc tgaccgccca acgacccccg | 120 |
| cccattgacg tcaataatga cgtatgttcc catagtaacg ccaataggga ctttccattg | 180 |
| acgtcaatgg gtggagtatt tacggtaaac tgcccacttg gcagtacatc aagtgtatca | 240 |
| tatgccaagt acgcccccta ttgacgtcaa tgacggtaaa tggcccgcct ggcattatgc | 300 |
| ccagtacatg accttatggg actttcctac ttggcagtac atctacgtat tagtcatcgc | 360 |
| tattaccatg gtgatgcggt tttggcagta catcaatggg cgtggatagc ggtttgactc | 420 |
| acggggattt ccaagtctcc accccattga cgtcaatggg agtttgtttt ggcaccaaaa | 480 |
| tcaacgggac tttccaaaat gtcgtaacaa ctccgcccca ttgacgcaaa tgggcggtag | 540 |
| gcgtgtacgg tgggaggtct atataagcag cgcgttttgc ctgtactggg tctctctggt | 600 |
| tagaccagat ctgagcctgg gagctctctg gctaactagg gaacccactg cttaagcctc | 660 |
| aataaagctt gccttgagtg cttcaagtag tgtgtgcccg tctgttgtgt gactctggta | 720 |
| actagagatc cctcagaccc ttttagtcag tgtggaaaat ctctagcagt ggcgcccgaa | 780 |
| cagggacttg aaagcgaaag ggaaaccaga ggagctctct cgacgcagga ctcggcttgc | 840 |

```
tgaagcgcgc acggcaagag gcgaggggcg gcgactggtg agtacgccaa aaattttgac    900
tagcggaggc tagaaggaga gagatggtg cgagagcgtc agtattaagc ggggagaat      960
tagatcgcga tgggaaaaaa ttcggttaag gccagggga aagaaaaaat ataaattaaa   1020
acatatagta tgggcaagca gggagctaga acgattcgca gttaatcctg gcctgttaga   1080
aacatcagaa ggctgtagac aaatactggg acagctacaa ccatcccttc agacaggatc   1140
agaagaactt agatcattat ataatacagt agcaaccctc tattgtgtgc atcaaaggat   1200
agagataaaa gacaccaagg aagctttaga caagatagag gaagagcaaa acaaaagtaa   1260
gaccaccgca cagcaagcgg ccgctgatct tcagacctgg aggaggagat atgagggaca   1320
attggagaag tgaattatat aaatataaag tagtaaaaat tgaaccatta ggagtagcac   1380
ccaccaaggc aaagaagaa gtggtgcaga gagaaaaaag agcagtggga ataggagctt    1440
tgttccttgg gttcttggga gcagcaggaa gcactatggg cgcagcgtca atgacgctga   1500
cggtacaggc cagacaatta ttgtctggta tagtgcagca gcagaacaat ttgctgaggg   1560
ctattgaggc gcaacagcat ctgttgcaac tcacagtctg gggcatcaag cagctccagg   1620
caagaatcct ggctgtggaa agatacctaa aggatcaaca gctcctgggg atttggggtt   1680
gctctggaaa actcatttgc accactgctg tgccttggaa tgctagttgg agtaataaat   1740
ctctggaaca gatttggaat cacacgacct ggatggagtg ggacagagaa attaacaatt   1800
acacaagctt aatacactcc ttaattgaag aatcgcaaaa ccagcaagaa aagaatgaac   1860
aagaattatt ggaattagat aaatgggcaa gtttgtggaa ttggtttaac ataacaaatt   1920
ggctgtggta tataaaatta ttcataatga tagtaggagg cttggtaggt ttaagaatag   1980
ttttttgctgt actttctata gtgaatagag ttaggcaggg atattcacca ttatcgtttc   2040
agacccacct cccaaccccg aggggacccg acaggcccga aggaatagaa gaagaaggtg   2100
gagagagaga cagagacaga tccattcgat tagtgaacgg atcggcactg cgtgcgccaa   2160
ttctgcagac aaatggcagt attcatccac aattttaaaa gaaaaggggg gattggggggg   2220
tacagtgcag gggaaagaat agtagacata atagcaacag acatacaaac taaagaatta   2280
caaaaacaaa ttacaaaaat tcaaaatttt cgggtttatt acaggacag cagagatcca    2340
gtttggttaa ttaacccgtg tcggctccag atctggcctc cgcgccgggt tttggcgcct   2400
cccgcgggcg ccccctcct cacggcgagc gctgccacgt cagacgaagg gcgcagcgag    2460
cgtcctgatc cttccgcccg gacgctcagg acagcggccc gctgctcata agactcggcc   2520
ttagaaccc agtatcagca gaaggacatt ttaggacggg acttgggtga ctctagggca    2580
ctggttttct ttccagagag cggaacaggc gaggaaaagt agtcccttct cggcgattct   2640
gcggagggat ctccgtgggg cggtgaacgc cgatgattat ataaggacgc gccgggtgtg   2700
gcacagctag ttccgtcgca gccgggattt gggtcgcggt tcttgtttgt ggggatcccc   2760
gggtaccggt gccaccatgc tcttgagca aggagtcag cactgcaagc ctgaagaagg     2820
ccttgaggcc cgaggagagg ccctgggcct ggtgggtgcg caggctcctg ctactgagga   2880
gcaggaggct gcctcctcct cttctactct agttgaagtc accctggggg aggtgcctgc   2940
tgccgagtca ccagatcctc cccagagtcc tcagggagcc tccagcctcc ccactaccat   3000
gaactaccct ctctggagcc aatcctatga ggactccagc aaccaagaag aggaggggcc   3060
aagcaccttc cctgacctgg agtccgagtt ccaagcagca ctcagtagga aggtggccga   3120
gttggttcat tttctgctcc tcaagtatcg agccagggag ccggtcacaa aggcagaaat   3180
```

```
gctggggagt gtcgtcggaa attggcagta tttctttcct gtgatcttca gcaaggcttc    3240
cagttccttg cagctggtct ttggcatcga gctgatggaa gtggacccca tcggccactt    3300
gtacatcttt gccacctgcc tgggcctctc ctacgatggc ctgctgggtg acaatcagat    3360
catgcccaag gcaggcctcc tgataatcgt cctggccata atcgcaagag agggcgactg    3420
tgcccctgag gagaaaatct ggaggagct gagtgtgtta gaggtgtttg aggggaggga     3480
agacagtatc ttgggcgatc caagaagct gctcacccaa catttcgtgc aggaaaacta     3540
cctggagtac cggcaggtcc ccggcagtga tcctgcatgt tatgagttcc tgtggggtcc    3600
aagggccctc gttgaaacca gctatgtgaa agtcctgcac acatggtaa agatcagtgg     3660
aggacctcac atttcctacc caccctgca tgagtgggtt ttgagagagg gggaagagga    3720
gggcagaggc agtcttctga catgtggaga tgtggaagaa aaccctggcc ccatgcaggc    3780
cgaaggccgg ggcacagggg gttcgacggg cgatgctgat ggcccaggag gccctggcat    3840
tcctgatggc ccaggggca atgctggcgg cccaggagag gcgggtgcca cgggcggcag    3900
aggtccccgg ggcgcagggg cagcaagggc ctcggggccg ggaggaggcg ccccgcgggg    3960
tccgcatggc ggcgcggctt cagggctgaa tggatgctgc agatgcgggg ccaggggcc    4020
ggagagccgc ctgcttgagt tctacctcgc catgcctttc gcgacaccca tggaagcaga    4080
gctggcccgc aggagcctgg cccaggatgc cccaccgctt cccgtgccag gggtgcttct    4140
gaaggagttc actgtgtccg gcaacatact gactatccga ctgactgctg cagaccaccg    4200
ccaactgcag ctctccatca gctcctgtct ccagcagctt tccctgttga tgtggatcac    4260
gcagtgcttt ctgccgtgt ttttggctca gcctccctca gggcagaggc gctagtgaga     4320
attcgatatc aagcttatcg ataatcaacc tctggattac aaaatttgtg aaagattgac    4380
tggtattctt aactatgttg ctccttttac gctatgtgga tacgctgctt taatgccttt    4440
gtatcatgct attgcttccc gtatggcttt catttctcc tccttgtata aatcctggtt     4500
gctgtctctt tatgaggagt tgtggcccgt tgtcaggcaa cgtggcgtgg tgtgcactgt    4560
gtttgctgac gcaaccccca ctggttgggg cattgccacc acctgtcagc tcctttccgg    4620
gactttcgct ttccccctcc ctattgccac ggcggaactc atcgccgcct gccttgcccg    4680
ctgctggaca ggggctcggc tgttgggcac tgacaattcc gtggtgttgt cggggaaatc    4740
atcgtccttt ccttggctgc tcgcctgtgt tgccacctgg attctgcgcg gacgtccttt    4800
ctgctacgtc ccttcggccc tcaatccagc ggaccttcct tcccgcggcc tgctgccggc    4860
tctgcggcct cttccgcgtc ttcgccttcg ccctcagacg agtcggatct ccctttgggc    4920
cgcctccccg catcgatacc gtcgacctcg agacctagaa aaacatggag caatcacaag    4980
tagcaataca gcagctacca atgctgattg tgcctggcta aagcacaag aggaggaga     5040
ggtgggtttt ccagtcacac ctcaggtacc tttaagacca atgacttaca aggcagctgt    5100
agatcttagc cactttttac tggaagggct aattcactcc caacgaagac aagatctgct    5160
ttttgcctgt actgggtctc tctggttaga ccagatctga gcctgggagc tctctggcta    5220
actagggaac ccactgctta agcctcaata aagcttgcct tgagtgcttc aagtagtgtg    5280
tgcccgtctg ttgtgtgact ctggtaacta gagatccctc agaccctttt agtcagtgtg    5340
gaaaatctct agcagggccc ggtaccaggt aagtgtaccc aattcgccct atagtgagtc    5400
gtattacaat tcactcgatc gcccttccca acagttgcgc agcctgaatg gcgaatggag    5460
atccaatttt taagtgtata atgtgttaaa ctactgattc taattgtttg tgtatttag     5520
attcacagtc ccaaggctca tttcaggccc ctcagtcctc acagtctgtt catgatcata    5580
```

```
atcagccata ccacatttgt agaggtttta cttgctttaa aaaacctccc acacctcccc   5640
ctgaacctga aacataaaat gaatgcaatt gttgttgtta acttgtttat tgcagcttat   5700
aatggttaca aataaagcaa tagcatcaca aatttcacaa ataaagcatt ttttcactg    5760 cattctagtt gtggtttgtc caaactcatc aatgtatctt aacgcgtaaa ttgtaagcgt   5820
taatattttg ttaaaattcg cgttaaattt ttgttaaatc agctcatttt ttaaccaata   5880
ggccgaaatc ggcaaaatcc cttataaatc aaaagaatag accgagatag ggttgagtgt   5940
tgttccagtt tggaacaaga gtccactatt aaagaacgtg gactccaacg tcaaagggcg   6000
aaaaaccgtc tatcagggcg atgcccact  acgtgaacca tcaccctaat caagtttttt   6060
ggggtcgagg tgccgtaaag cactaaatcg gaaccctaaa gggagccccc gatttagagc   6120
ttgacgggga aagccggcga acgtggcgag aaggaaggg  agaaagcga  aggagcggg    6180 cgctagggcg ctggcaagtg tagcggtcac gctgcgcgta accaccacac ccgccgcgct   6240
taatgcgccg ctacagggcg cgtcaggtgg cacttttcgg ggaaatgtgc gcggaacccc   6300
tatttgttta ttttctaaa  tacattcaaa tatgtatccg ctcatgagac aataaccctg   6360
ataaatgctt caataatatt gaaaaaggaa gaatcctgag gcggaaagaa ccagctgtgg   6420
aatgtgtgtc agttagggtg tggaaagtcc ccaggctccc cagcaggcag aagtatgcaa   6480
agcatgcatc tcaattagtc agcaaccagg tgtggaaagt ccccaggctc cccagcaggc   6540
agaagtatgc aaagcatgca tctcaattag tcagcaacca tagtcccgcc cctaactccg   6600
cccatcccgc ccctaactcc gcccagttcc gcccattctc cgccccatgg ctgactaatt   6660
ttttttattt atgcagaggc cgaggccgcc tcggcctctg agctattcca gaagtagtga   6720
ggaggctttt ttggaggcct aggcttttgc aaagatcgat caagagacag gatgaggatc   6780
gtttcgcatg attgaacaag atggattgca cgcaggttct ccggccgctt gggtggagag   6840
gctattcggc tatgactggg cacaacagac aatcggctgc tctgatgccg ccgtgttccg   6900
gctgtcagcg caggggcgcc cggttctttt tgtcaagacc gacctgtccg gtgccctgaa   6960
tgaactgcaa gacgaggcag cgcggctatc gtggctggcc acgacgggcg ttccttgcgc   7020
agctgtgctc gacgttgtca ctgaagcggg aagggactgg ctgctattgg gcgaagtgcc   7080
ggggcaggat ctcctgtcat ctcaccttgc tcctgccgag aaagtatcca tcatggctga   7140
tgcaatgcgg cggctgcata cgcttgatcc ggctacctgc ccattcgacc accaagcgaa   7200
acatcgcatc gagcgagcac gtactcggat ggaagccggt cttgtcgatc aggatgatct   7260
ggacgaagaa catcaggggc tcgcgccagc cgaactgttc gccaggctca aggcgagcat   7320
gcccgacggc gaggatctcg tcgtgaccca tggcgatgcc tgcttgccga atatcatggt   7380
ggaaaatggc cgcttttctg gattcatcga ctgtggccgg ctgggtgtgg cggaccgcta   7440
tcaggacata gcgttggcta cccgtgatat tgctgaagaa cttggcggcg aatgggctga   7500
ccgcttcctc gtgctttacg gtatcgccgc tcccgattcg cagcgcatcg ccttctatcg   7560
ccttcttgac gagttcttct gagcgggact ctggggttcg aaatgaccga ccaagcgacg   7620
cccaacctgc catcacgaga tttcgattcc accgccgcct tctatgaaag gttgggcttc   7680
ggaatcgttt tccgggacgc cggctggatg atcctccagc gcggggatct catgctggag   7740
ttcttcgccc acccta gggg gaggctaact gaaacacgga aggagacaat accggaagga   7800
acccgcgcta tgacggcaat aaaaagacag aataaaacgc acggtgttgg gtcgtttgtt   7860
cataaacgcg gggttcggtc ccagggctgg cactctgtcg ataccccacc gagacccat    7920
```

-continued

| | |
|---|---|
| tggggccaat acgcccgcgt ttcttccttt tccccaccec accccccaag ttcgggtgaa | 7980 |
| ggcccagggc tcgcagccaa cgtcggggcg gcaggccctg ccatagcctc aggttactca | 8040 |
| tatatactt agattgattt aaaacttcat ttttaattta aaaggatcta ggtgaagatc | 8100 |
| ctgacagagg tccatgcaca tgaagctgta catggaaggc accgtgaaca accaccactt | 8160 |
| caagtgcacc agcgagggcg agggcaagcc ttacgagggc acccagacca tgagaatcaa | 8220 |
| ggtggtgaca cttgtctttt gataatctca tgaccaaaat cccttaacgt gagttttcgt | 8280 |
| tccactgagc gtcagacccc gtagaaaaga tcaaggatc ttcttgagat cctttttttc | 8340 |
| tgcgcgtaat ctgctgcttg caaacaaaaa aaccaccgct accagcggtg gtttgtttgc | 8400 |
| cggatcaaga gctaccaact cttttccga aggtaactgg cttcagcaga gcgcagatac | 8460 |
| caaatactgt tcttctagtg tagccgtagt taggccacca cttcaagaac tctgtagcac | 8520 |
| cgcctacata cctcgctctg ctaatcctgt taccagtggc tgctgccagt ggcgataagt | 8580 |
| cgtgtcttac cgggttggac tcaagacgat agttaccgga taaggcgcag cggtcgggct | 8640 |
| gaacggggg ttcgtgcaca cagcccagct tggagcgaac gacctacacc gaactgagat | 8700 |
| acctacagcg tgagctatga gaaagcgcca cgcttcccga agggagaaag gcggacaggt | 8760 |
| atccggtaag cggcagggtc ggaacaggag agcgcacgag ggagcttcca gggggaaacg | 8820 |
| cctggtatct ttatagtcct gtcgggtttc gccacctctg acttgagcgt cgattttgt | 8880 |
| gatgctcgtc aggggcgg agcctatgga aaaacgccag caacgcggcc ttttacggt | 8940 |
| tcctggcctt ttgctggcct tttgctcaca tgttctttcc tgcgttatcc cctgattctg | 9000 |
| tggataaccg tattaccgcc | 9020 |

<210> SEQ ID NO 54
<211> LENGTH: 4307
<212> TYPE: DNA
<213> ORGANISM: Artificial Sequence
<220> FEATURE:
<223> OTHER INFORMATION: Synthetic polynucleotide

<400> SEQUENCE: 54

| | |
|---|---|
| atgggcgccc gggccagcgt gctgagcggc ggcgagctgg accggtggga aagatccgg | 60 |
| ctgcggcccg gcggcaagaa gaagtacaag ctgaagcaca tcgtgtgggc cagccgggag | 120 |
| ctggagcggt cgccgtgaa ccccggcctg ctggagacca gcgagggctg ccggcagatc | 180 |
| ctgggccagc tgcagcccag cctgcagacc ggcagcgagg agctgcggag cctgtacaac | 240 |
| accgtggcca ccctgtactg cgtgcaccag cggatcgaga tcaaggacac caaggaggcc | 300 |
| ctggacaaga tcgaggagga gcagaacaag agcaagaaga aggcccagca ggccgccgcc | 360 |
| gacaccggcc acagcaacca ggtgagccag aactacccca tcgtgcagaa catccagggc | 420 |
| cagatggtgc accaggccat cagccccgg accctgaacg cctgggtgaa ggtggtggag | 480 |
| gagaaggcct tcagccccga ggtgatcccc atgttcagcg ccctgagcga gggcgccacc | 540 |
| ccccaggacc tgaacaccat gctgaacacc gtgggcggcc accaggccgc catgcagatg | 600 |
| ctgaaggaga ccatcaacga ggaggccgcc gagtgggacc gggtgcaccc cgtgcacgcc | 660 |
| ggccccatcg cccccggcca gatgcgggag cccgggca gcgacatcgc cggcaccacc | 720 |
| agcaccctgc aggagcagat cggctggatg acccacaacc ccccatccc cgtgggcgag | 780 |
| atctacaagc ggtggatcat cctgggcctg aacaagatcg tgcggatgta cagccccacc | 840 |
| agcatcctgg acatccggca gggccccaag gagcccttcc gggactacgt ggaccggttc | 900 |
| tacaagaccc tgcgggccga gcaggccagc caggaggtga agaactggat gaccgagacc | 960 |

```
ctgctggtgc agaacgccaa ccccgactgc aagaccatcc tgaaggccct gggccccggc    1020
gccaccctgg aggagatgat gaccgcctgc cagggcgtgg gcggccccgg ccacaaggcc    1080
cgggtgctgg ccgaggccat gagccaggtg accaaccccg ccaccatcat gatccagaag    1140
ggcaacttcc ggaaccagcg gaagaccgtg aagtgcttca actgcggcaa ggagggccac    1200
atcgccaaga actgccgggc cccccggaaa aagggctgtt ggaaatgtgg aaaggaagga    1260
caccaaatga aagattgtac tgagagacag gctaattttt tagggaagat ctggccttcc    1320
cacaagggaa ggccagggaa ttttcttcag agcagaccag agccaacagc cccaccagaa    1380
gagagcttca ggtttgggga agagacaaca actccctctc agaagcagga gccgatagac    1440
aaggaactgt atcctttagc ttccctcaga tcactctttg gcagcgaccc ctcgtcacaa    1500
taaagatagg cggccagctg aaggaggccc tgctggacac cggcgccgac gacaccgtgc    1560
tggaggagat gaacctgccc ggccggtgga agcccaagat gatcggcggc atcggcggct    1620
tcatcaaggt gcggcagtac gaccagatcc tgatcgagat ctgcggccac aaggccatcg    1680
gcaccgtgct ggtgggcccc accccgtga acatcatcgg ccggaacctg ctgacccaga    1740
tcggctgcac cctgaacttc cccatcagcc ccatcgagac cgtgcccgtg aagctgaagc    1800
ccggcatgga cggccccaag gtgaagcagt ggcccctgac cgaggagaag atcaaggccc    1860
tggtggagat ctgcaccgag atggagaagg agggcaagat cagcaagatc ggcccccgaga    1920 accctacaa caccccgtg ttcgccatca agaagaagga cagcaccaag tggcggaagc    1980
tggtggactt ccgggagctg aacaagcgga cccaggactt ctgggaggtg cagctgggca    2040 tccccacc cgccggcctg aagcagaaga gagcgtgac cgtgctggac gtgggcgacg    2100
cctacttcag cgtgcccctg gacaaggact ccggaagta caccgccttc accatcccca    2160
gcatcaacaa cgagaccccc ggcatccggt accagtacaa cgtgctgccc cagggctgga    2220
agggcagccc cgccatcttc cagtgcagca tgaccaagat cctggagccc ttccggaagc    2280
agaaccccga catcgtgatc taccagtaca tggacgacct gtacgtgggc agcgacctgg    2340
agatcggcca gcaccggacc aagatcgagg agctgcggca gcacctgctg cggtggggct    2400
tcaccacccc cgacaagaag caccagaagg agccccct cctgtggatg ggctacgagc    2460 tgcacccccga caagtggacc gtgcagccca tcgtgctgcc cgagaaggac agctggaccg    2520
tgaacgacat ccagaagctg gtgggcaagc tgaactgggc cagccagatc tacgccggca    2580
tcaaggtgcg gcagctgtgc aagctgctgc ggggcaccaa ggccctgacc gaggtggtgc    2640
ccctgaccga ggaggccgag ctggagctgg ccgagaaccg ggagatcctg aaggagcccg    2700
tgcacggcgt gtactacgac cccagcaagg acctgatcgc cgagatccag aagcagggcc    2760
agggccagtg gacctaccag atctaccagg agcccttcaa gaacctgaag accggcaagt    2820
acgcccggat gaagggcgcc cacaccaacg acgtgaagca gctgaccgag gccgtgcaga    2880
agatcgccac cgagagcatc gtgatctggg gcaagacccc caagttcaag ctgcccatcc    2940
agaaggagac ctgggaggcc tggtggaccg agtactggca ggccacctgg atccccgagt    3000
gggagttcgt gaacaccccc cccctggtga agctgtggta ccagctggag aaggagccca    3060
tcatcggcgc cgagaccttc tacgtggacg gcgccgccaa ccgggagacc aagctgggca    3120
aggccggcta cgtgaccgac cggggccggc agaaggtggt gcccctgacc gacaccacca    3180
accagaagac cgagctgcag gccatccacc tggcccctgca ggacagcggc ctggaggtga    3240
acatcgtgac cgacagccag tacgccctgg gcatcatcca ggcccagccc gacaagagcg    3300
```

```
agagcgagct ggtgagccag atcatcgagc agctgatcaa gaaggagaag gtgtacctgg    3360
cctgggtgcc cgcccacaag ggcatcggcg gcaacgagca ggtggacaag ctggtgagcg    3420
ccggcatccg gaaggtgctg ttcctggacg gcatcgacaa ggcccaggag gagcacgaga    3480
agtaccacag caactggcgg gccatggcca gcgacttcaa cctgccccc gtggtggcca    3540
aggagatcgt ggccagctgc gacaagtgcc agctgaaggg cgaggccatg cacggccagg    3600
tggactgcag ccccggcatc tggcagctgg tgtgcaccca cctggagggc aaggtgatcc    3660
tggtggccgt gcacgtggcc agcggctaca tcgaggccga ggtgatcccc gccgagaccg    3720
gccaggagac cgcctacttc ctgctgaagc tggccggccg gtggcccgtg aagaccgtgc    3780
acaccgacaa cggcagcaac ttcaccagca ccaccgtgaa ggccgcctgc tggtgggccg    3840
gcatcaagca ggagttcggc atcccctaca accccagag ccaggcgtg atcgagagca    3900
tgaacaagga gctgaagaag atcatcggcc aggtgcggga ccaggccgag cacctgaaga    3960
ccgccgtgca gatggccgtg ttcatccaca acttcaagcg gaagggcggc atcggcggct    4020
acagcgccgg cgagcggatc gtggacatca tcgccaccca catccagacc aaggagctgc    4080
agaagcagat caccaagatc cagaacttcc gggtgtacta ccgggacagc cgggaccccg    4140
tgtggaaggg ccccgccaag ctgctgtgga agggcgaggg cgccgtggtg atccaggaca    4200
acagcgacat caaggtggtg ccccggcgga aggccaagat catccgggac tacggcaagc    4260
agatggccgg cgacgactgc gtggccagcc ggcaggacga ggactga                 4307
```

<210> SEQ ID NO 55
<211> LENGTH: 8549
<212> TYPE: DNA
<213> ORGANISM: Artificial Sequence
<220> FEATURE:
<223> OTHER INFORMATION: Synthetic polynucleotide

<400> SEQUENCE: 55

```
ggatccctg aggggccccc catgggctag aggatccggc tcggcctct gcataaataa       60
aaaaaattag tcagccatga gcttggccca ttgcatacgt tgtatccata tcataatatg    120
tacatttata ttggctcatg tccaacatta ccgccatgtt gacattgatt attgactagt    180
tattaatagt aatcaattac ggggtcatta gttcatagcc catatatgga gttccgcgtt    240
acataactta cggtaaatgg cccgcctggc tgaccgccca acgacccccg cccattgacg    300
tcaataatga cgtatgttcc catagtaacg ccaatagga ctttccattg acgtcaatgg    360
gtggagtatt tacggtaaac tgcccacttg gcagtacatc aagtgtatca tatgccaagt    420
acgccccta ttgacgtcaa tgacggtaaa tggcccgcct ggcattatgc ccagtacatg    480
accttatggg actttcctac ttggcagtac atctacgtat tagtcatcgc tattaccatg    540
gtgatgcggt tttggcagta catcaatggg cgtggatagc ggtttgactc acggggattt    600
ccaagtctcc accccattga cgtcaatggg agtttgtttt ggcaccaaaa tcaacgggac    660
tttccaaaat gtcgtaacaa ctccgcccca ttgacgcaaa tgggcggtag gcgtgtacgg    720
tgggaggtct atataagcag agctcgttta gtgaaccgtc agatcgcctg gagacgccat    780
ccacgctgtt ttgacctcca tagaagacac cgggaccgat ccagcctccc ctcgaagctt    840
acatgtggta ccgagctcgg atcctgagaa cttcagggtg agtctatggg acccttgatg    900
ttttcttcc ccttcttttc tatggttaag ttcatgtcat aggaagggga gaagtaacag    960
ggtacacata ttgaccaaat cagggtaatt ttgcatttgt aattttaaaa aatgctttct   1020
tcttttaata tactttttg tttatcttat ttctaatact ttccctaatc tctttctttc   1080
```

```
agggcaataa tgatacaatg tatcatgcct ctttgcacca ttctaaagaa taacagtgat    1140
aatttctggg ttaaggcaat agcaatattt ctgcatataa atatttctgc atataaattg    1200
taactgatgt aagaggtttc atattgctaa tagcagctac aatccagcta ccattctgct    1260
tttatttttat ggttgggata aggctggatt attctgagtc caagctaggc ccttttgcta   1320
atcatgttca tacctcttat cttcctccca cagctcctgg gcaacgtgct ggtctgtgtg    1380
ctggcccatc actttggcaa agcacgtgag atctgaattc gagatctgcc gccgccatgg    1440
gcgcccgggc cagcgtgctg agcggcggcg agctggaccg gtgggagaag atccggctgc    1500
ggcccggcgc caagaagaag tacaagctga agcacatcgt gtgggccagc cgggagctgg    1560
agcggttcgc cgtgaacccc ggcctgctgg agaccagcga gggctgccgg cagatcctgg    1620
gccagctgca gcccagcctg cagaccggca gcgaggagct gcggagcctg tacaacaccg    1680
tggccaccct gtactgcgtg caccagcgga tcgagatcaa ggacaccaag gaggccctgg    1740
acaagatcga ggaggagcag aacaagagca agaagaaggc ccagcaggcc gccgccgaca    1800
ccggccacag caaccaggtg agccagaact accccatcgt gcagaacatc cagggccaga    1860
tggtgcacca ggccatcagc ccccggaccc tgaacgcctg ggtgaaggtg gtggaggaga    1920
aggccttcag ccccgaggtg atccccatgt tcagcgccct gagcgagggc gccaccccc     1980
aggacctgaa caccatgctg aacaccgtgg gcggccacca ggccgccatg cagatgctga    2040
aggagaccat caacgaggag gccgccgagt gggaccgggt gcaccccgtg cacgccggcc    2100
ccatcgcccc cggccagatg cgggagcccc ggggcagcga catcgccggc accaccagca    2160
ccctgcagga gcagatcggc tggatgaccc acaaccccccc catcccccgtg ggcgagatct   2220
acaagcggtg gatcatcctg ggcctgaaca agatcgtgcg gatgtacagc cccaccagca    2280
tcctggacat ccggcagggc cccaaggagc ccttccggga ctacgtggac cggttctaca    2340
agaccctgcg ggccgagcag gccagccagg aggtgaagaa ctggatgacc gagaccctgc    2400
tggtgcagaa cgccaacccc gactgcaaga ccatcctgaa ggccctgggc ccggcgcca    2460
ccctggagga tgatgatgacc gcctgccagg gcgtgggcgg ccccggccac aaggcccggg   2520
tgctggccga ggccatgagc caggtgacca accccgccac catcatgatc cagaagggca    2580
acttccggaa ccagcggaag accgtgaagt gcttcaactg cggcaaggag ggccacatcg    2640
ccaagaactg ccgggccccc cggaaaaagg gctgttggaa atgtggaaag gaaggacacc    2700
aaatgaaaga ttgtactgag agacaggcta atttttttagg gaagatctgg ccttcccaca    2760
agggaaggcc agggaatttt cttcagagca gaccagagcc aacagccccca ccagaagaga    2820
gcttcaggtt tggggaagag acaacaactc cctctcagaa gcaggagccg atagacaagg    2880
aactgtatcc tttagcttcc ctcagatcac tctttggcag cgaccccctcg tcacaataaa    2940
gataggcggc cagctgaagg aggccctgct ggacaccggc gccgacgaca ccgtgctgga    3000
ggagatgaac ctgccccggcc ggtggaagcc caagatgatc ggcggcatcg gcggcttcat    3060
caaggtgcgg cagtacgacc agatcctgat cgagatctgc ggccacaagg ccatcggcac    3120
cgtgctggtg ggccccaccc ccgtgaacat catcggccgg aacctgctga cccagatcgg    3180
ctgcacccctg aacttcccca tcagccccat cgagaccgtg cccgtgaagc tgaagcccgg    3240
catggacggc cccaaggtga agcagtggcc cctgaccgag gagaagatca aggccctggt    3300
ggagatctgc accgagatgg agaaggaggg caagatcagc aagatcggcc ccgagaaccc    3360
ctacaacacc cccgtgttcg ccatcaagaa gaaggacagc accaagtggc ggaagctggt    3420
```

```
ggacttccgg gagctgaaca agcggaccca ggacttctgg gaggtgcagc tgggcatccc      3480
ccaccccgcc ggcctgaagc agaagaagag cgtgaccgtg ctggacgtgg gcgacgccta      3540
cttcagcgtg ccctggaca aggacttccg gaagtacacc gccttcacca tccccagcat      3600
caacaacgag accccggca tccggtacca gtacaacgtg ctgccccagg gctggaaggg      3660 cagcccgcc atcttccagt gcagcatgac caagatcctg gagcccttcc ggaagcagaa      3720
ccccgacatc gtgatctacc agtacatgga cgacctgtac gtgggcagcg acctggagat      3780
cggccagcac cggaccaaga tcgaggagct gcggcagcac ctgctgcggt ggggcttcac      3840
cacccccgac aagaagcacc agaaggagcc ccccttcctg tggatgggct acgagctgca      3900
ccccgacaag tggaccgtgc agcccatcgt gctgcccgag aaggacagct ggaccgtgaa      3960
cgacatccag aagctggtgg gcaagctgaa ctgggccagc cagatctacg ccggcatcaa      4020
ggtgcggcag ctgtgcaagc tgctgcgggg caccaaggcc ctgaccgagg tggtgcccct      4080
gaccgaggag gccgagctgg agctggccga gaaccgggag atcctgaagg agcccgtgca      4140
cggcgtgtac tacgacccca gcaaggacct gatcgccgag atccagaagc agggccaggg      4200
ccagtggacc taccagatct accaggagcc cttcaagaac ctgaagaccg gcaagtacgc      4260
ccggatgaag ggcgcccaca ccaacgacgt gaagcagctg accgaggccg tgcagaagat      4320
cgccaccgag agcatcgtga tctggggcaa gaccccaag ttcaagctgc ccatccagaa      4380
ggagacctgg gaggcctggt ggaccgagta ctggcaggcc acctggatcc ccgagtggga      4440
gttcgtgaac acccccccc tggtgaagct gtggtaccag ctggagaagg agcccatcat      4500
cggcgccgag accttctacg tggacggcgc cgccaaccgg gagaccaagc tgggcaaggc      4560
cggctacgtg accgaccggg ccggcagaa ggtggtgccc ctgaccgaca ccaccaacca      4620
gaagaccgag ctgcaggcca tccacctggc cctgcaggac agcggcctgg aggtgaacat      4680
cgtgaccgac agccagtacg ccctgggcat catccaggcc cagcccgaca gagcgagag      4740 cgagctggtg agccagatca tcgagcagct gatcaagaag gagaaggtgt acctggcctg      4800 ggtgccgcc cacaagggca tcggcggcaa cgagcaggtg gacaagctgg tgagcgccgg      4860
catccggaag gtgctgttcc tggacggcat cgacaaggcc caggaggagc acgagaagta      4920
ccacagcaac tggcgggcca tggccagcga cttcaacctg cccccgtgg tggccaagga      4980 gatcgtggcc agctgcgaca gtgccagct gaagggcgag gccatgcacg gccaggtgga      5040
ctgcagcccc ggcatctggc agctggtgtg caccacctg gagggcaagg tgatcctggt      5100
ggccgtgcac gtggccagcg gctacatcga ggccgaggtg atccccgccg agaccggcca      5160
ggagaccgcc tacttcctgc tgaagctggc cggccggtgg cccgtgaaga ccgtgcacac      5220
cgacaacggc agcaacttca ccagcaccac cgtgaaggcc gcctgctggt gggcggcat      5280 caagcaggag ttcggcatcc cctacaaccc ccagagccag ggcgtgatcg agagcatgaa      5340
caaggagctg aagaagatca tcggccaggt gcgggaccag gccgagcacc tgaagaccgc      5400
cgtgcagatg gccgtgttca tccacaactt caagcggaag ggcggcatcg gcggctacag      5460
cgccggcgag cggatcgtgg acatcatcgc caccgacatc cagaccaagg agctgcagaa      5520
gcagatcacc aagatccaga acttccgggt gtactaccgg acagccggg accccgtgtg      5580 gaagggcccc gccaagctgc tgtggaaggg cgagggcgcc gtggtgatcc aggacaacag      5640
cgacatcaag gtggtgcccc ggcggaaggc caagatcatc cgggactacg caagcagat      5700 ggccggcgac gactgcgtgg ccagccggca ggacgaggac tgacacatgg aattcacccc      5760
accagtgcag gctgcctatc agaaagtggt ggctggtgtg gctaatgccc tggcccacaa      5820
```

```
gtatcactaa gctcgctttc ttgctgtcca atttctatta aaggttcctt tgttccctaa    5880
gtccaactac taaactgggg gatattatga agggccttga gcatctggat tctgcctaat    5940
aaaaaacatt tattttcatt gcaatgatgt atttaaatta tttctgaata ttttactaaa    6000
aagggaatgt gggaggtcag tgcatttaaa acataaagaa atgaagagct agttcaaacc    6060
ttgggaaaat acactatatc ttaaactcca tgaagaagg tgaggctgca aacagctaat     6120
gcacattggc aacagcccct gatgcctatg ccttattcat ccctcagaaa aggattcaag    6180
tagaggcttg atttggaggt taaagttttg ctatgctgta ttttacatta cttattgttt    6240
tagctgtcct catgaatgtc ttttcactac ccatttgctt atcctgcatc tctcagcctt    6300
gactccactc agttctcttg cttagagata ccacctttcc cctgaagtgt tccttccatg    6360
ttttacggcg agatggtttc tcctcgcctg gccactcagc cttagttgtc tctgttgtct    6420
tatagaggtc tacttgaaga aggaaaaaca gggggcatgg tttgactgtc ctgtgagccc    6480
ttcttccctg cctcccccac tcacagtgac ccggaatccc tcgacctcga gccaccttg    6540 attctcatgg tctgggtgcc ctcgtaaggc ttgccctcgc cctcgctggt gcacttgaag    6600
tggtggttgt tcacggtgcc ttccatgtac agcttcatgt gcatgctcga gatggcagtc    6660
tagcactagt gcggccgcag atctgcttcc tcgctcactg actcgctgcg ctcggtcgtt    6720
cggctgcggc gagcggtatc agctcactca aaggcggtaa tacggttatc cacagaatca    6780
ggggataacg caggaaagaa catgtgagca aaaggccagc aaaaggccag gaaccgtaaa    6840
aaggccgcgt tgctggcgtt tttccatagg ctccgccccc ctgacgagca tcacaaaaat    6900
cgacgctcaa gtcagaggtg gcgaaacccg acaggactat aaagatacca ggcgtttccc    6960
cctggaagct ccctcgtgcg ctctcctgtt ccgaccctgc cgcttaccgg atacctgtcc    7020
gcctttctcc cttcgggaag cgtggcgctt tctcatagct cacgctgtag gtatctcagt    7080
tcggtgtagg tcgttcgctc caagctgggc tgtgtgcacg aaccccccgt tcagcccgac    7140
cgctgcgcct tatccggtaa ctatcgtctt gagtccaacc cggtaagaca cgacttatcg    7200
ccactggcag cagccactgg taacaggatt agcagagcga ggtatgtagg cggtgctaca    7260
gagttcttga agtggtggcc taactacggc tacactagaa gaacagtatt tggtatctgc    7320
gctctgctga agccagttac cttcggaaaa agagttggta gctcttgatc cggcaaacaa    7380
accaccgctg gtagcggtgg tttttttgtt tgcaagcagc agattacgcg cagaaaaaaa    7440
ggatctcaag aagatccttt gatcttttct acggggtctg acgctcagtg gaacgaaaac    7500
tcacgttaag ggattttggt catgagatta tcaaaaagga tcttcaccta gatccttta    7560 aattaaaaat gaagttttaa atcaatctaa agtatatatg agtaaacttg gtctgacagt    7620
cagaagaact cgtcaagaag gcgatagaag gcgatgcgct gcgaatcggg agcggcgata    7680
ccgtaaagca cgaggaagcg gtcagcccat tcgccgccaa gttcttcagc aatatcacgg    7740
gtagccaacg ctatgtcctg atagcggtcc gccacaccca gccggccaca gtcgatgaat    7800
ccagaaaagc ggccattttc caccatgata ttcggcaagc aggcatcgcc atgggtcacg    7860
acgagatcct cgccgtcggg catgctcgcc ttgagcctgg cgaacagttc ggctggcgcg    7920
agcccctgat gttcttcgtc cagatcatcc tgatcgacaa gaccggcttc catccgagta    7980
cgtgctcgct cgatgcgatg tttcgcttgg tggtcgaatg ggcaggtagc cggatcaagc    8040
gtatgcagcc gccgcattgc atcagccatg atggatactt tctcggcagg agcaaggtga    8100
gatgacagga gatcctgccc cggcacttcg cccaatagca gccagtccct tcccgcttca    8160
```

```
gtgacaacgt cgagcacagc tgcgcaagga acgcccgtcg tggccagcca cgatagccgc    8220
gctgcctcgt cttgcagttc attcagggca ccggacaggt cggtcttgac aaaaagaacc    8280
gggcgcccct gcgctgacag ccggaacacg gcggcatcag agcagccgat tgtctgttgt    8340
gcccagtcat agccgaatag cctctccacc caagcggccg gagaacctgc gtgcaatcca    8400
tcttgttcaa tcatactctt ccttttcaa tattattgaa gcatttatca gggttattgt    8460
ctcatgagcg gatacatatt tgaatgtatt tagaaaaata aacaaatagg ggttccgcgc    8520
acatttcccc gaaaagtgcc acctgacgt                                      8549
```

```
<210> SEQ ID NO 56
<211> LENGTH: 8
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (2)..(2)
<223> OTHER INFORMATION: Xaa is Val or Ile
<220> FEATURE:
<221> NAME/KEY: MISC_FEATURE
<222> LOCATION: (4)..(4)
<223> OTHER INFORMATION: Xaa is any amino acid

<400> SEQUENCE: 56

Asp Xaa Glu Xaa Asn Pro Gly Pro
1               5
```

```
<210> SEQ ID NO 57
<211> LENGTH: 18
<212> TYPE: PRT
<213> ORGANISM: Thosea asigna virus

<400> SEQUENCE: 57

Glu Gly Arg Gly Ser Leu Leu Thr Cys Gly Asp Val Glu Glu Asn Pro
1               5                   10                  15

Gly Pro
```

```
<210> SEQ ID NO 58
<211> LENGTH: 314
<212> TYPE: PRT
<213> ORGANISM: Homo sapiens

<400> SEQUENCE: 58

Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
                20                  25                  30

Thr Glu Glu Gln Glu Ala Ala Ser Ser Ser Ser Thr Leu Val Glu Val
            35                  40                  45

Thr Leu Gly Glu Val Pro Ala Ala Glu Ser Pro Asp Pro Pro Gln Ser
        50                  55                  60

Pro Gln Gly Ala Ser Ser Leu Pro Thr Thr Met Asn Tyr Pro Leu Trp
65                  70                  75                  80

Ser Gln Ser Tyr Glu Asp Ser Ser Asn Gln Glu Glu Glu Gly Pro Ser
                85                  90                  95

Thr Phe Pro Asp Leu Glu Ser Glu Phe Gln Ala Ala Leu Ser Arg Lys
                100                 105                 110

Val Ala Glu Leu Val His Phe Leu Leu Leu Lys Tyr Arg Ala Arg Glu
            115                 120                 125
```

```
Pro Val Thr Lys Ala Glu Met Leu Gly Ser Val Val Gly Asn Trp Gln
    130                 135                 140

Tyr Phe Phe Pro Val Ile Phe Ser Lys Ala Ser Ser Leu Gln Leu
145                 150                 155                 160

Val Phe Gly Ile Glu Leu Met Glu Val Asp Pro Ile Gly His Leu Tyr
                165                 170                 175

Ile Phe Ala Thr Cys Leu Gly Leu Ser Tyr Asp Gly Leu Leu Gly Asp
                180                 185                 190

Asn Gln Ile Met Pro Lys Ala Gly Leu Leu Ile Ile Val Leu Ala Ile
                195                 200                 205

Ile Ala Arg Glu Gly Asp Cys Ala Pro Glu Glu Lys Ile Trp Glu Glu
    210                 215                 220

Leu Ser Val Leu Glu Val Phe Glu Gly Arg Glu Asp Ser Ile Leu Gly
225                 230                 235                 240

Asp Pro Lys Lys Leu Leu Thr Gln His Phe Val Gln Glu Asn Tyr Leu
                245                 250                 255

Glu Tyr Arg Gln Val Pro Gly Ser Asp Pro Ala Cys Tyr Glu Phe Leu
                260                 265                 270

Trp Gly Pro Arg Ala Leu Val Glu Thr Ser Tyr Val Lys Val Leu His
                275                 280                 285

His Met Val Lys Ile Ser Gly Gly Pro His Ile Ser Tyr Pro Pro Leu
    290                 295                 300

His Glu Trp Val Leu Arg Glu Gly Glu Glu
305                 310

<210> SEQ ID NO 59
<211> LENGTH: 180
<212> TYPE: PRT
<213> ORGANISM: Homo sapiens

<400> SEQUENCE: 59

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Asn Ala Gly
            20                  25                  30

Gly Pro Gly Glu Ala Gly Ala Thr Gly Gly Arg Gly Pro Arg Gly Ala
            35                  40                  45

Gly Ala Ala Arg Ala Ser Gly Pro Gly Gly Ala Pro Arg Gly Pro
    50                  55                  60

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
                100                 105                 110

Ala Pro Pro Leu Pro Val Pro Gly Val Leu Leu Lys Glu Phe Thr Val
                115                 120                 125

Ser Gly Asn Ile Leu Thr Ile Arg Leu Thr Ala Ala Asp His Arg Gln
    130                 135                 140

Leu Gln Leu Ser Ile Ser Ser Cys Leu Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
```

<210> SEQ ID NO 60
<211> LENGTH: 23
<212> TYPE: DNA
<213> ORGANISM: Artificial Sequence
<220> FEATURE:
<223> OTHER INFORMATION: Synthetic primer

<400> SEQUENCE: 60
taaggccgag tcttatgagc agc                                           23

<210> SEQ ID NO 61
<211> LENGTH: 19
<212> TYPE: DNA
<213> ORGANISM: Artificial Sequence
<220> FEATURE:
<223> OTHER INFORMATION: Synthetic primer

<400> SEQUENCE: 61
aggactcggc ttgctgaag                                                19

<210> SEQ ID NO 62
<211> LENGTH: 21
<212> TYPE: DNA
<213> ORGANISM: Artificial Sequence
<220> FEATURE:
<223> OTHER INFORMATION: Synthetic primer

<400> SEQUENCE: 62
agcctgtctc tcagtacaat c                                             21

<210> SEQ ID NO 63
<211> LENGTH: 20
<212> TYPE: DNA
<213> ORGANISM: Artificial Sequence
<220> FEATURE:
<223> OTHER INFORMATION: Synthetic primer

<400> SEQUENCE: 63
tgtcttatgt ccagaatgct                                               20

<210> SEQ ID NO 64
<211> LENGTH: 18
<212> TYPE: DNA
<213> ORGANISM: Artificial Sequence
<220> FEATURE:
<223> OTHER INFORMATION: Synthetic primer

<400> SEQUENCE: 64
gcacggcaag aggcgagg                                                 18

<210> SEQ ID NO 65
<211> LENGTH: 20
<212> TYPE: DNA
<213> ORGANISM: Artificial Sequence
<220> FEATURE:
<223> OTHER INFORMATION: Synthetic primer

<400> SEQUENCE: 65
gccggatgtc caggatgctg                                               20

<210> SEQ ID NO 66
<211> LENGTH: 9
<212> TYPE: PRT
<213> ORGANISM: Lymphocytic choriomeningitis virus

<400> SEQUENCE: 66

Lys Ala Val Tyr Asn Phe Ala Thr Met
1               5

<210> SEQ ID NO 67
<211> LENGTH: 9
<212> TYPE: PRT
<213> ORGANISM: Mus musculus

<400> SEQUENCE: 67

Ser Pro Ser Tyr Val Tyr His Gln Phe
1               5

<210> SEQ ID NO 68
<211> LENGTH: 8
<212> TYPE: PRT
<213> ORGANISM: Homo sapiens

<400> SEQUENCE: 68

Arg Gly Pro Glu Ser Arg Leu Leu
1               5

<210> SEQ ID NO 69
<211> LENGTH: 937
<212> TYPE: DNA
<213> ORGANISM: Artificial Sequence
<220> FEATURE:
<223> OTHER INFORMATION: Synthetic polynucleotide

<400> SEQUENCE: 69
gcacggcaag aggcgagggg cggcgactgg tgagtacgcc aaaaattttg actagcggag     60
gctagaagga gagagatggg tgcgagagcg tcagtattaa gcgggggaga attagatcgc    120
gatgggaaaa aattcggtta aggccagggg gaaagaaaaa atataaatta aaacatatag    180
tatgggcaag cagggagcta gaacgattcg cagttaatcc tggcctgtta gaaacatcag    240
aaggctgtag acaaatactg ggacagctac aaccatccct tcagacagga tcagaagaac    300
ttagatcatt atataataca gtagcaaccc tctattgtgt gcatcaaagg atagagataa    360
aagacaccaa ggaagcttta gacaagatag aggaagagca aaacaaaagt aagaaaaaag    420
cacagcaagc agcagctgac acaggacaca gcaatcaggt cagccaaaat taccctatag    480
tgcagaacat ccagggggcaa atggtacatc aggccatatc acctagaact ttaaatgcat    540
gggtaaaagt agtagaagag aaggctttca gcccagaagt gatacccatg ttttcagcat    600
tatcagaagg agccacccca caagatttaa acaccatgct aaacacagtg gggggacatc    660
aagcagccat gcaaatgtta aaagagacca tcaatgagga agctgcagaa tgggatagag    720
tgcatccagt gcatgcaggg cctattgcac caggccagat gagagaacca aggggaagtg    780
acatagcagg aactactagt acccttcagg aacaaatagg atggatgaca cataatccac    840
ctatcccagt aggagaaatc tataaaagat ggataatcct gggattaaat aaaatagtaa    900
gaatgtatag ccctaccagc attctggaca taagaca                             937

<210> SEQ ID NO 70
<211> LENGTH: 1329
<212> TYPE: DNA
<213> ORGANISM: Artificial Sequence
<220> FEATURE:
<223> OTHER INFORMATION: Synthetic polynucleotide

<400> SEQUENCE: 70

-continued

```
gcacggcaag aggcgagggg cggcgactgg tgagtacgcc aaaaattttg actagcggag      60
gctagaagga gagagatggg tgcgagagcg tcagtattaa gcggggagga attagatcgc     120
gatgggaaaa aattcggtta aggccagggg gaaagaaaaa atataaatta aaacatatag     180
tatgggcaag cagggagcta gaacgattcg cagttaatcc tggcctgtta gaaacatcag     240
aaggctgtag acaaatactg ggacagctac aaccatccct tcagacagga tcagaagaac     300
ttagatcatt atataataca gtagcaaccc tctattgtgt gcatcaaagg atagagataa     360
aagacaccaa ggaagcttta gacaagatag aggaagagca aaacaaaagt aagaccaccg     420
cacagcaagc ggccgctgat cttcagacct ggaggaggag atatgaggga caattggaga     480
agtgaattat ataaatataa agtagtaaaa attgaaccat taggagtagc acccaccaag     540
gcaaagagaa gagtggtgca gagagaaaaa agagcagtgg gaataggagc tttgttcctt     600
gggttcttgg gagcagcagg aagcactatg ggcgcagcgt caatgacgct gacggtacag     660
gccagacaat tattgtctgg tatagtgcag cagcagaaca atttgctgag ggctattgag     720
gcgcaacagc atctgttgca actcacagtc tggggcatc aagcagctcc aggcaagaat     780
cctggctgtg gaaagatacc taaaggatca acagctcctg gggatttggg gttgctctgg     840
aaaactcatt tgcaccactg ctgtgccttg gaatgctagt tggagtaata aatctctgga     900
acagatttgg aatcacacga cctggatgga gtgggacaga gaaattaaca attacacaag     960
cttaatacac tccttaattg aagaatcgca aaaccagcaa gaaaagaatg aacaagaatt    1020
attggaatta gataaatggg caagtttgtg gaattggttt aacataacaa attggctgtg    1080
gtatataaaa ttattcataa tgatagtagg aggcttggta gatttaagaa tagttttttgc    1140 tgtactttct atagtgaata gagttaggca gggatattca ccattatcgt ttcagaccca    1200
cctcccaacc ccgaggggac ccgacaggcc cgaaggaata gaagaagaag gtgtacaagc    1260
ggtggatcat cctgggcctg aacaagatcg tgcggatgca cagccccacc agcatcctgg    1320
acatccggc                                                            1329
```

MATERIALS AND METHODS FOR PRODUCING IMPROVED LENTIVIRAL VECTOR PARTICLES

CROSS REFERENCE TO RELATED APPLICATIONS

This application is a continuation of U.S. patent application Ser. No. 15/612,192 filed Jun. 2, 2017, which is a continuation of U.S. patent application Ser. No. 14/389,131, filed Sep. 29, 2014, which is the U.S. national phase application under 35 U.S.C. § 371 of International Application No. PCT/US13/34640, filed Mar. 29, 2013, which claims priority to U.S. patent application Ser. No. 13/436,472, filed Mar. 30, 2012, now U.S. Pat. No. 8,323,662, issued Dec. 4, 2012; and U.S. Provisional Patent Application Nos. 61/666,103, filed Jun. 29, 2012; 61/732,756, filed Dec. 3, 2012; and 61/789,575, filed Mar. 15, 2013, all of which are incorporated herein by reference in their entirety.

INCORPORATION BY REFERENCE OF MATERIAL SUBMITTED ELECTRONICALLY

Incorporated by reference in its entirety is a computer-readable amino acid/nucleotide sequence listing submitted concurrently herewith and identified as follows: One 249,580 byte ASCII (Text) file named "46417C_SeqListing.txt" created on Jul. 16, 2019.

FIELD OF THE INVENTION

The disclosure relates to materials and methods useful for generating improved pseudotyped lentiviral vector particles.

BACKGROUND

Dendritic cells (DCs) are essential antigen presenting cells for the initiation and control of immune responses. DCs can capture and process antigens, migrate from the periphery to a lymphoid organ, and present the antigens to resting T cells in a major histocompatibility complex (MHC)-restricted fashion. These cells are derived from bone marrow (BM) and display dendritic morphology and high mobility. The discovery of DCs as specialized antigen-presenting cells (APCs) has fueled attempts at DC-based immunization/vaccination strategies that involve targeting DCs for display of specific antigens. Recombinant virus-based vectors have been developed as a mechanism to directly deliver a gene encoding a designated antigen(s) to host cells. Through induction of a desired adaptive immune response, the expressed gene product provides a therapeutic benefit.

Challenges in achieving a safe and effective system include designing a vector that efficiently targets a desired set of host cells, providing a suitable delivery system, and expressing a desired antigen to elicit an effective immune response so that it can be utilized broadly across a designated human subject population.

The envelope glycoproteins of Sindbis virus and other alphaviruses disclosed herein incorporate into the lipid bilayer of the viral particle membrane. Typically, the viral membrane (envelope) includes multiple copies of trimers of two glycoprotein heterodimers, E1 and E2, which are produced from cleavage of a single precursor protein. The precursor protein comprises, from its N- to C-terminus, E3, E2, 6K and E1 proteins. The small E3 glycoprotein serves as a signal sequence for translocation of the E2 protein into the membrane, and is cleaved from E2 by furin or some other $Ca^{2+}$-dependent serine proteinase. The 6K protein serves as a signal sequence for translocation of the E1 protein into the membrane and is then cleaved from the precursor protein. WO 2008/011636 and US 2011/0064763 disclose lentiviral packaging systems.

SUMMARY OF THE INVENTION

The inventors have discovered that lentiviral vector particles that exhibit two characteristics (a) pseudotyped with a highly mannosylated alphavirus glycoprotein and (b) comprising a Vpx protein, have unexpectedly improved transduction efficiency for cells expressing DC-SIGN. These particles infect cells expressing DC-SIGN, particularly dendritic cells, significantly more efficiently than lentiviral vector particles having only one of these two characteristics. In particular instances, highly mannosylated pseudotyped lentiviral vector particles are provided that comprise a Vpx protein and a lentiviral genome comprising a sequence of interest (e.g., a polynucleotide encoding an antigen).

Methods of Generating Pseudotyped Lentiviral Vector Particles

One aspect of the disclosure provides a method of generating a pseudotyped lentiviral vector particle comprising: (a) culturing in a culture medium comprising a mannosidase inhibitor, preferably a mannosidase I inhibitor, and a virus packaging cell comprising: (1) a lentiviral vector genome comprising a polynucleotide encoding an exogenous antigen, (2) a polynucleotide encoding an alphavirus glycoprotein that preferentially binds cells expressing DC-SIGN, and (3) a polynucleotide encoding a SAMHD1 inhibitor; and (b) isolating a pseudotyped lentiviral vector particle that preferentially binds cells expressing DC-SIGN.

Another aspect of the disclosure provides a method of generating a pseudotyped lentiviral vector particle comprising: (a) culturing in a culture medium comprising kifunensine a virus packaging cell comprising: (1) a lentiviral vector genome comprising a polynucleotide encoding an exogenous antigen, (2) a polynucleotide encoding a Sindbis E2 glycoprotein that preferentially binds dendritic cells expressing DC-SIGN, and (3) a polynucleotide encoding a Vpx protein or a Vpr protein that retains SAMHD1-inhibiting activity; and (b) isolating a pseudotyped lentiviral vector particle that preferentially binds dendritic cells expressing DC-SIGN. In some embodiments, the E2 glycoprotein is 90% identical to SEQ ID NO: 30 [SIN-Var1]. In some embodiments, (i) residue 160 of the E2 glycoprotein is absent or is an amino acid other than glutamic acid, (ii) one or more of residues 70, 76, or 159 of the E2 glycoprotein variant is a non-basic residue, and (iii) the E2 glycoprotein variant is not part of a fusion protein with Sindbis virus E3 glycoprotein. In some embodiments, the E2 glycoprotein is SEQ ID NO: 30 [SIN-Var1].

In some or any of the embodiments described herein, the Vpx protein comprises an amino acid sequence that is at least 80% identical to SIVmac Vpx (SEQ ID NO: 44).

In some or any of the embodiments described herein, the Vpx protein comprises an amino acid sequence at least 90% identical to SIVmac Vpx (SEQ ID NO: 44), SIVsm Vpx (SEQ ID NO: 45), SIVrcm Vpx (SEQ ID NO: 46), or HIV-2 Vpx (SEQ ID NO: 47).

In some or any of the embodiments described herein, the Vpr protein comprises an amino acid sequence at least 90% identical to SIVdeb Vpr (SEQ ID NO: 48) or SIVmus Vpr (SEQ ID NO: 49).

In some or any of the embodiments described herein, the antigen is a tumor-specific antigen or a virus-specific antigen. In some or any of the embodiments described herein, the tumor-specific antigen is selected from the group consisting of NY-ESO-1, MAGE, e.g., MAGE-A3 and MAGE-A1, MART-1/Melan-A, BAGE, RAGE, gp100, gp75, mda-7, tyrosinase, tyrosinase-related protein, e.g., TRP2, renal cell carcinoma antigen, 5T4, SM22-alpha, carbonic anhydrase I, carbonic anhydrase IX (also known as G250), HIF-1alpha, HIF-2alpha, VEGF, prostate specific membrane antigen (PSMA), prostate-specific antigen (PSA), prostatic acid phosphates, six-transmembrane epoithelial antigen of the prostate (STEAP), NKX3.1, telomerase enzyme, survivin, mesothelin, mutated ras, bcr/abl rearrangement, Her2/neu, mutated p53, wild-type p53, cytochrome P450 1B1, N-acetylglucosaminyltransferase-V, human papilloma virus protein E6, human papilloma virus protein E7, carcinoembryonic antigen, merkel cell virus T-antigen oncoproteins and alpha-fetoprotein. In some or any of the embodiments described herein, the virus-specific antigen is an HIV antigen, an SIV antigen, an adenovirus antigen, an enterovirus antigen, a coronavirus antigen, a calicivirus antigen, a distemper virus antigen, an Ebola virus antigen, a flavivirus antigen, a hepatitis virus antigen, a herpesvirus antigen, an infectious peritonitis virus antigen, an influenza virus antigen, a leukemia virus antigen, a Marburg virus antigen, an orthomyxovirus antigen, a papilloma virus antigen, a parainfluenza virus antigen, a paramyxovirus antigen, a parvovirus antigen, a pestivirus antigen, a picorna virus antigen, a poliovirus antigen, a pox virus antigen, a polyoma virus antigen, a rabies virus antigen, a reovirus antigen, a retrovirus antigen, or a rotavirus antigen.

In some or any of the embodiments described herein, the lentiviral vector genome further comprises a nucleotide sequence encoding a second antigen. In some or any of the embodiments described herein, the first and second antigen are expressed as a fusion protein that comprises a self-cleaving A2 peptide between the two antigens. In some or any of the embodiments described herein, the self-cleaving A2 peptide comprises the amino acid sequence of SEQ ID NO: 56 or SEQ ID NO: 57. In some or any of the embodiments described herein, the first antigen is MAGE-A3 and the second antigen is NY-ESO-1.

In some or any of the embodiments described herein, the kifunensine is present in the culture medium at a concentration of about 0.01 µg/ml to about 1 mg/ml. In some or any of the embodiments described herein, the kifunensine is present in the culture medium at a concentration of about 0.1 µg/ml to about 1 µg/ml. In some or any of the embodiments described herein, the kifunensine is present in the culture medium at a concentration of about 0.25 µg/ml to about 2 µg/ml.

In some or any of the embodiments described herein, the virus packaging cell further comprises: (i) a polynucleotide comprising gag and pol genes; and (ii) a polynucleotide encoding a rev protein. In some or any of the embodiments described herein, the gag and pol genes are human codon optimized and comprise a non-optimized window around position 1228 to 1509 of SEQ ID NO: 54. In some or any of the embodiments described herein, the polynucleotide comprising gag and pol genes lacks a functional rev responsive element (RRE). In some or any of the embodiments described herein, the polynucleotide comprising gag and pol genes lacks a functional RRE because the RRE has been deleted. In some or any of the embodiments described herein, the pol gene encodes an inactive integrase enzyme. In some or any of the embodiments described herein, the integrase enzyme has a D64V mutation.

In some or any of the embodiments described herein, the polynucleotide encoding the Vpx protein or Vpr protein is on the same or different plasmid as the polynucleotide encoding the rev protein, or the polynucleotide comprising the gag and pol genes.

In some or any of the embodiments described herein, the lentiviral vector genome is derived from HIV-1.

In some or any of the embodiments described herein, the lentiviral vector genome has an inactivated 3' long terminal repeat (LTR) or a self-inactivating 3' long terminal repeat (LTR). In some or any of the embodiments described herein, the lentiviral vector genome comprises a U3 element lacking at least one of an enhancer sequence, a TATA box, an Sp1 site, an NK-kappa B site, or a polypurine tract (PPT).

In some or any of the embodiments described herein, the lentiviral vector genome comprises the nucleotide sequence of any one of SEQ ID NOs: 21 [SIN vector], 22 [703 vector], or 23 [704 vector].

In some or any of the embodiments described herein, the lentiviral vector genome further comprises a nucleotide sequence encoding a dendritic cell maturation/stimulatory factor. In some or any of the embodiments described herein, the dendritic cell maturation/stimulatory factor is selected from the group consisting of GM-CSF, IL-2, IL-4, IL-6, IL-7, IL-15, IL-21, IL-23, TNFα, B7.1, B7.2, 4-1BB, CD40 ligand, and drug-inducible CD40.

In some or any of the embodiments described herein, the nucleotide sequence encoding an antigen is operably linked to a promoter selected from the group consisting of the human Ubiquitin-C promoter (UbiC), the cytomegalovirus immediate early promoter (CMV), the Rous sarcoma virus promoter (RSV), and the tetracycline-responsive promoter. In some or any of the embodiments described herein, the promoter is an intron-deficient promoter. In some or any of the embodiments described herein, the intron-deficient promoter is a UbiC Related aspects of the disclosure provide a lentiviral vector particle produced by any of the methods recited above.

Compositions Comprising Pseudotyped Lentiviral Vector Particles

Another aspect of the disclosure provides a composition comprising pseudotyped lentiviral vector particles comprising (a) a SAMHD1 inhibitor, (b) an exogenous polynucleotide encoding an antigen, and (c) an envelope glycoprotein that preferentially binds dendritic cells expressing DC-SIGN, wherein at least 60%, or at least 70%, or at least 80%, preferably at least 90% of N-linked glycans in said composition comprise a $Man_5$ through $Man_9$ structure, preferably $Man_9$.

Another aspect of the disclosure provides a composition comprising pseudotyped lentiviral vector particles comprising (a) a Vpx protein, (b) an exogenous polynucleotide encoding an antigen, and (c) an envelope glycoprotein that preferentially binds dendritic cells expressing DC-SIGN, wherein at least 80% of N-linked glycans in said composition comprise a $Man_9$ structure.

In some or any of the embodiments described herein, the Vpx protein comprises an amino acid sequence that is at least 80% identical to SIVmac Vpx protein (SEQ ID NO: 44).

In some or any of the embodiments described herein, the Vpx protein comprises an amino acid sequence at least 90% identical to SIVmac Vpx (SEQ ID NO: 44), SIVsm Vpx (SEQ ID NO: 45), SIVrcm Vpx (SEQ ID NO: 46), or HIV-2 Vpx (SEQ ID NO: 47).

In some or any of the embodiments described herein, the Vpr protein comprises an amino acid sequence at least 90% identical to SIVdeb Vpr (SEQ ID NO: 48) or SIVmus Vpr (SEQ ID NO: 49).

In some or any of the embodiments described herein, the pseudotyped lentiviral vector particle infects dendritic cells expressing DC-SIGN with an in vitro transduction efficiency of at least 1%, or at least 5%, or at least 10%, or at least 20%. See, e.g., the procedure of Example 8.

In some or any of the embodiments described herein, the glycoprotein is a Sindbis virus E2 glycoprotein. In some or any of the embodiments described herein, the E2 glycoprotein has at least 90% identity to SEQ ID NO: 30 [SIN-Var1]. In some or any of the embodiments described herein, (i) residue 160 of the E2 glycoprotein is absent or is an amino acid other than glutamic acid, (ii) one or more of residues 70, 76, or 159 of the E2 glycoprotein variant is a non-basic residue, and (iii) the E2 glycoprotein variant is not part of a fusion protein with Sindbis virus E3 glycoprotein.

In some or any of the embodiments described herein, the antigen is a tumor-specific antigen or a virus-specific antigen. In some or any of the embodiments described herein, the tumor-specific antigen is selected from the group consisting of NY-ESO-1, MAGE, e.g., MAGE-A3 and MAGE-A1, MART-1/Melan-A, BAGE, RAGE, gp100, gp75, mda-7, tyrosinase, tyrosinase-related protein, e.g., TRP2, renal cell carcinoma antigen, 5T4, SM22-alpha, carbonic anhydrase I, carbonic anhydrase IX (also known as G250), HIF-1alpha, HIF-2alpha, VEGF, prostate specific membrane antigen (PSMA), prostate-specific antigen (PSA), prostatic acid phosphates, six-transmembrane epoithelial antigen of the prostate (STEAP), NKX3.1, telomerase enzyme, survivin, mesothelin, mutated ras, bcr/abl rearrangement, Her2/neu, mutated p53, wild-type p53, cytochrome P450 1B1, N-acetylglucosaminyltransferase-V, human papilloma virus protein E6, human papilloma virus protein E7, carcinoembryonic antigen, merkel cell virus T-antigen oncoproteins and alpha-fetoprotein. In some or any of the embodiments described herein, the virus-specific antigen is an HIV antigen, an SIV antigen, an adenovirus antigen, an enterovirus antigen, a coronavirus antigen, a calicivirus antigen, a distemper virus antigen, an Ebola virus antigen, a flavivirus antigen, a hepatitis virus antigen, a herpesvirus antigen, an infectious peritonitis virus antigen, an influenza virus antigen, a leukemia virus antigen, a Marburg virus antigen, an orthomyxovirus antigen, a papilloma virus antigen, a parainfluenza virus antigen, a paramyxovirus antigen, a parvovirus antigen, a pestivirus antigen, a picorna virus antigen, a poliovirus antigen, a pox virus antigen, a rabies virus antigen, a reovirus antigen, a retrovirus antigen, or a rotavirus antigen.

In some or any of the embodiments described herein, the lentiviral vector genome further comprises a nucleotide sequence encoding a second antigen. In some or any of the embodiments described herein, the first and second antigen are expressed as a fusion protein that comprises a self-cleaving A2 peptide between the two antigens. In some or any of the embodiments described herein, the self-cleaving A2 peptide comprises the amino acid sequence of SEQ ID NO: 56 or SEQ ID NO: 57. In some or any of the embodiments described herein, the first antigen is NY-ESO-1 and the second antigen is MAGE-A3.

In some or any of the embodiments described herein, the lentiviral vector genome is derived from HIV-1.

In some or any of the embodiments described herein, the lentiviral vector genome has an inactivated 3' long terminal repeat (LTR) or a self-inactivating 3' long terminal repeat (LTR). In some aspects, the lentiviral vector genome comprises a U3 element lacking at least one of an enhancer sequence, a TATA box, an Sp1 site, an NK-kappa B site, or a polypurine tract (PPT).

In some or any of the embodiments described herein, the lentiviral vector genome comprises the nucleotide sequence of any one of SEQ ID NOs: 21 [SIN vector], 22 [703 vector], or 23 [704 vector].

In some or any of the embodiments described herein, the lentiviral vector genome further comprises a nucleotide sequence encoding a dendritic cell maturation/stimulatory factor. In some or any of the embodiments described herein, the dendritic cell maturation/stimulatory factor is selected from the group consisting of GM-CSF, IL-2, IL-4, IL-6, IL-7, IL-15, IL-21, IL-23, TNFα, B7.1, B7.2, 4-1BB, CD40 ligand, and drug-inducible CD40.

In some or any of the embodiments described herein, the nucleotide sequence encoding an antigen is operably linked to a promoter selected from the group consisting of the human Ubiquitin-C promoter (UbiC), the cytomegalovirus immediate early promoter (CMV), the Rous sarcoma virus promoter (RSV), and the tetracycline-responsive promoter. In some or any of the embodiments described herein, the promoter is an intron-deficient promoter. In some or any of the embodiments described herein, the intron-deficient promoter is a human Ubiquitin-C (UbiC) promoter.

In some or any of the embodiments described herein, the pseudotyped lentiviral vector particles have an IU of at least $10^5$/mL.

In some or any of the embodiments described herein, the composition further comprises an immunostimulating agent.

In some or any of the embodiments described herein, the composition further comprises an adjuvant. For example, as disclosed herein, adjuvants include alum, or 3 De-O-acylated monophosphoryl lipid A (MPL). Classes of adjuvants disclosed herein include (a) aluminum salts, (b) oil-in-water emulsion formulations, optionally with or without other specific immunostimulating agents such as muramyl peptides or other bacterial cell wall components, (c) saponin adjuvants, including ISCOMs (immunostimulating complexes) and ISCOMATRIX; (d) Complete Freund's Adjuvant (CFA) and Incomplete Freund's Adjuvant (IFA); (e) cytokines; and (f) adjuvants of formula (I).

(I)

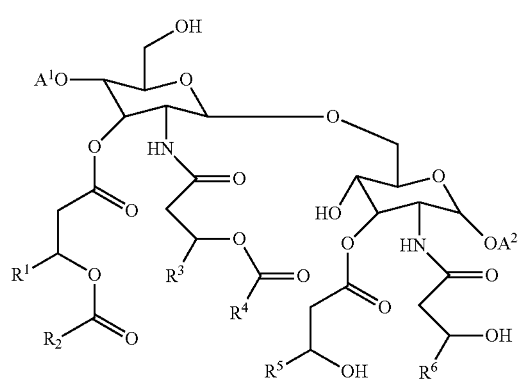

wherein the moieties A1 and A2 are independently selected from the group of hydrogen, phosphate, and phosphate salts. Sodium and potassium are exemplary counterions for the phosphate salts. The moieties $R^1$, $R^2$, $R^3$, $R^4$, $R^5$, and $R^6$ are independently selected from the group of hydrocarbyl having 3 to 23 carbons, represented by $C_3$-$C_{23}$. For added clarity it will be explained that when a moiety is "independently selected from" a specified group having multiple members, it should be understood that the member chosen for the first moiety does not in any way impact or limit the choice of the member selected for the second moiety. The carbon atoms to which $R^1$, $R^3$, $R^5$ and $R^6$ are joined are asymmetric, and thus may exist in either the R or S stereochemistry. In one embodiment all of those carbon atoms are in the R stereochemistry, while in another embodiment all of those carbon atoms are in the S stereochemistry.

In various embodiments of the disclosure, the adjuvant has the chemical structure of formula (I) but the moieties A1, A2, R1, R2, R3, R4, R5, and R6 are selected from subsets of the options previously provided for these moieties, where these subsets are identified below by E1, E2, etc.

E1: $A_1$ is phosphate or phosphate salt and $A_2$ is hydrogen.
E2: $R^1$, $R^3$, $R^5$ and $R^6$ are $C_3$-$C_{21}$ alkyl; and $R^2$ and $R^4$ are $C_5$-$C_{23}$ hydrocarbyl.
E3: $R^1$, $R^3$, $R^5$ and $R^6$ are $C_5$-$C_{17}$ alkyl; and $R^2$ and $R^4$ are $C_7$-$C_9$ hydrocarbyl.
E4: $R^1$, $R^3$, $R^5$ and $R^6$ are $C_7$-$C_{15}$ alkyl; and $R^2$ and $R^4$ are $C_9$-$C_{17}$ hydrocarbyl.
E5: $R^1$, $R^3$, $R^5$ and $R^6$ are $C_9$-$C_{13}$ alkyl; and $R^2$ and $R^4$ are $C_{11}$-$C_{15}$ hydrocarbyl.
E6: $R^1$, $R^3$, $R^5$ and $R^6$ are $C_9$-$C_{15}$ alkyl; and $R^2$ and $R^4$ are $C_{11}$-$C_{17}$ hydrocarbyl.
E7: $R^1$, $R^3$, $R^5$ and $R^6$ are $C_7$-$C_{13}$ alkyl; and $R^2$ and $R^4$ are $C_9$-$C_{15}$ hydrocarbyl.
E8: $R^1$, $R^3$, $R^5$ and $R^6$ are $C_{11}$-$C_{20}$ alkyl; and $R^2$ and $R^4$ are $C_{12}$-$C_{20}$ hydrocarbyl.
E9: $R^1$, $R^3$, $R^5$ and $R^6$ are $C_{11}$ alkyl; and $R^2$ and $R^4$ are $C_{13}$ hydrocarbyl.
E10: $R^1$, $R^3$, $R^5$ and $R^6$ are undecyl and $R^2$ and $R^4$ are tridecyl.

In certain options, each of E2 through E10 is combined with embodiment E1, and/or the hydrocarbyl groups of E2 through E9 are alkyl groups, preferably straight chain alkyl groups. A preferred adjuvant is E1 in combination with E10, where (i) $A_1$ is phosphate or phosphate salt and $A_2$ is hydrogen and (ii) $R^1$, $R^3$, $R^5$ and $R^6$ are undecyl and $R^2$ and $R^4$ are tridecyl.

In some or any of the embodiments described herein, the envelope glycoproteins also bind cells expressing mouse SIGNR1.

In some or any of the embodiments described herein, the pseudotyped lentiviral vector particles also more efficiently transduce cells expressing mouse SIGNR1 compared to cells not expressing mouse SIGNR1.

Other features and advantages of the present disclosure will become apparent from the following detailed description. It should be understood, however, that the detailed description and the specific examples, while indicating specific embodiments of the disclosure, are given by way of illustration only, because various changes and modifications within the spirit and scope of the disclosure will become apparent to those skilled in the art from this detailed description.

BRIEF DESCRIPTION OF THE DRAWINGS

FIGS. 1A and 1B illustrate the ability of pseudotyped lentiviral vector particles produced in the presence of various mannosidase inhibitors (e.g., kifunensine, DMNJ, and swainsonine) to infect HT1080 cells stably expressing the DC-SIGN receptor (1A) or lacking DC-SIGN (1B). Efficiency of infection was assessed by determining GFP expression from the lentiviral vector. The y-axis is the percentage of GFP positive cells.

FIGS. 2A and 2B illustrate the ability of pseudotyped lentiviral vector particles produced in the presence of 400 μg/ml DMNJ or various concentrations of kifunensine to infect HT1080 cells stably expressing the DC-SIGN receptor (2A) or lacking DC-SIGN (2B). Efficiency of infection was assessed as in FIG. 1.

FIG. 3A is a diagram illustrating the substrate specificity for the PNGaseF and EndoH. PNGaseF is a general endoglycosidase that will cleave all N-linked glycosylation regardless of glycosylation profile. EndoH is a specialized endoglycosidase that will only cleave high-mannose N-linked glycosylation. EndoH cleaves only hi-mannose N-linked glycosylation (i.e., EndoH will target 2 of 4 sites on SINVar1 in the absence of kifunensine, and 4 of 4 sites on SINVar1 in the presence of kifunensine). FIG. 3B illustrates the results of an experiment to determine the glycosylation status of the glycoproteins on pseudotyped lentiviral vector particles produced in the presence of kifunensine or DMNJ using gel shifts by running on an SDS-PAGE gel and immunoblotting with antibody against the Sindbis viral envelope.

FIG. 4A illustrates the ability of pseudotyped lentiviral vector particles produced in the presence of 400 μg/ml DMNJ or various concentrations of kifunensine to infect HT1080 cells stably expressing the DC-SIGN receptor. Efficiency of infection was assessed as in FIG. 1. FIG. 4B illustrates the results of an experiment to determine the glycosylation status of the E2 glycoprotein on pseudotyped lentiviral vector particles produced in FIG. 4A.

FIG. 5A is a Western blot (anti-HA) of HA-tagged SIVmacVpx expressed in 293T cells. was cloned into a mammalian expression vector driven by a CMV promoter (construct named pENV-SIVmacVpx). FIG. 5B is a Western blot (anti-HA) of viral protein extracts from viral particles comprising HA-tagged SIVmacVpx. 100 ng of p24 was loaded per well onto a gel for immunoblotting with anti-HA antibody. Anti-p24 antibody was used as a loading control.

FIG. 6 is a scatter plot of transduction events measured by gating on dendritic cells that were positive for CD11c and assessing the percentage of cells positive for GFP (x-axis; as a result of infection by the VSV-G pseudotyped, integration-defective lentivirus with or without Vpx) with DC-SIGN on the y-axis.

FIG. 7 is a scatter plot of transduction events measured by gating on dendritic cells that were positive for CD11c and assessing the percentage of cells positive for GFP (x-axis; as a result of infection by the VSV-G pseudotyped, integration-competent lentivirus with or without Vpx) with DC-SIGN on the y-axis.

FIG. 8 is a scatter plot of transduction events measured by gating on dendritic cells infected with SINvar1-pseudotyped, integration-defective lentivirus with or without Vpx and produced in the presence of absence of kifunensine. The y-axis measures cells that were positive for CD11c or DC-SIGN and the x-axis measures the percentage of cells positive for GFP.

FIG. 9A is a Western blot of Sindbis virus glycoproteins prepared according to Example 1 with no treatment (lanes 1-3), 400 μg/ml of DMNJ (lanes 4-6), or 1 μg/ml of kifunensine (lanes 7-9). The particles were not treated with endoglycosidase (lanes 1, 4, 7), incubated with EndoH for 1 hour (lanes 2, 5, 8), or incubated with PNGaseF for 1 hour (lanes 3, 6, 9). Samples were then analyzed using a gel-shift assay and immunoblotting with antibody against the Sindbis virus envelope. FIG. 9B (no mannosidase inhibitor) is an intensity profile of each band from lanes 1-3 and its location on the lane. FIG. 9C (DMNJ treated) is an intensity profile of each band from lanes 4-6 and its location on the lane. FIG. 9D (kifunensine treated) is an intensity profile of each band from lanes 7-9 and its location on the lane.

For FIG. 10A, 293T huDC-SIGN cells were transduced with vectors packaged with the Wild Type (WT) or defective integrase (D64V) and a vector genome containing the extended 3'PPT (703) or 3'PPT deletion (704). At 48 hours post-transduction, nested Alu-PCR analysis was performed on genomic DNA extracted from the transduced cells. Error bars indicate standard error of the mean from transductions performed in triplicate. FIGS. 10B and 10C demonstrate the integration rate of WT/703 and D64V/704 vectors encoding GFP-T2A-NeoR using two independent methods. For FIG. 10B, HT1080 huDC-SIGN cells were transduced with serial dilutions of the indicated vectors. Transduced cells were grown under G418 selection and neomycin resistant colonies, representing individual integration events, were counted. Integration Events were calculated as described in Example 10. For FIG. 10C, HT1080 huDC-SIGN cells were transduced with the indicated vectors. Flow cytometry was performed at multiple time points post-transduction to determine the percentage of GFP-expressing cells. Error bars indicate standard error of the mean from flow cytometry triplicates.

Figure 11:
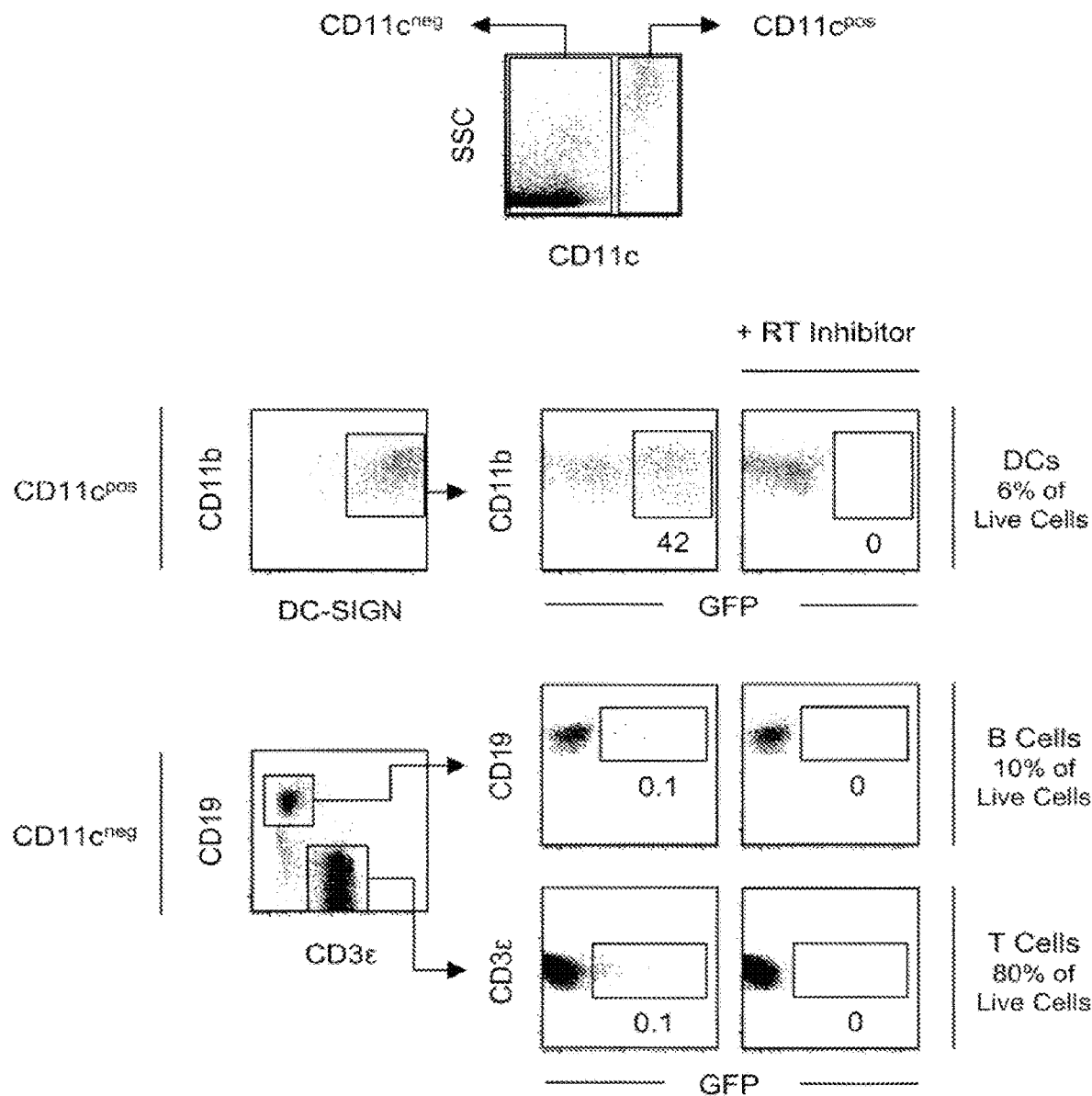

FIG. 11: Human PBMCs were treated with GM-CSF and IL-4 for 3 days, then incubated with 20 ng p24 of ID-VP02 encoding GFP. At the time of vector addition, the culture consisted primarily of DCs, B-cells, and T-cells. Three days after transduction, cells were analyzed for surface markers and categorized as either DCs (CD11c$^{pos}$) 6%, B-cells (CD11c$^{neg}$, CD19$^{pos}$) 10%, or T-cells (CD11c$^{neg}$, CD3ε$^{pos}$) 80%. Transduction events were measured by assessing percent of cells positive for GFP within each population of cells. Numbers in plots are the percentage of cells within the GFP$^{+}$ gate.

Figure 12:
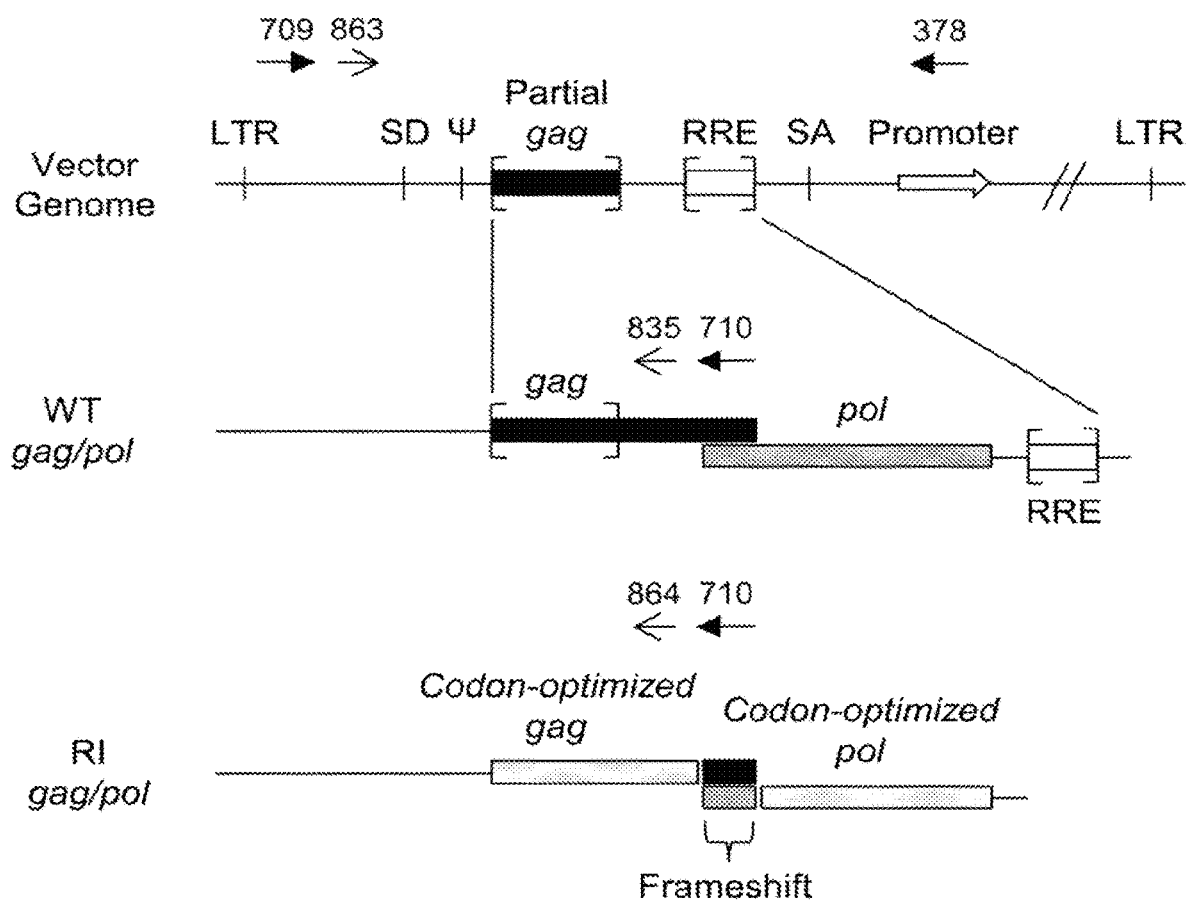

FIG. 12: A portion of the vector genome (top) is represented containing long terminal repeats (LTR) at each end. The splice donor (SD) and splice acceptor (SA) sites flank the psi packaging signal (Ψ), the partial gag sequence and the Rev-responsive element (RRE). Components between the antigen promoter (Promoter) and the 3' LTR are not highlighted and therefore forward slash marks (//) are used. A portion of the WT gag/pol (middle) is represented showing the gag (black box) and pol (grey box) genes followed by the RRE. The two components that are homologous between the WT gag/pol and the vector genome (the RRE and the first 354 bp of gag) are represented in brackets (not drawn to scale). The hypothesized region of recombination between the vector genome and the WT gag/pol are shown with connecting lines. A portion of the RI gag/pol (bottom) is represented showing the codon-optimized gag and pol genes (white boxes to distinguish from wild-type). The non-codon-optimized frameshift between the gag and pol genes is represented in its native codon sequence (overlapping black and grey boxes). Primers used for the psi-gag recombination assay are shown with their approximate locations on the constructs. First round PCR primers are represented with closed arrows and are the pairs 709 and 710 (to detect the psi-gag recombinant) or 709 and 378 (to detect integrated vector genome). The expected amplicon for integrated vector with primer pairs 709 and 378 is 1697 bp. The nested PCR primers are represented with open arrows and are the pairs 863 and 835 (to detect psi-gag recombinant with the WT gag/pol) or 863 and 864 (to detect psi-gag recombination with the RI gag/pol). The expected amplicon with either of the psi-gag recombinant primer pairs is 937 bp.

Figure 13:
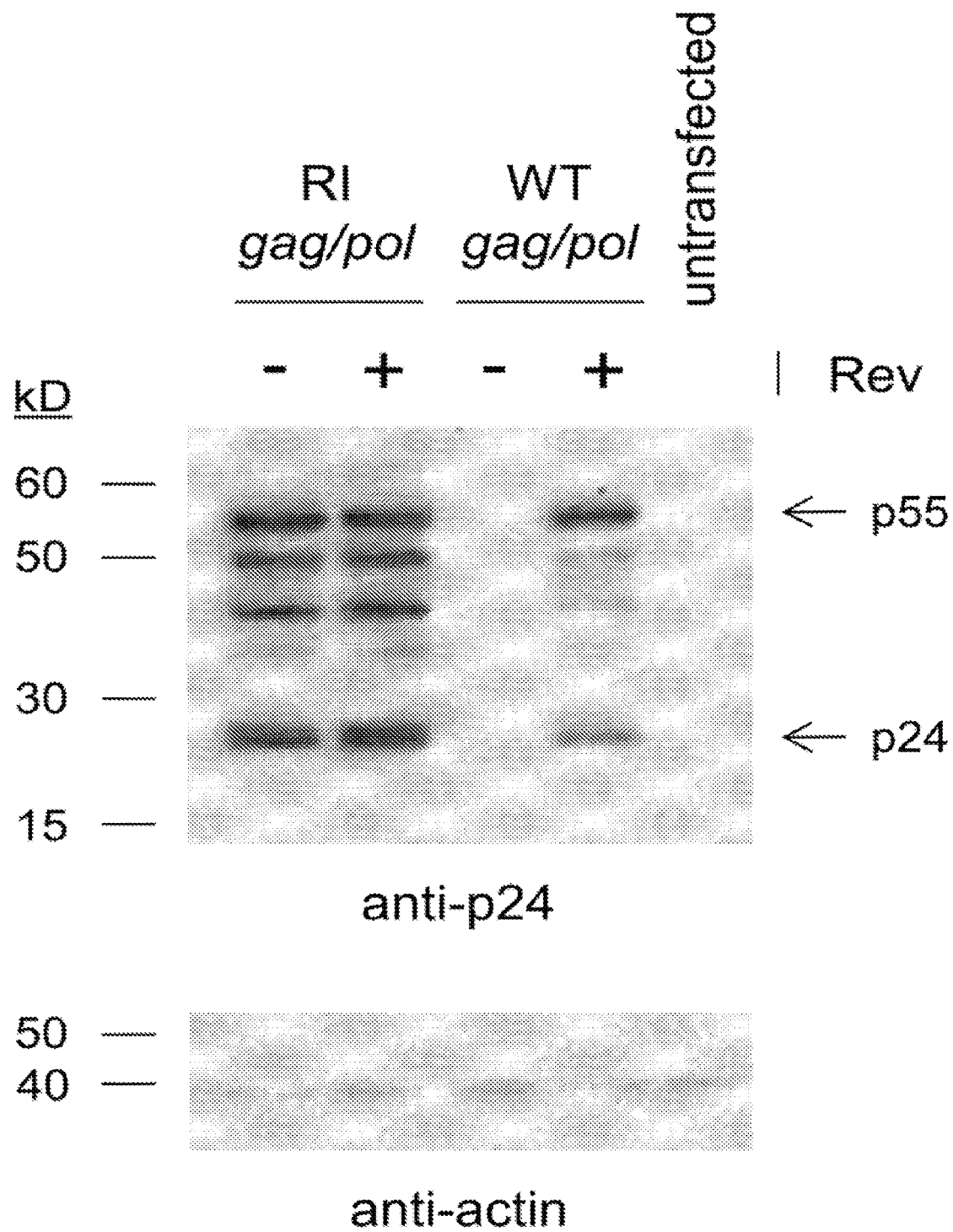

FIG. 13: 293T cells were transfected with either WT gag/pol or RI gag/pol plasmids in the presence of either Rev plasmid (+) or empty backbone plasmid (−). Twenty-four hours later cells were lysed and analyzed for expression of Gag proteins using anti-p24 antibody. Unprocessed Gag protein (p55) and p24 are indicated with arrows. Lysate from untransfected cells was included as a control. Equal loading of wells was confirmed with anti-actin antibody.

Figures 14A, 14B:
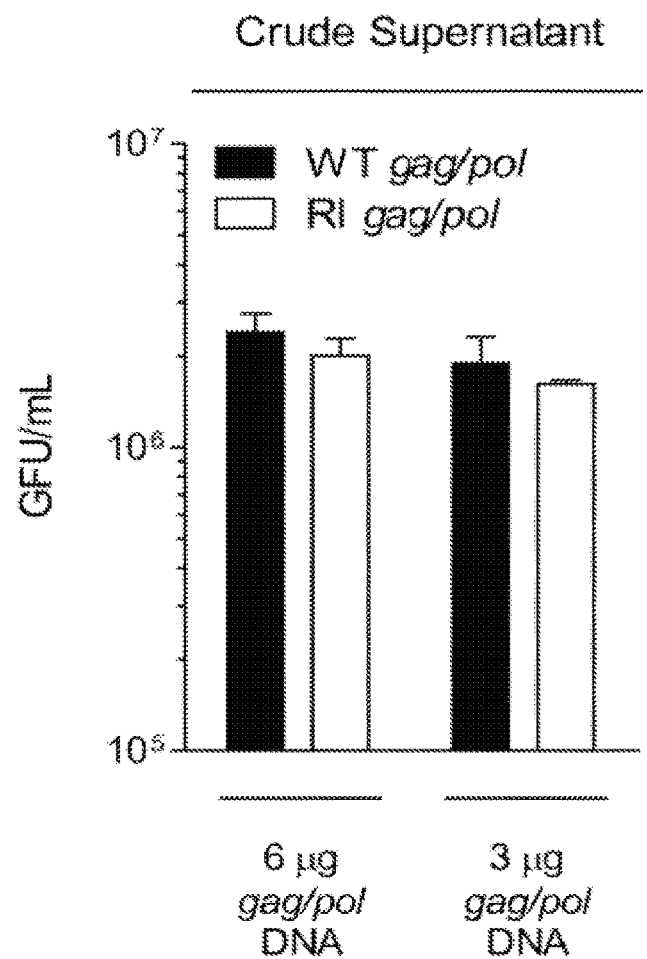

FIG. 14A: GFP-encoding vector was produced with two plasmid amounts (6 μg or 3 μg) of either WT gag/pol or RI gag/pol. Resulting p24 levels in vector supernatant is shown in the table. FIG. 14B: 293T cells were transduced with 2-fold dilutions of vectors produced in 14A and analyzed for GFP expression after 2 days. GFU/mL were calculated and plotted on the y-axis. The μg amount of gag/pol plasmid used to make vector (6 μg or 3 μg) are plotted on the x-axis. WT gag/pol and RI gag/pol are shown in black or white columns respectively.

Figure 15:
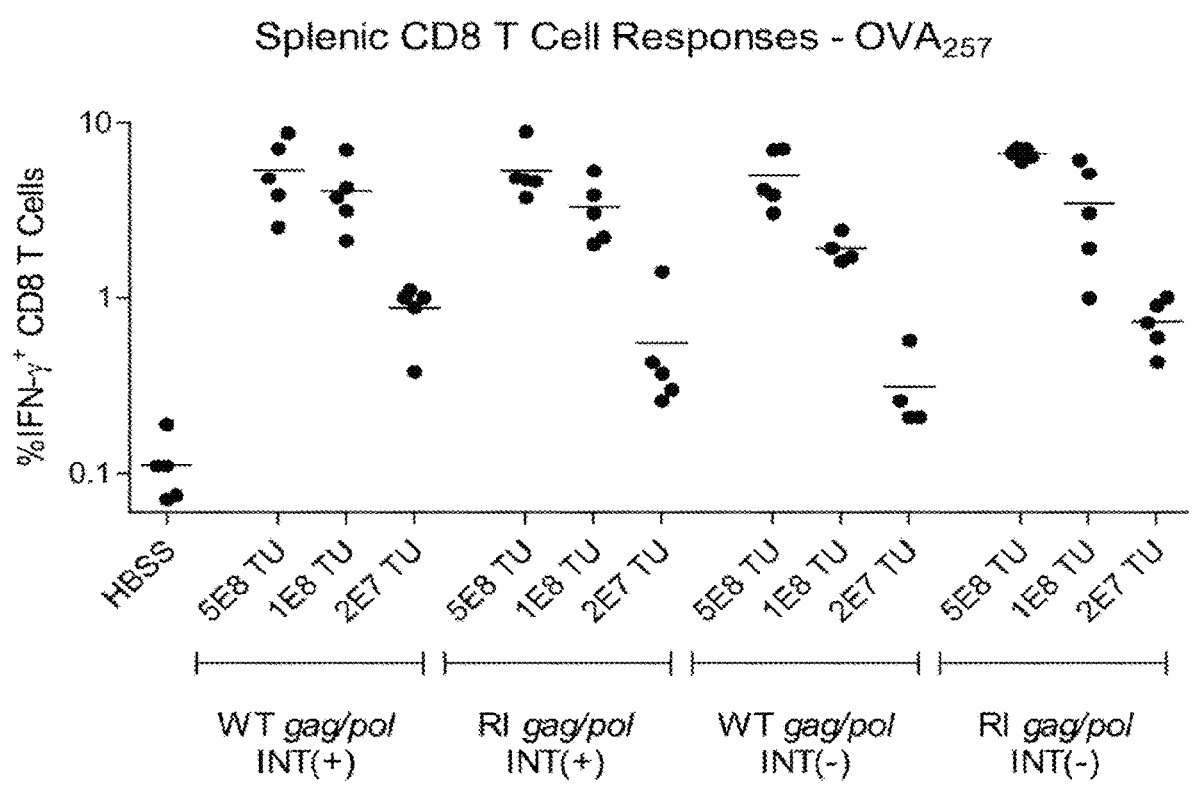

FIG. 15: C57BL/6 mice were immunized with the indicated doses ($2×10^7$, $1×10^8$, or $5×10^8$ TU) of LV encoding full-length OVA or HBSS vehicle alone. LVs were either integration-competent (INT+) or integration-deficient (INT−) and generated with either WT- or RI gag/pol, as indicated. At day 12 post immunization, the percentage of OVA$_{257}$-specific splenic CD8 T cells was measured by ICS for IFN-γ after ex vivo peptide restimulation.

Figure 16:
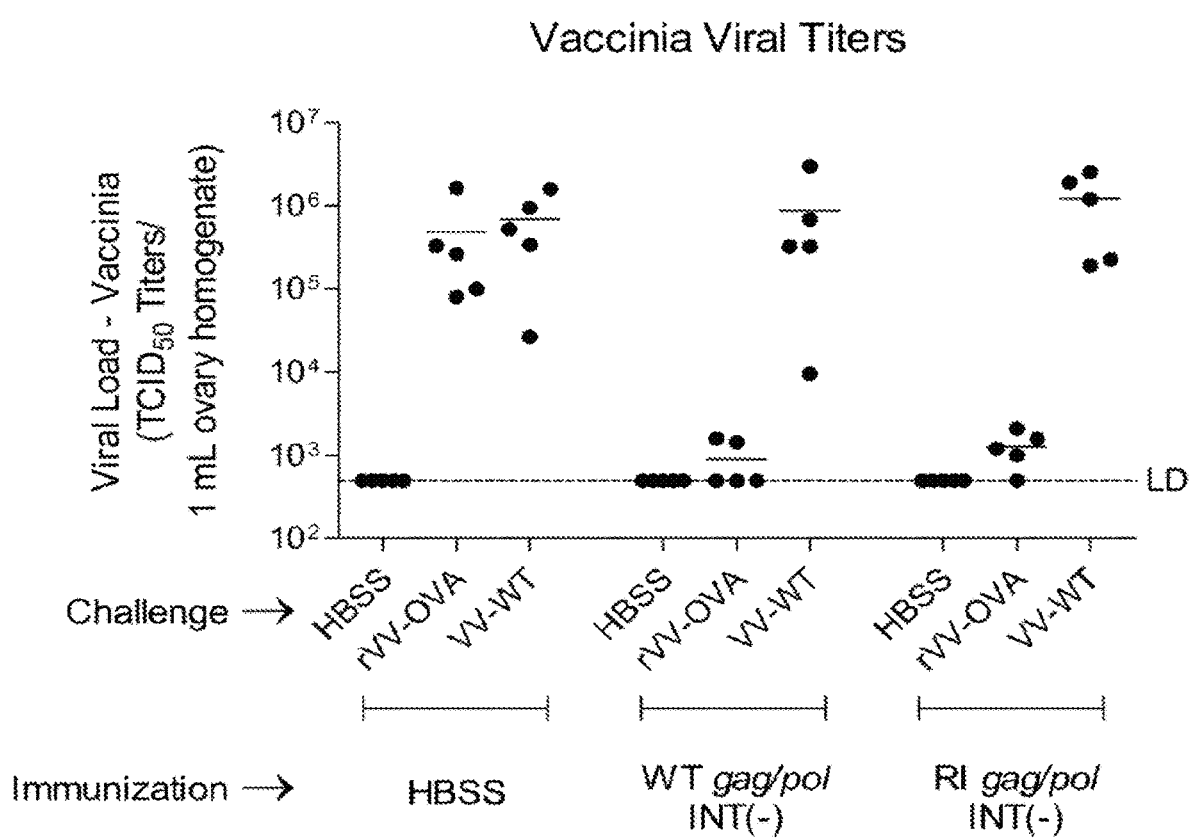

FIG. 16: C57BL/6 mice (5 per group) were immunized with $5×10^8$ TU of Integration-deficient (INT−) LV generated with either WT or RI gag/pol encoding a polyepitope antigen (LV1b) that contains the H-2$^b$-restricted OVA$_{257}$ CD8 T cell epitope and then challenged on day 28 post-immunization with $1×10^7$ TCID$_{50}$ wild type WR-strain vaccine virus (VV-WT), WR-strain recombinant OVA vaccine virus (rVV-OVA), or left unchallenged. On day 33 (day 5 post-challenge) viral load in the ovaries of each animal were measured by TCID$_{50}$ assay.

Figure 17A:
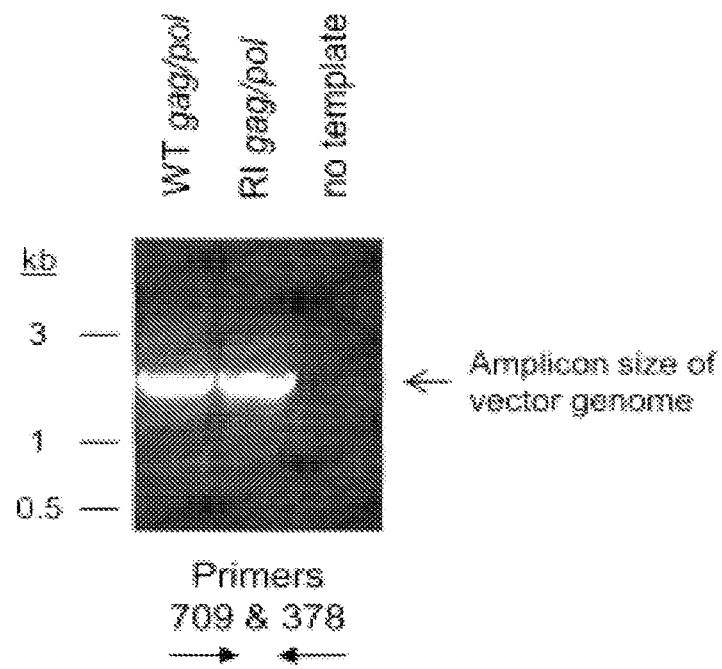
Figure 17B:
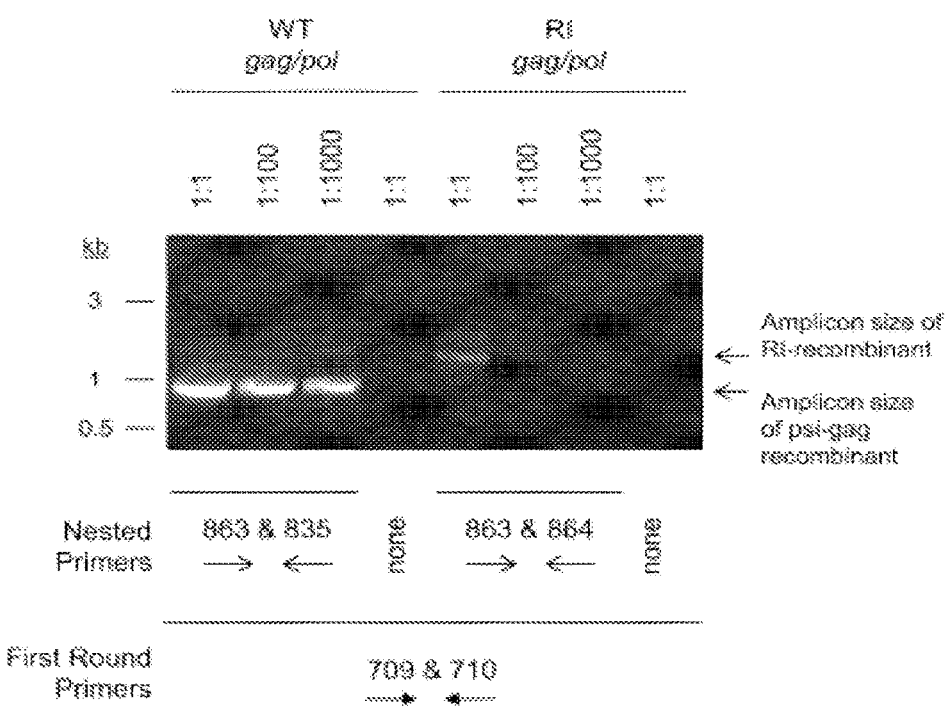
Figure 18A:
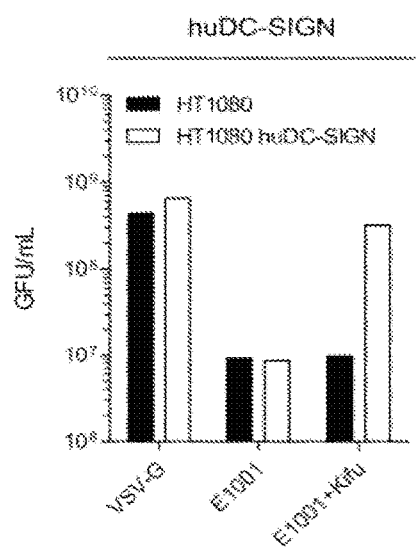
Figure 18B:
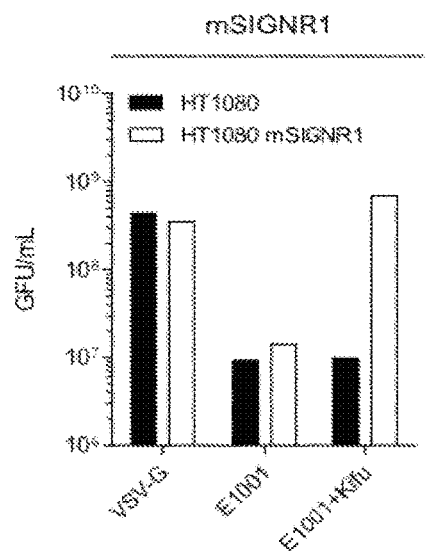
Figures 18C, 18D:
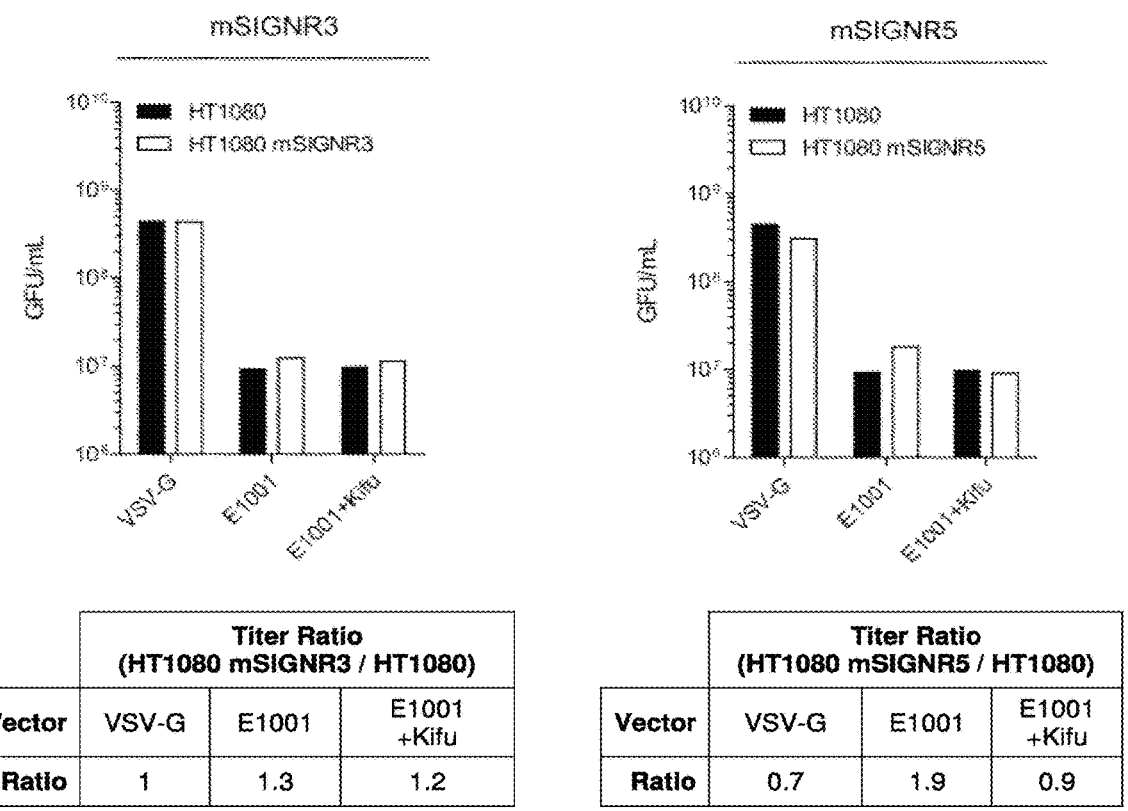

FIG. 17A: 293T cells were transduced with either WT gag/pol or RI gag/pol vectors. Two days later, genomic DNA was isolated and analyzed for integrated proviral DNA by PCR using primer pair 709 and 378 that binds within the vector genome as schematized in FIG. 12. PCR products were visualized on a 1% agarose gel. The amplicon size of the vector genome is indicated with an arrow. No template control was included in the PCR and gel. FIG. 17B: Genomic DNA from FIG. 17A was analyzed for proviral psi-gag recombinants with first round PCR followed by nested PCR. The first round PCR used primer pairs 709 and 710 that bind in the vector genome and the frameshift within gag/pol respectively. 1 μl of the first round PCR product was used as template either undiluted (1:1), or with 1:100, or 1:1000 dilutions in a nested PCR. Primer pairs for nested PCR were either 863 and 835, or 863 and 864. The former pair (863, 835) binds in the vector genome and the WT gag/pol respectively. The latter pair (863, 864) binds in the vector genome and the RI gag/pol. All primers and their binding sites are schematized in FIG. 12. Template only controls were included. Resulting nested PCR products were visualized on a 1% agarose gel. The amplicon size of the psi-gag recombinant is shown with an arrow. FIG. 17C: The band from the nested PCR for WT gag/pol (the bright band below 1 kb) was cloned into a TOPO-TA vector and sequenced. Sequence of the WT gag/pol psi-gag recombinant band is shown with regions marked for aligning with the vector genome, partial gag or WT gag/pol. Double slashes (//) and dots indicate sequences not shown for simplicity. Numbers on sequence indicate nucleotide position on the amplicon. Base pairs 1-414 of the psi-gag recombinant aligns with the vector genome, while bp 120-937 aligns with the WT gag/pol. For reference, the partial gag sequence is bp 76-439 of the recombinant. FIG. 17D: The band from nested PCR for the RI gag/pol (faint band between 1 kb and 3 kb) was cloned into a TOPO-TA vector and sequenced. Sequence of the RI gag/pol recombinant band is shown with regions marked for aligning with the vector genome or the RI gag/pol. Dots indicate sequences not shown for simplicity. Numbers on sequence indicate nucleotide position on the amplicon. Base pairs 1-1253 of the RI recombinant aligns with the vector genome, while bp 1254-1329 aligns with the RI gag/pol. For reference, the partial gag sequence is bp 76-439 of the recombinant. Full sequence and alignment are shown in (Supplementary Figure S1B).

FIGS. 18A-18D: HT1080 cells and HT1080 cells stably expressing (FIG. 18A) human DC-SIGN (HT1080 huDC-SIGN), (FIG. 18B) mouse SIGNR1 (HT1080 mSIGNR1), (FIG. 18C) mouse SIGNR3 (HT1080 mSIGNR3), or (FIG. 18D) mouse SIGNR5 (HT1080 mSIGNR5), were incubated with concentrated (1,000-fold) integration-deficient VSV-G pseudotyped vector encoding GFP, or ID-VP02 pseudotyped vectors encoding GFP that were produced either in the absence or presence of kifunensine (kifu).

Figure 19A:
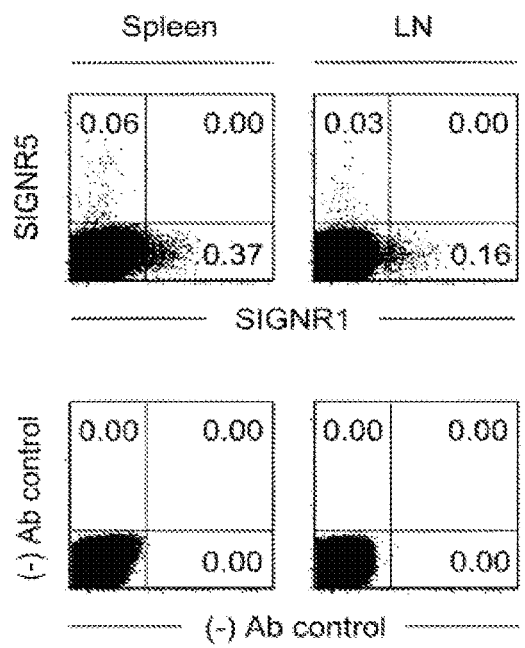
Figure 19B:
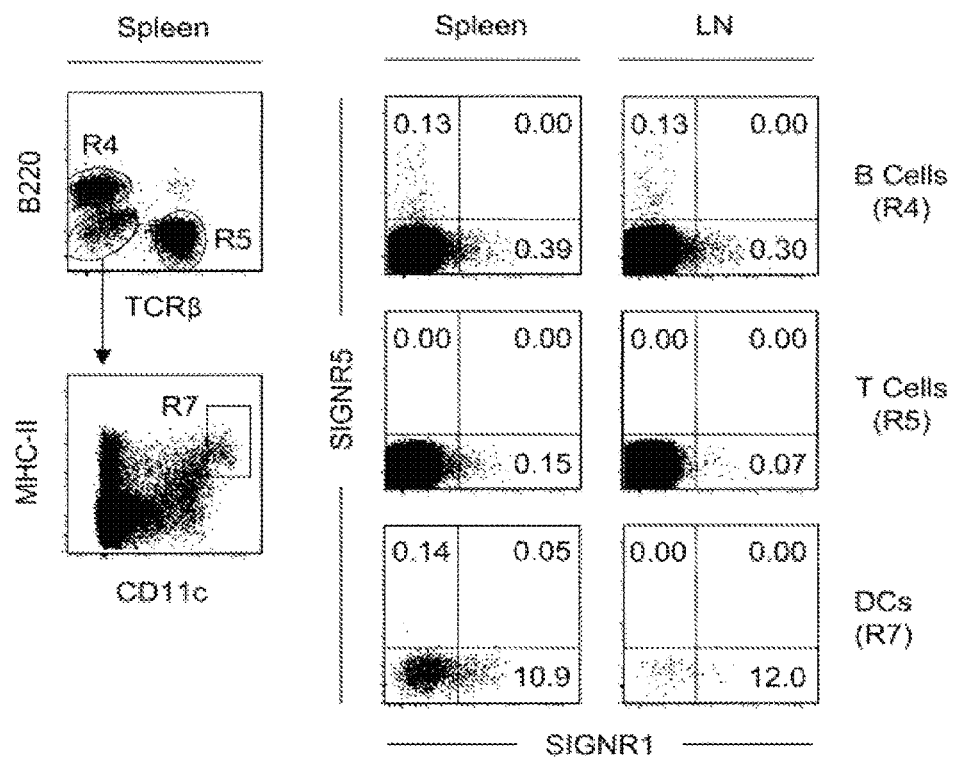

FIG. 19A: The expression of SIGNR1 and SIGNR5 on spleen and lymph cells was analyzed on live, single cell events. Control staining pattern lacking SIGNR1 or SIGNR5-specific antibodies is shown. FIG. 19B: Live, single cell events from spleen and lymph node were subdivided into B cells (B220+ TCRβ−, labeled R4), T cells (TCRβ+, B220−, labeled R5), and DCs (B220−TCRβ− MHC-II+ CD11c$^{hi}$, labeled R7) and subsequently analyzed for expression of SIGNR5 and SIGNR1. For all subsets, frequencies of positive events were ≤0.00 in negative control stains lacking SIGNR1- and SIGNR5-specific antibodies.

FIGS. 20A-20C: The phenotype of GFP-expressing cells in the draining lymph node after subcutaneous injection with GFP-encoding ID-VP02 was analyzed by flow cytometry. Female BALB/c mice (15 per group) were injected subcutaneously in the footpad with $3 \times 10^{10}$ genomes of ID-VP02 encoding GFP, control ID-VP02 encoding a non-fluorescent protein, or left untreated. Four days later, the popliteal and cervical lymph nodes were separately pooled from 5 mice (3 pools per treatment group) and analyzed for the presence of GFP-expressing cells. (FIG. 20A) Live, singlet events from the popliteal (draining) or cervical (non-draining) lymph nodes were analyzed for GFP expression. Popliteal lymph node cells from naïve or negative control ID-VP02 served as negative controls. (FIG. 20B) Frequency of CD11c and MHC-II on GFP+ events from the popliteal lymph nodes of mice injected with GFP-encoding ID-VP02 are shown as black dots overlayed on total B220− TCRβ− events, shown in gray, as a reference. (FIG. 20C) Expression of SIGNR1 on GFP+ CD11c+ MHC-II+ events, shown with (left panel) and without (right panel) inclusion of SIGNR1-specific antibody. Gate statistics are the mean value of three biological replicates. Values in panel (FIG. 20A) are number of positive events per $1 \times 10^6$ cells, whereas all other gate values are percentages.

Figure 21:
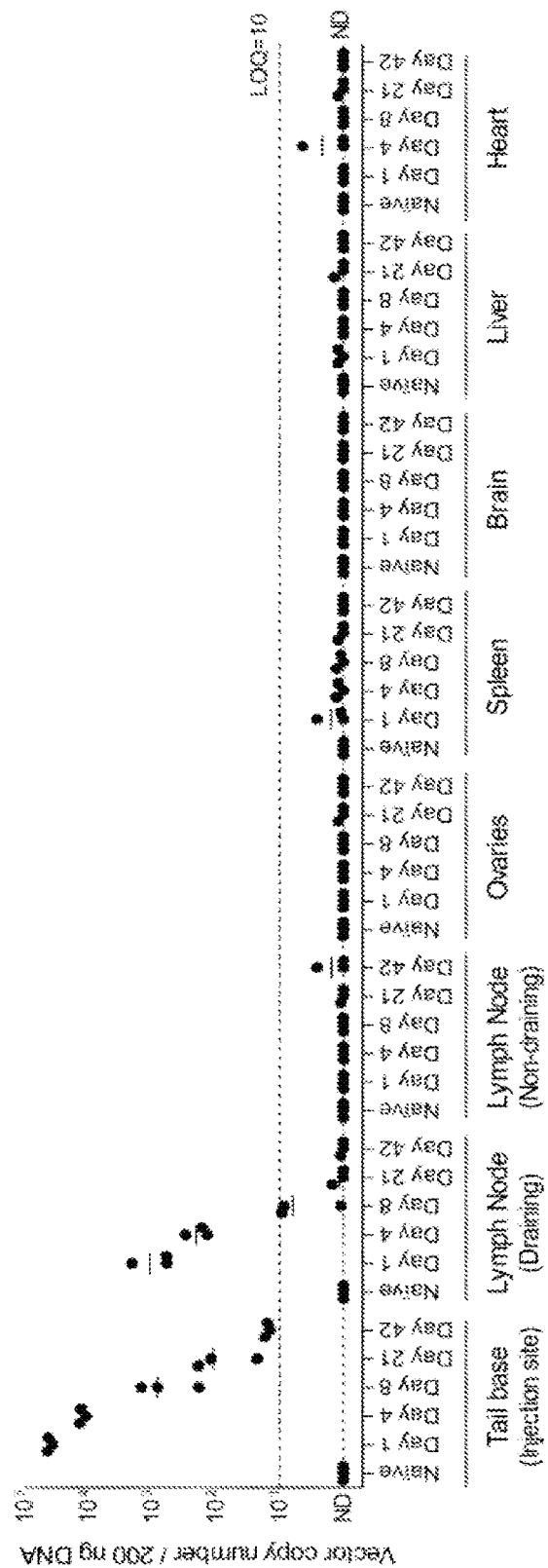

FIG. 21: C57BL/6 mice (3 per group) received a single subcutaneous injection of $3 \times 10^{10}$ genomes of ID-VP02 at the base of the tail. Biodistribution, as determined by the presence of reverse-transcribed vector DNA, of ID-VP02 in the indicated tissues was evaluated by quantitative PCR at 1, 4, 8, 21, or 42 days post-injection. Inguinal and cervical lymph nodes are indicated as draining and non-draining, respectively. Input DNA was normalized to 200 ng. The limit of quantitation (LOQ) of 10 copies per reaction was defined by the lowest copy number on the standard curve. Samples that did not amplify within 40 qPCR cycles were designated as not detected (ND).

FIGS. 22A-22E: (FIG. 22A) C57BL/6 mice were immunized with indicated doses (vector genomes) of ID-VP02 encoding full-length OVA or HBSS vehicle alone. At day 12 post immunization, the percentage of $OVA_{257}$-specific splenic CD8 T cells was measured by ICS. (FIG. 22B) The kinetics of the primary and secondary CD8 T cell response to ID-VP02 encoding OVA was determined by immunizing mice (5 per group) with $1 \times 10^{10}$ genomes of ID-VP02 in a prime-boost regimen with a 35 day interval and analyzing splenic CD8 T cell responses at the indicated timepoints. Immunizations were staggered such that all groups were analyzed by ICS on the same day. (FIG. 22C) Representative intracellular IFN-γ, TNF-α, and IL-2, and surface CD107a staining on viable CD8 T cells after peptide restimulation. (FIG. 22D) Frequency of CD8 T cells expressing combinations of IFN-γ, TNF-α, IL-2, and CD107a around the peak and post contraction of the primary and secondary responses. Negligible numbers of CD8 T cells that were IFN-γ negative expressed any other effector molecule. (FIG. 22E) The effector/memory phenotype of CD44$^{hi}$ H-2K$^b$-$OVA_{257}$ pentamer+ CD8 T cells was assessed by staining with CD127 and KLRG1 at the indicated timepoints.

FIGS. 23A-23D: (FIG. 23A) Experimental schedule: C57BL/6 mice (5 per group) were immunized with $5 \times 10^{10}$, $1 \times 10^{10}$, or $2 \times 10^9$ vector genomes of ID-VP02 encoding a polyepitope antigen (LV1b) that contains the H-2$^b$-restricted $OVA_{257}$ and LCMV GP33 CD8 T cell epitopes and then challenged on day 35 post-immunization with $1 \times 10^7$ TCID50 wild-type WR-strain vaccine virus (VV-WT), WR-strain recombinant OVA vaccine virus (rVV-OVA), or left unchallenged. On day 40 (day 5 post-challenge) splenic CD8 T cell responses and viral load in the ovaries were measured. (FIG. 23B) $OVA_{257}$− and LCMV GP33-specific CD8 T cell responses were measured by staining for intracellular IFN-γ and TNF-α after ex vivo peptide restimulation. Representative dot plots of the CD8 T cell cytokine profile is shown. (FIG. 23C) Frequency of $OVA_{257}$-specific IFN-γ+ CD8 T cells for each animal. (FIG. 23D) Viral load (measured by TCID$_{50}$ assay) within the ovaries of each animal.

FIGS. 24A-24D: (FIG. 24A) BALB/c mice (5 per group) were immunized with indicated doses, in vector genomes, of ID-VP02 encoding AH1A5, a heteroclitic mutant of the endogenous CT26 tumor rejection epitope AH1, linked to OVA (OVA-AH1A5) or HBSS vehicle alone. At day 12 post immunization, the percentage of AH1A5- or AH1-specific splenic CD8 T cells was measured by ICS. (FIG. 24B) Twelve days after immunization, a 1:1:1 mixture of dye-labeled target cells each pulsed with AH1, AH1A5, or a control peptide were transferred intravenously into immunized and naive mice (3 per group). The following day, spleens were harvested and the relative recovery of each population was compared between naïve and immunized mice to calculate specific killing. (FIG. 24C) BALB/c mice (10 per group) were immunized with $4 \times 10^9$ vector genomes of ID-VP02 encoding OVA-AH1A5. Four weeks later, mice were injected subcutaneously with $8 \times 10^4$ CT26 tumor cells on the right flank and mice were euthanized when tumors exceeded 100 mm$^2$. (FIG. 24D) Therapeutic immunization: BALB/c mice (10 per group) were injected subcutaneously with 8×10⁴ CT26 tumor cells. Four days later, mice were either immunized with 4×10⁹ vector genomes of ID-VP02 encoding OVA-AH1A5 or left untreated and mice were euthanized when tumors exceeded 100 mm².

DETAILED DESCRIPTION

This disclosure relates to methods and materials useful for generating pseudotyped lentiviral vector particles that efficiently bind to and productively infect cells expressing DC-SIGN (e.g., dendritic cells). The methods and materials in this disclosure relate to the unexpected discovery that the combination of a Vpx protein in a lentiviral vector particle with highly mannosylated (e.g., by culturing the virus packaging cells in the presence of kifunensine) alphavirus glycoproteins (e.g., Sindbis virus glycoproteins) in the envelope results in lentiviral vector particles that infect non-dividing cells expressing DC-SIGN (e.g., dendritic cells) significantly more efficiently than lentiviral vector particles that either lack a Vpx protein or highly mannosylated glycoproteins in the envelope. One advantageous aspect of the disclosure is that lentiviral vector particles pseudotyped with a Sindbis virus E2 glycoprotein and produced in the presence of kifunensine infect dendritic cells significantly more efficiently if the particles also comprise a Vpx protein in the virion, thus allowing for delivery and expression of a sequence of interest (e.g., a polynucleotide encoding an antigen) to a dendritic cell.

Definitions

The term "functional fragment" when used in reference to a polypeptide means a polypeptide that is truncated, i.e., missing one or more amino acids from the N-terminus or C-terminus, and that retains the desired activity. When used in reference to a Vpx protein, "functional fragment" means a fragment that retains the ability to inhibit the activity of SAMHD1. The term may analogously be applied to polynucleotides that are truncated.

The term "variant" when used in reference to a polypeptide means a polypeptide that has one or more substitutions, deletions or insertions relative to a parent polypeptide. In some contexts, the variant is one that retains the desired activity. When used in reference to a Vpx protein, "functional variant" means a variant that retains the ability to inhibit the activity of SAMHD1. The term may analogously be applied to polynucleotides that have one or more substitutions, deletions or insertions relative to a parent polynucleotide.

As used herein, the term "conservative amino acid substitution" is the replacement of one amino acid with another amino acid having similar properties, e.g. size, charge, hydrophobicity, hydrophilicity, and/or aromaticity, and includes exchanges as indicated below:

| Original | Exemplary |
| --- | --- |
| Ala (A) | val; leu; ile |
| Arg (R) | lys; gln; asn |
| Asn (N) | gln; his; asp, lys; gln |
| Asp (D) | glu; asn |
| Cys (C) | ser; ala |
| Gln (Q) | asn; glu |
| Glu (E) | asp; gln |
| Gly (G) | ala |
| His (H) | asn; gln; lys; arg |

| Original | Exemplary |
| --- | --- |
| Ile (I) | leu; val; met; ala; phe; norleucine |
| Leu (L) | norleucine; ile; val; met; ala; phe |
| Lys (K) | arg; gln; asn |
| Met (M) | leu; phe; ile |
| Phe (F) | leu; val; ile; ala; tyr |
| Pro (P) | ala |
| Ser (S) | thr |
| Thr (T) | ser |
| Trp (W) | tyr; phe |
| Tyr (Y) | trp; phe; thr; ser |
| Val (V) | ile; leu; met; phe; ala; norleucine |

Amino acid residues which share common side-chain properties are often grouped as follows.
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

As used herein, the terms "integration deficient" and "integration defective" are used interchangeably. An integration deficient viral vector is one that is at least 10-fold (preferably, at least 20-fold, at least 30-fold, at least 40-fold, at least 50-fold, at least 60-fold, at least 70-fold, at least 80-fold, at least 90-fold, at least 100-fold, at least 150-fold, at least 200-fold, at least 250-fold, at least 300-fold, at least 350-fold, at least 400-fold, at least 450-fold, at least 500-fold, at least 550-fold, at least 600-fold, at least 650-fold, at least 700-fold, at least 750-fold, at least 800-fold, at least 850-fold, at least 900-fold, at least 950-fold, or at least 1000-fold) less efficient at integrating than an integration-competent viral vector. For example, integration-deficient may mean at least about 20-fold to about 100-fold less efficient at integrating than a viral vector which has not been modified to be integration defective. Integration can be measured by any method known in the art, e.g., by PCR detection of integration events near an Alu element.

A "pseudotyped" lentivirus is a lentiviral particle having one or more envelope glycoproteins that are encoded by a virus that is distinct from the lentiviral genome. The envelope glycoprotein may be modified, mutated or engineered as described herein.

As used herein, the term "exogenous antigen" refers to an antigen that has been genetically engineered to be expressed in the lentiviral vectors disclosed herein. Accordingly, the term explicitly includes antigens derived from HIV that have been genetically engineered to be expressed in the lentiviral vectors disclosed herein.

As used herein, a Sindbis E2 glycoprotein that "preferentially binds dendritic cells expressing DC-SIGN" is a glycoprotein that binds dendritic cells expressing DC-SIGN more efficiently than cells that do not express DC-SIGN.

The Sindbis virus envelope protein contains four N-linked glycans—two on the E2 protein and two on the E1 protein. Two N-glycans of the virus produced in mammalian cells in the absence of a mannosidase I inhibitor have a high-mannose structure (one E2 N-linked glycan and one E1 N-linked glycan), while the remaining two have a complex structure. The two complex structure N-glycans are exposed on the surface of the envelope protein, while the two high-mannose structure N-glycans are buried within the center of the trimer of the envelope proteins. See Morizono et al., *J Virol,* 84:14, 6923-34 (2010), incorporated by reference. Accordingly, typically 50% of the N-linked glycans on a viral particle with a Sindbis virus glycoprotein produced in mammalian cells would have the high-mannose structure. A "highly mannosylated" viral particle is a particle wherein at least 60%, at least 70%, at least 80%, at least 90%, at least 95%, at least 99%, or 100% of N-linked glycans on the viral envelope glycoproteins comprise at least a $Man_5$ structure, preferably $Man_9$, measured by, for example, mass spectrometry (see Crispin et al., JBC 2009).

SAMHD1 Inhibitors

Vpx and Vpr

In some or any embodiments, the SAMHD1 inhibitor is a Vpx protein or a Vpr protein. Vpx is encoded by viruses of the HIV-2, SIV sooty mangabey (SIVsm), SIV red capped mangabey (SIVrcm), and SIV macaque (SIVmac), among others. Vpx of HIV-2 and SIV is a 112-amino-acid (aa), 18-kDa protein and is packaged in the virion in significant quantities through its interaction with the p6 region of the $p55^{gag}$ precursor. Vpx was recently shown to inhibit the activity of a restriction factor expressed in human dendritic and myeloid cells, SAMHD1. Laguette et al., *Nature,* 474, 654-657 (2011). SAMHD1 was identified as the restriction factor that renders human dendritic and myeloid cells largely refractory to HIV-1 infection.

Vpx from SIV and HIV-2 are 83% identical at the amino acid level. See Goujon et al., *J Virol,* 82:24, 12335-12345 (2008). Accordingly, it may be assumed that residues that differ between SIV and HIV-2 are not important for Vpx function. Moreover, mutational analysis of Vpx from SIV and HIV-2 has been carried out by others and can be used as a guide in generating Vpx variants for use in the materials and methods of this disclosure. See Goujon et al. Asn26Ala, Ser52Ala, and Ser63Ala/Ser65Ala mutants do not affect Vpx function. Deletion of the proline-rich C-terminal 11 residue, Ser13Ala, Lys84Ala/Lys85Ala, Thr17Ala, Thr28Ala, Gly86Ala/Cys87Ala, Ser13 Ala/Thr17Ala/Thr28Ala, His39Ala, and Tyr66Ala/Tyr68Ala/Tyr71Ala, Trp49Ala/Trp53Ala/Trp56Ala, and Lys68Ala/Lys77Ala mutations abolish Vpx activity.

In some or any embodiments, the lentiviral vector particles described herein comprise a Vpx protein or a variant thereof. In some or any embodiments, the variant retains the ability to inhibit SAMHD1. In some or any embodiments, the variant comprises an amino acid sequence at least 75%, 80%, 85%, 90% or 95% identical to SEQ ID NO: 45 (SIVsm Vpx). In some or any embodiments, the variant comprises an amino acid sequence at least 75%, 80%, 85%, 90% or 95% identical to SEQ ID NO: 46 (SIVrcm Vpx). In some or any embodiments, the variant comprises an amino acid sequence at least 75%, 80%, 85%, 90% or 95% identical to SEQ ID NO: 44 (SIVmac Vpx). In some or any embodiments, the variant comprises an amino acid sequence at least 75%, 80%, 85%, 90% or 95% identical to SEQ ID NO: 47 (HIV-2).

The anti-SAMHD1 activity of Vpx has been localized to the N-terminal 86 residues of Vpx. Gramberg et al., *J Virol,* 84:3, 1387-1396. Accordingly, in some or any embodiments, the functional fragment comprises the SAMHD1 inhibitory region of Vpx, i.e., amino acid residues 1 through 86 of SEQ ID NO: 44.

While Vpx is only present in some lentiviruses, all primate lentiviruses encode a gene closely related to Vpx called Vpr. Vpr is known to cause cell-cycle arrest. Recently, however, Vpr proteins isolated from SIVdeb and SIVmus were shown to inhibit human SAMHD1. Lim et al., *Cell Host & Microbe,* 11, 194-204 (2012). Accordingly, in some or any embodiments, the lentiviral vector particles described herein comprise a SAMHD1-inhibiting Vpr protein or a variant thereof that retains the ability to inhibit SAMHD1. In some or any embodiments, the variant comprises an amino acid sequence at least 75%, 80%, 85%, 90% or 95% identical to SEQ ID NO: 48 (SIVdeb Vpr). In some or any embodiments, the variant comprises an amino acid sequence at least 75%, 80%, 85%, 90% or 95% identical to SEQ ID NO: 49 (SIVmus Vpr).

Information from sequence alignments of Vpx proteins can be used to generate functional variants and functional fragment variants of Vpx, as defined above. Techniques for deleting and mutating amino acids are well known in the art. See Ausubel, F. M. et al., *Current Protocols in Molecular Biology,* John Wiley & Sons, (1998), including all supplements through 2011. Generally, to construct functional variants, either non-conservative or conservative substitutions or deletions can be introduced at the positions that differ between viruses encoding a Vpx protein, as these positions tend to be permit non-conservative substitutions while retaining function. For positions with amino acid residues conserved across viruses, the residue is either retained or conservative substitutions are introduced. Vpx, Vpr and variants thereof are tested for the ability to inhibit the activity of SAMHD1 according to the methods disclosed herein or known in the art. See Lim et al., *Cell Host & Microbe,* 11, 194-204 (2012) and Lahouassa et al., *Nature Immunol,* 13:3, 223-229 (2012), incorporated by reference in their entirety.

Despite previous reports indicating that packaging of SIVmac Vpx into HIV-1 virions required modification of the p6 region of the Gag protein to resemble the SIVmac p6 (Sunseri et al., *J Virol,* 86:6 (2012)), the inventors have unexpectedly discovered that SIVmac Vpx is efficiently packaged into the HIV-1-based pseudotyped lentiviral vectors disclosed herein without the need for modifying p6 or fusing Vpx to HIV-1 Vpr. Accordingly, in some or any embodiments, the Vpx protein is not fused to a Vpr protein. Similarly, in some or any embodiments, the gag protein in the packaging cell is not modified from its native sequence.

In some or any embodiments, the Vpx protein is fused to HIV-1 Vpr protein.

Typically, the Vpx protein is packaged in the viral particle. However, in some or any embodiments, a gene encoding a Vpx protein is included on the lentiviral genome and is expressed when the viral particle infects a target cell.

Viral Vector Envelope

Arthropod-borne viruses (Arboviruses) are viruses that are transmitted to a host, such as humans, horses, or birds by an infected arthropod vector such as a mosquito. Arboviruses are further divided into sub-families of viruses including alphaviruses and flaviviruses, which have a single-stranded RNA genome of positive polarity and a glycoprotein-containing envelope. For example, dengue fever virus, yellow fever virus and West Nile virus belong to the flavivirus family, and Sindbis virus, Semliki Forest virus and Venezuelan Equine Encephalitis virus, are members of the alphavirus family (Wang et al. J. Virol. 66, 4992 (1992)). The envelope of Sindbis virus includes two transmembrane glycoproteins (Mukhopadhyay et al. *Nature Rev. Microbio.* 3, 13 (2005)): E1, believed to be responsible for fusion, and E2, believed to be responsible for cell binding. Sindbis virus envelope glycoproteins are known to pseudotype other retroviruses, including oncoretroviruses and lentiviruses.

The envelope of Sindbis virus and other alphaviruses incorporates into the lipid bilayer of the viral particle membrane, and typically includes multiple copies of two glycoproteins, E1 and E2. Each glycoprotein has membrane-spanning regions; E2 has an about 33 residue cytoplasmic domain whereas the cytoplasmic tail of E1 is very short (about 2 residues). Both E1 and E2 have palmitic acids attached in or near the membrane-spanning regions. E2 is initially synthesized as a precursor protein that is cleaved by furin or other Ca2+-dependent serine proteinase into E2 and a small glycoprotein called E3. Located between sequences encoding E2 and E1 is a sequence encoding a protein called 6K. E3 and 6K are signal sequences which serve to translocate the E2 and E1 glycoproteins, respectively, into the membrane. In the Sindbis virus genome, the coding region for Sindbis envelope proteins includes sequence encoding E3, E2, 6K, and E1. As used herein, the "envelope" of an arbovirus virus includes at least E2, and may also include E1, 6K and E3. An exemplary sequence of envelope glycoproteins of Sindbis virus, strain HR, is presented as SEQ ID No. 17 (E3, E2, 6K, and E1 polyprotein). Sequences of envelope glycoproteins for other arboviruses can be found in e.g., GenBank. For example, sequence encoding Dengue virus glycoproteins can be found in Accession GQ252677 (among others in GenBank) and in the virus variation database at NCBI (GenBank accessions and virus variation database are incorporated by reference for envelope glycoprotein sequences) and sequence encoding Venezuelan equine encephalitis virus envelope glycoproteins in Accession NP 040824 (incorporated by reference for sequences of envelope glycoproteins).

It is understood that references to a "residue number of the E2 glycoprotein" (such as residue 160, 70, 76 or 159) are defined by reference to the amino acid sequence of the protein of SEQ ID NO: 18, which is the E2 glycoprotein of Sindbis strain HR (i.e., "Sindbis HR reference strain"). For example, if a variant of Sindbis E2 glycoprotein has been produced in which residue 70 has been deleted from SEQ ID NO: 18, then "residue 160" will refer to actual residue 159 of such a variant. Analogous positions in other alphaviruses can be determined through alignments that maximize homology.

The use of the terms "attachment," "binding," "targeting" and the like are used interchangeably and are not meant to indicate a mechanism of the interaction between Sindbis virus envelope glycoprotein and a cellular component. DC-SIGN (Dendritic Cell Specific ICAM-3 (Intracellular Adhesion Molecules 3)-Grabbing Nonintegrin; also known as CD209) is a C-type lectin-like receptor capable of rapid binding and endocytosis of materials (Geijtenbeek, T. B., et al. Annu. Rev. Immunol. 22: 33-54, 2004). E2 appears to target virus to dendritic cells through DC-SIGN. As shown herein, cells expressing DC-SIGN are transduced by viral vector particles pseudotyped with Sindbis virus E2 better (at least 2-fold, at least 3-fold, at least 4-fold, at least 5-fold, at least 6-fold, at least 7-fold, at least 8-fold, at least 9-fold, or at least 10-fold better) than isogenic cells that don't express DC-SIGN. The mechanism of how E2 glycoprotein facilitates viral infection appears to involve DC-SIGN, possibly through direct binding to DC-SIGN or causing a change in conformation or some other mechanism. Regardless of the actual mechanism, the targeting by E2 is preferential for cells expressing DC-SIGN, namely dendritic cells.

Sindbis virus also binds to cells via heparan sulfate (Klimstra et al., *J Virol* 72: 7357, 1998; Burmes and Griffin, *J Virol* 72: 7349, 1998). Because heparan sulfate and other cell surface glycosaminoglycans are found on the surface of most cell types, it is desirable to reduce interaction between heparan sulfate and Sindbis envelope glycoproteins. This can be accomplished by diminishing the binding of Sindbis virus envelope to heparan sulfate or increasing the binding, e.g., increasing avidity, of Sindbis virus envelope to dendritic cells or both. As a result, nonspecific binding to other molecules, which may be expressed by other cell types and which may occur even if the envelope is specific for DC-SIGN, is reduced, and the improved specificity may serve to avoid undesired side effects, such as side effects that may reduce the desired immune response, or side effects associated with off-target transduction of other cell types. Alternatively or in addition to the advantages of relatively specific transduction of cells expressing DC-SIGN, viral particles pseudotyped with Sindbis virus envelope E2 glycoprotein may offer other advantages over viral particles pseudo-typed with glycoproteins such as VSVG. Examples of such advantages include reduced complement-mediated lysis and/or reduced neuronal cell targeting, both of which are believed to associate with administration of VSV-G pseudo-typed viral particles.

In various embodiments, the lentiviral vector particles disclosed herein specifically bind to cells expressing DC-SIGN and have reduced or abrogated binding to heparan sulfate. That is, a Sindbis virus envelope E2 glycoprotein may be modified to preferentially direct the virus to dendritic cells that express DC-SIGN relative to other cell types. Based on information obtained from structural studies and molecular modeling among other studies, variant sequences of envelope proteins, especially E2 and E1 glycoproteins, are designed and generated such that the glycoproteins maintain their functions as envelope proteins, but have the desired binding specificity, avidity, or level of binding. Candidate variant sequences may be created for each glycoprotein and assayed using the methods described below, or other methods known in the art, to identify envelope glycoproteins with the most desirable characteristics.

Certain variant sequences of Sindbis E2 have at least one amino acid alteration at residue 160 as compared to SEQ ID NO: 1 or SEQ ID NO: 18 (E2 Sindbis HR reference sequence). Residue 160 is deleted or changed to an amino acid other than glutamic acid. An alteration is most commonly a substitution of at least one amino acid, but alternatively can be an addition or deletion of one or more amino acids. Preferably, any additional amino acids are few in number and do not comprise an antigenic epitope (e.g., hemagglutinin tag sequence), which may compromise safety. When there are two or more alterations, they can both be of the same type (e.g., substitution) or differing types (e.g., a substitution and a deletion). Multiple alterations can be scattered or located contiguously in the protein sequence.

In some embodiments, variant sequences comprise at least one amino acid alteration in the region of about residue 50 to about residue 180 of Sindbis virus E2 (SEQ ID NO: 18). Within this region are amino acids that are involved with binding to heparan sulfate. By reducing the net positive charge of E2, electrostatic interaction with heparan sulfate can be reduced, resulting in decreased binding to heparan sulfate. Candidate positively charged amino acids in this region include lysines at residues 63, 70, 76, 84, 97, 104, 129, 131, 133, 139, 148, 149, 159 and arginine at residues 65, 92, 128, 137, 157, 170, 172 (Bear et al., Virology 347: 183-190, 2006) of SEQ ID NO: 18. At least several of these amino acids are directly implicated in E2 binding to heparan sulfate. Net positive charge can be reduced by deletion of lysine or arginine or substitution of lysine or arginine with a neutral or negatively charged amino acid. For example, one or more of these lysines and arginines may be replaced with glutamic or aspartic acid. Certain embodiments have at least one substitution of lysine 70, 76 or 159. In cases where E2 is expressed as a polyprotein with E3, the lysine located adjacent to the natural E3/E2 cleavage site is maintained—that is, the recognition sequence and cleavage site is unaltered. Alternatively, the native endopeptidase cleavage site sequence is replaced with a recognition sequence for a different endopeptidase.

Certain variants of Sindbis virus E2 are also modified in a way that positively impacts binding to dendritic cells. Alteration of the glutamic acid found at residue 160 in the reference HR sequence (SEQ ID NO: 18) can improve binding to dendritic cells (see Gardner et al., *J Virol* 74, 11849, 2000, which is incorporated in its entirety). Alterations, such as a deletion of residue 160 or substitution of residue 160 are found in certain variants. In particular variants, a non-charged amino acid is substituted for Glu, in other variants, a non-acidic amino acid is substituted for Glu. Typically, Glu160 is replaced with one of the small or aliphatic amino acids, including glycine, alanine, valine, leucine or isoleucine.

Other variants comprise two or more (e.g., 3, 4, or 5) amino acid alterations. Typically in these variants one of the alterations is Glu 160 and the remaining alteration(s) are changes of one or more of the lysines and arginines in the region spanning residue about 50 to about 180. Certain of the variants comprise an alteration of Glu160 to a non-acidic residue or deletion and one or more alterations of lysine 70, lysine 76, or lysine 159 with a non-basic amino acid. Some specific variants comprise a Glu160 to Gly, Lys 70 to Glu, and Lys 159 to Glu; a Glu 160 to Gly, Lys 70, 76 and 159 to Glu; a deletion of Glu 160 and Lys 70 and 159 to Glu; and a deletion of Glu 160 and Lys 70, 76, and 159 to Glu. In some embodiments, the E2 variant is between 80 and 100% (e.g., 82%, 85%, 87%, 90%, 92%, 95%, 97%, or 99%) identical to any one of SEQ ID NOs: 30-43 [SINvar1-14 E2].

In certain cases, E2 protein is first expressed as a polyprotein in fusion with at least E3 or in fusion with a leader sequence. Regardless of whether the leader sequence is E3 or another sequence, E2 in the viral envelope should be free of the E3 or other leader sequence. In other words, E2 is preferably not an E3/E2 fusion protein. In certain embodiments, E2 is expressed as part of E3-E2-6K-E1 polyprotein. In these embodiments, the polyprotein is between 80 and 100% (e.g., 82%, 85%, 87%, 90%, 92%, 95%, 97%, or 99%) identical to any one of SEQ ID NOs: 3-16 [SINvar1-14 polyprotein]. Sindbis virus naturally expresses E2 as part of a polyprotein and the junction regions for E3/E2, E2/6K, and 6K/E1 have sequences recognized and cleaved by endopeptidases. Normally, the E3/E2 junction is cleaved by furin or a furin-like serine endopeptidase between residues 65 and 66. Furin has specificity for paired arginine residues that are separated by two amino acids. To maintain E3/E2 cleavage by furin, residues 62-66 (RSKRS; SEQ ID NO: 26) should maintain the two arginine residues with two amino acid separation and the serine residue. Alternatively, a different cleavage sequence can be used in place of the E3/E2 furin cleavage sequence or any of the other cleavage sequences. Recognition and cleavage sites can be incorporated for endopeptidases, including, without limitation, aspartic endopeptidases (e.g., cathepsin D, chymosin, HIV protease), cysteine endopeptidases (bromelains, papain, calpain), metalloendopeptidases, (e.g., collagenase, thermolysin), serine endopeptidases (e.g., chymotrypsin, factor IXa, factor X, thrombin, trypsin), streptokinases. The recognition and cleavage site sequences for these enzymes are well known.

Amino acids in Sindbis virus E2, other than those already mentioned, may also be altered. Generally, a variant E2 sequence will have at least 80% sequence amino acid identity to the reference E2 sequence, or it may have at least 82%, at least 85%, at least 87%, at least 90%, at least 92%, at least 95%, or at least 98% sequence identity. In some embodiments, a variant E2 sequence has at least 80% sequence amino acid identity to SEQ ID NO: 30 [SINvar1], or it may have at least 82%, at least 85%, at least 87%, at least 90%, at least 92%, at least 95%, or at least 98% sequence identity. In some embodiments, a variant E2 sequence has at least 80% sequence amino acid identity to SEQ ID NO: 31 [SINvar2], or it may have at least 82%, at least 85%, at least 87%, at least 90%, at least 92%, at least 95%, or at least 98% sequence identity. In some embodiments, a variant E2 sequence has at least 80% sequence amino acid identity to SEQ ID NO: 32 [SINvar3], or it may have at least 82%, at least 85%, at least 87%, at least 90%, at least 92%, at least 95%, or at least 98% sequence identity.

The variant glycoprotein should exhibit biological function, such as the ability to facilitate infection of dendritic cells by a viral particle having an envelope comprising E2. Experiments have identified regions of envelope glycoproteins that appear to have an important role in various aspects of viral assembly, attachment to cell surface, and infection. When making variants, the following information can be used as guidelines. The cytoplasmic tail of E2—approximately residues 408 to 415—is important for virus assembly (West et al. J Virol 80: 4458-4468, 2006; incorporated in its entirety). Other regions are involved in forming secondary structure (approximately residues 33-53); and involved in transport and protein stability (approximately residues 86-119) (Navaratmarajah et al., J Virol 363: 124-147, 2007; incorporated in its entirety). The variant may retain hydrophobic character of a region that spans the membrane, approximately residues 370-380. The variant may retain one or both N-linked glycosylation sites residues NIT (residues 196-198) and NFT (residues 318-320) and may retain one or more of the sites that are palmitoylated (C-396, C416 and C417) (Strauss and Strauss Microbiol Rev 58, 491-562, 1994; pp. 499-509 incorporated). On the other hand, many regions of E2 may be altered without deleterious event. For example, insertions of transposons at many different locations in E2 still resulted in viable virus (Navaratmarajah, ibid).

In certain embodiments, a tag peptide may be incorporated into E3, 6K, or E1 proteins. For some purposes, a tag may be incorporated into E2, but a tag is not desirable for use in a product for administration to human patients. A tag peptide, which is a short sequence (e.g., 5-30 amino acids), can be used to facilitate detection of envelope expression and its presence in viral particles. For detection purposes, a tag sequence will typically be detectable by antibodies or chemicals. Another use for a tag is to facilitate purification of viral particles. A substrate containing a binding partner for the tag can be used to absorb virus. Elution of the virus can be accomplished by treatment with a moiety that displaces the tag from the binding partner or when the tag sequence is in linkage with a cleavable sequence, treatment with the appropriate endopeptidase will conveniently allow release of virus. (See, for example, Qiagen catalog, Factor Xa Protease System). Removal of the tag peptide is generally desirable for safety purposes of the virus particles use in animal subjects. If the tag is not removed, an immune response to the tag may occur.

Suitable tags include, without limitation, FLAG (DYKDDDDK) (SEQ ID NO: 28) (U.S. Pat. No. 4,703,004, incorporated in its entirety), for which antibodies are commercially available, chitin binding protein, maltose binding protein, glutathione-S-transferase, poly(His) (U.S. Pat. No. 4,569,794, incorporated in its entirety), thioredoxiin, HA (hemagglutinin)-tag, among others. Poly(His) can be adsorbed onto affinity media containing bound metal ions, e.g., nickel or cobalt, and eluted with a low pH medium.

The viral particles may be evaluated to determine the specificity of the envelope glycoprotein incorporated into the virus that targets dendritic cells. For example, a mixed population of bone marrow cells can be obtained from a subject and cultured in vitro. Alternatively, isogenic cells lines that express or don't express DC-SIGN can be obtained and used. The recombinant virus can be administered to the mixed population of bone marrow cells or isogenic cell lines, and expression of a reporter gene incorporated into the virus can be assayed in the cultured cells. Certain embodiments may employ a limiting dilution analysis, in which the mixed population of cells is split into separate parts, which are then separately incubated with decreasing amounts of virus (e.g., 2-fold, 5-fold, 10-fold less virus in each part). In some embodiments, at least about 50%, more preferably at least about 60%, 70%, 80% or 90%, still more preferably at least about 95% of infected cells in the mixed cell population are dendritic cells that express DC-SIGN. In certain embodiments, the ratio of infected dendritic cells to infected non-dendritic cells (or non DC-SIGN expressing cells) is at least about 2:1, at least about 3:1, at least about 4:1, at least about 5:1, at least about 6:1, at least about 7:1, at least about 8:1, at least about 9:1, at least about 10:1, at least about 20:1, at least about 30:1, at least about 40:1, at least about 50:1, at least about 100:1, at least about 200:1, at least about 500:1, at least about 1000:1, at least about 5000:1, at least about 10,000:1, or more. For limiting dilution, greater selectivity is typically seen at higher dilutions (i.e., lower amounts) of input virus.

Activity of pseudotyped viral particles can be determined by any of a variety of techniques. For example, a preferred method to measure infectivity efficiency (IU, infectious units) is by administering viral particles to cells and measuring expression of a product encoded in the vector genome. Any product that can be assayed may be used. One convenient type of product is a fluorescent protein, such as green fluorescent protein (GFP). Other products that can be used include proteins expressed on a cell surface (e.g., detection by antibody binding), enzymes, and the like. If the product is an antigen and cells are dendritic cells, infectivity/ activity can be assessed by determining an immune response. Furthermore, it is possible to ascertain side effects in a mammal. The ability to specifically target dendritic cells can also be tested directly, for example, in cell culture as described below.

Viral particles can also be prepared and tested for their selectivity and/or their ability to facilitate penetration of the target cell membrane. Viral particles that have an envelope with unmodified glycoproteins can be used as controls for comparison. Briefly, cells expressing a receptor for an envelope glycoprotein are infected by the virus using a standard infection assay. After a specified time, for example 48 hours post-infection, cells can be collected and the percentage of cells infected by the virus can be determined by flow cytometry, for example. Selectivity can be scored by calculating the percentage of cells infected by virus. Similarly, the effect of a variant envelope glycoprotein on viral titer can be quantified by dividing the percentage of cells infected by virus comprising a variant envelope by the percentage of cells infected by virus comprising the corresponding wild type (unmodified) envelope glycoprotein. A particularly suitable variant will have the best combination of selectivity and infectious titer. Once a variant is selected, viral concentration assays may be performed to confirm that these viruses can be concentrated without compromising activity. Viral supernatants are collected and concentrated by ultracentrifugation. The titers of viruses can be determined by limited dilution of viral stock solution and infection of cells expressing the receptor for the envelope glycoprotein, measuring the expression of a product expressed by the viruses as described above.

The entry of a lentiviral vector particle into a target cell is another type of evaluation of activity. BlaM-Vpr (beta-lactamase Vpr) fusion protein has been utilized to evaluate HIV-1 viral penetration; a fusion of BlaM and a Sindbis virus envelope glycoprotein, such as E1 or an E2/E1 fusion protein can be used to assess the efficacy of an envelope protein in facilitating fusion and penetration into a target cell. Viral particles may be prepared, for example, by transient transfection of packaging cells with one or more vectors comprising the viral elements, BlaM-Vpr, and the variant envelope of interest (and an affinity molecule if appropriate). The resulting viruses can be used to infect cells expressing a molecule the targeting molecule (or affinity molecule) specifically binds in the absence or presence of the free inhibitor of binding (such as an antibody). Cells can then be washed with $CO_2$-independent medium and loaded with CCF2 dye (Aurora Bioscience). After incubation at room temperature to allow completion of the cleavage reaction, the cells can be fixed by paraformaldehyde and analyzed by flow cytometry and microscopy. The presence of blue cells indicates the penetration of viruses into the cytoplasm; fewer blue cells would be expected when blocking antibody is added (Cavrois et al. *Nat Biotechnol* 20: 1151-1154, 2002; incorporated in its entirety).

To investigate whether penetration is dependent upon a low pH, and to identify envelope glycoproteins with the desired pH dependence, $NH_4Cl$ or other compound that alters pH can be added at the infection step ($NH_4Cl$ will neutralize the acidic compartments of endosomes). In the case of $NH_4Cl$, the disappearance of blue cells will indicate that penetration of viruses is low pH-dependent. In addition, to confirm that the activity is pH-dependent, lysosomotropic agents, such as ammonium chloride, chloroquine, concanamycin, bafilomycin A1, monensin, nigericin, etc., may be added into the incubation buffer. These agents elevate the pH within the endosomal compartments (e.g., Drose and Altendorf, *J. Exp. Biol.* 200, 1-8, 1997). The inhibitory effect of these agents will reveal the role of pH for viral fusion and entry. The different entry kinetics between viruses displaying different fusogenic molecules may be compared and the most suitable selected for a particular application.

PCR-based entry assays can be utilized to monitor reverse transcription and measure kinetics of viral DNA synthesis as an indication of the kinetics of viral entry. For example, viral particles comprising a particular envelope protein molecule are incubated with target cells, such as 293T cells, DCs, or any other cells that have been engineered to express, or which naturally express, the appropriate binding partner (receptor) for the envelope protein molecule. Either immediately, or after a time increment (to allow infection to occur), unbound viruses are removed and aliquots of the cells are analyzed for viral nucleic acids. DNA is extracted from these aliquots and subjected to amplification analysis, generally in a semi-quantitative assay, primed with LTR-specific primers. The appearance of LTR-specific DNA products indicates the success of viral entry.

Lentiviral Vector Genome The viral vector particle comprises a genome, which comprises at least one sequence (e.g., 1, 2, 3, 4, or 5) of interest. Other sequences may be included, such as sequences that allow the genome to be packaged into the virus particle and sequences that promote expression of the sequence(s) of interest following transduction of the target cell. The genome can be derived from any of a large number of suitable, available lentiviral genome based vectors, including those identified for human gene therapy applications, such as those described by Pfeifer and Verma (*Annu. Rev. Genomics Hum. Genet.* 2:177-211, 2001; which is incorporated herein by reference in its entirety). For the sake of simplicity, the genome is also referred to as "viral vector genome" or "vector genome."

Backbone

Suitable lentiviral vector genomes include those based on Human Immunodeficiency Virus (HIV-1), HIV-2, feline immunodeficiency virus (FIV), equine infectious anemia virus, Simian Immunodeficiency Virus (SIV) and maedi/visna virus. A desirable characteristic of lentiviruses is that they are able to infect both dividing and non-dividing cells, it is not necessary for target cells to be dividing (or to stimulate the target cells to divide). Generally, the genome and envelope glycoproteins will be based on different viruses, such that the resulting viral vector particle is pseudotyped. Safety features of the vector genome are desirably incorporated. Safety features include self-inactivating LTR and a non-integrating genome.

In some exemplary embodiments, the viral vector genome comprises sequences from a lentivirus genome, such as the HIV-1 genome or the SIV genome. The viral genome construct may comprise sequences from the 5' and 3' LTRs of a lentivirus, and in particular may comprise the R and U5 sequences from the 5' LTR of a lentivirus and an inactivated or self-inactivating 3' LTR from a lentivirus. The LTR sequences may be LTR sequences from any lentivirus from any species. For example, they may be LTR sequences from HIV, SIV, FIV or BIV. Typically, the LTR sequences are HIV LTR sequences.

The vector genome may comprise an inactivated or self-inactivating 3' LTR (Zufferey et al. *J Virol* 72: 9873, 1998; Miyoshi et al., *J Virol* 72:8150, 1998; US2010/0323403, all incorporated in their entirety). A self-inactivating vector generally has a deletion of the enhancer and promoter sequences from the 3' long terminal repeat (LTR), which is copied over into the 5' LTR during vector integration. In one instance, the U3 element of the 3' LTR contains a deletion of its enhancer sequence, the polypurine tract (PPT), the TATA box, Sp1 and NF-kappa B sites. As a result of the self-inactivating 3' LTR, the provirus that is generated following entry and reverse transcription will comprise an inactivated 5' LTR. The rationale is to improve safety by reducing the risk of mobilization of the vector genome and the influence of the LTR on nearby cellular promoters. The self-inactivating 3' LTR may be constructed by any method known in the art. In various embodiments, the pseudotyped lentiviral vector comprises a lentiviral vector genome comprising the sequence of SEQ ID NO: 23. This vector comprises a deletion of the 3' PPT and TATA box. Thus, the vector is self-inactivating such that (a) transcription of the full-length vector genome from reversed transcribed dsDNA vectors in the infected target cell is prevented, (b) the risk of insertional activation that can occur when a 3'LTR can function as a promoter after integration is minimized, and (c) the extended U3 deletion can be complemented by additional, redundant safety mechanisms (e.g., mutation of integrase).

Optionally, the U3 sequence from the lentiviral 5' LTR may be replaced with a promoter sequence in the viral construct, such as a heterologous promoter sequence. This can increase the titer of virus recovered from the packaging cell line. An enhancer sequence may also be included. Any enhancer/promoter combination that increases expression of the viral RNA genome in the packaging cell line may be used. In one example, the CMV enhancer/promoter sequence is used (U.S. Pat. Nos. 5,385,839 and 5,168,062, each of which is incorporated in its entirety).

In certain embodiments, the risk of insertional mutagenesis is minimized by constructing the lentiviral vector genome to be integration defective. A variety of approaches can be pursued to produce a non-integrating vector genome. These approaches entail engineering a mutation(s) into the integrase enzyme component of the pol gene, such that it encodes a protein with an inactive integrase. The vector genome itself can be modified to prevent integration by, for example, mutating or deleting one or both attachment sites, or making the 3' LTR-proximal polypurine tract (PPT) non-functional through deletion or modification. In addition, non-genetic approaches are available; these include pharmacological agents that inhibit one or more functions of integrase. The approaches are not mutually exclusive, that is, more than one of them can be used at a time. For example, both the integrase and attachment sites can be non-functional, or the integrase and PPT site can be non-functional, or the attachment sites and PPT site can be non-functional, or all of them can be non-functional.

As stated above, one approach is to make and use a non-functional integrase. Integrase is involved in cleavage of viral double-stranded blunt-ended DNA and joining the ends to 5'-phosphates in the two strands of a chromosomal target site. Integrase has three functional domains: N-terminal domain, which contains a zinc-binding motif (HHCC), the central domain core, which contains the catalytic core and a conserved DD35E motif (D64, D116, E152 in HIV-1), and a C-terminal domain, which has DNA binding properties. Point mutations introduced into integrase are sufficient to disrupt normal function. Many integrase mutations have been constructed and characterized (see, Philpott and Thrasher, *Human Gene Therapy* 18:483, 2007; Apolonia, Thesis submitted to University College London, April 2009, pp, 82-97; Engelman et al. *J Virol* 69: 2729, 1995; Nightingale et al. Mol Therapy, 13: 1121, 2006; all of which are incorporated in their entirety). The sequence encoding the integrase protein can be deleted or mutated to render the protein inactive, preferably without significantly impairing reverse transcriptase activity or nuclear targeting, thereby only preventing integration of the provirus into the target cell genome. Acceptable mutations can reduce integrase catalysis, strand transfer, binding to att sites, binding to host chromosomal DNA, and other functions. For example, a single aspartic acid to asparagine substitution at residue 35 of HIV or SIV integrase completely abolishes viral DNA integration. Deletions of integrase will generally be confined to the C-terminal domain. Deletion of coding sequence for residues 235-288 result in a useful non-functional integrase (Engelman et al. J Virol 69:2729, 1995). As further examples, mutations can be generated, for example, Asp64 (residue numbers are given for HIV-1, corresponding residue numbers for integrase from other lentiviruses or retroviruses can be readily determined by one of ordinary skill) (e.g., D64E, D64V), Asp116 (e.g., D116N), Asn120 (e.g., N120K), Glu152, Gln148 (e.g., Q148A), Lys156, Lys159, Trp235 (e.g. W235E), Lys264 (e.g., K264R), Lys266 (e.g., K266R), Lys273 (e.g., K273R). Other mutations can be constructed and tested for integration, transgene expression, and any other desirable parameter. Assays for these functions are well known. Mutations can be generated by any of a variety of techniques, including site-directed mutagenesis and chemical synthesis of nucleic acid sequence. One mutation may be made or more than one of these mutations can be present in integrase. For example, an integrase may have mutations at two amino acids, three amino acids, four amino acids, and so on.

Alternatively or in combination with the use of integrase mutant(s), the attachment sites (att) in U3 and U5 can also be mutated. Integrase binds to these sites and the 3'-terminal dinucleotide is cleaved at both ends of the vector genome. A CA dinucleotide is located at the recessed 3' end; the CA is required for processing, mutation of the nucleotides blocks integration into the host chromosome. The A of the CA dinucleotide is the most critical nucleotide for integration, and mutations at both ends of the genome will give the best results (Brown et al *J Virol* 73:9011 (1999). In one exemplification, the CA at each end is changed to TG. In other exemplifications, the CA at each end is changed to TG at one end and GT at the other end. In other exemplifications, the CA at each end is deleted; in other exemplifications, the A of the CA is deleted at each end.

Integration can also be inhibited by mutation or deletion of polypurine tract (PPT) (WO 2009/076524; incorporated in its entirety), located proximally to the 3' LTR. The PPT is a polypurine sequence of about 15 nucleotides that can serve as a primer binding site for plus-strand DNA synthesis. In this case, mutations or deletions of PPT targets the reverse transcription process. Without wishing to be held to a mechanism, by mutating or deleting PPT, production of linear DNA is radically reduced and essentially only 1-LTR DNA circles are produced. Integration requires a linear double-stranded DNA vector genome, and integration is essentially eliminated without it. As stated above, a PPT can be made non-functional by mutation or by deletion. Typically, the entire about 15 nt PPT is deleted, although in some embodiments, shorter deletions of 14 nt, 13, nt, 12 nt, 11 nt, 10 nt, 9 nt, 8 nt, 7 nt, 6 nt, 5 nt, 4 nt, 3 nt and 2 nt may be made. When mutations are made, typically multiple mutations are made, especially in the 5' half of the PPT (McWilliams et al., *J Virol* 77:11150, 2003), although single and double mutations in the first four bases will still reduce transcription. Mutations made at the 3' end of PPT generally have a more dramatic effect (Powell and Levin *J Virol* 70:5288, 1996).

These different approaches to make a vector genome non-integrating can be used individually or in combination. Using more than one approach may be used to build a fail-safe vector through redundant mechanisms. Thus, PPT mutations or deletions can be combined with att site mutations or deletions or with Integrase mutations or PPT mutations or deletions can be combined with both att site mutations or deletions and Integrase mutations. Similarly, att site mutations or deletions and Integrase mutations may be combined with each other or with PPT mutations or deletions.

An additional approach to enhancing the safety of the pseudotyped lentiviral particles involves modifying the plasmid comprising the gag/pol genes to remove sites of potential recombination with the lentiviral vector. This approach can be used individually or in combination with any of the approaches described herein. For example, the gag and pol genes can be mammalian or human "codon optimized", i.e., at least 50%, 60%, 70%, 75%, 80%, 85%, 90% of 95% of the codons of the gag and/or pol genes are replaced with codons that encode the same amino acid but that are preferred by mammalian cells, e.g., human cells, thus improving or optimizing expression in the mammalian, e.g. human, cells. To codon optimize the gag and pol genes, a polynucleotide is generated that alters "wild-type" codons to codons more frequently utilized in the human genome. In HIV, however, certain portions of the genome should retain substantially the original codons (e.g., at least 75%, 80%, 85%, 90%, 95% or 100% of the original codons) in order to permit frameshifting that is required to synthesize Gag and Pol starting from the same initiation codon of its mRNA. Translation of Gag-Pol requires a shift of the reading frame in the 5' direction (−1 shift) at the p7/p1 junction, around codon 432 of the mRNA. Translation of Gag-Pol then proceeds in this new reading frame until a stop codon is reached about 3,000 nucleotides later. Ribosomal-1 frameshifting is a very controlled event requiring both a specific consensus slippery sequence and a downstream secondary RNA structure which causes the ribosome to pause. Thus, according to the present disclosure, the nucleic acid encoding gag and pol contains a "non-optimized window": a region starting at around position 1228 (or starting around position 1218-1298, or 1218-1238, or 1228-1238, or 1218-1228, or 1228-1298, or 1238-1248, or 1248-1258, or 1258-1268, or 1268-1278, or 1278-1288, or 1288-1298) of SEQ ID NO: 54 (the gag-pol open reading frame) and ending at position 1509 (or ending around position 1373-1558, or 1373-1509, or 1373-1500, or 1373-1470, or 1373-1440, or 1373-1410, or 1373-1401, or 1373-1392, or 1373-1383, or 1401-1509, or 1440-1509, or 1499-1519, or 1499-1509, or 1509-1519) of SEQ ID NO: 54 that is not substantially changed from the wild-type gag-pol sequence. In other words, the non-optimized window retains substantially the original codons (e.g., at least 90%, 95%, or 100% of the original codons). It is understood that the non-optimized window corresponding to nucleotides 1228-1509 of SEQ ID NO: 54 may have a different actual nucleotide numbering when SEQ ID NO: 54 is mutated or is part of a larger nucleotide sequence; for example, if a plasmid contains 100 nucleotides 5' to SEQ ID NO: 54, then the non-optimized window will correspond to nucleotides 1328-1609 in the plasmid. In some embodiments, the region from nucleotides 1229 to 1298 retains substantially the original codons, and/or the region from nucleotides 1510-1558 is codon optimized. In some embodiments, the codon optimized polynucleotide encoding Gag and Pol comprises SEQ ID NO: 54. In some embodiments, the plasmid encoding the codon optimized gag-pol polynucleotide comprises the sequence of SEQ ID NO: 55.

In some or any embodiments, the plasmid encoding the human codon optimized gag and pol genes (and comprising the non-optimized window described above) also lacks a Rev responsive element (RRE). Deletion of the RRE removes yet another region of homology and potential recombination between the gag/pol plasmid and the lentiviral vector plasmid. In combination, such an approach eliminates or minimizes regions of homology between the gag/pol plasmid and the lentiviral vector, thus minimizing the chances for recombination between these plasmids that could result in a replication-competent virus. It is understood that the RRE may still be present in the packaging cell and process, but is present on a different plasmid.

Regulatory Elements

As discussed herein, the viral vector genome comprises a sequence of interest that is desirable to express in target cells. Typically, the sequence of interest is located between the 5' LTR and 3' LTR sequences. Further, the sequence of interest is preferably in a functional relationship with other genetic elements, for example transcription regulatory sequences including promoters or enhancers, to regulate expression of the sequence of interest in a particular manner. In certain instances, the useful transcriptional regulatory sequences are those that are highly regulated with respect to activity, both temporally and spatially. Expression control elements that may be used for regulating the expression of the components are known in the art and include, but are not limited to, inducible promoters, constitutive promoters, secretion signals, enhancers and other regulatory elements.

The sequence of interest and any other expressible sequence is typically in a functional relationship with internal promoter/enhancer regulatory sequences. An "internal" promoter/enhancer is one that is located between the 5' LTR and the 3' LTR sequences in the viral vector construct and is operably linked to the sequence of interest. The internal promoter/enhancer may be any promoter, enhancer or promoter/enhancer combination known to increase expression of a gene with which it is in a functional relationship. A "functional relationship" and "operably linked" mean, without limitation, that the sequence is in the correct location and orientation with respect to the promoter and/or enhancer that the sequence of interest will be expressed when the promoter and/or enhancer is contacted with the appropriate molecules.

The choice of an internal promoter/enhancer is based on the desired expression pattern of the sequence of interest and the specific properties of known promoters/enhancers. Thus, the internal promoter may be constitutively active. Non-limiting examples of constitutive promoters that may be used include the promoter for ubiquitin (U.S. Pat. No. 5,510,474; WO 98/32869, each of which is incorporated herein by reference in its entirety), CMV (Thomsen et al., *PNAS* 81:659, 1984; U.S. Pat. No. 5,168,062, each of which is incorporated herein by reference in its entirety), beta-actin (Gunning et al. 1989 *Proc. Natl. Acad. Sci. USA* 84:4831-4835, which is incorporated herein by reference in its entirety) and pgk (see, for example, Adra et al. 1987 *Gene* 60:65-74; Singer-Sam et al. 1984 Gene 32:409-417; and Dobson et al. 1982 *Nucleic Acids Res.* 10:2635-2637, each of the foregoing which is incorporated herein by reference in its entirety). In some embodiments, the promoter used to control expression of the antigens encoded by the pseudotyped lentiviral vector genome is an intron-deficient promoter. In some embodiments, the human Ubiquitin-C (UbiC) promoter is used to control expression of the antigens encoded by the pseudotyped lentiviral vector genome. In various embodiments, the UbiC promoter has been modified to remove introns, i.e., the promoter is intron deficient. The full-length UbiC promoter is 1250 nucleotides. The intron begins at 412 and goes all the way to the end (412-1250). This region can be deleted for the purpose of minimizing heterogeneous viral genomic transcripts. The HIV viral genome has a native intron within it. Thus, a lentivirus comprising a UbiC promoter would have a total of 2 introns in the lentivirus genome. The UbiC intron can exist in both spliced and unspliced forms. Deletion of the UbiC intron eliminates the possibility of heterogenous viral transcripts and ensures homogeneity in the delivered pseudotyped lentiviral particles.

Alternatively, the promoter may be a tissue specific promoter. In some preferred embodiments, the promoter is a target cell-specific promoter. For example, the promoter can be from any product expressed by dendritic cells, including CD11c, CD103, TLRs, DC-SIGN, BDCA-3, DEC-205, DCIR2, mannose receptor, Dectin-1, Clec9A, MHC classII. In addition, promoters may be selected to allow for inducible expression of the sequence of interest. A number of systems for inducible expression are known in the art, including the tetracycline responsive system, the lac operator-repressor system, as well as promoters responsive to a variety of environmental or physiological changes, including heat shock, metal ions, such as metallothionein promoter, interferons, hypoxia, steroids, such as progesterone or glucocorticoid receptor promoter, radiation, such as VEGF promoter. A combination of promoters may also be used to obtain the desired expression of the gene of interest. The artisan of ordinary skill will be able to select a promoter based on the desired expression pattern of the gene in the organism or the target cell of interest.

The viral genome may comprise at least one RNA Polymerase II or III responsive promoter. This promoter can be operably linked to the sequence of interest and can also be linked to a termination sequence. In addition, more than one RNA Polymerase II or III promoters may be incorporated. RNA polymerase II and III promoters are well known to one of skill in the art. A suitable range of RNA polymerase III promoters can be found, for example, in Paule and White, Nucleic Acids Research, Vol. 28, pp 1283-1298 (2000), which is incorporated herein by reference in its entirety. RNA polymerase II or III promoters also include any synthetic or engineered DNA fragment that can direct RNA polymerase II or III to transcribe downstream RNA coding sequences. Further, the RNA polymerase II or III (Pol II or III) promoter or promoters used as part of the viral vector genome can be inducible. Any suitable inducible Pol II or III promoter can be used with the methods of the disclosure. Particularly suited Pol II or III promoters include the tetracycline responsive promoters provided in Ohkawa and Taira, Human Gene Therapy, Vol. 11, pp 577-585 (2000) and in Meissner et al. Nucleic Acids Research, Vol. 29, pp 1672-1682 (2001), each of which is incorporated herein by reference in its entirety.

An internal enhancer may also be present in the viral construct to increase expression of the gene of interest. For example, the CMV enhancer (Boshart et al. *Cell,* 41:521, 1985; which is incorporated herein by reference in its entirety) may be used. Many enhancers in viral genomes, such as HIV, CMV, and in mammalian genomes have been identified and characterized (see GenBank). An enhancer can be used in combination with a heterologous promoter. One of ordinary skill in the art will be able to select the appropriate enhancer based on the desired expression pattern.

A viral vector genome will usually contain a promoter that is recognized by the target cell and that is operably linked to the sequence of interest, viral components, and other sequences discussed herein. A promoter is an expression control element formed by a nucleic acid sequence that permits binding of RNA polymerase and transcription to occur. Promoters may be inducible, constitutive, temporally active or tissue specific. The activity of inducible promoters is induced by the presence or absence of biotic or abiotic factors. Inducible promoters can be a useful tool in genetic engineering because the expression of genes to which they are operably linked can be turned on or off at certain stages of development of an organism, its manufacture, or in a particular tissue. Inducible promoters can be grouped as chemically-regulated promoters, and physically-regulated promoters. Typical chemically-regulated promoters include, not are not limited to, alcohol-regulated promoters (e.g., alcohol dehydrogenase I (alcA) gene promoter), tetracycline-regulated promoters (e.g., tetracycline-responsive promoter), steroid-regulated promoter (e.g., rat glucocorticoid receptor (GR)-based promoter, human estrogen receptor (ER)-based promoter, moth ecdysone receptor-based promoter, and the promoters based on the steroid/retinoid/thyroid receptor superfamily), metal-regulated promoters (e.g., metallothionein gene-based promoters), and pathogenesis-related promoters (e.g., *Arabidopsis* and maize pathogen-related (PR) protein-based promoters). Typical physically-regulated promoters include, but are not limited to, temperature-regulated promoters (e.g., heat shock promoters), and light-regulated promoters (e.g., soybean SSU promoter).

One of skill in the art will be able to select an appropriate promoter based on the specific circumstances. Many different promoters are well known in the art, as are methods for operably linking the promoter to the gene to be expressed. Both native promoter sequences and many heterologous promoters may be used to direct expression in the packaging cell and target cell. Heterologous promoters are preferred, however, as they generally permit greater transcription and higher yields of the desired protein as compared to the native promoter.

The promoter may be obtained, for example, from the genomes of viruses such as polyoma virus, fowlpox virus, adenovirus, bovine papilloma virus, avian sarcoma virus, cytomegalovirus, a retrovirus, hepatitis-B virus and Simian Virus 40 (SV40). The promoter may also be, for example, a heterologous mammalian promoter, e.g., the actin promoter or an immunoglobulin promoter, a heat-shock promoter, or the promoter normally associated with the native sequence, provided such promoters are compatible with the target cell. In one embodiment, the promoter is the naturally occurring viral promoter in a viral expression system. In some embodiments, the promoter is a dendritic cell-specific promoter. The dendritic cell-specific promoter can be, for example, CD11c promoter.

Transcription may be increased by inserting an enhancer sequence into the vector(s). Enhancers are typically cis-acting elements of DNA, usually about 10 to 300 bp in length, that act on a promoter to increase its transcription. Many enhancer sequences are now known from mammalian genes (globin, elastase, albumin, alpha-fetoprotein, and insulin) and from eukaryotic cell viruses. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the antigen-specific polynucleotide sequence, but is preferably located at a site 5' from the promoter.

Expression vectors may also contain sequences necessary for the termination of transcription and for stabilizing the mRNA. These sequences are often found in the 5' and, occasionally 3', untranslated regions of eukaryotic or viral DNAs or cDNAs and are well known in the art.

The viral vector genome may also contain additional genetic elements. The types of elements that may be included in the construct are not limited in any way and may be chosen to achieve a particular result. For example, a signal that facilitates nuclear entry of the viral genome in the target cell may be included. An example of such a signal is the HIV-1 flap signal. Further, elements may be included that facilitate the characterization of the provirus integration site in the target cell. For example, a tRNA amber suppressor sequence may be included in the construct. An insulator sequence from e.g., chicken 3-globin may also be included in the viral genome construct. This element reduces the chance of silencing an integrated provirus in the target cell due to methylation and heterochromatinization effects. In addition, the insulator may shield the internal enhancer, promoter and exogenous gene from positive or negative positional effects from surrounding DNA at the integration site on the chromosome. In addition, the vector genome may contain one or more genetic elements designed to enhance expression of the gene of interest. For example, a woodchuck hepatitis virus responsive element (WRE) may be placed into the construct (Zufferey et al. 1999. *J. Virol.* 74:3668-3681; Deglon et al. 2000. *Hum. Gene Ther.* 11:179-190, each of which is incorporated herein by reference in its entirety).

The viral vector genome is typically constructed in a plasmid form that may be transfected into a packaging or producer cell line. The plasmid generally comprises sequences useful for replication of the plasmid in bacteria. Such plasmids are well known in the art. In addition, vectors that include a prokaryotic origin of replication may also include a gene whose expression confers a detectable or selectable marker such as a drug resistance. Typical bacterial drug resistance products are those that confer resistance to ampicillin or tetracycline.

Plasmids containing one or more of the components described herein are readily constructed using standard techniques well known in the art. For analysis to confirm correct sequences in plasmids constructed, the plasmid may be replicated in *E. coli*, purified, and analyzed by restriction endonuclease digestion or its DNA sequence determined by conventional methods.

Vectors constructed for transient expression in mammalian cells may also be used. Transient expression involves the use of an expression vector that is able to replicate efficiently in a host cell, such that the host cell accumulates many copies of the expression vector and, in turn, synthesizes high levels of a the polypeptide encoded by the antigen-specific polynucleotide in the expression vector. See Sambrook et al., supra, pp. 16.17-16.22. Other vectors and methods suitable for adaptation to the expression of polypeptides are well known in the art and are readily adapted to the specific circumstances.

Using the teachings provided herein, one of skill in the art will recognize that the efficacy of a particular expression system can be tested by transfecting packaging cells with a vector comprising a gene encoding a reporter protein and measuring the expression using a suitable technique, for example, measuring fluorescence from a green fluorescent protein conjugate. Suitable reporter genes are well known in the art.

Types of Sequences of Interest

The sequence of interest is not limited in any way and includes any nucleic acid that one of ordinary skill desires to have integrated, transcribed, and expressed in the target cell. The product can be a protein or a nucleic acid. The sequence of interest can encode a protein or a nucleic acid molecule, including siRNA, microRNA, a self-complementary double stranded RNA in which the complementary region is greater than about 20 ribonucleotides in length, or an RNA that is complementary to a message RNA, where binding of said complementary (anti-sense) RNA to the message RNA blocks its ability to be translated into protein. In some instances, the sequence of interest can encode an antigen against which an immune response is desired. In particular, tumor antigens and infectious diseases antigens from agents such as HIV, HSV, HCV, HPV, malaria, or tuberculosis are desirable. Moreover, multiple sequences of interest may be included in a single vector.

In certain cases, the sequence of interest can be a gene encoding a small inhibiting RNA (siRNA) or a microRNA (miRNA) of interest that down-regulates expression of a molecule. For example, the gene encoding an siRNA or a microRNA can be used to down-regulate expression of negative regulators in a cell, including those that inhibit activation or maturation of dendritic cells. siRNAs and microRNAs are well known in the art (Fire et al., *Nature* 391:806, 1998; see also "The RNA Interference Resource" of Applied Biosystems, Trang et al., *Oncogene Suppl* 2:S52, 2008; Taganov, K., et al. 2007. *Immunity* 26:133-137; Dahlberg, J. E. and E. Lund. 2007. *Sci. STKE* 387:pe25; Tiemann and Rossi, *EMBO Mol Med* 1: 142, 2009). Alternatively, the sequence of interest can encode a self-complementary double stranded RNA in which the complementary region is greater than about 20 ribonucleotides in length, or an anti-sense RNA that is greater than about 20 ribonucleotides in length. Those of ordinary skill in the art will appreciate that siRNA, miRNA, dsRNA and anti-sense RNA molecules can be expressed from an RNA polymerase III promoter, or, alternatively, can be a component of a non-coding RNA that is transcribed from an RNA polymerase II promoter.

In addition, the sequence of interest may encode more than one product. In some configurations, the sequence to be delivered can comprise multiple genes encoding at least one protein, at least one siRNA, at least one microRNA, at least one dsRNA or at least one anti-sense RNA molecule or any combinations thereof. For example, the sequence to be delivered can include one or more genes that encode one or more antigens against which an immune response is desired. The one or more antigens can be associated with a single disease or disorder, or they can be associated with multiple diseases and/or disorders. In some instances, a gene encoding an immune regulatory protein can be included along with a gene encoding an antigen against which an immune response is desired, and the combination can elicit and regulate the immune response to the desired direction and magnitude. In other instances, a sequence encoding an siRNA, microRNA, dsRNA or anti-sense RNA molecule can be constructed with a gene encoding an antigen against which an immune response is desired, and the combination can regulate the scope of the immune response. The products may be produced as an initial fusion product in which the encoding sequence is in functional relationship with one promoter. Alternatively, the products may be separately encoded and each encoding sequence in functional relationship with a promoter. The promoters may be the same or different.

In certain configurations, vectors contain polynucleotide sequences that encode dendritic cell maturation/stimulatory factors. Exemplary stimulatory molecules include GM-CSF, IL-2, IL-4, IL-6, IL-7, IL-15, IL-21, IL-23, TNFα, B7.1, B7.2, 4-1BB, CD40 ligand (CD40L), drug-inducible CD40 (iCD40), and the like. These polynucleotides are typically under the control of one or more regulatory elements that direct the expression of the coding sequences in dendritic cells. Maturation of dendritic cells contributes to successful vaccination (Banchereau, J and Palucka, A. K. Nat. Rev. Immunol. 5:296-306 (2005); Schuler, G. et al. Curr. Opin. Immunol. 15:138-147 (2003); Figdor, C. G. et al. Nat. Med. 10:475-480 (2004)). Maturation can transform DCs from cells actively involved in antigen capture into cells specialized for T cell priming. For example, engagement of CD40 by CD40L on CD4-helper T cells is a critical signal for DC maturation, resulting in potent activation of CD8 T cells. Such stimulatory molecules are also referred to as maturation factors or maturation stimulatory factors. Immune checkpoints represent significant barriers to activation of functional cellular immunity in cancer, and antagonistic antibodies specific for inhibitory ligands on T cells including CTLA4 and programmed death-1 (PD-1) are examples of targeted agents being evaluated in the clinics. A significant tolerance mechanism in chronic infections and cancer is the functional exhaustion of Ag-specific T cells that express high levels of PD-1. As the potency of therapeutic immunization has been shown to be significantly enhanced by combination with immune checkpoint control, as a non-limiting example, it can be appreciated by those of ordinary skill in the art that an alternative approach to inhibiting immune checkpoint is to inhibit the expression of programmed death (PD) ligands one and two (PD-L1/L2). One way to accomplish inhibition is by the expression of RNA molecules such as those described herein, which repress the expression of PD-L1/L2 in the DCs transduced with the lentivirus vector encoding one or more of the RNA molecules. Maturation of DCs or expression of particular elements such as immune checkpoints, for example PD-1 ligands, can be characterized by flow cytometry analysis of up-regulation of surface marker such as MHC II, and profile of expressed chemokines and cytokines.

A sequence encoding a detectable product, usually a protein, can be included to allow for identification of cells that are expressing the desired product. For example, a fluorescent marker protein, such as green fluorescent protein (GFP), is incorporated into the construct along with a sequence of interest (e.g., encoding an antigen). In other cases, the protein may be detectable by an antibody or the protein may be an enzyme that acts on a substrate to yield a detectable product, or a product that allows selection of a transfected or transduced target cell, for example confers drug resistance, such as hygromycin resistance. Typical selection genes encode proteins that confer resistance to antibiotics or other toxins suitable for use in eukaryotic cells, e.g., neomycin, methotrexate, blasticidine, among others known in the art, or complement auxotrophic deficiencies, or supply critical nutrients withheld from the media. The selectable marker can optionally be present on a separate plasmid and introduced by co-transfection.

One or more multicistronic expression units may be utilized that include two or more of the elements (e.g., sequence(s) of interest, the envelope molecule, DC maturation factors) necessary for production of the desired virus in packaging cells. The use of multicistronic vectors reduces the total number of nucleic acid molecules required and thus avoids the possible difficulties associated with coordinating expression from multiple vector genomes. In a multicistronic vector the various elements to be expressed are operably linked to one or more promoters (and other expression control elements as necessary). In some configurations, a multicistronic vector comprises a sequence of interest, a sequence encoding a reporter product, and viral elements. The sequence of interest typically encodes an antigen and, optionally, a DC maturation factor. At times, the multicistronic vector comprises a gene encoding an antigen, a gene encoding a DC maturation factor and viral elements.

The disclosed pseudotyped lentiviral vectors can be engineered to express more than one, e.g., two, three, or four, antigens at a time. Several methods are known in the art for simultaneously expressing more than one gene from a single vector. For example, the vectors can comprise multiple promoters fused to the genes' open reading frames (ORFs), insertion of splicing signals between genes, fusion of genes whose expressions are driven by a single promoter, insertion of proteolytic cleavage sites between genes, insertion of internal ribosomal entry sites (IRESs) between genes, insertion of bi-directional promoters between genes, and/or "self-cleaving" 2A peptides. Each component to be expressed in a multicistronic expression vector may be separated, for example, by an internal ribosome entry site (IRES) element or a viral 2A element, to allow for separate expression of the various proteins from the same promoter. IRES elements and 2A elements are known in the art (U.S. Pat. No. 4,937,190; de Felipe et al. 2004. *Traffic* 5: 616-626, each of which is incorporated herein by reference in its entirety). In one embodiment, oligonucleotides encoding furin cleavage site sequences (RAKR) (Fang et al. 2005. Nat. Biotech 23: 584-590, which is incorporated herein by reference in its entirety) linked with 2A-like sequences from foot-and-mouth diseases virus (FMDV; F2A), porcine teschovirus-1 (P2A), equine rhinitis A virus (ERAV; E2A), and thosea asigna virus (TaV; T2A) (Szymczak et al. 2004. *Nat. Biotechnol.* 22: 589-594, which is incorporated herein by reference in its entirety) are used to separate genetic elements in a multicistronic vector. The 2A peptide consensus sequence is D(V/I)EXNPGP (SEQ ID NO: 56). In some embodiments, the lentiviral vector comprises a polynucleotide encoding T2A (SEQ ID NO: 57). In some embodiments, the 2A peptide is encoded by the polynucleotide of SEQ ID NO: 52. The efficacy of a particular multicistronic vector can readily be tested by detecting expression of each of the genes using standard protocols.

Expression of two or more antigens can also be accomplished using Internal Ribosome Entry Sites (IRES). IRES enable eukaryotic ribosomes to enter and scan an mRNA at a position other than the 5' $m^7$ G-cap structure. If positioned internally, e.g., 3' of a first coding region (or cistron), an IRES will enable translation of a second coding region within the same transcript. The second coding region is identified by the first ATG encountered after the IRES. Exemplary IRES elements include viral IRES such as the picornavirus IRES and the cardiovirus IRES (see, e.g., U.S. Pat. No. 4,937,190) and non-viral IRES elements found in 5' UTRs (e.g., those elements of transcripts encoding immunoglobulin heavy chain binding protein (BiP) (Macejak et al., *Nature*, 35390-4, 1991); *Drosophila Antennapedia* (Oh et al., *Genes Dev.* 6:1643-53, 1992) and Ultrabithorax (Ye et al., *Mol. Cell Biol.*, 17:1714-21, 1997); fibroblast growth factor 2 (Vagner et al., *Mol. Cell Biol.*, 15:35-44, 1995); initiation factor eIF4G (Gan et al., *J. Biol. Chem.* 273:5006-12, 1998); proto-oncogene c-myc (Nanbru et al., *J. Biol. Chem.*, 272:32061-6, 1995; Stoneley, *Oncogene*, 16:423-8, 1998); and vascular endothelial growth factor (VEGF) (Stein et al., *Mol. Cell Biol.*, 18:3112-9, 1998).

Expression of two or more antigens can also be accomplished using bidirectional promoters, i.e., a promoter region or two back-to-back cloned promoters whose reading directions point away from each other, and from which two open reading frames flanking the promoter region are transcribed. Examples of such promoters include the PDGF-A, neurotropic JC virus, BRCA1, transcobalamin II, and dipeptidylpeptidase IV promoters.

In a specific exemplification, the viral vector genome comprises: a cytomegalovirus (CMV) enhancer/promoter sequence; the R and U5 sequences from the HIV 5' LTR; a packaging sequence (ψ); the HIV-1 flap signal; an internal enhancer; an internal promoter; a gene of interest; the woodchuck hepatitis virus responsive element; a tRNA amber suppressor sequence; a U3 element with a deletion of its enhancer sequence; the chicken β-globin insulator; and the R and U5 sequences of the 3' HIV LTR. In some exemplifications, the vector genome comprises an intact lentiviral 5' LTR and a self-inactivating 3' LTR (Iwakuma et al. Virology 15:120, 1999, incorporated by reference in its entirety).

Construction of the vector genome can be accomplished using any suitable genetic engineering techniques known in the art, including, without limitation, the standard techniques of restriction endonuclease digestion, ligation, transformation, plasmid purification, and DNA sequencing, for example as described in Sambrook et al. (1989. Molecular Cloning: A Laboratory Manual. Cold Spring Harbor Laboratory Press, N.Y.), Coffin et al. (Retroviruses. Cold Spring Harbor Laboratory Press, N.Y. (1997)) and "RNA Viruses: A Practical Approach" (Alan J. Cann, Ed., Oxford University Press, (2000), each of the foregoing which is incorporated herein by reference in its entirety.

In some embodiments, the sequence of interest encodes at least one antigen. Any antigen that is associated with a disease or disorder can be delivered to dendritic cells using the viral particles as described herein. An antigen that is associated with the disease or disorder is identified for preparation of a viral particle that targets dendritic cells. Antigens associated with many diseases and disorders are well known in the art. An antigen may be previously known to be associated with the disease or disorder, or may be identified by any method known in the art. For example, an antigen to a type of cancer from which a patient is suffering may be known, such as a tumor-associated antigen or may be identified from the tumor itself by any of a variety of methods known in the art.

Tumor-associated antigens are known for a variety of cancers including, for example, renal cell carcinoma, prostate cancer, melanoma, and breast cancer. In some breast cancers, for example, the Her-2 receptor is overexpressed on the surface of cancerous cells. Exemplary tumor antigens include, but are not limited to, MAGE, e.g., MAGE-A3 and MAGE-A1, BAGE, RAGE, and NY-ESO-1, which are unmutated antigens expressed in the immune-privileged areas of the testes and in a variety of tumor cells; lineage-specific tumor antigens such as the melanocyte-melanoma lineage antigens, MART-1/Melan-A, gp100, gp75, mda-7, tyrosinase and tyrosinase-related protein, e.g., TRP2; renal cell carcinoma-5T4, SM22-alpha, carbonic anhydrases I and IX (also known as G250), hypoxia-inducible factors (e.g., HIF-1alpha and HIF-2alpha), VEGF or prostate specific membrane antigen (PSMA), prostate-specific antigen (PSA), prostatic acid phosphates, and six-transmembrane epithelial antigen of the prostate (STEAP), NKX3.1, which are antigens expressed in normal and neoplastic cells derived from the same tissue; epitope proteins/peptides derived from genes mutated in tumor cells or genes transcribed at different levels in tumor compared to normal cells, such as telomerase enzyme, survivin, mesothelin, mutated ras, bcr/abl rearrangement, Her2/neu, mutated or wild-type p53, cytochrome P450 1B1, and abnormally expressed intron sequences such as N-acetylglucosaminyltransferase-V; clonal rearrangements of immunoglobulin genes generating unique idiotypes in myeloma and B-cell lymphomas; epitope proteins/peptides derived from oncoviral processes, such as human papilloma virus proteins E6 and E7; non-mutated oncofetal proteins with a tumor-selective expression, such as carcinoembryonic antigen and alpha-fetoprotein. A number of tumor associated antigens have been reviewed (see, for example, "Tumor-Antigens Recognized By T-Lymphocytes," Boon T, Cerottini J C, Vandeneynde B, Vanderbruggen P, Vanpel A, Annual Review Of Immunology 12: 337-365, 1994; "A listing of human tumor antigens recognized by T cells," Renkvist N, Castelli C, Robbins P F, Parmiani G. Cancer Immunology Immunotherapy 50: (1) 3-15 Mar. 2001, each of which is incorporated herein by reference in its entirety.)

In some or any embodiments described herein, the pseudotyped lentiviral vector comprises a polynucleotide encoding MAGE-A3 (SEQ ID NO: 58). In some embodiments, MAGE-A3 is encoded by the polynucleotide of SEQ ID NO: 50. In some embodiments, MAGE-A3 is encoded by the polynucleotide of at least 40, 50, 60, 70, 80, 90, 95, 99 percent identity to SEQ ID NO: 50. In some embodiments, the pseudotyped lentiviral vector comprises a polynucleotide encoding a fragment of MAGE-A3 of at least 40, 50, 60, 70, 80, 90, 100, 110, 120, 130, 140, 150, 160, 170, 180, 190, 200, 210, 220, 230, 240, 250, 260, 270, 280, 290, 300, or 310 amino acids of SEQ ID NO: 58. In some embodiments, the polynucleotide encodes a variant of MAGE-A3 that is at least 40, 50, 60, 70, 80, 90, 95, 99 percent identity to SEQ ID NO: 58. In some embodiments, the pseudotyped lentiviral vector comprises a polynucleotide encoding NY-ESO-1 (SEQ ID NO: 59). In some embodiments, NY-ESO-1 is encoded by the polynucleotide of SEQ ID NO: 51. In some embodiments, MAGE-A3 is encoded by the polynucleotide of at least 40, 50, 60, 70, 80, 90, 95, 99 percent identity to SEQ ID NO: 51. In some embodiments, the pseudotyped lentiviral vector comprises a polynucleotide encoding a fragment of NY-ESO-1 of at least 40, 50, 60, 70, 80, 90, 100, 110, 120, 130, 140, 150, 160, or 170 amino acids of SEQ ID NO: 59. In some embodiments, the polynucleotide encodes a variant of NY-ESO-1 that is at least 40, 50, 60, 70, 80, 90, 95, 99 percent identity to SEQ ID NO: 59. In some embodiments, the pseudotyped lentiviral vector comprises a polynucleotide encoding MAGE-A3 (SEQ ID NO: 58) and a polynucleotide encoding NY-ESO-1 (SEQ ID NO: 59). In some or any embodiments, NY-ESO-1 and MAGE-A3 are expressed from the same transcript as a fusion protein that comprises NY-ESO-1 and MAGE-A3 and a self-cleaving A2 peptide between the two antigens, e.g., SEQ ID NO: 56 or 57. The antigens may be in any order (e.g., NY-ESO-1 first and MAGE-A3 second, or MAGE-A3 first and NY-ESO-1 second).

The antigen can also be an antigen associated with an infectious disease, such as, for example, HIV/AIDS. The antigen can be, for example, gp120 (Klimstra, W. B., et al. 2003. *J Virol* 77:12022-12032; Bernard, K. A., et al. 2000. *Virology* 276:93-103; Byrnes, A. P., et al. 1998. J Virol 72: 7349-7356, each of which is incorporated herein by reference in its entirety). Other exemplary antigens include, but are not limited to: gag, pol, env, tat, nef and rev (Lieberman, J. et al. 1997. *AIDS Res Hum Retroviruses* 13(5): 383-392; Menendez-Arias, L. et al. 1998. *Viral Immunol* 11(4): 167-181, each of which is incorporated herein by reference in its entirety).

Examples of viral antigens include, but are not limited to, adenovirus polypeptides, alphavirus polypeptides, calicivirus polypeptides, e.g., a calicivirus capsid antigen, coronavirus polypeptides, distemper virus polypeptides, Ebola virus polypeptides, enterovirus polypeptides, flavivirus polypeptides, hepatitis virus (AE) polypeptides, e.g., a hepatitis B core or surface antigen, or a hepatitis C virus E1 or E2 glycoproteins, core, or non-structural proteins, herpesvirus polypeptides, e.g., a herpes simplex virus or varicella zoster virus glycoprotein, immunodeficiency virus polypeptides, e.g., the human immunodeficiency virus envelope or protease, infectious peritonitis virus polypeptides, influenza virus polypeptides, e.g., an influenza A hemagglutinin, neuraminidase, or nucleoprotein, leukemia virus polypeptides, Marburg virus polypeptides, orthomyxovirus polypeptides, papilloma virus polypeptides, parainfluenza virus polypeptides, e.g., the hemagglutinin/neuraminidase, paramyxovirus polypeptides, parvovirus polypeptides, pestivirus polypeptides, picorna virus polypeptides, e.g., a poliovirus capsid polypeptide, pox virus polypeptides, e.g., a vaccinia virus polypeptide, rabies virus polypeptides, e.g., a rabies virus glycoprotein G, reovirus polypeptides, retrovirus polypeptides, and rotavirus polypeptides.

Examples of bacterial antigens include, but are not limited to, *Actinomyces* polypeptides, *Bacillus* polypeptides, *Bacteroides* polypeptides, *Bordetella* polypeptides, *Bartonella* polypeptides, *Borrelia* polypeptides, e.g., *B. burgdorferi* OspA, *Brucella* polypeptides, *Campylobacter* polypeptides, *Capnocytophaga* polypeptides, *Chlamydia* polypeptides, *Clostridium* polypeptides, *Corynebacterium* polypeptides, *Coxiella* polypeptides, Dermatophilus polypeptides, *Enterococcus* polypeptides, *Ehrlichia* polypeptides, *Escherichia* polypeptides, *Francisella* polypeptides, *Fusobacterium* polypeptides, *Haemobartonella* polypeptides, *Haemophilus* polypeptides, e.g., *H. influenzae* type b outer membrane protein, *Helicobacter* polypeptides, *Klebsiella* polypeptides, L-form bacteria polypeptides, *Leptospira* polypeptides, *Listeria* polypeptides, Mycobacteria polypeptides, *Mycoplasma* polypeptides, *Neisseria* polypeptides, *Neorickettsia* polypeptides, *Nocardia* polypeptides, *Pasteurella* polypeptides, *Peptococcus* polypeptides, *Peptostreptococcus* polypeptides, *Pneumococcus* polypeptides, *Proteus* polypeptides, *Pseudomonas* polypeptides, *Rickettsia* polypeptides, *Rochalimaea* polypeptides, *Salmonella* polypeptides, *Shigella* polypeptides, *Staphylococcus* polypeptides, *Streptococcus* polypeptides, e.g., *S. pyogenes* M proteins, *Treponema* polypeptides, and *Yersinia* polypeptides, e.g., *Y. pestis* F1 and V antigens.

Examples of fungal antigens include, but are not limited to, *Absidia* polypeptides, *Acremonium* polypeptides, *Alternaria* polypeptides, *Aspergillus* polypeptides, *Basidiobolus* polypeptides, *Bipolaris* polypeptides, *Blastomyces* polypeptides, *Candida* polypeptides, *Coccidioides* polypeptides, *Conidiobolus* polypeptides, *Cryptococcus* polypeptides, *Curvalaria* polypeptides, *Epidermophyton* polypeptides, *Exophiala* polypeptides, *Geotrichum* polypeptides, *Histoplasma* polypeptides, *Madurella* polypeptides, *Malassezia* polypeptides, *Microsporum* polypeptides, *Moniliella* polypeptides, *Mortierella* polypeptides, *Mucor* polypeptides, *Paecilomyces* polypeptides, *Penicillium* polypeptides, *Phialemonium* polypeptides, *Phialophora* polypeptides, *Prototheca* polypeptides, *Pseudallescheria* polypeptides, *Pseudomicrodochium* polypeptides, *Pythium* polypeptides, *Rhinosporidium* polypeptides, *Rhizopus* polypeptides, *Scolecobasidium* polypeptides, *Sporothrix* polypeptides, *Stemphylium* polypeptides, *Trichophyton* polypeptides, *Trichosporon* polypeptides, and *Xylohypha* polypeptides.

Examples of protozoan parasite antigens include, but are not limited to, *Babesia* polypeptides, *Balantidium* polypeptides, *Besnoitia* polypeptides, *Cryptosporidium* polypeptides, *Eimeria* polypeptides, *Encephalitozoon* polypeptides, *Entamoeba* polypeptides, *Giardia* polypeptides, *Hammondia* polypeptides, *Hepatozoon* polypeptides, *Isospora* polypeptides, *Leishmania* polypeptides, *Microsporidia* polypeptides, *Neospora* polypeptides, *Nosema* polypeptides, *Pentatrichomonas* polypeptides, *Plasmodium* polypeptides, e.g., *P. falciparum* circumsporozoite (PfCSP), sporozoite surface protein 2 (PfSSP2), carboxyl terminus of liver state antigen 1 (PfLSA1 c-term), and exported protein 1 (PfExp-1), *Pneumocystis* polypeptides, *Sarcocystis* polypeptides, *Schistosoma* polypeptides, *Theileria* polypeptides, *Toxoplasma* polypeptides, and *Trypanosoma* polypeptides.

Examples of helminth parasite antigens include, but are not limited to, *Acanthocheilonema* polypeptides, *Aelurostrongylus* polypeptides, *Ancylostoma* polypeptides, *Angiostrongylus* polypeptides, *Ascaris* polypeptides, *Brugia* polypeptides, *Bunostomum* polypeptides, *Capillaria* polypeptides, *Chabertia* polypeptides, *Cooperia* polypeptides, *Crenosoma* polypeptides, *Dictyocaulus* polypeptides, *Dioctophyme* polypeptides, *Dipetalonema* polypeptides, *Diphyllobothrium* polypeptides, *Diplydium* polypeptides, *Dirofilaria* polypeptides, *Dracunculus* polypeptides, *Enterobius* polypeptides, *Filaroides* polypeptides, *Haemonchus* polypeptides, *Lagochilascaris* polypeptides, *Loa* polypeptides, *Mansonella* polypeptides, *Muellerius* polypeptides, *Nanophyetus* polypeptides, *Necator* polypeptides, *Nematodirus* polypeptides, *Oesophagostomum* polypeptides, *Onchocerca* polypeptides, *Opisthorchis* polypeptides, *Ostertagia* polypeptides, *Parafilaria* polypeptides, *Paragonimus* polypeptides, *Parascaris* polypeptides, *Physaloptera* polypeptides, *Protostrongylus* polypeptides, *Setaria* polypeptides, *Spirocerca* polypeptides *Spirometra* polypeptides, *Stephanofilaria* polypeptides, *Strongyloides* polypeptides, *Strongylus* polypeptides, *Thelazia* polypeptides, *Toxascaris* polypeptides, *Toxocara* polypeptides, *Trichinella* polypeptides, *Trichostrongylus* polypeptides, *Trichuris* polypeptides, *Uncinaria* polypeptides, and *Wuchereria* polypeptides.

Examples of ectoparasite antigens include, but are not limited to, polypeptides (including protective antigens as well as allergens) from fleas; ticks, including hard ticks and soft ticks; flies, such as midges, mosquitoes, sand flies, black flies, horse flies, horn flies, deer flies, tsetse flies, stable flies, myiasis-causing flies and biting gnats; ants; spiders, lice; mites; and true bugs, such as bed bugs and kissing bugs.

Once an antigen has been identified and selected, a sequence that encodes the desired antigen is identified. Preferably the sequence comprises a cDNA. Following viral infection, the sequence of interest (e.g., one encoding the antigen) is expressed by the target dendritic cells. If contacted ex vivo, the target dendritic cells are then transferred back to the patient, for example by injection, where they interact with immune cells that are capable of generating an immune response against the desired antigen. In preferred embodiments, the recombinant virus is injected into the patient where it transduces the targeted dendritic cells in situ. The dendritic cells then express the particular antigen associated with a disease or disorder to be treated, and the patient is able to mount an effective immune response against the disease or disorder.

The viral vector genome may contain a polynucleotide sequence encoding more than one antigen, and upon transduction of a target dendritic cell, generates immune responses to the multitude of antigens delivered to the cell. In some embodiments, the antigens are related to a single disease or disorder. In other embodiments, the antigens are related to multiple diseases or disorders. In some embodiments, the viral vector genome contains a polynucleotide sequence encoding MART-1/Melan-A, NY-ESO-1, and MAGE.

Production of Viral Particles

Any of a variety of methods already known in the art may be used to produce infectious viral, e.g., lentiviral, particles whose genome comprises an RNA copy of the viral vector genome. In one method, the viral vector genome is introduced into a packaging cell line that contains all the components necessary to package viral genomic RNA, transcribed from the viral vector genome, into viral particles. Alternatively, the viral vector genome may comprise one or more genes encoding viral components in addition to the one or more sequences of interest. In order to prevent replication of the genome in the target cell, however, endogenous viral genes required for replication will usually be removed and provided separately in the packaging cell line.

In general, the lentiviral vector particles are produced by a cell line that is transfected with one or more plasmid vectors containing the components necessary to generate the particles. These lentiviral vector particles are typically not replication-competent, i.e., they are only capable of a single round of infection. Most often, multiple plasmid vectors are utilized to separate the various genetic components that generate the lentiviral vector particles, mainly to reduce the chance of recombination events that might otherwise generate replication competent viruses. A single plasmid vector having all of the lentiviral components can be used if desired, however. As one example of a system that employs multiple plasmid vectors, a cell line is transfected with at least one plasmid containing the viral vector genome (i.e., the vector genome plasmid), including the LTRs, the cis-acting packaging sequence, and the sequence(s) of interest, which are often operably linked to a heterologous promoter, at least one plasmid encoding the virus enzymatic and structural components (i.e., the packaging plasmid that encodes components such as, Gag and Pol), and at least one envelope plasmid encoding an Arbovirus envelope glycoprotein. Additional plasmids can be used to enhance retrovirus particle production, e.g., Rev-expression plasmids, as described herein and known in the art. Viral particles bud through the cell membrane and comprise a core that includes a genome containing the sequence of interest and an Arbovirus envelope glycoprotein that targets dendritic cells. When the Arbovirus glycoprotein is Sindbis virus E2 glycoprotein, the glycoprotein is engineered to have reduced binding to heparan sulfate compared to the reference strain HR E2 glycoprotein (SEQ ID NO: 18).

Transfection of packaging cells with plasmid vectors of the present disclosure can be accomplished by well-known methods, and the method to be used is not limited in any way. A number of non-viral delivery systems are known in the art, including for example, electroporation, lipid-based delivery systems including liposomes, delivery of "naked" DNA, and delivery using polycyclodextrin compounds, such as those described in Schatzlein A G. (2001. *Non-Viral Vectors in Cancer Gene Therapy: Principles and Progresses*. Anticancer Drugs, which is incorporated herein by reference in its entirety). Cationic lipid or salt treatment methods are typically employed, see, for example, Graham et al. (1973. *Virol.* 52:456; Wigler et al. (1979. *Proc. Natl. Acad. Sci. USA* 76:1373-76), each of the foregoing which is incorporated herein by reference in its entirety. The calcium phosphate precipitation method is most often used. However, other methods for introducing the vector into cells may also be used, including nuclear microinjection and bacterial protoplast fusion.

The packaging cell line provides the components, including viral regulatory and structural proteins, that are required in trans for the packaging of the viral genomic RNA into lentiviral vector particles. The packaging cell line may be any cell line that is capable of expressing lentiviral proteins and producing functional lentiviral vector particles. Some suitable packaging cell lines include 293 (ATCC CCL X), 293T, HeLa (ATCC CCL 2), D17 (ATCC CCL 183), MDCK (ATCC CCL 34), BHK (ATCC CCL-10) and Cf2Th (ATCC CRL 1430) cells. The packaging cell line may stably express the necessary viral proteins. Such a packaging cell line is described, for example, in U.S. Pat. No. 6,218,181, which is incorporated herein by reference in its entirety. Alternatively a packaging cell line may be transiently transfected with nucleic acid molecules encoding one or more necessary viral proteins along with the viral vector genome. The resulting viral particles are collected and used to infect a target cell. The gene(s) encoding envelope glycoprotein(s) is usually cloned into an expression vector, such as pcDNA3 (Invitrogen, CA USA). Eukaryotic cell expression vectors are well known in the art and are available from a number of commercial sources. Packaging cells, such as 293T cells are then co-transfected with the viral vector genome encoding a sequence of interest (typically encoding an antigen), at least one plasmid encoding virus packing components, and a vector for expression of the targeting molecule. The envelope is expressed on the membrane of the packaging cell and incorporated into the viral vector.

Production of virus is measured as described herein and expressed as IU per volume. IU is infectious unit, or alternatively transduction units (TU); IU and TU can be used interchangeably as a quantitative measure of the titer of a viral vector particle preparation. As described herein, virus is produced in which the genome can express a product that is readily measurable. A fluorescent protein, green fluorescent protein, is preferred. The lentiviral vector is typically non-integrating. The virus is then administered to target cells and the number of target cells that express GFP is determined, such as by flow cytometry. The titer is then calculated. The titer is preferably as high as possible, but at least $1 \times 10^5$ IU/mL, at least $3 \times 10^5$ IU/mL, at least $1 \times 10^6$ IU/mL, at least $3 \times 10^6$ IU/mL, or at least $1 \times 10^7$ IU/mL of cell supernatant (before any concentration). Alternatively, the titer is at least 80%, at least 90%, at least 95%, at least 100% of the titer of the same lentiviral vector pseudotyped in the same cells with VSV-G envelope.

Production of Highly Mannosylated Viral Particles

The Sindbis virus envelope protein contains four N-linked glycans-two on the E2 protein and two on the E1 protein. Two N-glycans of the virus produced in mammalian cells in the absence of a mannosidase I inhibitor have a high-mannose structure (one E2 N-linked glycan and one E1 N-linked glycan), while the remaining two have a complex structure. The two complex structure N-glycans are exposed on the surface of the envelope protein, while the two high-mannose structure N-glycans are buried within the center of the trimer of the envelope proteins. Sindbis virus particles with complex N-linked glycans do not bind DC-SIGN as efficiently as particles with less complex, highly mannosylated glycoproteins.

In the present disclosure, the inventors demonstrate that viral particles produced in mammalian cells in the presence of the mannosidase I inhibitor, kifunensine, unexpectedly exhibit significantly increased DC-SIGN-binding as compared to particles produced in the presence of DMNJ.

In some or any embodiments, a virus packaging cell is cultured in the presence of a mannosidase I inhibitor. In some or any embodiments, the mannosidase I inhibitor is kifunensine. In some embodiments, kifunensine is present in the media at a concentration of about 0.01 µg/ml to about 1 mg/ml, about 0.1 µg/ml to about 10 µg/ml, about 0.1 µg/ml to about 9 µg/ml, about 0.1 µg/ml to about 8 µg/ml, about 0.1 µg/ml to about 7 µg/ml, about 0.1 µg/ml to about 6 µg/ml, about 0.1 µg/ml to about 5 µg/ml, about 0.1 µg/ml to about 4 µg/ml, about 0.1 µg/ml to about 3 µg/ml, about 0.1 µg/ml to about 2 µg/ml, about 0.1 µg/ml to about 1 µg/ml, about 0.25 µg/ml to about 10 µg/ml, about 0.25 µg/ml to about 9 µg/ml, about 0.25 µg/ml to about 8 µg/ml, about 0.25 µg/ml to about 7 µg/ml, about 0.25 µg/ml to about 6 µg/ml, about 0.25 µg/ml to about 5 µg/ml, about 0.25 µg/ml to about 4 µg/ml, about 0.25 µg/ml to about 3 µg/ml, about 0.25 µg/ml to about 2 µg/ml, or about 0.25 µg/ml to about 1 µg/ml.

In some or any embodiments wherein a pseudotyped lentiviral vector particle comprises an Sindibis virus E2 glycoprotein and a Vpx protein, the lentiviral particles are produced in the presence of a mannosidase I inhibitor. In some embodiments, the mannosidase inhibitor is deoxymannojirimycin (DMNJ). In preferred embodiments, the mannosidase inhibitor is kifunensine. In some embodiments, DMNJ is present in the media at a concentration of about 1.0 µg/ml to about 1.0 mg/ml, about 1.0 µg/ml to about 900 µg/ml, about 1.0 µg/ml to about 800 µg/ml, about 1.0 µg/ml to about 700 µg/ml, about 1.0 µg/ml to about 600 µg/ml, about 1.0 µg/ml to about 500 µg/ml, about 1.0 µg/ml to about 400 µg/ml, about 1.0 µg/ml to about 300 µg/ml, about 1.0 µg/ml to about 200 µg/ml, about 1.0 g/ml to about 100 µg/ml, about 50 µg/ml to about 500 µg/ml, about 50 µg/ml to about 400 g/ml, about 50 µg/ml to about 300 µg/ml, about 50 µg/ml to about 200 µg/ml, about 50 g/ml to about 100 µg/ml, about 100 µg/ml to about 500 µg/ml, about 100 µg/ml to about 400 µg/ml, about 100 µg/ml to about 300 µg/ml, about 100 µg/ml to about 200 µg/ml, about 200 µg/ml to about 500 µg/ml, or about 200 µg/ml to about 400 µg/ml.

In some or any embodiments, a pseudotyped lentiviral vector particle produced in the presence of a mannosidase I inhibitor (e.g., kifunensine) comprises an envelope glycoprotein (e.g., Sindibis virus E2), wherein at least 60% of N-linked glycans comprise a Mannose$_5$ (Man$_5$), Man$_6$, Man$_7$, Man$_8$, and/or Man$_9$ structure. In some embodiments, at least 65%, at least 70%, at least 75%, at least 80%, at least 85%, at least 90%, at least 95%, at least 96%, at least 97%, at least 98%, at least 99%, or 100% of N-linked glycans comprise a Man$_5$, Man$_6$, Man$_7$, Man$_8$, and/or Man$_{9+}$ structure.

In one scenario, one or more vectors are used to introduce polynucleotide sequences into a packaging cell line for the preparation of a lentiviral vector particle pseudotyped with a Sindbis virus envelope glycoprotein such as E2, as described herein. In some embodiments, the lentiviral vector particle is highly mannosylated. In some embodiments, the lentiviral vector particle also comprises a Vpx protein or variant thereof. In yet other embodiments, the lentiviral vector particle is highly mannosylated and comprises a Vpx protein or variant thereof. The vectors can contain polynucleotide sequences encoding the various components of the virus including the Sindbis virus envelope, a sequence(s) of interest (typically encoding an antigen), and any components necessary for the production of the virus that are not provided by the packaging cell.

The glycosylation profile of a viral envelope protein can be determined by any method known in the art. For example, gel shift assays on viral glycoproteins treated with glycosidases (e.g., EndoH or PNGaseF) or left untreated may be compared. Other methods include cleaving glycans from the viral glycoproteins and separating and identifying the components via HPLC and mass spectrometry methods.

Delivery of the Virus

The virus may be delivered to a target cell in any way that allows the virus to contact the target cell, e.g., dendritic cell (DC), in which delivery of a polynucleotide of interest is desired. At times, a suitable amount of virus will be introduced into a human or other animal directly (in vivo), e.g., though injection into the body. Suitable animals include, without limitation, horses, dogs, cats, cattle, pigs, sheep, rabbits, chickens or other birds. Viral particles may be injected by a number of routes, such as intravenous, intradermal, subcutaneous, intranodal, intra-peritoneal cavity, or mucosal. The virus may be delivered using a subdermal injection device such the devices disclosed in U.S. Pat. Nos. 7,241,275, 7,115,108, 7,108,679, 7,083,599, 7,083,592, 7,047,070, 6,971,999, 6,808,506, 6,780,171, 6,776,776, 6,689,118, 6,670,349, 6,569,143, 6,494,865, 5,997,501, 5,848,991, 5,328,483, 5,279,552, 4,886,499, all of which are incorporated by reference in their entirety. Other injection locations also are suitable, such as directly into organs comprising target cells. For example, intra-lymph node injection, intra-spleen injection, or intra-bone marrow injection may be used to deliver virus to the lymph node, the spleen and the bone marrow, respectively. Depending on the particular circumstances and nature of the target cells, introduction can be carried out through other means including for example, inhalation, or direct contact with epithelial tissues, for example those in the eye, mouth or skin.

Alternatively, target cells are provided and contacted with the virus in vitro, such as in culture plates. The target cells are typically populations of cells comprising dendritic cells obtained from a healthy subject or a subject in need of treatment or in whom it is desired to stimulate an immune response to an antigen. Methods to obtain cells from a subject are well known in the art and includes phlebotomy, surgical excision, and biopsy. Human DCs may also be generated by obtaining CD34α+ human hematopoietic progenitors and using an in vitro culture method as described elsewhere (e.g., Banchereau et al. *Cell* 106, 271-274 (2001) incorporated by reference in its entirety).

The virus may be suspended in media and added to the wells of a culture plate, tube or other container. Media containing the virus may be added prior to the plating of the cells or after the cells have been plated. Cells are typically incubated in an appropriate amount of media to provide viability and to allow for suitable concentrations of virus in the media such that transduction of the host cell occurs. The cells are preferably incubated with the virus for a sufficient amount of time to allow the virus to infect the cells. Preferably the cells are incubated with virus for at least 1 hour, at least 5 hours or at least 10 hours.

In both in vivo and in vitro delivery, an aliquot of viral particles containing sufficient number to infect the desired target cells may be used. When the target cell is to be cultured, the concentration of the viral particles is generally at least 1 IU/μL, more preferably at least 10 IU/μl, even more preferably at least 300 IU/μL, even more preferably at least $1 \times 10^4$ IU/μL, even more preferably at least $1 \times 10^5$ IU/μL, even more preferably at least $1 \times 10^6$ IU/μL, or even more preferably at least $1 \times 10^7$ IU/μL.

Following infection with the virus in vitro, target cells can be introduced (or re-introduced) into a human or other animal. The cells can be introduced into the dermis, under the dermis, or into the peripheral blood stream. The cells introduced into an animal are preferably cells derived from that animal, to avoid an adverse immune response. Cells derived from a donor having a similar immune background may also be used. Other cells that also can be used include those designed to avoid an adverse immunologic response.

Target cells may be analyzed for integration, transcription and/or expression of the sequence or gene(s) of interest, the number of copies of the gene integrated, and the location of the integration, for example. Such analysis may be carried out at any time and may be carried out by any method known in the art.

Subjects in which a virus, or virus-infected dendritic cells, are administered can be analyzed for location of infected cells, expression of the virus-delivered polynucleotide or gene of interest, stimulation of an immune response, and monitored for symptoms associated with a disease or disorder by any methods known in the art.

The methods of infecting cells disclosed above do not depend upon individual-specific characteristics of the cells. As a result, they are readily extended to a variety of animal species. In some instances, viral particles are delivered to a human or to human dendritic cells, and in other instances they are delivered to an animal such as a mouse, horse, dog, cat, or mouse or to birds. As discussed herein, the viral vector genome is pseudotyped to confer upon it a broad host range as well as target cell specificity. One of skill in the art would also be aware of appropriate internal promoters and other elements to achieve the desired expression of a sequence of interest in a particular animal species. Thus, one of skill in the art will be able to modify the method of infecting dendritic cells from any species.

Therapeutic and Prophylactic Immunizations

Dendritic cells may be infected with a lentivirus vector particle as described herein for the prevention of, or treatment of, a disease or disorder, particularly those for which activation of an immune response in a patient would be beneficial. Many such diseases are well known. For example, diseases or disorders that are amenable to treatment or prevention by the methods of the present disclosure include, without limitation, cancers, autoimmune diseases, and infections, including viral, bacterial, fungal and parasitic infections. In one method, a disease is treated by viral particles (e.g., highly mannosylated viral particles comprising a Vpx protein) described herein in order to deliver a sequence of interest to dendritic cells, wherein expression of the sequence of interest produces a disease-specific antigen and leads to stimulation of antigen-specific cellular immune responses and humoral immune responses. Generally, the sequence of interest encodes an antigen against which an immune response is desired, but is not normally expressed in a dendritic cell. The antigen is expressed and presented by the dendritic cell. The viral vector genome may further encode a DC maturation factor.

In a typical usage, viral particles deliver to dendritic cells sequences encoding an antigen against which an immune response is desired. The delivery can be achieved by contacting dendritic cells with the virus in vitro, whereupon the infected dendritic cells are provided to a patient. Other times, delivery can be achieved by delivering the virus to a subject for infecting dendritic cells in vivo. The dendritic cells then stimulate antigen-specific T cells or B cells in a patient to induce cellular and humoral immune responses to the expressed antigen. In such ways, a patient that is suffering from a disease or disorder is treated by generating immune cells with a desired specificity.

In some of the viruses, DC maturation factors that activate and/or stimulate maturation of the DCs are delivered in conjunction with the sequence of interest. In alternatives, the DCs are activated by delivery of DC maturation factors prior to, simultaneously with, or after delivery of the virus. DC maturation factors may be provided separately from administration of the virus.

As described herein, one or more immune modulation or DC maturation factors can be encoded by one or more sequences that are contained in the viral genome and expressed after the virus infects a dendritic cell. The sequences encoding immune modulation factors can also be provided in a separate vector that is co-transfected with the viral vector encoding one or more antigens in a packaging cell line.

The methods described herein can be used for adoptive immunotherapy in a patient. As described above, an antigen against which an immune response is desired is identified. A polynucleotide encoding the desired antigen is obtained and packaged into a recombinant virus. Target dendritic cells are obtained from the patient and transduced with a recombinant virus containing a polynucleotide that encodes the desired antigen. The dendritic cells are then transferred back into the patient.

The viral particles may be injected in vivo, where they infect DCs and deliver a sequence of interest, typically encoding an antigen. The amount of viral particles is at least $3 \times 10^6$ IU, and can be at least $1 \times 10^7$ IU, at least $3 \times 10^7$ IU, at least $1 \times 10^8$ IU, at least $3 \times 10^8$ IU, at least $1 \times 10^9$ IU, or at least $3 \times 10^9$ IU. At selected intervals, DCs from the recipient's lymphoid organs may be used to measure expression, for example, by observing marker expression, such as GFP or luciferase. Nucleic acid monitoring techniques and measurements of reverse transcriptase (RT) activity can also be used to analyze the biodistribution of viral particles. T cells from peripheral blood mononuclear cells, lymph nodes, spleens, or malignant or target pathogen-infected tissue of lentiviral vector particle-treated recipients may be measured from the magnitude and durability of response to antigen stimulation. Tissue cells other than DCs, such as epithelial cells and lymphoid cells, may be analyzed for the specificity of in vivo gene delivery.

Vaccines often include an adjuvant. The lentiviral vector particles described herein may also be administered along with an adjuvant. The adjuvant may be administered with the recombinant virus particles, before the recombinant virus particles, or after the recombinant virus particles. If administered with the virus particles, desirable adjuvants do not significantly disrupt the integrity of the virus particle, such as disrupting the viral membrane containing the envelope glycoproteins.

A variety of adjuvants can be used in combination with the virus to elicit an immune response to the antigen encoded in the viral vector genome. Preferred adjuvants augment the intrinsic response to an antigen without causing conformational changes in the antigen that affect the qualitative form of the response. Preferred adjuvants include alum, 3 De-O-acylated monophosphoryl lipid A (MPL) (see GB 2220211). QS21 is a triterpene glycoside or saponin isolated from the bark of the *Quillaja Saponaria* Molina tree found in South America (see Kensil et al., in Vaccine Design: The Subunit and Adjuvant Approach (eds. Powell and Newman, Plenum Press, N Y, 1995); U.S. Pat. No. 5,057,540). Other adjuvants are oil in water emulsions (such as squalene or peanut oil), optionally in combination with immune stimulants, such as monophosphoryl lipid A (see Stoute et al., *N. Engl. J. Med.* 336, 86-91 (1997)). Another adjuvant is CpG (*Bioworld Today*, Nov. 15, 1998). Adjuvants can be administered as a component of a therapeutic composition with an active agent or can be administered separately, before, concurrently with, or after administration of the therapeutic agent.

One class of adjuvants is aluminum salts (alum), such as aluminum hydroxide, aluminum phosphate, aluminum sulfate. Such adjuvants can be used with or without other specific immunostimulating agents such as MPL or 3-DMP, QS21, polymeric or monomeric amino acids such as polyglutamic acid or polylysine. Another class of adjuvants is oil-in-water emulsion formulations. Such adjuvants can be used with or without other specific immunostimulating agents such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'dipalmitoyl-sn-glycero-3-hydroxyphosphoryloxy)-ethylamine (MTP-PE), N-acetylglucsaminyl-N-acetylmuramyl-L-A1-D-isoglu-L-Ala-dipalmitoxy propylamide (DTP-DPP) Theramide™), or other bacterial cell wall components. Oil-in-water emulsions include (a) MF59 (WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton Mass.), (b) SAF, containing 10% Squalane, 0.4% Tween 80, 5% pluronic-blocked polymer L121, and thr-MDP, either microfluidized into a submicron emulsion or vortexed to generate a larger particle size emulsion, and (c) Ribi adjuvant system (RAS), (Ribi Immunochem, Hamilton, Mont.) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™). Another class of preferred adjuvants is saponin adjuvants, such as Stimulon™ (QS21, Aquila, Worcester, Mass.) or particles generated there from such as ISCOMs (immunostimulating complexes) and ISCOMATRIX. Other adjuvants include Complete Freund's Adjuvant (CFA) and Incomplete Freund's Adjuvant (IFA). Other adjuvants include cytokines, such as interleukins (IL-1, IL-2, and IL-12), macrophage colony stimulating factor (M-CSF), tumor necrosis factor (TNF).

Another adjuvant that can be used with the compositions herein is identified by chemical formula (I):

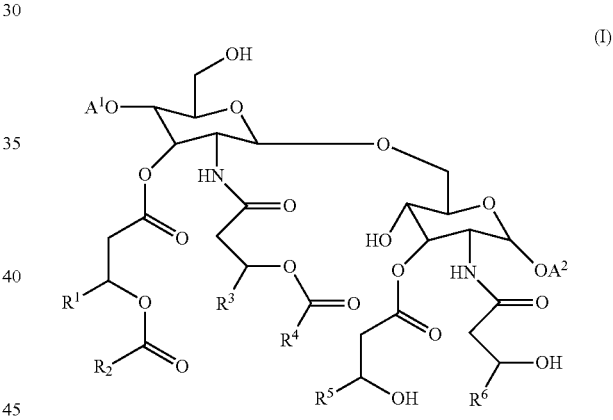

wherein the moieties A1 and A2 are independently selected from the group of hydrogen, phosphate, and phosphate salts. Sodium and potassium are exemplary counterions for the phosphate salts. The moieties $R^1$, $R^2$, $R^3$, $R^4$, $R^5$, and $R^6$ are independently selected from the group of hydrocarbyl having 3 to 23 carbons, represented by $C_3$-$C_{23}$. For added clarity it will be explained that when a moiety is "independently selected from" a specified group having multiple members, it should be understood that the member chosen for the first moiety does not in any way impact or limit the choice of the member selected for the second moiety. The carbon atoms to which $R^1$, $R^3$, $R^5$ and $R^6$ are joined are asymmetric, and thus may exist in either the R or S stereochemistry. In one embodiment all of those carbon atoms are in the R stereochemistry, while in another embodiment all of those carbon atoms are in the S stereochemistry.

"Hydrocarbyl" refers to a chemical moiety formed entirely from hydrogen and carbon, where the arrangement of the carbon atoms may be straight chain or branched, noncyclic or cyclic, and the bonding between adjacent carbon atoms maybe entirely single bonds, i.e., to provide a saturated hydrocarbyl, or there may be double or triple bonds present between any two adjacent carbon atoms, i.e., to provide an unsaturated hydrocarbyl, and the number of carbon atoms in the hydrocarbyl group is between 3 and 24 carbon atoms. The hydrocarbyl may be an alkyl, where representative straight chain alkyls include methyl, ethyl, n-propyl, n-butyl, n-pentyl, n-hexyl, and the like, including undecyl, dodecyl, tridecyl, tetradecyl, pentadecyl, hexadecyl, heptadecyl, octadecyl, etc.; while branched alkyls include isopropyl, sec-butyl, isobutyl, tert-butyl, isopentyl, and the like. Representative saturated cyclic hydrocarbyls include cyclopropyl, cyclobutyl, cyclopentyl, cyclohexyl, and the like; while unsaturated cyclic hydrocarbyls include cyclopentenyl and cyclohexenyl, and the like. Unsaturated hydrocarbyls contain at least one double or triple bond between adjacent carbon atoms (referred to as an "alkenyl" or "alkynyl", respectively, if the hydrocarbyl is non-cyclic, and cycloalkeny and cycloalkynyl, respectively, if the hydrocarbyl is at least partially cyclic). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

The adjuvant of formula (I) may be obtained by synthetic methods known in the art, for example, the synthetic methodology disclosed in PCT International Publication No. WO 2009/035528, which is incorporated herein by reference, as well as the publications identified in WO 2009/035528, where each of those publications is also incorporated herein by reference. Certain of the adjuvants may also be obtained commercially. A preferred adjuvant is Product No. 699800 as identified in the catalog of Avanti Polar Lipids, Alabaster, Ala., see E1 in combination with E10, below.

In various embodiments of the disclosure, the adjuvant has the chemical structure of formula (I) but the moieties $A_1$, $A_2$, $R^1$, $R^2$, $R^3$, $R^4$, $R^5$, and $R^6$ are selected from subsets of the options previously provided for these moieties, where these subsets are identified below by E1, E2, etc.

E1: $A_1$ is phosphate or phosphate salt and $A_2$ is hydrogen.
E2: $R^1$, $R^3$, $R^5$ and $R^6$ are $C_3$-$C_{21}$ alkyl; and $R^2$ and $R^4$ are $C_5$-$C_{23}$ hydrocarbyl.
E3: $R^1$, $R^3$, $R^5$ and $R^6$ are $C_5$-$C_{17}$ alkyl; and $R^2$ and $R^4$ are $C_7$-$C_{19}$ hydrocarbyl.
E4: $R^1$, $R^3$, $R^5$ and $R^6$ are $C_7$-$C_{15}$ alkyl; and $R^2$ and $R^4$ are $C_9$-$C_{17}$ hydrocarbyl.
E5: $R^1$, $R^3$, $R^5$ and $R^6$ are $C_9$-$C_{13}$ alkyl; and $R^2$ and $R^4$ are $C_{11}$-$C_{15}$ hydrocarbyl.
E6: $R^1$, $R^3$, $R^5$ and $R^6$ are $C_9$-$C_{15}$ alkyl; and $R^2$ and $R^4$ are $C_{11}$-$C_{17}$ hydrocarbyl.
E7: $R^1$, $R^3$, $R^5$ and $R^6$ are $C_7$-$C_{13}$ alkyl; and $R^2$ and $R^4$ are $C_9$-$C_{15}$ hydrocarbyl.
E8: $R^1$, $R^3$, $R^5$ and $R^6$ are $C_{11}$-$C_{20}$ alkyl; and $R^2$ and $R^4$ are $C_{12}$-$C_{20}$ hydrocarbyl.
E9: $R^1$, $R^3$, $R^5$ and $R^6$ are $C_{11}$ alkyl; and $R^2$ and $R^4$ are $C_{13}$ hydrocarbyl.
E10: $R^1$, $R^3$, $R^5$ and $R^6$ are undecyl and $R^2$ and $R^4$ are tridecyl.

In certain options, each of E2 through E10 is combined with embodiment E1, and/or the hydrocarbyl groups of E2 through E9 are alkyl groups, preferably straight chain alkyl groups.

The adjuvant of formula (I) may be formulated into a pharmaceutical composition, optionally with a co-adjuvant, each as discussed below. In this regard reference is made to US Patent Publication No. 2008/0131466 which provides formulations, e.g., aqueous formulation (AF) and stable emulsion formulations (SE) for GLA adjuvant, where these formulations may be utilized for any of the adjuvants of formula (I).

An adjuvant can be administered with the virus of the disclosure as a single composition, or can be administered before, concurrent with or after administration of the recombinant virus of the disclosure. Immunogen and adjuvant can be packaged and supplied in the same vial or can be packaged in separate vials and mixed before use. Immunogen and adjuvant are typically packaged with a label indicating the intended therapeutic application. If immunogen and adjuvant are packaged separately, the packaging typically includes instructions for mixing before use. The choice of an adjuvant and/or carrier depends on the stability of the vaccine containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, Complete Freund's adjuvant is not suitable for human administration. Alum, MPL and QS21 are preferred. Optionally, two or more different adjuvants can be used simultaneously, such as alum with MPL, alum with QS21, MPL with QS21, and alum, QS21 and MPL together. Also, Incomplete Freund's adjuvant can be used (Chang et al., Advanced Drug Delivery Reviews 32, 173-186 (1998)), optionally in combination with any of alum, QS21, and MPL and all combinations thereof.

Pharmaceutical Compositions and Kits

Also contemplated herein are pharmaceutical compositions and kits containing a virus provided herein and one or more components. Pharmaceutical compositions can include viral vector particles as provided herein and a pharmaceutical carrier. Kits can include the pharmaceutical compositions and/or combinations provided herein, and one or more components, such as instructions for use, a device for administering a compound to a subject, and a device for administering a compound to a subject.

Provided herein are pharmaceutical compositions containing viral particles as provided herein and a suitable pharmaceutical carrier. Pharmaceutical compositions provided herein can be in various forms, e.g., in solid, liquid, powder, aqueous, or lyophilized form. Examples of suitable pharmaceutical carriers are known in the art. Such carriers and/or additives can be formulated by conventional methods and can be administered to the subject at a suitable dose. Stabilizing agents such as lipids, nuclease inhibitors, polymers, and chelating agents can preserve the compositions from degradation within the body.

The viral vector particles provided herein can be packaged as kits. Kits can optionally include one or more components such as instructions for use, devices, and additional reagents, and components, such as tubes, containers and syringes for practice of the methods. Exemplary kits can include the viruses provided herein, and can optionally include instructions for use, a device for detecting a virus in a subject, a device for administering the virus to a subject, and a device for administering a compound to a subject.

Kits comprising polynucleotides encoding a gene of interest (typically an antigen) are also contemplated herein. The kit may include at least one plasmid encoding virus packaging components and vector encoding Sindbis virus E2 glycoprotein variant. Some kits will contain at least one plasmid encoding virus packaging components, a vector encoding Sindbis virus E2 glycoprotein variant, and a vector encoding at least one DC maturation factor.

Kits comprising a viral vector encoding a sequence of interest (typically an antigen) and optionally, a polynucleotide sequence encoding a DC maturation factor are also contemplated herein. In some kits, the kit includes at least one plasmid encoding virus packaging components and a vector encoding Sindbis virus E2 glycoprotein variant.

A kit may also contain instructions. Instructions typically include a tangible expression describing the virus and, optionally, other components included in the kit, and methods for administration, including methods for determining the proper state of the subject, the proper dosage amount, and the proper administration method, for administering the virus. Instructions can also include guidance for monitoring the subject over the duration of the treatment time.

Kits provided herein also can include a device for administering a virus to a subject. Any of a variety of devices known in the art for administering medications or vaccines can be included in the kits provided herein. Exemplary devices include, but are not limited to, a hypodermic needle, an intravenous needle, a catheter, a needle-less injection device, an inhaler, and a liquid dispenser, such as an eyedropper. Typically, the device for administering a virus of the kit will be compatible with the virus of the kit; for example, a needle-less injection device such as a high pressure injection device can be included in kits with viruses not damaged by high pressure injection, but is typically not included in kits with viruses damaged by high pressure injection.

Kits provided herein also can include a device for administering a compound, such as a DC activator or stimulator, to a subject. Any of a variety of devices known in the art for administering medications to a subject can be included in the kits provided herein. Exemplary devices include a hypodermic needle, an intravenous needle, a catheter, a needle-less injection, but are not limited to, a hypodermic needle, an intravenous needle, a catheter, a needle-less injection device, an inhaler, and a liquid dispenser such as an eyedropper. Typically the device for administering the compound of the kit will be compatible with the desired method of administration of the compound.

EXEMPLARY EMBODIMENTS

Methods of Generating Pseudotyped Lentiviral Vector Particles

In some embodiments of the disclosure, a method of generating a pseudotyped lentiviral vector particle comprises:
(a) culturing in a culture medium comprising a mannosidase I inhibitor a virus packaging cell comprising:
    (1) a lentiviral vector genome comprising a polynucleotide encoding an exogenous antigen,
    (2) a polynucleotide encoding an alphavirus glycoprotein that preferentially binds dendritic cells expressing DC-SIGN, and
    (3) a polynucleotide encoding a SAMHD1 inhibitor; and
(b) isolating a pseudotyped lentiviral vector particle that preferentially binds dendritic cells expressing DC-SIGN.

In specific aspects, the mannosidase inhibitor is kifunensine or DMNJ.

In specific aspects, the alphavirus glycoprotein is a Sindbis virus E2 glycoprotein.

In specific aspects, the SAMHD1 inhibitor is a Vpx protein, e.g., a SIVmac Vpx protein, a SIVsm protein, a SIVrcm, or an HIV-2 Vpx protein. In specific aspects, the SAMHD1 inhibitor is an antibody or fragment thereof. In specific aspects, the SAMHD1 inhibitor is a Vpr protein with SAMHD1-inhibiting ability, e.g., a SIVdeb Vpr protein or a SIVmus Vpr protein.

In some embodiments of the disclosure, a method of generating a pseudotyped lentiviral vector particle comprises:
(a) culturing in a culture medium comprising kifunensine a virus packaging cell comprising:
    (1) a lentiviral vector genome comprising a polynucleotide encoding an exogenous antigen,
    (2) a polynucleotide encoding a Sindbis E2 glycoprotein that preferentially binds dendritic cells expressing DC-SIGN, and
    (3) a polynucleotide encoding a Vpx protein or a Vpr protein that retains SAMHD1-inhibiting activity; and
(b) isolating a pseudotyped lentiviral vector particle that preferentially binds dendritic cells expressing DC-SIGN.

In specific aspects, the E2 glycoprotein is 90% identical to SEQ ID NO: 30 [SIN-Var1]. In some aspects, (i) residue 160 of the E2 glycoprotein is absent or is an amino acid other than glutamic acid, (ii) one or more of residues 70, 76, or 159 of the E2 glycoprotein variant is a non-basic residue, and (iii) the E2 glycoprotein variant is not part of a fusion protein with Sindbis virus E3 glycoprotein. In some aspects, the E2 glycoprotein is SEQ ID NO: 30 [SIN-Var1].

In specific aspects, the Vpx protein comprises an amino acid sequence that is at least 80% identical to SIVmac Vpx (SEQ ID NO: 44).

In specific aspects, the Vpx protein comprises an amino acid sequence at least 80% identical to SIVmac Vpx (SEQ ID NO: 44), SIVsm Vpx (SEQ ID NO: 45), SIVrcm Vpx (SEQ ID NO: 46), or HIV-2 Vpx (SEQ ID NO: 47). In specific aspects, the Vpx protein comprises an amino acid sequence at least 90% identical to SIVmac Vpx (SEQ ID NO: 44), SIVsm Vpx (SEQ ID NO: 45), SIVrcm Vpx (SEQ ID NO: 46), or HIV-2 Vpx (SEQ ID NO: 47).

In specific aspects, the Vpr protein of the pseudotyped lentiviral vector particle or lentiviral vector packaging system of any of the preceding embodiments comprises an amino acid sequence at least 80% identical to SIVdeb Vpr (SEQ ID NO: 48) or SIVmus Vpr (SEQ ID NO: 49). In specific aspects, the Vpr protein of the pseudotyped lentiviral vector particle or lentiviral vector packaging system of any of the preceding embodiments comprises an amino acid sequence at least 90% identical to SIVdeb Vpr (SEQ ID NO: 48) or SIVmus Vpr (SEQ ID NO: 49).

In specific aspects, the antigen is a tumor-specific antigen or a virus-specific antigen. In some aspects, the tumor-specific antigen is selected from the group consisting of NY-ESO-1, MAGE, e.g., MAGE-A3 and MAGE-A1, MART-1/Melan-A, BAGE, RAGE, gp100, gp75, mda-7, tyrosinase, tyrosinase-related protein, e.g., TRP2, renal cell carcinoma antigen, 5T4, SM22-alpha, carbonic anhydrase I, carbonic anhydrase IX (also known as G250), HIF-1alpha, HIF-2alpha, VEGF, prostate specific membrane antigen (PSMA), prostate-specific antigen (PSA), prostatic acid phosphates, six-transmembrane epithelial antigen of the prostate (STEAP), NKX3.1, telomerase enzyme, survivin, mesothelin, mutated ras, bcr/abl rearrangement, Her2/neu, mutated p53, wild-type p53, cytochrome P450 1B1, N-acetylglucosaminyltransferase-V, human papilloma virus protein E6, human papilloma virus protein E7, carcinoembryonic antigen, merkel cell virus T-antigen oncoproteins, and alpha-fetoprotein. In some aspects, the virus-specific antigen is an HIV antigen, an SIV antigen, an adenovirus antigen, an enterovirus antigen, a coronavirus antigen, a calicivirus antigen, a distemper virus antigen, an Ebola virus antigen, a flavivirus antigen, a hepatitis virus antigen, a herpesvirus antigen, an infectious peritonitis virus antigen, an influenza virus antigen, a leukemia virus antigen, a Marburg virus antigen, an orthomyxovirus antigen, a papilloma virus antigen, a parainfluenza virus antigen, a paramyxovirus antigen, a parvovirus antigen, a pestivirus antigen, a picorna virus antigen, a poliovirus antigen, a pox virus antigen, a rabies virus antigen, a reovirus antigen, a retrovirus antigen, or a rotavirus antigen.

In specific aspects, the lentiviral vector genome further comprises a nucleotide sequence encoding a second antigen. In specific aspects, the first and second antigen are expressed as a fusion protein that comprises a self-cleaving A2 peptide between the two antigens. In some aspects, the self-cleaving A2 peptide comprises the amino acid sequence of SEQ ID NO: 56 or SEQ ID NO: 57. In some aspects, the first antigen is NY-ESO-1 and the second antigen is MAGE-A3.

In specific aspects, the kifunensine is present in the culture medium at a concentration of about 0.1 µg/ml to about 10 µg/ml. In some aspects, the kifunensine is present in the culture medium at a concentration of about 0.25 µg/ml to about 2 µg/ml. In some aspects, the kifunensine is present in the culture medium at a concentration of about 0.01 µg/ml to about 1 mg/ml.

In specific aspects, the virus packaging cell further comprises:

(i) a polynucleotide comprising gag and pol genes; and
(ii) a polynucleotide encoding a rev protein. In some aspects, the polynucleotide encoding the Vpx protein is on the same or different plasmid as the polynucleotide encoding the rev protein, or the polynucleotide comprising the gag and pol genes. In some aspects, the gag and pol genes are human codon optimized and comprise a non-optimized window around position 1228 to 1509 of SEQ ID NO: 54. In some aspects, the polynucleotide comprising gag and pol genes lacks a functional rev responsive element (RRE). In some aspects, the pol gene encodes an inactive integrase enzyme. In some aspects, the integrase enzyme has a D64V mutation.

In specific aspects, the lentiviral vector genome is derived from HIV-1.

In specific aspects, the lentiviral vector genome of the pseudotyped lentiviral vector particle or packaging system of any of the preceding embodiments is capable of integrating.

In specific aspects, the lentiviral vector genome of the pseudotyped lentiviral vector particle or packaging system of any of the preceding embodiments is integration defective or integration deficient. For example, the lentiviral vector may integrate at a frequency at least 10-fold (e.g., at least 20-fold, at least 30-fold, at least 40-fold, at least 50-fold, at least 60-fold, at least 70-fold, at least 80-fold, at least 90-fold, at least 100-fold, at least 150-fold, at least 200-fold, at least 250-fold, at least 300-fold, at least 350-fold, at least 400-fold, at least 450-fold, at least 500-fold, at least 550-fold, at least 600-fold, at least 650-fold, at least 700-fold, at least 750-fold, at least 800-fold, at least 850-fold, at least 900-fold, at least 950-fold, or at least 1000-fold) less efficient at integrating than an integration-competent viral vector. In exemplary embodiments, the lentiviral vector may be at least about 20-fold to about 100-fold less efficient at integrating.

In specific aspects, the lentiviral vector genome has an inactivated 3' long terminal repeat (LTR) or a self-inactivating 3' long terminal repeat (LTR). In some aspects, the lentiviral vector genome comprises a U3 element lacking at least one of an enhancer sequence, a TATA box, an Sp site, an NK-kappa B site, or a polypurine tract (PPT). In some aspects, the pol gene encodes an inactive integrase enzyme and the lentiviral vector genome lacks a functional polypurine tract (PPT).

In specific aspects, the lentiviral vector genome comprises the nucleotide sequence of any one of SEQ ID NOs: 21 [SIN vector], 22 [703 vector], or 23 [704 vector].

In specific aspects, the lentiviral vector genome further comprises a nucleotide sequence encoding a dendritic cell maturation/stimulatory factor. In some aspects, the dendritic cell maturation/stimulatory factor is selected from the group consisting of GM-CSF, IL-2, IL-4, IL-6, IL-7, IL-15, IL-21, IL-23, TNFα, B7.1, B7.2, 4-1BB, CD40 ligand, and drug-inducible CD40.

In specific aspects, the nucleotide sequence encoding an antigen is operably linked to a promoter selected from the group consisting of the human Ubiquitin-C promoter (UbiC), the cytomegalovirus immediate early promoter (CMV), the Rous sarcoma virus promoter (RSV), and the tetracycline-responsive promoter. In some aspects, the promoter is an intron-deficient promoter. In some aspects, the intron-deficient promoter is a UbiC.

In specific aspects, a lentiviral vector particle produced by the methods described herein is provided.

In specific aspects, a lentiviral vector particle produced by the methods described herein is provided, wherein the lentiviral vector genome further comprises a nucleotide sequence encoding a second antigen. In specific aspects, the first and second antigen are expressed as a fusion protein that comprises a self-cleaving A2 peptide between the two antigens. In some aspects, the self-cleaving A2 peptide comprises the amino acid sequence of SEQ ID NO: 56 or SEQ ID NO: 57. In some aspects, the first antigen is NY-ESO-1 and the second antigen is MAGE-A3.

Compositions Comprising Pseudotyped Lentiviral Vector Particles

In some or any embodiments of the disclosure, there is provided a composition comprising pseudotyped lentiviral vector particles comprising (a) a Vpx protein or a Vpr protein that retains SAMHD1-inhibiting activity, (b) an exogenous polynucleotide encoding an antigen, and (c) a plurality of envelope glycoproteins that preferentially bind cells expressing DC-SIGN, wherein the composition is more highly mannosylated compared to a control composition of the same pseudotyped lentiviral vector particles prepared in the absence of a mannosidase inhibitor. For example, such a highly mannosylated composition is characterized by containing envelope glycoproteins that are more EndoH-sensitive than envelope glycoproteins of a control composition prepared in the absence of a mannosidase inhibitor. As another example, such a highly mannosylated composition is characterized by containing envelope glycoproteins exhibiting an increased amount of EndoH-sensitive glycan as compared to envelope glycoproteins of a control composition prepared in the absence of a mannosidase inhibitor. It is understood that the control composition will contain approximately the same number of pseudotyped lentiviral vector particles comprising envelope glycoproteins having the same amino acid sequence(s). It is also understood that while the disclosure is primarily focused on alphavirus E2 glycoprotein, which is responsible for recognition and binding to dendritic cells, and highly mannosylated versions thereof, the alphavirus envelope also contains E1 glycoproteins that are susceptible to high mannosylation. Thus, references to envelope glycoproteins and highly mannosylated envelope glycoproteins include references to highly mannosylated alphavirus E2 and/or E1 glycoproteins, specifically highly mannosylated Sindbis E2 and/or E1 glycoproteins. High mannosylation of other types of virus envelopes, specifically retrovirus envelopes, also improves recognition of dendritic cells.

In some embodiments of the disclosure, there is provided a composition comprising pseudotyped lentiviral vector particles comprising (a) a Vpx protein or a Vpr protein that retains SAMHD1-inhibiting activity, (b) an exogenous polynucleotide encoding an antigen, and (c) a plurality of Sindbis E2 glycoproteins that preferentially bind cells expressing DC-SIGN, wherein the composition is more highly mannosylated compared to a control composition of pseudotyped lentiviral vector particles prepared in the absence of a mannosidase inhibitor. A substantial number of E2 glycoproteins in such compositions are more highly mannosylated, e.g. more EndoH-sensitive, than E2 glycoprotein in control compositions prepared in the absence of a mannosidase inhibitor.

EndoH is a specialized endoglycosidase that will only cleave high-mannose N-linked glycosylation (see FIG. 3A), e.g., Man5-9 glycans; Man3-4 glycans are resistant to EndoH. In contrast, PNGase F will cleave all types of glycosylation, including low-mannose glycans<Man5. When viral particles are produced in the presence of a mannosidase I inhibitor, such as kifunensine, the glycoproteins in the viral envelope will contain more high-mannose glycans that are susceptible to cleavage by EndoH (i.e., will be more "EndoH-sensitive"). One way of detecting the presence of high-mannose glycans in a composition of viral particles is to determine the molecular weight of the envelope glycoproteins by electrophoresis by sodium dodecyl sulfate-polyacrylamide gel electrophoresis (SDS-PAGE) after EndoH treatment. This "gel shift" assay is illustrated in Example 3. Samples of the viral particles, and control compositions of the same viral particles prepared in the absence of mannosidase inhibitor, can be run on a 10% SDS-PAGE gel and immunoblotted with antibody against the Sindbis glycoproteins. Virus envelope produced in the presence of mannosidase I inhibitors is more EndoH-sensitive and consequently runs faster on the gel (a farther distance) after EndoH treatment, compared to control virus. Thus, the presence of high-mannose glycoprotein can be measured using a gel-shift assay after EndoH treatment.

Control virus may be partially sensitive to EndoH treatment due to the presence of glycosylation sites in the Sindbis glycoproteins that are normally high mannose because they are internal and not exposed to mannosidase I during production. Thus, when run on 10% SDS-PAGE, control virus may exhibit some shift in molecular weight after EndoH treatment, due to EndoH cleavage of such internal high mannose glycans. This shift, however, may be only about 35% of the shift seen when control virus is treated with PNGase F, which cleaves all of the glycans.

Thus, in specific aspects, the amount of EndoH-sensitive glycan is detected by determining molecular weight of the Sindbis glycoproteins by sodium dodecyl sulfate-polyacrylamide gel electrophoresis (SDS-PAGE) after EndoH treatment. An increased amount of endoH-sensitive glycan in the composition, which indicates that the composition of viral particles is highly mannosylated, is detected when EndoH treatment results in the band corresponding to the envelope (E2 and/or E1) glycoproteins on a 10% SDS-PAGE gel shifting to a lower molecular weight compared to control envelope glycoproteins, as determined by visual inspection.

In some illustrative embodiments, the molecular weight of said envelope glycoproteins after treatment with EndoH has shifted completely, and is substantially the same as the molecular weight of said envelope glycoproteins after treatment with PNGaseF. In other illustrative embodiments, the molecular weight of said envelope glycoproteins after treatment with EndoH has shifted approximately 90% or more of the distance between (a) envelope glycoproteins not treated with endoglycosidase, and (b) envelope glycoproteins treated with PNGase F. In other illustrative embodiments, the molecular weight of said envelope glycoproteins after treatment with EndoH has shifted approximately 90% or more of the distance between (a) envelope glycoproteins not treated with endoglycosidase, and (b) envelope glycoproteins treated with PNGase F. In yet other illustrative embodiments, the molecular weight of said envelope glycoproteins has shifted about 40% or more, or preferably about 45% or more, or about 50% or more, or about 55% or more, or about 60% or more, or about 65% or more, or about 70% or more, or about 75% or more, or about 80% or more, or about 85% or more of the distance between (a) envelope glycoproteins not treated with endoglycosidase, and (b) envelope glycoproteins treated with PNGase F. As noted above, reference to envelope glycoproteins specifically includes reference to Sindbis E2 and/or E1 glycoproteins.

In specific aspects, at least 30%, at least 35%, at least 40%, at least 45%, at least 50%, at least 55%, at least 60%, at least 65%, at least 70%, at least 75%, at least 80%, at least 85%, at least 90%, or at least 95% of the envelope glycoproteins in said composition, e.g. the Sindbis E2 and/or E1 glycoproteins in said composition, have an increased amount of EndoH-sensitive glycan as compared to control envelope glycoproteins having the same amino acid sequence(s) in a control composition of pseudotyped lentiviral vector particles prepared in the absence of a mannosidase inhibitor.

In some embodiments of the disclosure, a composition comprises pseudotyped lentiviral vector particles comprising (a) a SAMHD1 inhibitor, (b) a lentiviral genome comprising a sequence of interest, and (c) an envelope glycoprotein that preferentially binds cells expressing DC-SIGN, wherein at least 80% of N-linked glycans in said composition comprise a $Man_9$ structure.

In specific aspects, the SAMHD1 inhibitor is a Vpx protein, e.g., a SIVmac Vpx protein, a SIVsm Vpx protein, a SIVrcm Vpx protein, or an HIV-2 Vpx protein. In specific aspects, the SAMHD1 inhibitor is an antibody or fragment thereof. In specific aspects, the SAMHD1 inhibitor is a Vpr protein with SAMHD1-inhibiting ability, e.g., a SIVdeb Vpr protein or a SIVmus Vpr protein.

In specific aspects, the sequence of interest encodes a protein or a nucleic acid molecule, such as a siRNA, microRNA, a self-complementary double stranded RNA in which the complementary region is greater than about 20 ribonucleotides in length, or an RNA that is complementary to a message RNA, where binding of said complementary (anti-sense) RNA to the message RNA blocks its ability to be translated into protein. In some instances, the sequence of interest encodes an antigen against which an immune response is desired. In specific aspects, the sequence of interest encodes a tumor antigen or an infectious disease antigens (e.g., from agents such as HIV, HSV, HCV, HPV, malaria, or tuberculosis). In specific aspects, multiple sequences of interest are included in a single vector.

In some embodiments of the disclosure, a composition comprises pseudotyped lentiviral vector particles comprising (a) a Vpx protein, (b) an exogenous polynucleotide encoding an antigen, and (c) an envelope glycoprotein that preferentially binds dendritic cells expressing DC-SIGN, wherein at least 80% of N-linked glycans in said composition comprise a Man$_9$ structure.

In specific aspects, the Vpx protein comprises an amino acid sequence that is at least 80% identical to SIVmac Vpx protein (SEQ ID NO: 44).

In specific aspects, the Vpx protein comprises an amino acid sequence at least 80% identical to SIVmac Vpx (SEQ ID NO: 44), SIVsm Vpx (SEQ ID NO: 45), SIVrcm Vpx (SEQ ID NO: 46), or HIV-2 Vpx (SEQ ID NO: 47). In specific aspects, the Vpx protein comprises an amino acid sequence at least 90% identical to SIVmac Vpx (SEQ ID NO: 44), SIVsm Vpx (SEQ ID NO: 45), SIVrcm Vpx (SEQ ID NO: 46), or HIV-2 Vpx (SEQ ID NO: 47).

In specific aspects, the Vpr protein of the pseudotyped lentiviral vector particle or lentiviral vector packaging system of any of the preceding embodiments comprises an amino acid sequence at least 80% identical to SIVdeb Vpr (SEQ ID NO: 48) or SIVmus Vpr (SEQ ID NO: 49). In specific aspects, the Vpr protein of the pseudotyped lentiviral vector particle or lentiviral vector packaging system of any of the preceding embodiments comprises an amino acid sequence at least 90% identical to SIVdeb Vpr (SEQ ID NO: 48) or SIVmus Vpr (SEQ ID NO: 49).

In specific aspects, the pseudotyped lentiviral vector particle infects dendritic cells expressing DC-SIGN with an in vitro transduction efficiency of at least at least 1%, or at least 5%, or at least 10%, or at least 20%.

In specific aspects, the glycoprotein is a Sindbis virus E2 glycoprotein. In some aspects, the E2 glycoprotein has at least 90% identity to SEQ ID NO: 30 [SIN-Var1]. In some aspects, (i) residue 160 of the E2 glycoprotein is absent or is an amino acid other than glutamic acid, (ii) one or more of residues 70, 76, or 159 of the E2 glycoprotein variant is a non-basic residue, and (iii) the E2 glycoprotein variant is not part of a fusion protein with Sindbis virus E3 glycoprotein.

In specific aspects, the antigen is a tumor-specific antigen or a virus-specific antigen. In some aspects, the tumor-specific antigen is selected from the group consisting of NY-ESO-1, MAGE, MAGE-A3 and MAGE-A1, MART-1/Melan-A, BAGE, RAGE, gp100, gp75, mda-7, tyrosinase, tyrosinase-related protein, e.g., TRP2, renal cell carcinoma antigen, 5T4, SM22-alpha, carbonic anhydrase I, carbonic anhydrase IX (also known as G250), HIF-1alpha, HIF-2alpha, VEGF, prostate specific membrane antigen (PSMA), prostate-specific antigen (PSA), prostatic acid phosphates, six-transmembrane epoithelial antigen of the prostate (STEAP), NKX3.1, telomerase enzyme, survivin, mesothelin, mutated ras, bcr/abl rearrangement, Her2/neu, mutated p53, wild-type p53, cytochrome P450 1B1, N-acetylglucosaminyltransferase-V, human papilloma virus protein E6, human papilloma virus protein E7, carcinoembryonic antigen, merkel cell virus T-antigen oncoproteins, and alpha-fetoprotein. In some aspects, the virus-specific antigen is an HIV antigen, an SIV antigen, an adenovirus antigen, an enterovirus antigen, a coronavirus antigen, a calicivirus antigen, a distemper virus antigen, an Ebola virus antigen, a flavivirus antigen, a hepatitis virus antigen, a herpesvirus antigen, an infectious peritonitis virus antigen, an influenza virus antigen, a leukemia virus antigen, a Marburg virus antigen, an orthomyxovirus antigen, a papilloma virus antigen, a parainfluenza virus antigen, a paramyxovirus antigen, a parvovirus antigen, a pestivirus antigen, a picorna virus antigen, a poliovirus antigen, a pox virus antigen, a rabies virus antigen, a reovirus antigen, a retrovirus antigen, or a rotavirus antigen.

In specific aspects, the lentiviral vector genome further comprises a nucleotide sequence encoding a second antigen. In specific aspects, the first and second antigen are expressed as a fusion protein that comprises a self-cleaving A2 peptide between the two antigens. In some aspects, the self-cleaving A2 peptide comprises the amino acid sequence of SEQ ID NO: 56 or SEQ ID NO: 57. In some aspects, the first antigen is MAGE-A3 and the second antigen is NY-ESO-1.

In specific aspects, the lentiviral vector genome is derived from HIV-1.

In specific aspects, the lentiviral vector genome of the pseudotyped lentiviral vector particle or packaging system of any of the preceding embodiments is capable of integrating.

In specific aspects, the lentiviral vector genome of the pseudotyped lentiviral vector particle or packaging system of any of the preceding embodiments is integration deficient or integration defective.

In specific aspects, the lentiviral vector genome has an inactivated 3' long terminal repeat (LTR) or a self-inactivating 3' long terminal repeat (LTR). In some aspects, the lentiviral vector genome comprises a U3 element lacking at least one of an enhancer sequence, a TATA box, an Sp site, an NK-kappa B site, or a polypurine tract (PPT).

In specific aspects, the lentiviral vector genome comprises the nucleotide sequence of any one of SEQ ID NOs: 21 [SIN vector], 22 [703 vector], or 23 [704 vector].

In specific aspects, the lentiviral vector genome further comprises a nucleotide sequence encoding a dendritic cell maturation/stimulatory factor. In some aspects, the dendritic cell maturation/stimulatory factor is selected from the group consisting of GM-CSF, IL-2, IL-4, IL-6, IL-7, IL-15, IL-21, IL-23, TNFα, B7.1, B7.2, 4-1BB, CD40 ligand, and drug-inducible CD40.

In specific aspects, the nucleotide sequence encoding an antigen is operably linked to a promoter selected from the group consisting of the human Ubiquitin-C promoter (UbiC), the cytomegalovirus immediate early promoter (CMV), the Rous sarcoma virus promoter (RSV), and the tetracycline-responsive promoter. In some aspects, the promoter has been modified to be intron-deficient.

In some aspects, pseudotyped lentiviral vector particles comprise a Rev protein.

In specific aspects, the pseudotyped lentiviral vector particles have an IU of at least $10^5$/mL.

In specific aspects, the composition further comprises an immunostimulating agent.

In specific aspects, the composition further comprises an adjuvant. For example, as noted above, adjuvants include alum, or 3 De-O-acylated monophosphoryl lipid A (MPL). Classes of adjuvants disclosed herein include (a) aluminum salts, (b) oil-in-water emulsion formulations, optionally with or without other specific immunostimulating agents such as muramyl peptides or other bacterial cell wall components, (c) saponin adjuvants, including ISCOMs (immunostimulating complexes) and ISCOMATRIX; (d) Complete Freund's Adjuvant (CFA) and Incomplete Freund's Adjuvant (IFA); (e) cytokines; and (f) adjuvants of formula (I). Within formula (I), a preferred adjuvant is Product No. 699800 as identified in the catalog of Avanti Polar Lipids, Alabaster, Ala., see E1 in combination with E10, where (i) $A_1$ is phosphate or phosphate salt and $A_2$ is hydrogen and (ii) $R^1$, $R^3$, $R^5$ and $R^6$ are undecyl and $R^2$ and $R^4$ are tridecyl. In specific aspects, the envelope glycoproteins also bind cells expressing mouse SIGNR1.

In specific aspects, the pseudotyped lentiviral vector particles also more efficiently transduce cells expressing mouse SIGNR1 compared to cells not expressing mouse SIGNR1.

In some embodiments of the disclosure, the above-mentioned pseudotyped lentiviral vector particles are for use in a method of treatment or prevention of a disease or disorder in a patient. In specific aspects, the disease or disorder is a cancer, an autoimmune disease, or an infection, for example, a viral infection, a bacterial infection, a fungal infection or a parasitic infection.

Viral Vector Particles Comprising a Vpx Protein

In some embodiments of the disclosure, there is provided a pseudotyped lentiviral vector particle capable of targeting a cell expressing comprising:
(a) a non-native envelope glycoprotein;
(b) a lentiviral vector genome comprising an exogenous polynucleotide of interest; and
(c) a Vpx protein or other SAMHD1 inhibitor.

In some aspects, pseudotyped lentiviral vector particle further comprises a Rev protein.

In some embodiments of the disclosure, a lentiviral vector packaging system for producing a pseudotyped lentiviral vector particle is provided, comprising:
(i) a first polynucleotide encoding a non-native envelope glycoprotein;
(ii) a second polynucleotide comprising gag and pol genes;
(iii) a third polynucleotide encoding a rev protein;
(iv) a fourth polynucleotide encoding a Vpx protein or other SAMHD1 inhibitor; and
(v) a lentiviral vector genome comprising an exogenous polynucleotide of interest;
wherein two or more polynucleotides are on the same plasmid or on different plasmids. In specific aspects, the polynucleotide of (iv) is on the same plasmid as any one or more of the polynucleotides of (i), (ii), (iii) or (v).

In specific aspects, the packaging cell is selected from the group consisting of 293, 293T, HeLa, D17, MDCK, BHK and Cf2Th cells.

In specific aspects, the Vpx protein of the pseudotyped lentiviral vector particle or lentiviral vector packaging system of any of the preceding embodiments comprises an amino acid sequence that is at least 80% identical to SEQ ID NO: 44 (SIVmac), optionally an SIVmac Vpx protein (SEQ ID NO: 44), SIVsm Vpx protein (SEQ ID NO: 45), SIVrcm Vpx protein (SEQ ID NO: 46), or an HIV-2 VPX protein (SEQ ID NO: 47). In specific aspects, the Vpx protein of the pseudotyped lentiviral vector particle or lentiviral vector packaging system of any of the preceding embodiments comprises an amino acid sequence that is at least 90% identical to SEQ ID NO: 44 (SIVmac), optionally an SIVmac Vpx protein (SEQ ID NO: 44), SIVsm Vpx protein (SEQ ID NO: 45), SIVrcm Vpx protein (SEQ ID NO: 46), or an HIV-2 VPX protein (SEQ ID NO: 47).

In specific aspects, the Vpr protein of the pseudotyped lentiviral vector particle or lentiviral vector packaging system of any of the preceding embodiments comprises an amino acid sequence at least 80% identical to SIVdeb Vpr (SEQ ID NO: 48) or SIVmus Vpr (SEQ ID NO: 49). In specific aspects, the Vpr protein of the pseudotyped lentiviral vector particle or lentiviral vector packaging system of any of the preceding embodiments comprises an amino acid sequence at least 90% identical to SIVdeb Vpr (SEQ ID NO: 48) or SIVmus Vpr (SEQ ID NO: 49).

In specific aspects, the lentiviral vector genome of the pseudotyped lentiviral vector particle or lentiviral vector packaging system of any of the above embodiments is derived from HIV-1 or MLV.

In specific aspects, the lentiviral vector genome of the pseudotyped lentiviral vector particle or packaging system of any of the preceding embodiments is capable of integrating.

In specific aspects, the lentiviral vector genome of the pseudotyped lentiviral vector particle or packaging system of any of the preceding embodiments is non-integrating.

In specific aspects, the non-native envelope glycoprotein of the pseudotyped lentiviral vector particle or packaging system of any of the preceding embodiments is selected from the group consisting of an alphavirus glycoprotein, including Sindbis E2 glycoprotein, VEE E2 glycoprotein, rhabdovirus or vesiculovirus glycoprotein, including VSV-G glycoprotein, arenavirus glycoprotein, coronavirus glycoprotein, paramyxovirus glycoprotein, flavirvirus glycoprotein, orthomyxovirus glycoprotein, and baculovirus glycoprotein, preferably an alphavirus such as Sindbis virus.

In specific aspects, the non-native envelope glycoprotein of the pseudotyped lentiviral vector particle or packaging system of any of the preceding embodiments is a Sindbis virus E2 glycoprotein comprising an amino acid sequence at least 80% identical to SEQ ID NO: 30 [SINVar1].

In specific aspects, the non-native envelope glycoprotein of the pseudotyped lentiviral vector particle or packaging system of any of the preceding embodiments preferentially binds a cell expressing SAMHD1. In some aspects, the cell expressing SAMHD1 is a myeloid cell, optionally a dendritic cell, monocyte or a macrophage.

In specific aspects, the non-native envelope glycoprotein of the pseudotyped lentiviral vector particle or packaging system of any of the preceding embodiments preferentially binds dendritic cells expressing DC-SIGN.

In specific aspects, the polynucleotide of interest encodes (i) an antigen, (ii) a therapeutic polypeptide, or (iii) an inhibitory oligonucleotide. In some aspects, the polynucleotide of interest encodes an siRNA.

In specific aspects, the polynucleotide of interest encodes a viral, bacterial, fungal, protozoal or cancer antigen.

In specific aspects, the envelope glycoproteins also bind cells expressing mouse SIGNR1.

In specific aspects, the pseudotyped lentiviral vector particles also more efficiently transduce cells expressing mouse SIGNR1 compared to cells not expressing mouse SIGNR1.

In some embodiments of the disclosure, there is provided a method of producing a pseudotyped lentiviral vector particle of any of the preceding embodiments comprising culturing the packaging system of any of the preceding embodiments in a culture medium. In some aspects, the culture medium comprises a mannosidase I inhibitor, optionally kifunensine or DMNJ.

In some embodiments of the disclosure, there is provided a composition comprising the pseudotyped lentiviral vector particles of any of the preceding embodiments wherein the vector particles are highly mannosylated.

In some embodiments of the disclosure, there is provided a composition comprising the pseudotyped lentiviral vector particles of any of the preceding embodiments wherein at least 80% of N-linked glycans in said composition comprise a $Man_9$ structure.

In some embodiments of the disclosure, there is provided a method of delivering a lentiviral vector genome to a cell expressing SAMHD1, in vitro or in vivo, comprising contacting the cell with the vector particle of any of the above embodiments. In some aspects, the cell expressing SAMHD1 is a dendritic cell, a monocyte, or a macrophage.

In some embodiments of the disclosure, there is provided a method of eliciting an immune response or immunizing an individual comprising administering the vector particle of any of the above embodiments to an individual, preferably a vector particle that preferentially binds dendritic cells expressing DC-SIGN.

In some embodiments of the disclosure, the above-mentioned pseudotyped lentiviral vector particles are for use in a method of treatment or prevention of a disease or disorder in a patient. In specific aspects, the disease or disorder is a cancer, an autoimmune disease, or an infection, for example, a viral infection, a bacterial infection, a fungal infection or a parasitic infection.

Methods of Generating Viral Vector Particles with Highly Mannosylated Envelope Glycoproteins In some embodiments of the disclosure, there is provided a method of generating a virus vector particle that preferentially binds dendritic cells expressing DC-SIGN comprising: culturing a virus packaging cell comprising viral particle components in a culture medium, said components comprising a polynucleotide encoding an envelope glycoprotein that preferentially binds to dendritic cells expressing DC-SIGN, and wherein the culture medium comprises kifunensine at a concentration of about 0.01 µg/ml to about 1 mg/ml, preferably about 0.1 µg/ml to about 10 µg/ml.

In specific aspects, the kifunensine is present in the culture medium at a concentration of about 0.25 µg/ml to about 2 µg/ml.

In specific aspects, the kifunensine is present in the culture medium at a concentration of about 0.1 µg/ml to about 10 µg/ml, or about 0.25 µg/ml to about 2 µg/ml, or about 0.5 µg/ml to about 5 µg/ml.

In specific aspects, the viral particle components comprise a lentiviral vector genome.

In specific aspects, the viral particle infects cells expressing DC-SIGN with a transduction efficiency at least 5-fold higher than a viral particle produced in a culture medium lacking kifunensine.

In specific aspects, the virus packaging cell comprises:
(i) a first polynucleotide encoding a envelope glycoprotein;
(ii) a second polynucleotide comprising gag and pol genes;
(iii) a third polynucleotide encoding a rev protein; and
(iv) a lentiviral vector genome comprising a fourth polynucleotide encoding an antigen.

In specific aspects, the envelope glycoprotein is a Sindbis virus E2 glycoprotein. In some aspects, the E2 glycoprotein comprises [SINVar1] or a variant thereof having at least 80% amino acid sequence identity thereto. In some aspects, the E2 glycoprotein is 90% identical to SEQ ID NO: 30 [SIN-Var1]. In some aspects, (i) residue 160 of the E2 glycoprotein is absent or is an amino acid other than glutamic acid, (ii) one or more of residues 70, 76, or 159 of the E2 glycoprotein variant is a non-basic residue, and (iii) the E2 glycoprotein variant is not part of a fusion protein with Sindbis virus E3 glycoprotein. In some aspects, the E2 glycoprotein is SEQ ID NO: 30 [SIN-Var1].

In specific aspects, the lentiviral vector genome is derived from HIV-1.

In specific aspects, the lentiviral vector genome of the pseudotyped lentiviral vector particle or packaging system of any of the preceding embodiments is capable of integrating.

In specific aspects, the lentiviral vector genome of the pseudotyped lentiviral vector particle or packaging system of any of the preceding embodiments is integration deficient or integration defective. In some aspects, the pol gene encodes an inactive integrase enzyme and the lentiviral vector genome lacks a functional polypurine tract (PPT).

In specific aspects, the virus packaging cell further comprises a polynucleotide encoding a Vpx protein that retains SAMHD1-inhibiting activity, optionally comprising an amino acid sequence at least 80% identical to SIVmac Vpx (SEQ ID NO: 44).

In some embodiments of the disclosure, there is provided a composition comprising virus particles displaying an alphavirus E2 glycoprotein, wherein at least 80% of N-linked glycans in said composition comprise a $Man_9$ structure.

In specific aspects, the alphavirus E2 glycoprotein is a Sindbis E2 glycoprotein that binds preferentially to dendritic cells expressing DC-SIGN.

In some embodiments of the disclosure, there is provided a method of delivering a viral vector genome to a cell expressing DC-SIGN comprising administering the virus particle or composition of any of the preceding embodiments.

Additional Embodiments

1. A method of generating a pseudotyped lentiviral vector particle comprising:
(a) culturing in a culture medium comprising kifunensine a virus packaging cell comprising:
(1) a lentiviral vector genome comprising a polynucleotide encoding an exogenous antigen,
(2) a polynucleotide encoding a Sindbis E2 glycoprotein that preferentially binds dendritic cells expressing DC-SIGN, and
(3) a polynucleotide encoding a Vpx protein or a Vpr protein that retains SAMHD1-inhibiting activity; and
(b) isolating a pseudotyped lentiviral vector particle that preferentially binds dendritic cells expressing DC-SIGN.

2. The method of embodiment 1, wherein the E2 glycoprotein is 90% identical to SEQ ID NO: 30 [SIN-Var1].

3. The method of embodiment 1 or 2, wherein (i) residue 160 of the E2 glycoprotein is absent or is an amino acid other than glutamic acid, (ii) one or more of residues 70, 76, or 159 of the E2 glycoprotein variant is a non-basic residue, and (iii) the E2 glycoprotein variant is not part of a fusion protein with Sindbis virus E3 glycoprotein.

4. The method of embodiment 2, wherein the E2 glycoprotein is SEQ ID NO: 30 [SIN-Var1].

5. The method of any one of the above embodiments, wherein the Vpx protein comprises an amino acid sequence that is at least 80% identical to SIVmac Vpx [SEQ ID NO: 44].

6. The method of any one of embodiments 1 to 4, wherein the Vpx protein comprises an amino acid sequence at least 90% identical to SIVmac Vpx (SEQ ID NO: 44), SIVsm Vpx (SEQ ID NO: 45), SIVrcm Vpx (SEQ ID NO: 46), or HIV-2 Vpx (SEQ ID NO: 47).

7. The method of any one of embodiments 1 to 4, wherein the Vpx protein comprises an amino acid sequence at least 90% identical to SIVdeb Vpr (SEQ ID NO: 48) or SIVmus Vpr (SEQ ID NO: 49).

8. The method of any one of the above embodiments, wherein the antigen is a tumor-specific antigen or a virus-specific antigen.

9. The method of embodiment 8, wherein the tumor-specific antigen is selected from the group consisting of NY-ESO-1, MAGE, MART-1/Melan-A, BAGE, RAGE, gp100, gp75, mda-7, tyrosinase, tyrosinase-related protein, renal cell carcinoma antigen, 5T4, SM22-alpha, carbonic anhydrase I, carbonic anhydrase IX (also known as G250), HIF-1alpha, HIF-2alpha, VEGF, prostate specific membrane antigen (PSMA), prostate-specific antigen (PSA), prostatic acid phosphates, six-transmembrane epithelial antigen of the prostate (STEAP), NKX3.1, telomerase enzyme, survivin, mesothelin, mutated ras, bcr/abl rearrangement, Her2/neu, mutated p53, wild-type p53, cytochrome P450 1B1, N-acetylglucosaminyltransferase-V, human papilloma virus protein E6, human papilloma virus protein E7, carcinoembryonic antigen, and alpha-fetoprotein.

10. The method of embodiment 8, wherein the virus-specific antigen is an HIV antigen, an SIV antigen, an adenovirus antigen, an enterovirus antigen, a coronavirus antigen, a calicivirus antigen, a distemper virus antigen, an Ebola virus antigen, a flavivirus antigen, a hepatitis virus antigen, a herpesvirus antigen, an infectious peritonitis virus antigen, an influenza virus antigen, a leukemia virus antigen, a Marburg virus antigen, an orthomyxovirus antigen, a papilloma virus antigen, a parainfluenza virus antigen, a paramyxovirus antigen, a parvovirus antigen, a pestivirus antigen, a picorna virus antigen, a poliovirus antigen, a pox virus antigen, a rabies virus antigen, a reovirus antigen, a retrovirus antigen, or a rotavirus antigen.

11. The method of any one of the above embodiments, wherein the lentiviral vector genome further comprises a nucleotide sequence encoding a second antigen.

12. The method of embodiment 11 wherein the first and second antigen are expressed as a fusion protein that comprises a self-cleaving A2 peptide between the two antigens.

13. The method of embodiment 12, wherein self-cleaving A2 peptide comprises the amino acid sequence of SEQ ID NO: 56 or SEQ ID NO: 57.

14. The method of any one of embodiments 11 to 13, wherein the first antigen is NY-ESO-1 and the second antigen is MAGE-A3.

15. The method of embodiment 11, wherein the first and second antigen are expressed from a bi-directional promoter.

16. The method of any one of the above embodiments, wherein the kifunensine is present in the culture medium at a concentration of about 0.1 µg/ml to about 10 µg/ml.

17. The method of embodiment 16, wherein the kifunensine is present in the culture medium at a concentration of about 0.25 µg/ml to about 2 µg/ml.

18. The method of any one of the above embodiments, wherein the virus packaging cell further comprises:
(i) a polynucleotide comprising gag and pol genes; and
(ii) a polynucleotide encoding a rev protein.

19. The method of embodiment 18, wherein the gag and pol genes are human codon optimized and comprise a non-optimized window around position 1228 to 1509 of SEQ ID NO: 54.

20. The method of embodiment 18 or 19, wherein the polynucleotide comprising gag and pol genes lacks a functional rev responsive element (RRE).

21. The method of any one of embodiments 18 to 20, wherein the pol gene encodes an inactive integrase enzyme.

22. The method of embodiment 21, wherein the integrase enzyme has a D64V mutation.

23. The method of any one of embodiments 18 to 22, wherein the polynucleotide encoding the Vpx protein is on the same or different plasmid as the polynucleotide encoding the rev protein, or the polynucleotide comprising the gag and pol genes.

24. The method of any one of the above embodiments, wherein the lentiviral vector genome is derived from HIV-1.

25. The method of any one of the above embodiments, wherein the lentiviral vector genome has an inactivated 3' long terminal repeat (LTR) or a self-inactivating 3' long terminal repeat (LTR).

26. The method of embodiment 25, wherein the lentiviral vector genome comprises a U3 element lacking at least one of an enhancer sequence, a TATA box, an Sp1 site, an NK-kappa B site, or a polypurine tract (PPT).

27. The method of any one of the above embodiments, wherein the lentiviral vector genome comprises the nucleotide sequence of any one of SEQ ID NOs: 21, 22, or 23.

28. The method of any one of the above embodiments, wherein the lentiviral vector genome further comprises a nucleotide sequence encoding a dendritic cell maturation/stimulatory factor.

29. The method of embodiment 28, wherein the dendritic cell maturation/stimulatory factor is selected from the group consisting of GM-CSF, IL-2, IL-4, IL-6, IL-7, IL-15, IL-21, IL-23, TNFα, B7.1, B7.2, 4-1BB, CD40 ligand, and drug-inducible CD40.

30. The method of any one of the above embodiments, wherein the nucleotide sequence encoding an antigen is operably linked to a promoter selected from the group consisting of the human Ubiquitin-C promoter (UbiC), the cytomegalovirus immediate early promoter (CMV), the Rous sarcoma virus promoter (RSV), and the tetracycline-responsive promoter.

31. The method of embodiment 30, wherein the promoter is an intron-deficient promoter.

32. The method of embodiment 31, wherein the intron-deficient promoter is a UbiC promoter.

33. The lentiviral vector particle produced by the embodiment of claim 1.

34. The lentiviral vector particle produced by the embodiment of claim 18.

35. A method of generating a pseudotyped lentiviral vector particle comprising:
(a) culturing in a culture medium comprising kifunensine a virus packaging cell comprising:
(1) a lentiviral vector genome comprising a polynucleotide encoding MAGE-A3 and NY-ESO-1, wherein a polynucleotide encoding a self-cleaving TA2 peptide is positioned between the polynucleotide encoding MAGE-A3 and NY-ESO-1, wherein the lentiviral genome lacks a polypurine tract (PPT), and wherein expression of MAGE-A3 and NY-ESO-1 is controlled by a UbiC promoter lacking an intron,
(2) a polynucleotide encoding a Sindbis E2 glycoprotein that preferentially binds dendritic cells expressing DC-SIGN,
(3) a polynucleotide comprising human codon optimized gag and pol genes, wherein the polynucleotide lacks a functional rev responsive element (RRE) and wherein the pol gene encodes an inactive integrase enzyme,
(4) a polynucleotide encoding a Vpx protein or a Vpr protein that retains SAMHD1-inhibiting activity; and
(b) isolating a pseudotyped lentiviral vector particle that preferentially binds dendritic cells expressing DC-SIGN.

36. A composition comprising pseudotyped lentiviral vector particles comprising (a) a Vpx protein or a Vpr protein that retains SAMHD1-inhibiting activity, (b) an exogenous polynucleotide encoding an antigen, and (c) a plurality of envelope glycoproteins that preferentially bind cells expressing DC-SIGN, wherein said composition is more highly mannosylated compared to a control composition of the same pseudotyped lentiviral vector particles prepared in the absence of a mannosidase inhibitor.

37. The composition of embodiment 36, wherein the envelope glycoproteins are alphavirus glycoproteins.

38. The composition of embodiment 37, wherein the envelope glycoproteins are Sindbis glycoproteins.

39. The composition of any of embodiments 36-38, wherein high mannosylation is characterized by being more EndoH-sensitive than a control composition prepared in the absence of a mannosidase inhibitor.

40. The composition of any of embodiments 36-38, wherein EndoH sensitivity is determined by assessing the molecular weight of the envelope glycoproteins by sodium dodecyl sulfate-polyacrylamide gel electrophoresis (SDS-PAGE) after EndoH treatment.

41. The composition of any one of embodiments 36-38, wherein the molecular weight of the envelope glycoproteins after treatment with EndoH has shifted about 45% or more of the distance between (a) envelope glycoproteins not treated with an endoglycosidase, and (b) envelope glycoproteins treated with PNGase F.

42. The composition of embodiment 41, wherein the molecular weight of the envelope glycoproteins after treatment with EndoH has shifted approximately 70% or more of the distance between (a) envelope glycoproteins not treated with endoglycosidase, and (b) envelope glycoproteins treated with PNGase F.

43. The composition of embodiment 41, wherein the molecular weight of the envelope glycoproteins after treatment with EndoH has shifted approximately 90% or more of the distance between (a) envelope glycoproteins not treated with endoglycosidase, and (b) envelope glycoproteins treated with PNGase F.

44. The composition of any one of embodiments 36-43, wherein at least 30% of the envelope glycoproteins in said composition have an increased amount of EndoH-sensitive glycan as compared to control glycoproteins having the same amino acid sequence(s) in a control composition of pseudotyped lentiviral vector particles prepared in the absence of a mannosidase inhibitor.

45. The composition of any one of embodiments 36-44, wherein a majority of the envelope glycoproteins are highly mannosylated.

46. The composition of any one of embodiments 36-45, wherein the pseudotyped lentiviral vector particles are integration deficient.

47. The composition of any one of embodiments 36-46, wherein the composition comprises a Sindbis E2 glycoprotein.

48. The composition of embodiment 47, wherein the E2 glycoprotein is 90% identical to SEQ ID NO: 30 [SIN-Var1].

49. The composition of embodiment 47 or 48, wherein (i) residue 160 of the E2 glycoprotein is absent or is an amino acid other than glutamic acid, (ii) one or more of residues 70, 76, or 159 of the E2 glycoprotein variant is a non-basic residue, and (iii) the E2 glycoprotein variant is not part of a fusion protein with Sindbis virus E3 glycoprotein.

50. The composition of embodiment 49, wherein the E2 glycoprotein is SEQ ID NO: 30 [SIN-Var1].

51. The composition of any one of embodiments 36-50, wherein the Vpx protein comprises an amino acid sequence that is at least 80% identical to SIVmac Vpx [SEQ ID NO: 44].

52. The composition of any one of embodiments 36-50, wherein the Vpx protein comprises an amino acid sequence at least 90% identical to SIVmac Vpx (SEQ ID NO: 44), SIVsm Vpx (SEQ ID NO: 45), SIVrcm Vpx (SEQ ID NO: 46), or HIV-2 Vpx (SEQ ID NO: 47).

53. The composition of any one of embodiments 36-49, wherein the Vpx protein comprises an amino acid sequence at least 90% identical to SIVdeb Vpr (SEQ ID NO: 48) or SIVmus Vpr (SEQ ID NO: 49).

54. The composition of any one of embodiments 36-53, wherein the antigen is a tumor-specific antigen or a virus-specific antigen.

55. The composition of embodiment 54, wherein the tumor-specific antigen is selected from the group consisting of NY-ESO-1, MAGE, MART-1/Melan-A, BAGE, RAGE, gp100, gp75, mda-7, tyrosinase, tyrosinase-related protein, renal cell carcinoma antigen, 5T4, SM22-alpha, carbonic anhydrase I, carbonic anhydrase IX (also known as G250), HIF-1alpha, HIF-2alpha, VEGF, prostate specific membrane antigen (PSMA), prostate-specific antigen (PSA), prostatic acid phosphates, six-transmembrane epoithelial antigen of the prostate (STEAP), NKX3.1, telomerase enzyme, survivin, mesothelin, mutated ras, bcr/abl rearrangement, Her2/neu, mutated p53, wild-type p53, cytochrome P450 1B1, N-acetylglucosaminyltransferase-V, human papilloma virus protein E6, human papilloma virus protein E7, carcinoembryonic antigen, and alpha-fetoprotein.

56. The composition of embodiment 54, wherein the virus-specific antigen is an HIV antigen, an SIV antigen, an adenovirus antigen, an enterovirus antigen, a coronavirus antigen, a calicivirus antigen, a distemper virus antigen, an Ebola virus antigen, a flavivirus antigen, a hepatitis virus antigen, a herpesvirus antigen, an infectious peritonitis virus antigen, an influenza virus antigen, a leukemia virus antigen, a Marburg virus antigen, an orthomyxovirus antigen, a papilloma virus antigen, a parainfluenza virus antigen, a paramyxovirus antigen, a parvovirus antigen, a pestivirus antigen, a picorna virus antigen, a poliovirus antigen, a pox virus antigen, a rabies virus antigen, a reovirus antigen, a retrovirus antigen, or a rotavirus antigen.

57. The composition of any one of embodiments 36-56, wherein the lentiviral vector genome further comprises a nucleotide sequence encoding a second antigen.

58. The composition of embodiment 57 wherein the first and second antigen are expressed as a fusion protein that comprises a self-cleaving A2 peptide between the two antigens.

59. The composition of embodiment 58, wherein self-cleaving A2 peptide comprises the amino acid sequence of SEQ ID NO: 56 or SEQ ID NO: 57.

60. The composition of any one of embodiments 57-59, wherein the first antigen is NY-ESO-1 and the second antigen is MAGE-A3.

61. The composition of embodiment 57, wherein the first and second antigen are expressed from a bi-directional promoter.

EXAMPLES

The following examples are provided for illustration and are not intended to limit the scope of the disclosure.

Example 1

Lentiviral Vector Particles Pseudotyped with Sindbis Virus Glycoproteins Produced in the Presence of Kifunensine Efficiently Infect DC-SIGN-Expressing Cells The goal of the following experiments was to attempt to produce and characterize pseudotyped lentiviral vectors with highly mannosylated envelope glycoproteins. In so doing, the inventors unexpectedly discovered that kifunensine was far more effective at producing pseudotyped lentiviral vectors with the capability to efficiently infect cells expressing DC-SIGN (e.g., dendritic cells) using significantly smaller concentrations as compared to other mannosidase I inhibitors including DMNJ.

293T cells were transfected with four separate plasmids encoding the lentiviral genome, the Gag/Pol, Rev, and the Envelope, respectively, using polyethyleneimine (PEI). Five hours after transfection, mix+media was removed. Media was added back to the vessel along with the indicated amount of mannosidase inhibitor (i.e., DMNJ, kifunensine, and swainsonine). 48 hours later, supernatant (containing vector) was collected and filtered with a 0.45 μm filter. HT1080 cells stably expressing the human DC-SIGN receptor were then transduced with the indicated volumes of vector. The parental HT1080 cells (lacking DC-SIGN), were used as controls, and were not transduced by any of the vectors. 48 hours after transduction, cells were analyzed for GFP expression (gfp %). The results are shown in FIGS. 1A (HT1080 expressing DC-SIGN) and 1B (parental HT1080).

Figure 4A:
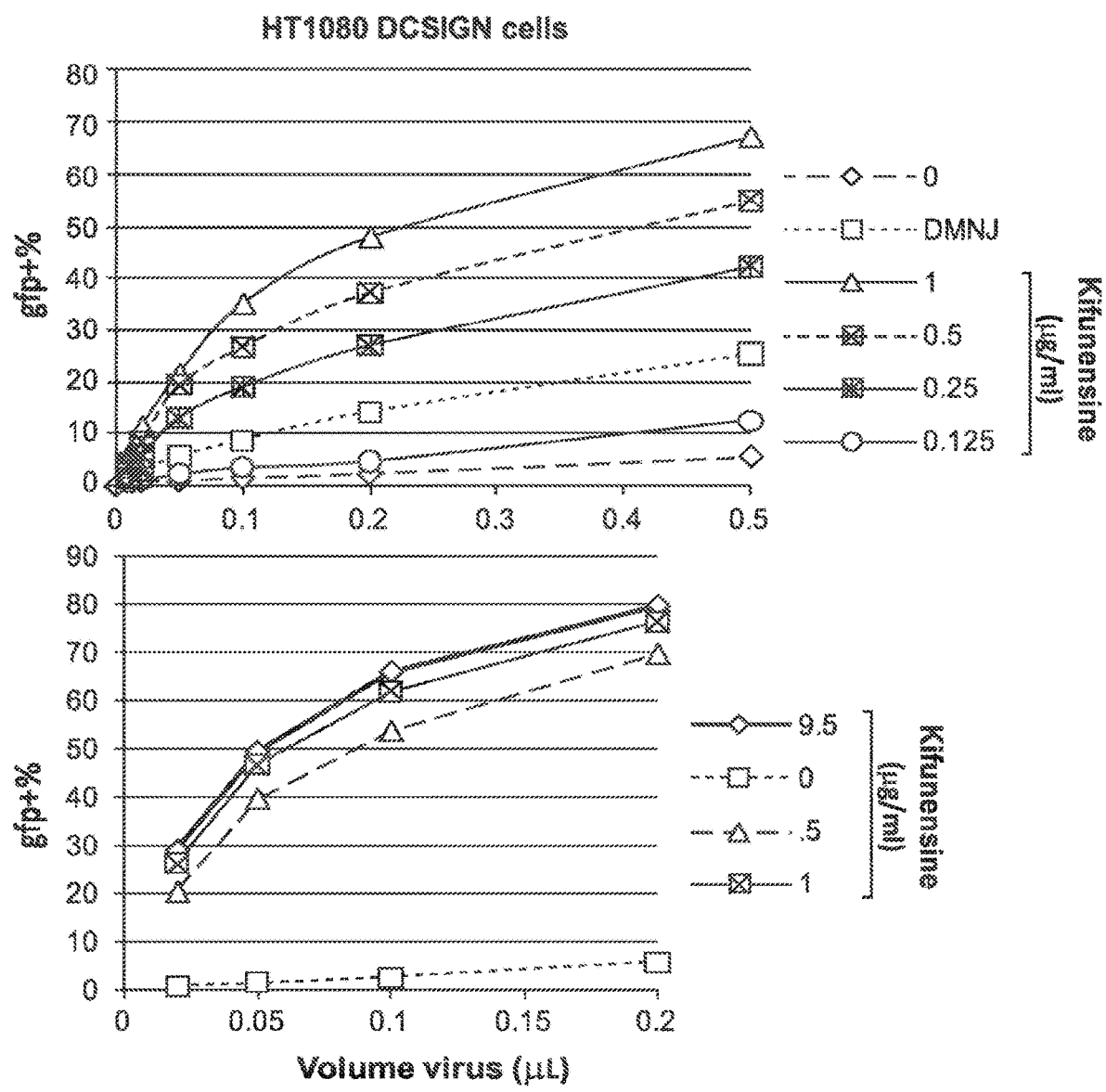

Lentiviral vector particles pseudotyped with Sindbis virus glycoproteins and produced in the presence of low concentrations of kifunensine (1 μg/ml) unexpectedly transfect cells expressing DC-SIGN significantly better than those produced in the presence of higher concentrations of DMNJ (400 μg/ml) or swainsonine (10 μg/ml). Accordingly, production of lentiviral vector particles pseudotyped with Sindbis virus glycoproteins in the presence of the mannosidase I inhibitor kifunensine results in significantly enhanced infection of DC-SIGN-expressing cells as compared to particles produced in the presence of other mannosidase I inhibitors.

Example 2

Low Amounts of Kifunensine are Required to Generate Pseudotyped Lentiviral Vector Particles that Efficiently Infect DC-SIGN-Expressing Cells The goal of this experiment was to determine the concentration of kifunensine most effective at producing pseudotyped lentiviral vector particles with the capability of infecting DC-SIGN-expressing cells.

293T cells were transfected with the plasmids described in Example 1 using PEI. Five hours after transfection, mix+media was removed. Media was added back to the vessel along with the indicated amount of Kifunensine (μg/ml), or with 400 μg/ml of DMNJ. 48 hours later supernatant (containing lentiviral vector particles) was collected and filtered with a 0.45 μm filter. HT1080 cells stably expressing the human DC-SIGN receptor were then transduced with the indicated volumes of supernatant containing vector. The parental HT1080 cells, which are not transduced by the vector, were used as controls. 48 hours after transduction, cells were analyzed for gfp expression (gfp+%). The results are shown in FIGS. 2A (HT1080 cells expressing DC-SIGN) and 2B (parental HT1080 cells).

Particles produced in the presence of 0.125 μg/ml kifunensine matched the ability of particles produced in the presence of 400 μg/ml DMNJ to infect DC-SIGN-expressing cells (FIG. 2A). Particles produced in the presence of all kifunensine concentrations exceeding 0.125 μg/ml infected DC-SIGN-expressing cells much more efficiently that particles produced in the presence of 400 μg/ml DMNJ. The titration of kifunensine revealed that the ability of lentiviral vector particles pseudotyped with Sindbis virus glycoproteins to infect DC-SIGN-expressing cells peaks with particles produced in the presence of 0.25 μg/ml.

Example 3

The goal of this experiment was to characterize the glycosylation profile of pseudotyped lentiviral particles produced in the presence of DMNJ or kifunensine.

Lentiviral vector particles pseudotyped with Sindbis virus glycoproteins were prepared according to Example 1 in the presence of 1 μg/ml kifunensine, DMNJ, or no mannosidase I inhibitor. The particles were incubated with either PNGaseF or EndoH for 1 hour. PNGaseF is a general endoglycosidase that will cleave all N-linked glycosylation regardless of glycosylation profile (see FIG. 3A). EndoH is a specialized endoglycosidase that will only cleave high-mannose N-linked glycosylation (see FIG. 3A). When viral particles are produced in the presence of a mannosidase I inhibitor, the viral envelope would be expected to have glycoproteins with high $Man_9$ content and susceptible to cleavage by EndoH. Samples were analyzed using a gel-shift assay by running on an SDS-PAGE gel and immunoblotting with antibody against the Sindbis viral envelope. The results are illustrated in FIG. 3B.

The degree of mobility of the viral envelope (SIN-Var1) of virus produced in the presence or absence of kifunensine or DMNJ, combined with the treatment of PNGaseF or EndoH, is indicative of the degree of glycosylation of Var1. Control virus (lane 1) is glycosylated (consequently running slower on the gel) and this glycosylation can be completely removed by PNGaseF (as evidenced by the faster mobility seen in lane 2). As expected due to the ability of PNGaseF to cleave any N-linked glycosylation, virus produced in the presence of either DMNJ or Kifunensine is sensitive to PNGaseF treatment (lanes 5 and 8). However, only virus produced in the presence of mannosidase I inhibitors (Var1+DMNJ or +kifunensine) are sensitive to EndoH treatment (lanes 6 and 9) whereas the control virus (Var1) is only partially sensitive to EndoH. The partial sensitivity likely comes from sites in E2-Var1 that are normally not exposed to mannosidase I during production and do not contribute to binding to dendritic cells. These results indicate that the efficiency of the mannosidase I inhibitor kifunensine in producing viral particles with high-mannose glycoproteins can be measured using a gel-shift assay after EndoH treatment and comparing its efficiency to particles produced in the presence of DMNJ.

Example 4

Mannose Content in Envelope Glycoproteins Correlates with Kifunensine Concentration in Media Used to Prepare Viral Particles The goal of this experiment was to characterize the glycosylation profile of pseudotyped lentiviral particles produced in the presence of varying concentrations of kifunensine.

Lentiviral vector particles pseudotyped with Sindbis virus glycoproteins were prepared according to Example 1 with varying concentrations of kifunensine or 400 μg/ml of DMNJ. The particles were incubated with EndoH for 1 hour. Samples were then analyzed using a gel-shift assay and immunoblotting with antibody against the Sindbis virus envelope. In parallel, HT1080 cells stably expressing the human DC-SIGN receptor were transduced with the indicated volumes of pseudotyped lentiviral vector particles prepared with or without kifunensine or DMNJ. 48 hours after transduction, cells were analyzed for GFP expression (shown on the y-axis as percent of GFP positive cells) to create the graphs. The results are illustrated in FIG. 4.

Figure 4B:
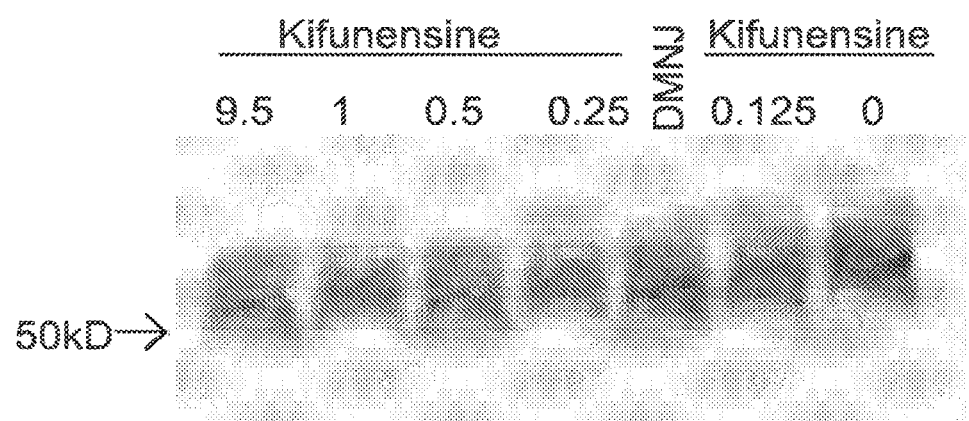

The degree of mannose content correlates with the degree of transduction of HT1080 DC-SIGN cells, as indicated by the degree of shift on the gel of EndoH treated samples (FIG. 4A) and the percent GFP transduction graphs (FIG. 4B). I.e., increasingly higher kifunensine concentrations in the media used to prepare viral particles resulted in higher mannose content envelope glycoproteins, as demonstrated by greater shifts with EndoH treatment and higher GFP expression (i.e., infection) in HT1080 cells expressing DC-SIGN. These results indicate that kifunensine directly affects the degree of mannose content on the viral envelope and this correlates directly with the ability to transduce HT1080 cells expressing the human DC-SIGN receptor.

Example 5

Confirmation of Vpx Expression in Pseudotyped Lentiviral Vector Particles

The goal of this experiment was to determine if SIVmac Vpx could be expressed and detected in pseudotyped lentiviral vector particles.

Figures 5A, 5B:
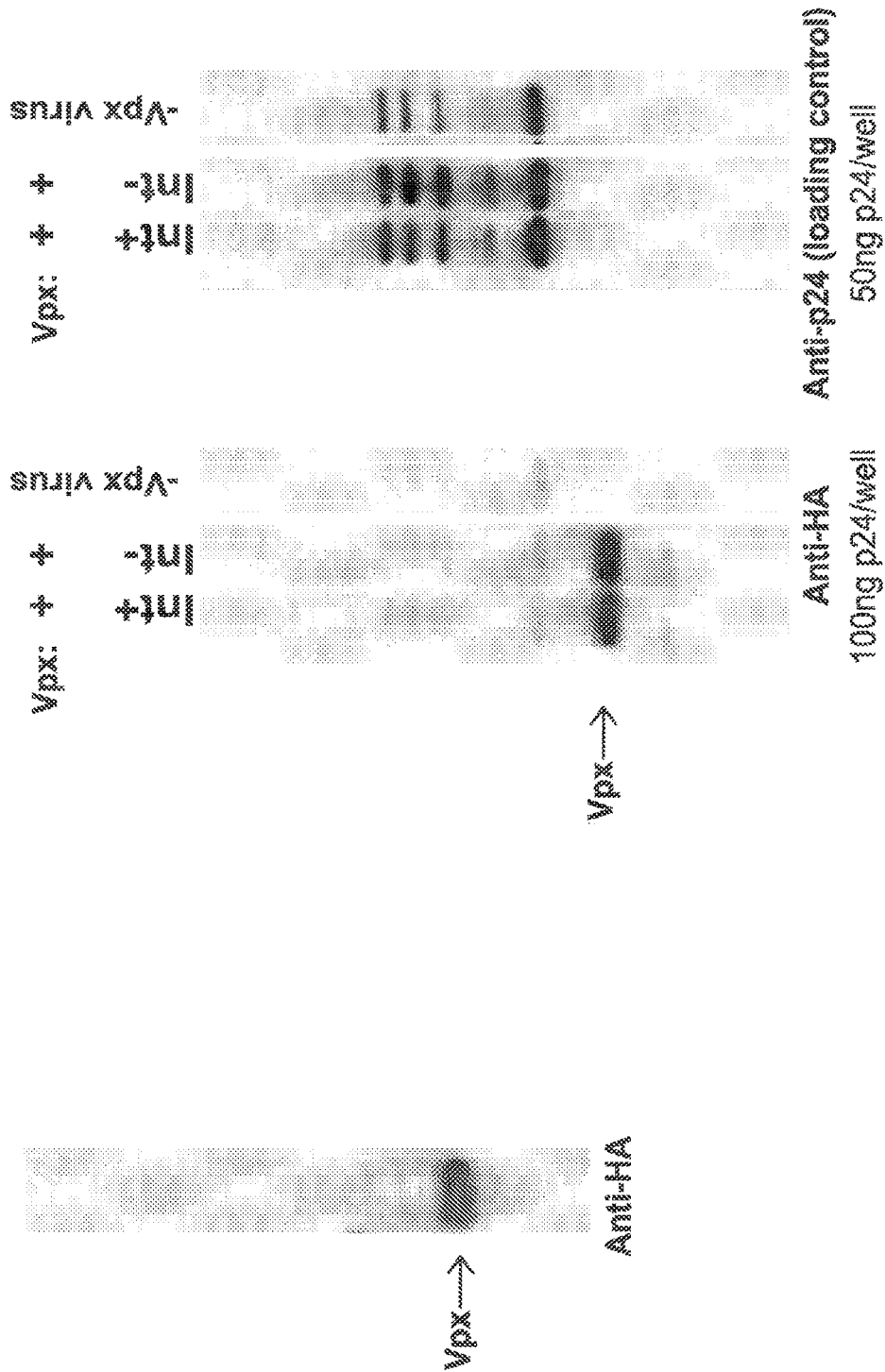
Figure 6:
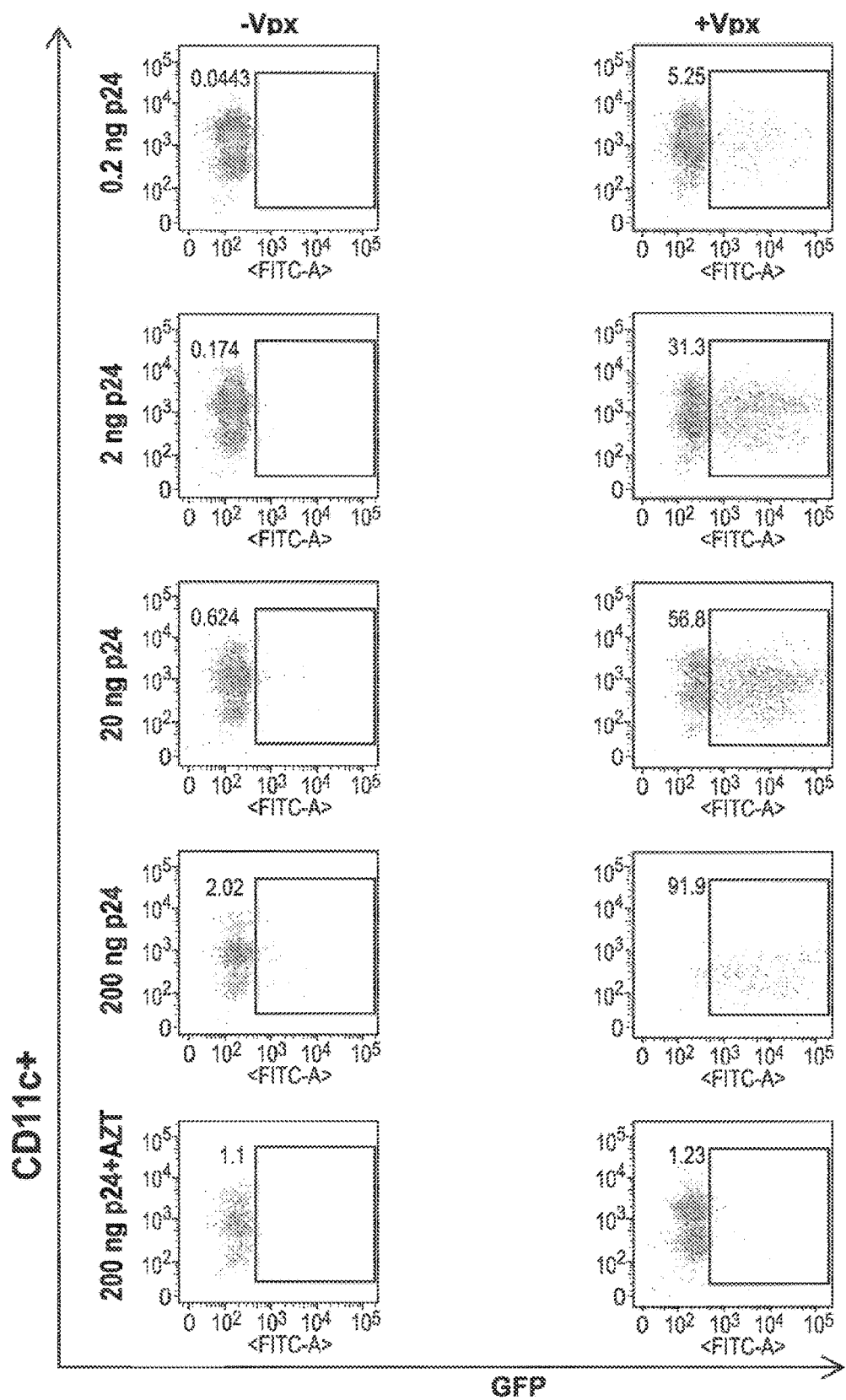
Figure 7:
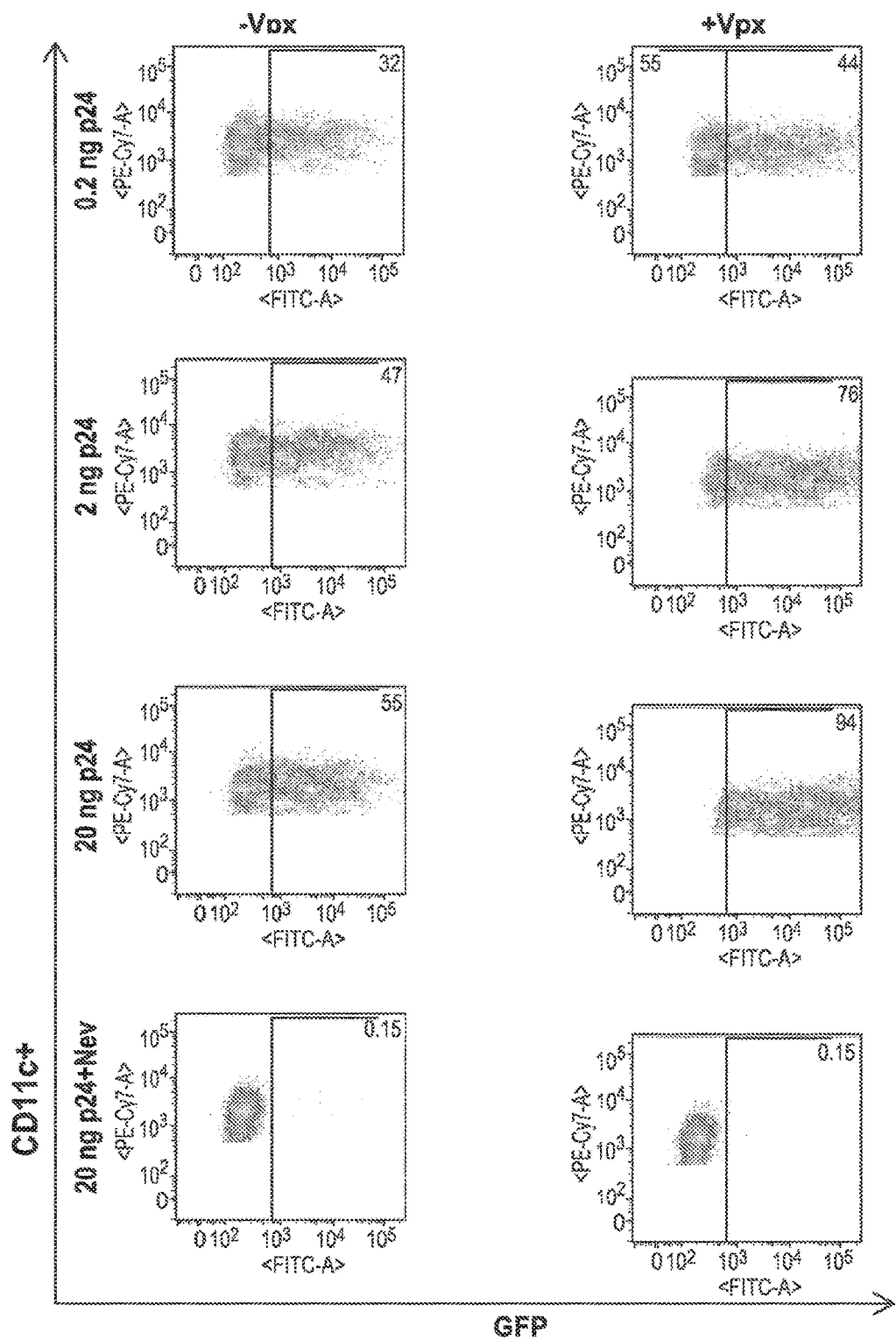
Figure 8:
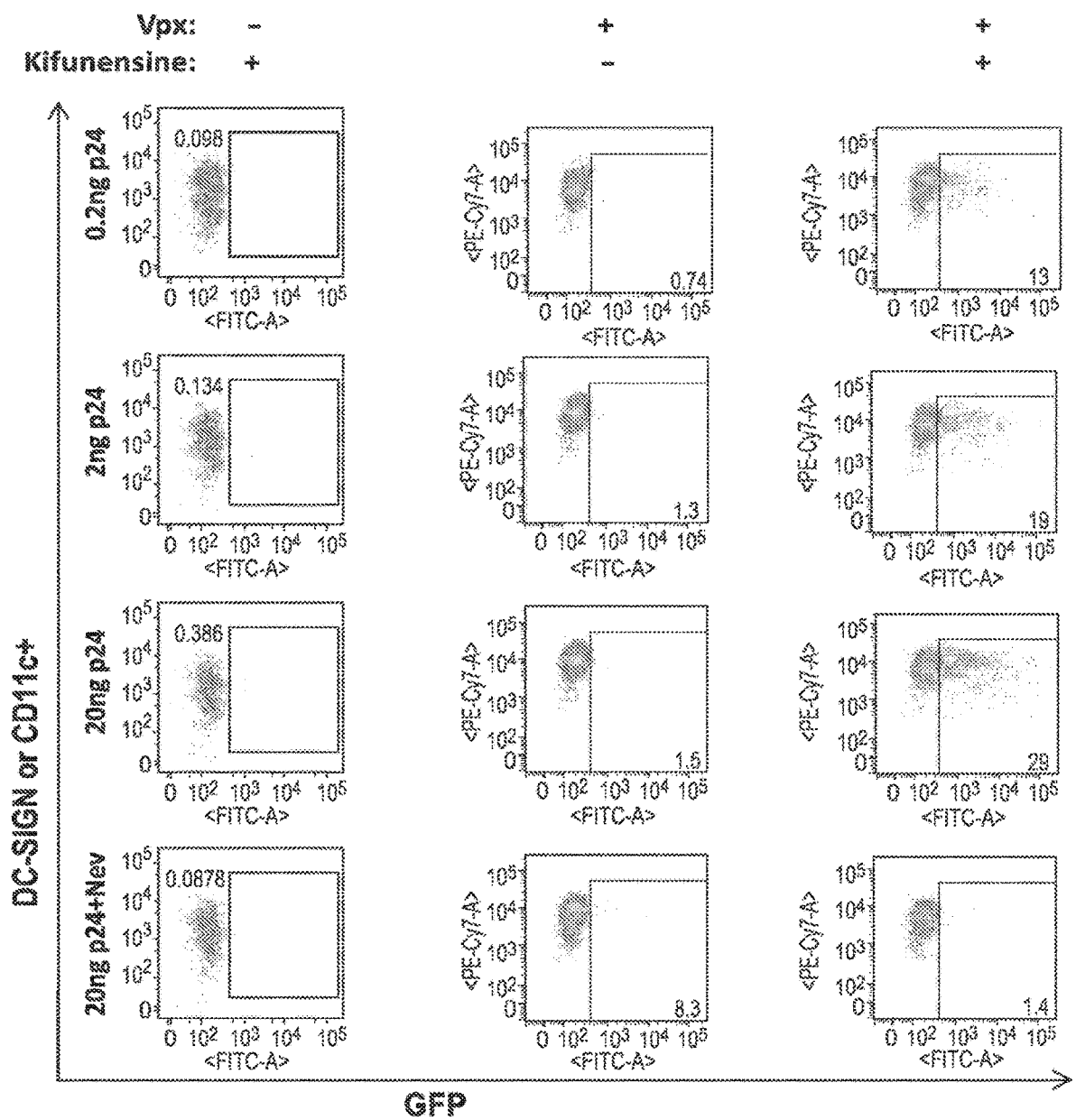

SIVmac Vpx with an N-terminal HA tag was cloned into a mammalian expression vector driven by a CMV promoter (construct named pENV-SIVmacVpx). To confirm that the Vpx protein was expressed, 293T cells were transfected with this construct and lysed 24 hours after transfection. Lysates were analyzed via immunoblotting using anti-HA antibody (FIG. 5A). To confirm that Vpx was packaged into lentivirus particles, lentiviruses were prepared using four plasmids transfected into 293T packaging cells. These four plasmids encode the lentiviral genome, the Gag/Pol (either integration competent [Int+], or integration-defective [Int−]), Rev, and the Envelope. A fifth plasmid was either included for Vpx or not. Virus was collected two days after transfection and concentrated using centrifugation. 100 ng of p24 was loaded per well onto a gel for immunoblotting with anti-HA antibody (FIG. 5B). As a loading control anti-p24 antibody was used.

In 293T cells transfected with the plasmid encoding the Vpx gene, Vpx protein is efficiently expressed (FIG. 5A). Similarly, Vpx is packaged into both integration-competent (Int+) and integration-defective (Int−) lentivirus particles (FIG. 5B).

Example 6

Vpx is Necessary for Efficient Transduction of Human Dendritic Cells by VSV-G-Pseudotyped Integration-Deficient Lentiviral Vector Particles The goal of this experiment was to determine if Vpx was required for a productive infection of dendritic cells by VSV-G-pseudotyped integration-deficient lentiviral vector particles.

Human peripheral blood mononuclear cells (PBMCs) were enriched for CD14+ monocytes, followed by enrichment for dendritic cells using GMCSF and IL-4. These PBMC-derived human dendritic cells were transduced with increasing amounts VSV-G-pseudotyped integration-deficient lentiviral vector particle (0.2 ng, 2 ng, 20 ng or 200 ng of p24) constructs which either did or did not contain Vpx. Five days after infection, transduction events were measured by gating on cells that were positive for CD11c, and assessing percent of cells positive for GFP (x-axis) with DC-SIGN on the y-axis. AZT (a reverse-transcriptase inhibitor) was used on the highest dose of lentiviral vector particles (200 ng).

The results are illustrated in FIG. 6. Vpx was required for integration-deficient VSV-G-pseudotyped lentiviral particles to transduce human dendritic cells derived from PBMCs. Efficient transduction is dependent on reverse transcription because it was inhibited by AZT.

Example 7

Vpx Improves Transduction of Human Dendritic Cells by VSV-G-Pseudotyped Integration-Competent Lentiviral Vector Particles The goal of this experiment was to determine if Vpx was required for a productive infection of dendritic cells by VSV-G-pseudotyped integration-competent lentiviral vector particles.

Human PBMCs were enriched for CD14+ monocytes, followed by enrichment for dendritic cells using GMCSF and IL-4. These PBMC-derived human dendritic cells were transduced with increasing amounts of VSV-G-pseudotyped integration-competent lentiviral vector particle (0.2 ng, 2 ng, or 20 ng of p24) constructs which either did or did not contain Vpx. Five days after infection, transduction events were measured by gating on cells that were positive for CD11c, and assessing percent of cells positive for GFP (x-axis) with CD11c on the y-axis. Nevirapine (Nev, a reverse-transcriptase inhibitor) was used on the highest dose of lentiviral vector particles (20 ng).

The results are illustrated in FIG. 7. Vpx enhanced the ability of integration-competent lentiviral vector particles to transduce human dendritic cells derived from PBMCs. The improved transduction is dependent on reverse transcription because it was inhibited by Nevirapine.

Example 8

Vpx and Highly Mannosylated Envelope Glycoproteins are Necessary for Efficient Transduction of Human Dendritic Cells by Lentiviral Vector Particles Pseudotyped with Sindbis Virus Envelope Glycoproteins The goal of this experiment was to test the capability of Sindbis virus E2 glycoprotein pseudotyped lentiviral vector particles comprising a Vpx protein and produced in the presence of kifunensine to productively infect dendritic cells.

Human PBMCs were enriched for CD14+ monocytes, followed by enrichment for dendritic cells using GMCSF and IL-4. These PBMC-derived human dendritic cells were transduced with varying amounts SINvar1-pseudotyped integration-defective lentiviral vector particle (0.2 ng, 2 ng, or 20 ng of p24) constructs which either did or did not contain Vpx, or were produced in the presence or absence of the mannosidase I inhibitor, kifunensine. Five days after infection, transduction events were measured by gating on cells that were positive for CD11c, and assessing percent of cells positive for GFP (x-axis) with either DC-SIGN or CD11c on the y-axis. Nevirapine (Nev, a reverse-transcriptase inhibitor) was used on the highest dose of lentiviral vector particles (20 ng).

As shown in FIG. 8, unexpectedly, both Vpx and production of the viral particles in the presence of kifunensine are required to efficiently transduce human dendritic cells using a lentivirus pseudotyped with Sindbis virus glycoproteins. Accordingly, these results show that particles comprising the combination of highly mannosylated glycoproteins (a result of particle formation in the presence of kifunensine) and Vpx act synergistically to efficiently infect and express lentiviral genome-encoded proteins. I.e., if either one of Vpx or highly mannosylated glycoproteins are missing from the Sindbis envelope glycoprotein-pseudotyped integration-defective lentiviral particles, dendritic cells are not efficiently transduced.

Example 9

Quantifying the Mannosylation of the Lentiviral Vector Particle Envelopes

Figure 9A:
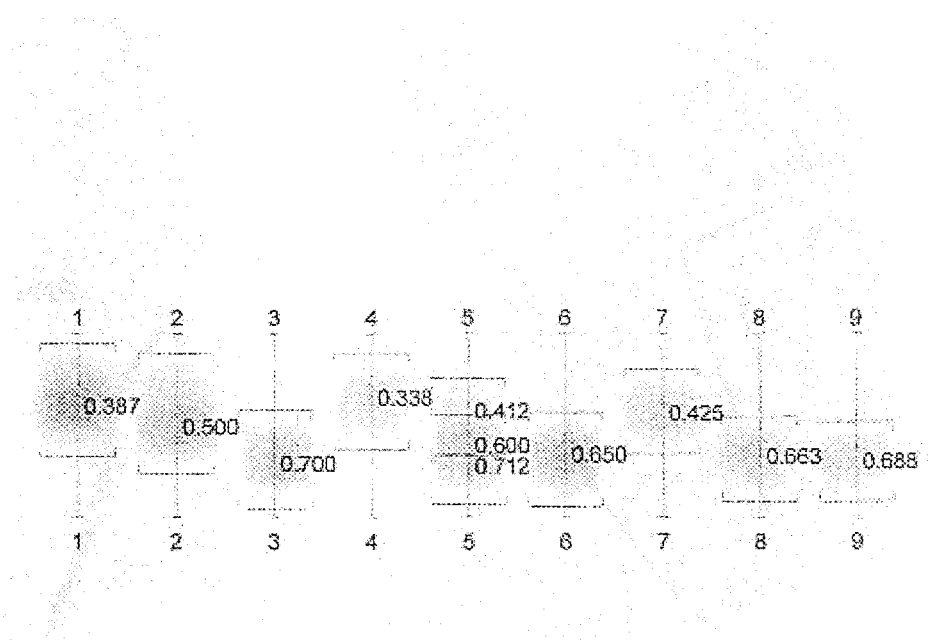

Lentiviral vector particles pseudotyped with Sindbis virus glycoproteins were prepared according to Example 1 with no treatment (FIG. 9A, lanes 1-3), 400 µg/ml of DMNJ (FIG. 9A, lanes 4-6), or 1 µg/ml of kifunensine (FIG. 9A, lanes 7-9). The particles were not treated (lanes 1, 4, 7), incubated with EndoH for 1 hour (lanes 2, 5, 8), or incubated with PNGaseF for 1 hour (lanes 3, 6, 9). Samples were then analyzed using a gel-shift assay and immunoblotting with antibody against the Sindbis virus envelope.

Analysis of the gel shift data was performed using Quantity One software from Biorad. In brief, using the "Lane" function, vertical lines were drawn through each of the 9 lanes shown in FIG. 9A. This specifies the area to be analyzed to the program. Next, using the "Band attributes" function, the peak intensity for each band was determined. These values are also shown in FIG. 9A. This gives us the peak intensity value of each band on the gel through the previously indicated "lane."

Figure 9B:
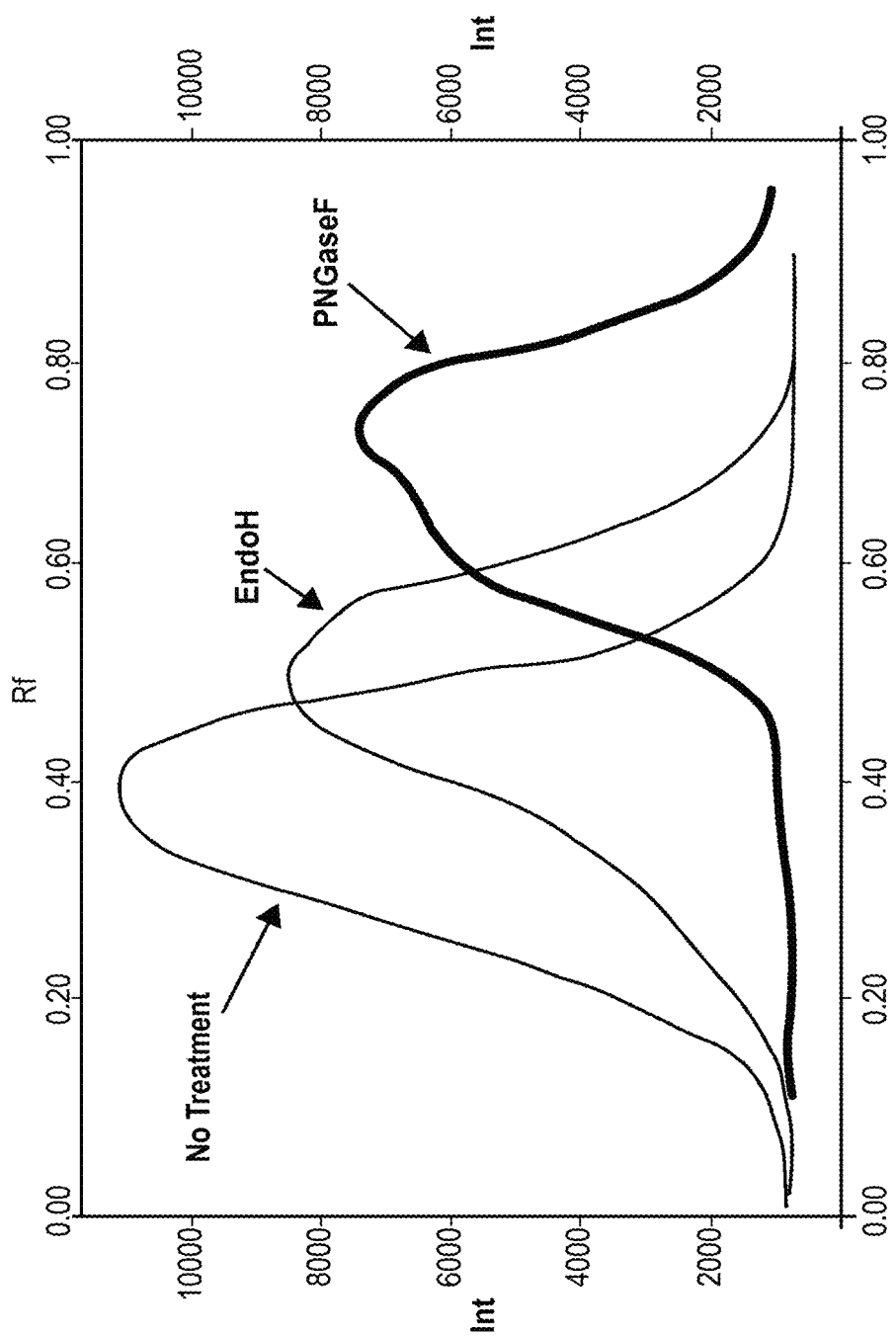
Figure 9C:
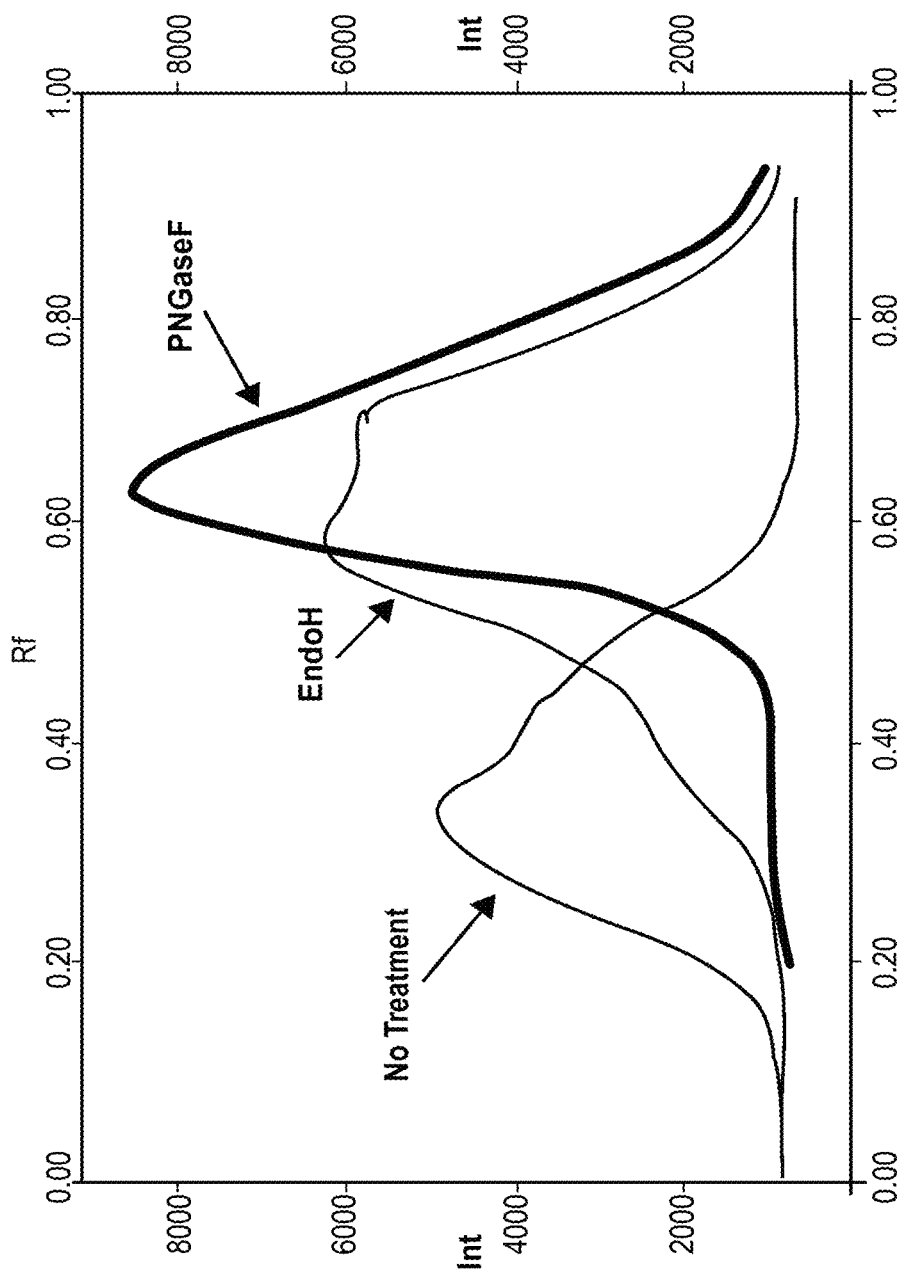
Figure 9D:
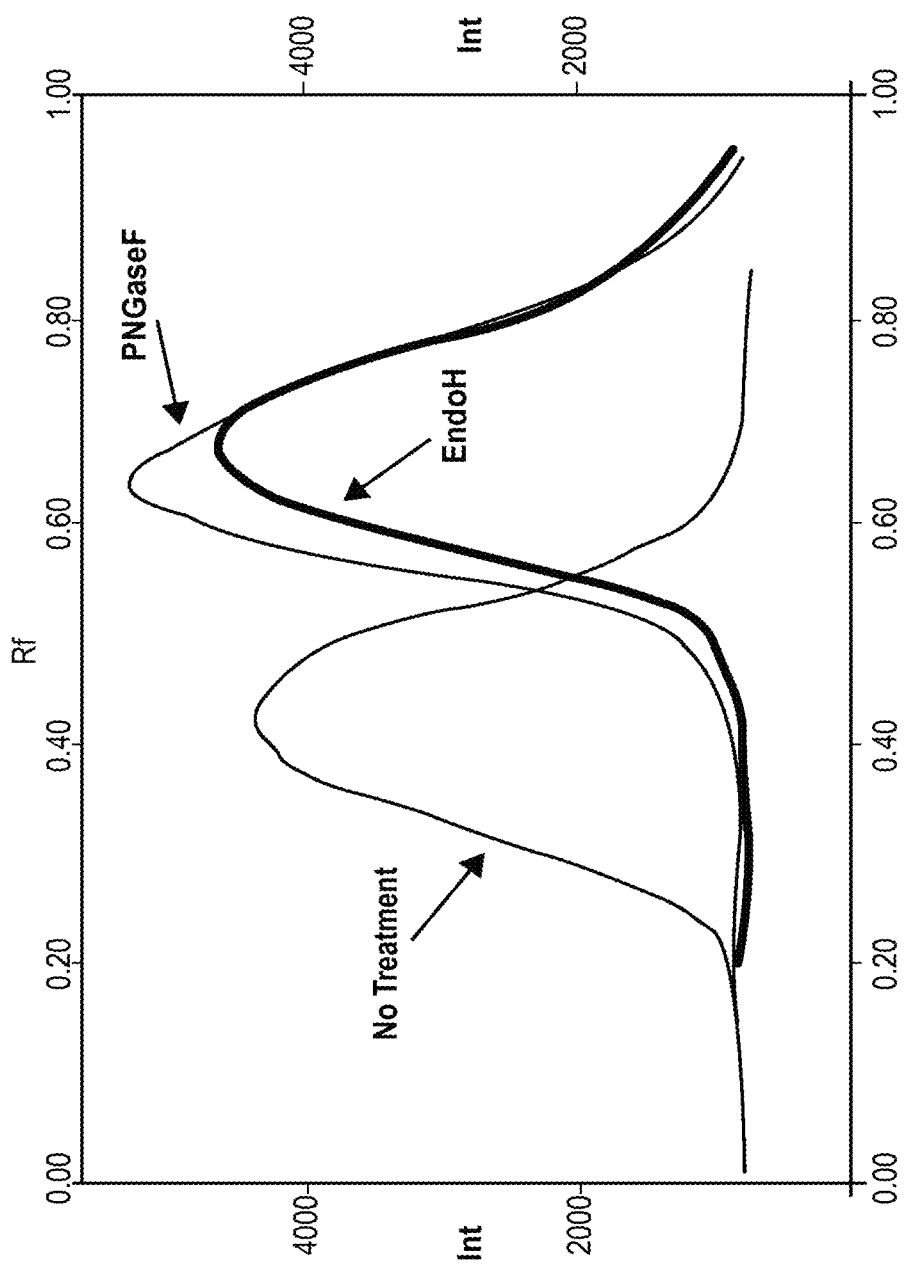

Next, graphs were assembled from the intensity profile of each band and its location on the lane. The results are shown in FIG. 9B (no mannosidase treatment), FIG. 9C (DMNJ treatment, and FIG. 9D (kifunensine treatment).

Each graph depicts each of the envelope types digested with no enzyme, Endo H, or PNGaseF, as indicated. The Y-axis is the intensity of the band and the X-axis is the location of the band along the described lane (i.e., the "relative front" (rf) value; the rf value is the distance of the band from the top of the gel over the total length of the lane). To quantify the shift, the peak intensity of a band that was not cut with a digestive enzyme (i.e., full glycosylation) was compared with a band that was cut with the PNGaseF enzyme (i.e., all glycosylation sites removed). Thus, a peak intensity that is equal to a band that has not been digested with any enzyme will be a 0% shift and a peak intensity that is equal to a band that has been digested with PNGaseF will be considered a 100% shift. Without the addition of kifunensine (Lane 2), the EndoH gel shift is 36% of a PNGaseF shift. Significantly, the kifunensine-treated sample digested with EndoH (i.e., high-mannose-specific digestion) shifted 90% of the distance of the PNGaseF shift. Accordingly, nearly all of the glycosylated sites on the viral vector envelope are in a high-mannose state after treatment with 1 µg/ml of kifunensine.

All of the quantitative analysis is shown in Table 1.

TABLE 1

| Envelope | Digestion enzyme | Peak intensity value | Spectrum intensity value | % shift |
|---|---|---|---|---|
| var1 | None | 0.387 | 0 | 0 |
| var1 | endoH | 0.5 | 0.113 | 36.10224 |
| var1 | PNGaseF | 0.7 | 0.313 | 100 |
| var1 + DMNJ | None | 0.338 | | |
| var1 + DMNJ | endoH | .412, .6, .712 | | |

TABLE 1-continued

| Envelope | Digestion enzyme | Peak intensity value | Spectrum intensity value | % shift |
|---|---|---|---|---|
| var1 + DMNJ | PNGaseF | 0.65 | | |
| var1 + kif | None | 0.425 | 0 | 0 |
| var1 + kif | endoH | 0.663 | 0.238 | 90.4943 |
| var1 + kif | PNGaseF | 0.688 | 0.263 | 100 |

Spectrum intensity value is peak intensity value minus the peak intensity value of the envelope digested with no enzyme. This is done to normalize the values in a spectrum from 0% shift to 100% shift, as explained above. % shift is the spectrum intensity value divided by the spectrum intensity value of PNGaseF treated samples multiplied by 100. This generates a percentage that quantifies the shift of a band cut with EndoH as related to bands treated with no enzyme or with PNGaseF. DMNJ treated envelopes were excluded from this analysis because they had heterogenous N-linked glycosylation patterns.

Example 10

Viral Vectors with Integration-Deficiency Design Elements

For clinical applications that require the direct administration of viral vectors but do not require sustained expression of the vector-delivered gene, such as for vaccines and antigen-directed immunotherapies, integration-deficient lentiviral vectors represent an appropriate and viable alternative to fully integration-competent lentiviral vectors for delivery of their genetic payload. The D64V integrase mutation within the gag/pol gene and the cPPT deletion within the vector genome were tested alone and in combination for their impact on integration rate of a viral vector.

Materials and Methods

Quantification of Integration by Alu-PCR.

293T huDC-SIGN cells seeded at 5E5 cells/well in 6-well plates were transduced in triplicate with 2E9 genomes per well of vector. At 48 hours post-transduction, cells were harvested and genomic DNA extracted using the DNeasy Kit (Qiagen, Valencia, Calif.). Genomic DNA was analyzed using an Alu-LTR based nested-PCR assay, which amplifies only provirus sequences that have been integrated into the host genomic DNA. The following modifications were introduced into the previously published method of Brussel et al., *Methods Mol. Biol.* 304, 139 (2005). Platinum Taq (Life Technologies, Grand Island, N.Y.) was used for the first round of amplification in a final reaction volume of 25 al. The first-round PCR cycle conditions were as follows: a denaturation step of 2 min at 95° C. and then 20 cycles of amplification (95° C. for 30 s, 55° C. for 30 seconds, 72° C. for 90 seconds). Nested PCR was performed using EXPRESS qPCR Supermix Universal (Life Technologies) and 100 nM of probe MH60310 in a final volume of 25 µl. The nested PCR protocol began with a 2 minute hold at 50° C. and a 10 minute denaturation step at 95° C., followed by 40 cycles of amplification (95° C. for 15 seconds, 60° C. for 30 seconds). All amplification reactions were performed using the Bio-Rad CFX (-96 or -384 model, Bio-Rad Laboratories, Hercules, Calif.). The copy number of integrated provirus was calculated in reference to a standard curve generated by parallel nested Alu-PCR of a reference 293T cell line containing integrated provirus of known copy number, diluted over a 5-log range. The total genomic DNA in the standard curve was normalized by mixing with genomic DNA from non-transduced cells; each standard and unknown sample contained 100 ng total genomic DNA. This assay allowed the detection of 58 proviruses (Experiment 1) or 4 proviruses (Experiment 2) in 100 ng of genomic DNA.

Quantification of Integration by Neomycin Resistance.

Vectors encoding GFP-T2A-NeoR antigen were independently analyzed for integration rate by neomycin resistant colony formation. HT1080 huDC-SIGN cells were transduced in 6-well plates with 0.5 ml of serially diluted vector (normalized by genomes) for 2 hours, after which 2 ml of complete medium was added. At 24 hours post-transduction, cells were fed with medium containing 800 µg/ml G418 (Life Technologies, Grand Island, N.Y.). Cells were then grown without passaging for 11-13 days under G418 selection, after which colonies were visualized by staining with crystal violet (BD Biosciences, Rockville, Md.). Total integration events were calculated as follows: (# of colonies)×(dilution factor)=Integration Events.

Quantification of Integration by GFP Expression.

For vectors encoding GFP-T2A-NeoR antigen, relative integration rate was measured by GFP expression over time in bulk culture. HT1080 huDC-SIGN cells were transduced in 6-well plates with equal amounts of WT/703 or D64V/704 vector (normalized by genomes) in 0.5 ml for 2 hours, followed by the addition of 2 ml of complete medium. Transduced cells were maintained in medium without drug selection for up to 30 days, passaging at regular intervals. During this period, cells were periodically analyzed for GFP expression by flow cytometry (Guava EasyCyte Plus, Millipore, Billerica, Mass.).

Results 293T huDC-SIGN cells were transduced with WT- or D64V-integrase VSV-G pseudotyped vectors packaging WT ("703") or cPPT-deleted genomes ("704"). At 48 hours post-transduction, cells were analyzed for the presence of integrated provirus by nested Alu-PCR analysis. As shown in FIG. 10A, the WT/704 and D64V/703 vectors each had integration rates that were decreased by approximately 2 logs as compared to WT/703 vector. In comparison, the integration rate of the D64V/704 vector was decreased by greater than 2 logs. These results demonstrate that the ID-VP02 (Sindbis virus E2 glycoprotein pseudotyped lentiviral vector particles with SIVmac Vpx and highly mannosylated envelope glycoproteins and prepared using packaging cells comprising the rev-independent gag/pol system described in Example 12) genome has significantly reduced integration potential, and that the D64V and 704 elements independently contribute to this phenotype.

To complement the nested Alu-PCR analysis, two additional methods were employed to investigate the integration rate of the viral vector genome. In both methods, HT1080 huDC-SIGN cells were transduced with WT/703 or D64V/704 vector encoding GFP and neomycin resistance (NeoR) separated by a self-cleaving T2A linker (GFP-T2A-NeoR). Transduction with either of these vectors results in both GFP and NeoR expression. Integration rate was measured as a function of antigen expression, either by outgrowth of neomycin-resistant colonies following G418 selection or by GFP expression over time in bulk culture.

In the first method of measuring integration rate (i.e., neomycin resistance), HT1080 huDC-SIGN cells were transduced with serial dilutions of vector and grown without passaging in the presence of G418 selection. Input vector was normalized by genome copy number. Cells that expressed NeoR and survived prolonged exposure to G418, forming colonies, were presumed to harbor integrated provirus. These colonies were counted and total integration events were calculated. Using this experimental approach, the integration rate of D64V/704 vector was decreased by 3 logs relative to that of WT/703, in two independent experiments (FIG. 10B).

In the second method (i.e., GFP expression), transduced cells were serially passaged in the absence of selection and analyzed by flow cytometry at varying times post-transduction. At day 2 post-transduction, approximately 40 percent of the cells transduced with WT/703 vector were GFP-positive (FIG. 10C). This population remained consistent for the duration of the experiment, suggesting that GFP expression was primarily from integrated provirus. In contrast, the percent of GFP-positive cells transduced with D64V/704 vector dropped approximately 100-fold by day 6 post-transduction and remained low, albeit higher than the mock-transduced control, for the remainder of the experiment. These results suggest that the majority of D64V/704 transduction events yielded non-integrated vector DNA, which expressed GFP at early times post-transduction, but was lost during subsequent cell divisions. The small percentage of GFP-expressing cells remaining by day 9 post-transduction likely represents the minority of transduction events that yielded integrated provirus. At the completion of the experiment (day 30) it was calculated that the D64V/704 vector was 386-fold decreased in its ability to undergo integration, compared to the WT/703 vector. These findings are comparable to the results from nest Alu-PCR analysis.

Taken together, the results from all three methods of measuring integration rate (nested Alu-PCR, NeoR colony outgrowth, and % GFP expression) demonstrate that the integration rate of the viral vector genome is 2-3 logs reduced relative to that of the standard, integration-competent 3rd generation lentiviral vector (WT/703).

Example 11

Pseudotyped Lentiviral Vector Particles Specifically Transduce Dendritic Cells in a Homogenous Population of Cells Viral vector specificity for dendritic cells was assessed within the context of a heterogenous population of potential target cells. Human PBMCs were placed in culture in the presence of GM-CSF and IL-4 for three days to generate a pool of primary cells that included a sufficient number of monocyte-derived DCs expressing DC-SIGN. On day three, 20 ng p24 of pseudotyped lentiviral vector encoding GFP that were produced in the presence of kifunensine and that contained Vpx were added to the culture. Three days after the introduction of the vector into the culture, cells were analyzed for the expression of GFP as a measure of transduction within the major populations of cells present at the time of analysis: DCs ($CD11c^{pos}$) 6%, B-cells ($CD11c^{neg}$, $CD19^{pos}$) 10%, and T-cells ($CD11c^{neg}$, $CD3\epsilon^{pos}$) 80%. As shown in FIG. 11, 42% of the cells within the $CD11c^{hi}$, DC-SIGN$^+$ population were transduced compared to 0.1% for both the B and T cell populations present within the culture. Transduction was completely ablated in all cell populations when the reverse transcriptase inhibitor nevirapine (RT inhibitor) was included in the culture. These results demonstrate that in a heterogeneous population of human cells of which DCs are a minority, the pseudotyped lentiviral vector specifically transduces DC-SIGN expressing DCs.

Example 12

Design of a Rev-Independent Gag/Pol Plasmid

Of the four plasmid system typical of pseudotyped third-generation LVs, two of the plasmids contain sequences within their transcripts that have the potential for recombining. Namely, the transfer vector (referred to here as the LV genome) and the gag/pol plasmid. There are two regions of sequence homology between transcripts of the LV genome and gag/pol (FIG. 12). First, the LV genome has a partial gag sequence following the psi packaging signal that consists of 354 base pairs (bp) that are identical to the 5' end of the gag sequence in the gag/pol plasmid. Recombination events that take place from this sequence overlap are referred to as psi-gag recombination events. Second, both the LV genome and gag/pol contain the Rev-responsive element (RRE), which consists of 234 bp that form a secondary RNA structure allowing Rev-dependent nuclear export of RRE-containing transcripts into the cytoplasm. These two homologous sequences were removed by deleting the RRE from the gag/pol plasmid and by codon-optimizing the gag/pol open reading frame (ORF), with the exception of a frame-shift region between gag and pol that is required for translation of pol protein products (FIG. 12). The frameshift region forms a secondary RNA structure at the gag and pol junction that causes a −1 register shift of the ribosome during translation that is essential for translating pol gene products. Watts et al., Nature, 460:711-716 (2009). For these experiments, a 282 bp region between base pairs 1228 and 1509 of the gag/pol ORF was not codon-optimized This region starts at bp 1563 of the pNL4-3 sequence of Wild Type HIV-1 which encodes Lysine409 of the Gag protein and extends to include the stop codon of Gag. The remaining regions (bp 1-1228 and bp 1510-4307 of gag/pol) were codon optimized based on the human codon table. Nakamura et al., *Nucleic Acids Res,* 28:292 (2000). The complete ORF of RI gag/pol was synthesized at Genscript and was cloned in place of the ORF consisting of WT gag/pol and the RRE.

Deletion of the RRE is known to eliminate Rev-dependent export of gag/pol transcripts from the nucleus because the RNA secondary structure of gag/pol retains transcripts in the nucleus. Banchereau and Steinman, *Nature,* 392(6673), 245 (1998). Therefore the codon-optimization serves both to eliminate these retentive secondary structures and to minimize sequence homology with the partial gag in the LV genome. Due to the fact that these modifications hypothetically relieve the gag/pol transcript from requiring Rev, the scheme is referred to as Rev-independent gag/pol (RI gag/pol), even though Rev is still required during vector production.

Example 13

Nuclear Export of RI Gag/Pol does not Require Rev

In order to demonstrate that the RI gag/pol transcript is indeed Rev-independent, 293T cells were transfected with either the Wild Type (WT gag/pol) or the RI gag/pol plasmids, in the presence or absence of a Rev encoding plasmid.
Materials and Methods
Expression of Gag Protein.

293T cells were plated in a 6-well dish at 1×10$^6$ cells/well. Twenty-four hours later, cells were transfected with 0.5 µg of either WT gag/pol or RI gag/pol plasmids in the presence of either 0.5 µg of Rev plasmid or 0.5 µg of empty backbone plasmid using Lipofectamine 2000 (Invitrogen). Twenty-four hours later, cells were lysed with cell extraction buffer (Invitrogen, catalog #FNN0011) and analyzed via SDS-PAGE using 4-12% NuPAGE Bis-Tris precast gels (Invitrogen, catalog #NP0321PK2) followed by transfer onto a nitrocellulose membrane. Blots were then probed with either anti-p24 antibody (Abcam, catalog #ab9071) or anti-actin antibody (Santa Cruz Biotech, catalog #sc-130656).
Results Cell lysates were analyzed for expression of gag protein products using SDS-PAGE and Western blotting with anti-p24 antibody. The RI gag/pol plasmid was able to express p24 and its precursors whether or not Rev was present, whereas the WT gag/pol transcript required Rev for protein expression (FIG. 13). The processing of p55 Gag protein appeared different between RI and WT gag/pol transcripts based on the ratio of p55:p24 protein, suggesting effects of codon-optimization on protein expression and/or processing. These results indicate that transcripts can undergo nuclear export in the absence of Rev, confirming that design changes to the RI gag/pol construct relieve the requirement for Rev.

Example 14

RI Gag/Pol Produces Infectious Vector with Comparable Titers to WT Gag/Pol

Previous studies have described reductions in titers of vectors produced in the absence of Rev. See Gasmi et al., *J. Virol.* 73:1828-1834(1999); Lucke et al., *J. Virol.* 79:9359-9362 (2005). Vector made with the "rev-independent" gag/pol construct was tested to determine if it would generate infectious particles with comparable titers to that of WT gag/pol.
Materials and Methods
Vector Production Vector was produced in either large scale (CF10) or small scale (10 cm dish). For large scale production, 293T cells were seeded at 5E8 cells/1 L in a 10-layer cell factory (Nunc, catalog #140400) in DMEM media containing 5% serum, L-glutamine, and antibiotics. Three days later, cells were transfected using PEI (stock 1 mg/mL) and total plasmid DNA at a ratio of 3:1 (mL PEI:mg DNA). Per 10-layer cell factory, 1 mg of vector genome plasmid and 0.5 mg of remaining plasmids (gag/pol, Rev, and VSV-G) were used. Five hours later, media was replaced with 1 L of serum-free media (Transfx-293 media, Hyclone catalog #SH30860.LS). Vector was harvested 2 and 3 days after transfection. Harvests were clarified using a pre-filter and 0.45 am stericup filter (Millipore). Vector was concentrated by spinning in a 1 L centrifuge bottle at 16,000 g for 5 hours. Pellet from each liter harvest was either resuspended in 1 mL of HBSS and aliquoted for storage at −80° C., or was resuspended in 1 mL of buffer for benzonase treatment (50 mM Tris-HCL pH7.5, 1 mM MgCl2, 5% v/v Sucrose). Benzonase nuclease was added at a final of 250 U/mL and incubated overnight at 4° C. in order to degrade any left-over plasmids from the transfection. Benzonase-treated vector preps were re-concentrated using a sucrose cushion (30% sucrose top, 5% sucrose bottom) and centrifuged at 116,000 g in an ultracentrifuge for 1.5 hours at 4° C. Vector pellet was resuspended in 1 mL HBSS, aliquoted and stored in −80° C. For small scale vector production, 293T cells were seeded in a 10 cm plate at 2.5E5 cells/plate and transfected the next day using PEI similar to as described above, but with 6 µg of vector genome plasmid and 3 µg of remaining plasmids, except varying amounts of gag/pol plasmids when comparing vector production. Small scale transfections were done in triplicates for accuracy. Five hours later, media was replaced with 4 mL of DMEM media containing 5% serum, L-glutamine, and antibiotics. Vector was harvested 2 and 3 days after transfection and was clarified using 0.45 am filter. Vector was stored at −80° C.

Vector Quantification—p24 Assay

Quantification of p24 was performed using the HIV-1 p24 ELISA kit by Advanced Bioscience Laboratories (Rockville, Md.), following the manufacturer's directions.

Vector Quantification—GFU Assay 293T cells were plated at 2E5 cells/well in a 12-well plate in 1 mL DMEM media containing 5% serum, L-glutamine, and antibiotics. Twenty-four hours later, cells in each well were transduced with 2-fold dilutions of vector encoding GFP. Each amount of vector is prepared in a 1 mL final volume in DMEM complete media. Five 2-fold serial dilutions of supernatant containing vector were prepared starting from 200 µL of vector per well. As a control to rule out pseudo-transduction, 10 µM of the reverse-transcriptase inhibitor nevirapine was used with the highest volume of vector in a parallel well. Forty-eight hours after transduction, cells were analyzed for GFP expression on a Guava machine (Guava technologies, now Millipore). Green Fluorescence Units (GFU) per mL was calculated by using a best fit (least squares) linear regression model based on the volumes of vector and the resulting percent GFP values in order to predict the number of GFP-positive cells per mL of vector using the FORECAST function in EXCEL. Events that resulted in less than 1% of GFP positive cells were set as the limit of quantification (LOQ).

Results

Two parallel vector preps pseudotyped with VSV-G were generated using a vector genome encoding green fluorescent protein (GFP) as a marker, and with two input DNA amounts of either the WT gag/pol or the RI gag/pol constructs. Both vector preps were assayed for p24 and were shown to have comparable physical particle titers, regardless of the gag/pol plasmid used to produce them (FIG. 14A). These preps were then assayed for their ability to transduce target cells. When normalized by volume, RI gag/pol vector resulted in transduction events comparable to WT gag/pol for both of the amounts of input gag/pol plasmid (3 µg or 6 µg) used during vector production (FIG. 14B). These results indicate that design elements introduced to generate the rev-independent gag/pol construct did not reduce the physical particle yield or infectivity of the lentiviral vector.

Example 15

RI and WT Gag/Pol Vectors Generate Equivalent Immune Responses

LVs are commonly used to deliver protein-encoding nucleic acids to various cell types in vitro for research applications and in clinical settings. However, directly injectable LVs are also being developed for both gene therapy and antigen-directed immunotherapy. To test whether a RI gag/pol vector would serve as an appropriate LV for immunotherapy applications, immune responses generated against an antigen transgene encoded by the RI gag/pol vector was evaluated.

Materials and Methods

Vector Quantification—TU Assay

Transduction units (TU) was determined using an assay in which transduction events in a target cell line are measured using a quantitative PCR assay that amplifies reverse-transcribed vector RNA sequences. Serial dilutions of test samples and reference material were incubated in duplicate in 96-well tissue culture plates in the presence of target 293T cells. The transduction step was performed both in the presence and absence of the reverse transcriptase inhibitor nevirapine as a means to asses background signal that may be contributed by residual plasmid DNA. At one day post-transduction, mock- or vector-transduced cells were lysed by the addition of a buffer containing sodium deoxycholate, Tween-20, sodium dodecyl sulfate (SDS), and proteinase K. The cell lysates were then incubated sequentially at 37° C., 55° C., and 95° C. to ensure proteolysis and DNA denaturation. Denatured cell lysates were then analyzed by qPCR using a primer/probe set that was designed to amplify a vector genome sequence of approximately 400-bp located upstream of the antigen promoter (EXPRESS qPCR Supermix Universal, Life technologies). The infectivity titer was calculated in reference to a standard curve comprised of linearized plasmid DNA containing the target sequences diluted over a 7-log range (5.3 copies-5.3×10$^6$ copies).

Immunizations

C57BL/6 mice were immunized subcutaneously in the tail base on day 0 with either 2×10$^7$, 1×10$^8$, or 5×10$^8$ TU of LV encoding LV1b, a polyepitope construct containing the OVA257 (SIINFEKL) (SEQ ID NO: 24) H-2Kb-restricted epitope, or HBSS vehicle. Aliquots of LV stored at −80° C. were thawed at room temperature and then kept on ice. Vector was serially diluted in cold sterile HBSS and transported to the animal facility for injection. Mice were placed in a conventional slotted restrainer with the tail base accessible. Vector was administered via 50 µL injection using a 29-gauge 0.3 mL insulin syringe (Becton Dickenson [BD]) inserted subcutaneously on the right side of the tail base, approximately 1 cm caudal to the anus, leading to minor but notable distension of the skin around the tail base.

Intracellular Cytokine Staining (ICS)

Spleens were homogenized by pressing through a 70 µM nylon filter. Red blood cells were lysed by hypotonic shock by brief exposure to ice-cold ultrafiltered water followed by immediate isotonic restoration with 10×PBS. For analysis of cytokines, cells were stimulated a 96-well with peptides are a concentration of 1 µg/mL per peptide in complete RPMI (10% FCS, 10 mM HEPES, 2 µM β-mercaptoethanol, and L-glutamine) for 5 hours at 37° C., 5% CO$_2$. OVA257 (SIINFEKL) peptide was manufactured at 95% purity by AnaSpec (Fremont, Calif.). After stimulation, surface staining was carried out in FACS buffer (PBS, 1% FCS, 2 mM EDTA, 0.01% sodium azide) in the presence of FcR blocking antibody 2.4G2 and LIVE/DEAD® Fixable Near-IR (L/D NIR, Invitrogen). Antibodies used for surface staining in in vivo experiments included anti-mouse CD4-PerCP-Cy5.5 (eBioscience) or CD4-Alexa Fluor 700 (eBioscience), CD8-Pacific Blue (eBioscience), and B220-V500 (BD). After surface staining, cells were fixed with Cytofix® (BD) and stored at 4° C. overnight in FACS buffer. Cells were then permeabilized with Perm/Wash™ buffer (BD) containing 5% rat serum (Sigma Aldrich). Antibodies for intracellular staining were diluted Perm/Wash™ buffer containing 5% rat serum and added to permeabilized cells. Antibodies included anti-mouse TNF-α-FITC (eBioscience), IFN-γ-PE (eBioscience), and IL-2-APC (eBioscience). Cells were washed twice with Perm/Wash™ buffer and resuspended in FACS buffer and analyzed on a 3-laser LSRFortessa with High Throughput Sampler (BD). Data were analyzed using FlowJo software (TreeStar, Ashland, Oreg.). Viable CD8 T cells were gated as follows: lymphocytes (FSC$^{int}$, SSC$^{lo}$), single cells (SSC-A=SSC-H), live (L/D NIR$^{lo}$), B220-CD4$^-$ CD8$^+$. Cytokine gates were based on the 99.9th percentile (0.1% of positive events in unstimulated cells).

Results

Mice were immunized with a dose range of WT or RI gag/pol vectors, containing either a Wild Type (INT(+)) or D64V mutant integrase (INT(−)), encoding a polyepitope construct termed LV1b which contains the OVA$_{257}$ (SIIN- FEKL) (SEQ ID NO: 24) H-2Kb-restricted CD8 T cell epitope. At 12 days post immunization, $OVA_{257}$-specific CD8 T cell responses in the spleen were measured by ICS for IFN-γ (FIG. 15). For both integration-competent and integration-deficient vectors, RI gag/pol and WT gag/pol vectors generated comparable CD8 T cell responses, confirming that codon optimization of the gag/pol gene did not negatively impact LV function as an immunotherapy vehicle.

Example 16

RI and WT Gag/Pol Vectors Both Induce Protective Anti-Viral Immunity

While it was observed that primary LV-induced CD8 T cell responses were equivalent with RI gag/pol vectors, the following experiments were performed to determine whether functional immunity induced by these was vectors was also similar. To address this, a recombinant live vaccinia virus challenge was employed as a model of viral infection.
Materials and Methods
Vaccina Virus Challenge C57BL/6 mice were immunized subcutaneously in the tail base on day 0 with $5\times10^8$ TU of vector encoding LV1b or HBSS vehicle. Four weeks later, mice were challenged intraperitoneally with $1\times10^7$ $TCID_{50}$ recombinant vaccinia virus expressing OVA (rVV-OVA), 1E7 $TCID_{50}$ wild-type vaccinia virus (VV-WT), or HBSS vehicle. Five days after challenge ovaries were harvested for quantitation of viral load by $TCID_{50}$ assay.
Results Mice were vaccinated with integration-deficient (INT(−)) LV vectors encoding $OVA_{257}$ with either a WT or RI gag/pol, and then challenged 4 weeks later with recombinant vaccinia virus encoding OVA (rVV-OVA) or wild type vaccinia virus (VV-WT) as a control (FIG. 16). Mice vaccinated with RI gag/pol and WT gag/pol vectors both showed dramatic reductions in viral load after challenge with rVV-OVA. Confirming that protection was antigen specific, the viral load after VV-WT challenge was similar between vehicle and LV treated groups. These data indicate that RI gag/pol LVs can induce memory CD8 T cells that respond to viral challenge and provide functional immunity.

Example 17

RI Gag/Pol Modifications Eliminate Psi-Gag Recombination, but not Other Recombination Events Between Vector Genome and Gag/Pol Transcripts The RI gag/pol was designed to attempt to eliminates psi-gag recombination, thus further minimizing the chances of RCL formation for third generation LVs. A nested PCR based approach was utilized to screen genomic DNA of cells transduced with integrating vector in order to detect psi-gag recombination.
Methods and Materials
Vector Quantification—Genomes Assay Genomic RNA was isolated from vector particles using the QIAamp Viral RNA Mini kit (Qiagen, Valencia, Calif.). To eliminate contaminating DNA, the extracted nucleic acid was then digested with DNAseI (Invitrogen) following the manufacturer's directions. Two dilutions of each DNAseI-treated RNA sample were then analyzed by quantitative RT-PCR using the RNA Ultrasense One-Step Quantitative RT-PCR System (Invitrogen) and previously-described vector-specific primers and probe. The RNA genome copy number was calculated in reference to a standard curve comprised of linearized plasmid DNA containing the target sequences, diluted over a 7-log range (10 copies—$1.0\times10^7$ copies). The genome titer as expressed here reflects the number of physical vector particles, calculated based on genomes, with each vector particle predicted to contain two single-stranded copies of genomic RNA.
Psi-Gag Recombination Assay 293T cells were plated at 2E6 cells in a 10 cm plate. Next day cells were transduced with 1E11 genomes of concentrated VSV-G pseudotyped vector made with either WT gag/pol or RI gag/pol. The titers for these vectors were 1.2E13 genomes/mL and 1.5 genomes/mL respectively. Forty-eight hours after transduction, cells were harvested and genomic DNA was isolated using a blood and cell culture DNA kit (Qiagen, catalog #13323). 100 ng of genomic DNA was used as template for the first round of PCR using high-fidelity platinum taq polymerase (Invitrogen, catalog #11304-011) and the following cycling parameters: 1 cycle at 94° C. for 2 minutes; 40 cycles at 94° C. for 30 seconds, 55° C. for 30 seconds, 68° C. for 90 seconds; 1 cycle at 68° C. for 5 minutes. 1 μl (out of 50 μl) of the first PCR was used as template either undiluted (1:1) or 1:100 diluted or 1:1000 diluted for the nested PCR. The nested PCR cycling parameters were identical to that used in the first round. No primer controls were included for all reactions. Primers used for PCRs were 378 (TAAGGCCGAGTCTTATGAGCAGC) (SEQ ID NO: 60), 709 (AGGACTCGGCTTGCTGAAG) (SEQ ID NO: 61), 710 (AGCCTGTCTCTCAGTACAATC) (SEQ ID NO: 62), 835 (TGTCTTATGTCCAGAATGCT) (SEQ ID NO: 63), 863 (GCACGGCAAGAGGCGAGG) (SEQ ID NO: 64), and 864 (GCCGGATGTCCAGGATGCTG) (SEQ ID NO: 65). 25 μl of total 50 μl of the nested PCR was visualized on a 1% agarose gel made with 1×TAE buffer and ethidium bromide. Bands were extracted and DNA was purified using a gel extraction kit (Qiagen, catalog #28704) followed by cloning into a TOPO-TA vector (Invitrogen, catalog #K4500-02) and sequencing (Davis Sequencing, CA) using M13 forward and reverse primers.
Results Using the nested PCR approach, a first round of PCR was performed using a forward primer (709) that binds the LV genome 5' of the psi packaging signal and a reverse primer (710) that binds within the frameshift region of both RI gag/pol and WT gag/pol (FIG. 12). The PCR product from this first round was then diluted and used as template for a second PCR using a nested forward primer (863) that binds the LV genome, and a nested reverse primer (835 or 864) that binds to the gag region within either the WT gag/pol or the RI gag/pol, respectively. These two reverse primers were designed to bind the same region in both constructs, with the only differences being due to codon-optimization. The amplicon size from a hypothetical psi-gag recombinant would be 937 bp when using either primer pairs 863 and 835, or primer pairs 863 and 864.

Vector preps encoding the LV1b polyepitope were generated with either the RI gag/pol or the WT gag/pol plasmids, and were used to transduce 293T cells. Forty-eight hours after transduction the genomic DNA was harvested and PCR was performed followed by analyzing on an agarose gel. First, a positive control PCR was performed using primers that bind only within the LV genome (primers 709 and 378). The predicted LV genome amplicon size with these primers is predicted to be 1697 bp. Cell cultures transduced with either WT gag/pol or RI gag/pol vector both yielded the expected amplicon size, thus confirming that transduction and integration of provirus are comparable for both vectors (FIG. 17A).

Next, the nested PCR was performed for psi-gag recombination as described above. Genomic DNA from cells transduced with the WT gag/pol vector produced a band at the expected size of 937 bp, consistent with psi-gag recombination (left half, FIG. 17B). In contrast, genomic DNA from cells transduced with RI gag/pol produced a larger, but fainter band at 1329 bp (right half, FIG. 17B). To determine the nature of the PCR bands, the 937 bp band from WT gag/pol as well as the 1329 bp band from the RI gag/pol were extracted and cloned into TOPO-TA plasmids. Sequencing revealed that the WT gag/pol band was consistent with a psi-gag recombinant in that the first half of the sequence aligned with the vector genome and the second half aligned with the gag/pol transcript that extended beyond the partial gag sequence (FIG. 17C). The fainter 1329 bp band from the RI gag/pol encoded a sequence that consisted of the first 1253 bp aligning with the LV genome but the last 77 bp aligning with a region of the RI gag/pol (FIG. 17D). These results indicate that psi-gag recombination was detectable in cells transduced with the WT gag/pol vector, but not in cells transduced with the RI gag/pol vector. Furthermore, these results present evidence that recombination, though apparently not dependent on psi-gag sequences, was still detectable in cells transduced with the RI gag/pol vector.

Example 18

Identification of the DC-SIGN Homolog SIGNR1 as a Mouse Receptor for SINvar1

ID-VP02 vector particles were investigated to determine whether they could utilize an endogenous mouse receptor for binding and entry. While humans encode DC-SIGN and one paralog, DC-SIGNR, mice have 8 homologs of DC-SIGN (termed SIGNR1 through SIGNR8). Of these, six are predicted to be membrane bound, namely SIGNR1, -R3, -R4, -R5, -R7, and -R8. Based on functional studies, SIGNR1, SIGNR3, and SIGNR5 (also referred to as mouse DC-SIGN), are reported to be the closest functional orthologs of human DC-SIGN. The ability of SINvar1 to mediate binding and entry via these receptors was therefore tested.

HT1080 cells stably expressing either mouse SIGNR1, SIGNR3, or SIGNR5 were generated. These cells were incubated with varying concentrations of integration-deficient GFP-encoding vector that was pseudotyped with SINvar1, kifunensine-modified high mannose SINvar1, or with pantropic VSV-G. In Example 8, it was established that a SINvar1 envelope produced in the presence of the mannosidase I inhibitor kifunensine is required for DC-SIGN binding and human DC transduction. In this experiment, therefore, HT1080 cells over-expressing human DC-SIGN were used as a positive control. Of the three mouse DC-SIGN orthologs tested, SINvar1-pseudotyped vector transduced only mouse SIGNR1 expressing cells and did so in a kifunensine-dependent manner (FIG. 18A-D), as had been observed for the human receptor. The transduction efficiency of kifunensine-modified SINvar1 vector on human DC-SIGN- and mouse SIGNR1-expressing cells was remarkably similar (FIG. 18A,B), indicating that SIGNR1 is a functionally orthologous receptor for ID-VP02 vector particles in the mouse.

Example 19

SIGNR1 is Expressed on Mouse DCs In Vivo

In order to further investigate the utility of the mouse model for functional studies that were reflective of the intended mechanism of action in humans, experiments were undertaken to determine whether SIGNR1 was expressed on mouse dendritic cells.

Materials and Methods

SIGNR1 and 5 Expression In Vivo

Cells from individual spleens or pools of 10 popliteal lymph nodes from 5 mice were stained in FACS buffer (PBS, 1% FCS, 2 mM EDTA, 0.01% sodium azide) in the presence of FcR blocking antibody 2.4G2 and LIVE/DEAD® Fixable Near-IR (L/D NIR, Invitrogen). Antibodies used for surface staining included anti-mouse CD4-PerCP-Cy5.5 (eBioscience) or CD4-Alexa Fluor 700 (eBioscience), CD8-Pacific Blue (eBioscience), and B220-V500 (BD). After surface staining, cells were fixed with Cytofix® (BD) and analyzed on a LSRFortessa multiparametric flow cytometer. Live, single cell events (L/D NIR$^-$, SSH=SSA) were subdivided into B cells (B220$^+$ TCRβ$^-$), T cells (TCRβ$^+$, B220$^-$), and DCs (B220$^-$ TCRβ$^-$ MHC-II$^+$ CD11c$^{hi}$). Gates for SIGNR5 and SIGNR1 expression each of these subsets was set using negative control stains lacking SIGNR1- and SIGNR5-specific antibodies, such that frequencies of positive events were ≤0.00.

Results

Single cell suspensions from three individual spleens or three pools of popliteal lymph nodes each were analyzed for SIGNR1 and SIGNR5 expression on T cells, B cells, and DCs. SIGNR5 expression was relatively rare in the steady state, being detected only on a small population of B cells (FIG. 19). By contrast, while SIGNR1 expression was limited on lymphocytes, approximately 10-12% of MHC-II$^+$ CD11c$^{hi}$ DCs expressed SIGNR1 (FIG. 19). Since SIGNR1 is also a functional receptor for ID-VP02 vector particles, these data led us to evaluate whether ID-VP02 vector particles could specifically target mouse DCs in vivo.

Example 20

ID-VP02 Vector Particles Target Mouse Draining Lymph Node DCs In Vivo

In order to determine whether the product of a Sindbis virus E2 glycoprotein pseudotyped lentiviral vector particle-encoded transgene could be detected in DCs after direct administration, particles encoding GFP or a non-fluorescent negative control protein were injected into the right footpad of recipient BALB/c mice.

Materials and Methods

ID-VP02-GFP Transduction In Vivo.

BALB/c mice (n=15/group) were injected subcutaneously in the footpad with 3×10$^{10}$ genomes of ID-VP02 vector particles encoding GFP, control particles encoding NY-ESO-1, or left untreated. Four days later, the draining popliteal or non-draining cervical lymph nodes from were pooled from 5 mice (3 pools per treatment group) and live (L/D singlet events (L/D NIR−, SSH=SSA) were analyzed for the presence of GFP. The phenotype of GFP$^+$ cells was determined by co-staining with anti-mouse CD11c-PE-Cy7 (eBioscience), MHC-II-Pacific Blue (eBioscience), SIGNR5-PE (eBioscience), and SIGNR1-APC (eBioscience).

Results

Four days after injecting ID-VP02 vector particles encoding GFP, the draining popliteal or non-draining cervical lymph nodes from 5 mice were pooled (3 pools per treatment group) and analyzed for GFP expression. Injection of ID-VP02 vector particles encoding GFP, but not a non-fluorescent control protein, led to detection of GFP$^+$ cells in the draining popliteal lymph node but not in the distal lymph node (FIG. 20A). Upon further surface marker analysis, approximately 90% of transduced cells were identified as DCs as indicated by CD11c and MHC-II expression (FIG. 20B), and more than one third of these GFP+ DCs were SIGNR1+ (FIG. 20C), supporting a likely role for this receptor in mouse DC transduction in vivo.

Example 21

ID-VP02 Vector Particle DNA has Limited Biodistribution

While analysis of lymph node cells was consistent with specific targeting of mouse DCs in vivo, biodistribution studies were performed to establish whether transduction events could be detected in other, particularly non-lymphoid, tissues and to characterize the clearance kinetics at positive tissue sites.
Materials and Methods
Vector Biodistribution C57BL/6 mice (n=3/group) received $3\times10^{10}$ genomes of ID-VP02 encoding the polyepitope construct LV1b subcutaneously at the base of the tail. The presence of reverse transcribed vector DNA was analyzed by qPCR at 1, 4, 8, 21, or 42 days post-injection in the following tissues: site of injection (tail base), spleen, liver, heart, ovaries, brain, and draining (inguinal) and non-draining (cervical) lymph node. Tissues were processed in Fastprep Lysing Matrix D tubes using a Fastprep-24 homogenizer (MP Biomedicals, Santa Ana, Calif.) and genomic DNA was isolated from homogenates using the Qiagen DNeasy Blood & Tissue Kit (Qiagen Inc., Valencia, Calif.). Eluted DNA (200 ng per sample) was analyzed by qPCR in quadruplicate using EXPRESS qPCR Supermix Universal (Life Technologies, Carlsbad, Calif.) and a primer/probe set designed to amplify a target sequence of 85-bp within the LV1b cassette. All reactions were performed using the Bio-Rad CFX384 and analyzed using Bio-Rad CFX Manager software (Bio-Rad Laboratories, Hercules, Calif.). The vector DNA copy number was calculated in reference to a standard curve comprised of plasmid DNA containing the target sequences diluted over a 7-log range ($10^1$ copies-$10^7$ copies).
Results ID-VP02 vector particles encoding a polyepitope model antigen construct designated as LV1b was utilized to determine biodistribution of the particles. After vector injection, the presence of reverse-transcribed vector genomes (vector DNA) can be measured by qPCR using a set of primers and probe specific for the LV1b cassette. Mice were administered $2.8\times10^{10}$ genomes of pseudotyped vector particle-LV1b in a single subcutaneous injection at the base of the tail. On a timecourse between 1 and 42 days post-injection, vector DNA was quantified at the injection site (tail base), draining (inguinal) and non-draining (cervical) lymph nodes, spleen, heart, liver, brain, and ovaries. At early time points after administration, vector DNA was detected exclusively at the injection site and in the draining lymph node. The vector signal in these tissues decreased over time, with no quantifiable signal at 8 days in draining lymph node and signal barely above the limit of quantitation (LOQ; 10 copies) at 42 days at the injection site (FIG. 21). These results indicate that the dispersal of ID-VP02 vector particles outside the injection site is limited to the draining lymph node, where its biological activity would be hypothesized to occur, and over 99% of vector DNA was cleared within three weeks.

Example 22

ID-VP02 Vector Particles Induce Polyfunctional Primary and Secondary CD8 T Cell Responses The following experiments were undertaken to measure the ability of Sindbis virus E2 glycoprotein pseudotyped lentiviral vector particles to generate an antigen-specific immune response in vivo.
Materials and Methods
Intracellular Cytokine Staining (ICS)

Figure 22A:
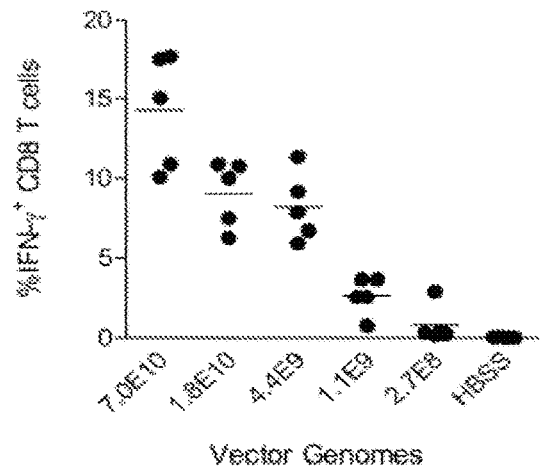

Spleens were homogenized by pressing through a 70 μM nylon filter. Red blood cells were lysed by hypotonic shock by brief exposure to ice-cold ultrafiltered water followed by immediate isotonic restoration with 10×PBS. For analysis of cytokines, cells were stimulated a 96-well with peptides are a concentration of 1 μg/mL per peptide in complete RPMI (10% FCS, 10 mM HEPES, 2 μM β-mercaptoethanol, and L-glutamine) for 5 h at 37° C., 5% $CO_2$. Peptides, including $OVA_{257}$ (SIINFEKL) (SEQ ID NO: 24), LCMV $GP_{33}$ (KAVYNFATM) (SEQ ID NO: 66), AH1 (SPSYVYHQF) (SEQ ID NO: 67), and AH1A5 (SPSYAYHQF) (SEQ ID NO: 25) were manufactured at 95% purity by AnaSpec (Fremont, Calif.). In some experiments, as noted, anti-mouse CD107a-PerCP-eF710 (eBioscience) was included in the stimulation cocktail to capture translocated CD107a on the surface of degranulating T cells. After stimulation, surface staining was carried out in FACS buffer (PBS, 1% FCS, 2 mM EDTA, 0.01% sodium azide) in the presence of FcR blocking antibody 2.4G2 and LIVE/DEAD® Fixable Near-IR (L/D NIR, Invitrogen). Antibodies used for surface staining in in vivo experiments included anti-mouse CD4-PerCP-Cy5.5 (eBioscience) or CD4-Alexa Fluor 700 (eBioscience), CD8-Pacific Blue (eBioscience), and B220-V500 (BD). After surface staining, cells were fixed with Cytofix® (BD) and stored at 4° C. overnight in FACS buffer. Cells were then permeabilized with Perm/Wash™ buffer (BD) containing 5% rat serum (Sigma Aldrich). Antibodies for intracellular staining were diluted Perm/Wash™ buffer containing 5% rat serum and added to permeabilized cells. Antibodies included anti-mouse TNF-α-FITC (eBioscience), IFN-γ-PE (eBioscience), and IL-2-APC (eBioscience). Cells were washed twice with Perm/Wash™ buffer and resuspended in FACS buffer and analyzed on a 3-laser LSRFortessa with High Throughput Sampler (BD). Data were analyzed using FlowJo software (TreeStar, Ashland, Oreg.). Viable CD8 T cells were gated as follows: lymphocytes ($FSC^{int}$, $SSC^{lo}$), single cells (SSC-A=SSC-H), live (L/D $NIR^{lo}$), B220⁻ CD4⁻ CD8⁺. Cytokine gates were based on the $99.9^{th}$ percentile (0.1% of positive events in unstimulated cells) and the CD107a gate was based on the $99^{th}$ percentile.
Results To assess the immunological activity of ID-VP02 vector particles in vivo, a dose range of vector encoding full length chicken ovalbumin (ID-VP02-OVA) was administered subcutaneously to C57BL/6 mice and the $OVA257$-specific CD8 T cell response in the spleen was measured by intracellular cytokine staining (ICS) (FIG. 22A). The frequency of IFN-γ+ effectors among splenic CD8 T cells range from a mean of around 15% at a dose of $7.0\times10^{10}$ genomes to around 1% at $2.7\times10^8$ genomes, indicating that ID-VP02 induces CD8 T cell responses in a dose-dependent manner across at least a 2-log dose range.

Figure 22B:
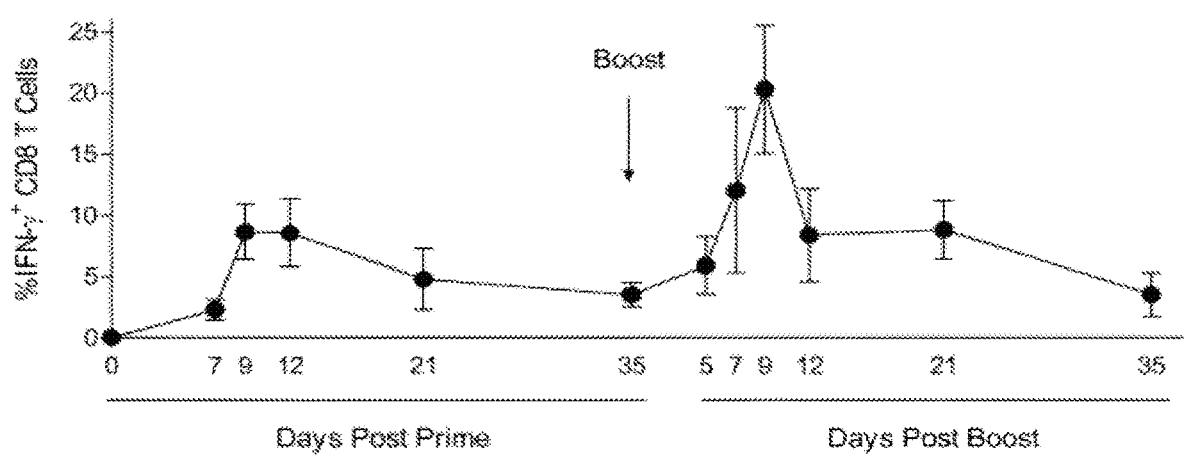

To address whether priming with ID-VP02 vector particles induced memory T cells that could be recalled through the administration of ID-VP02 as a homologous boost, animals were primed with a midrange dose of $1.0\times10^{10}$ genomes and then boosted with an equivalent dose 35 days post prime. At various timepoints post-prime and boost, the CD8 T cell response was measured by ICS. By analyzing the frequency of IFN-γ⁺ CD8 T cells, it was found that boosting with ID-VP02-OVA induced an OVA25$_7$-specific recall response that was both more rapid and of a more than two-fold greater magnitude than the primary response (FIG. 22B). These data indicate that the application of ID-VP02 is not limited to a single administration by vector-specific immunity, which is known to be a problem for other viral vectors, such as adenovirus-based vectors.

Figure 22C:
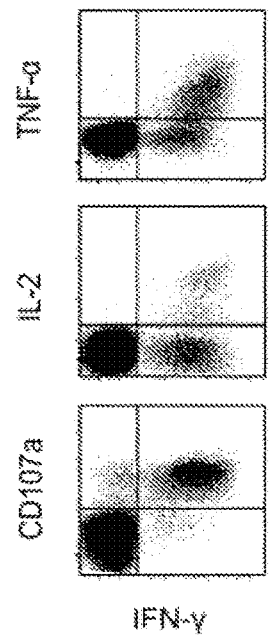
Figure 22D:
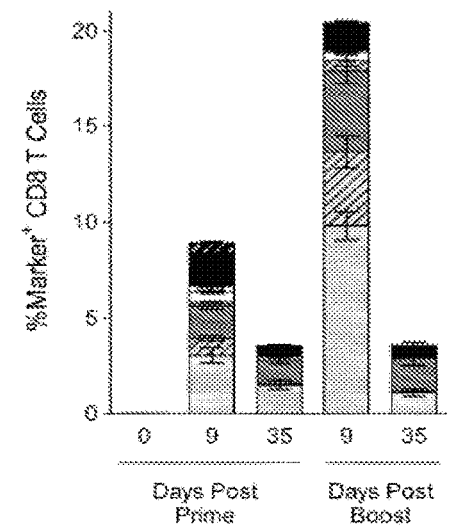

In addition to staining for IFN-γ, the quality of the primary and secondary CD8 T cell responses was analyzed by simultaneous staining for two additional cytokines, TNF-α and IL-2, as well as surface translocation of CD107a, a correlate of cytotoxic activity. After both the prime and boost, most of the responding CD8 T cells had a multifunctional phenotype, as evidenced by elucidation of CD107a, TNF-α, and IL-2 (FIG. 22C,D). Notably, 35 days after the boost, essentially 100% of the IFN-γ+ cells were CD107a$^+$, a majority also expressed TNF-α, and a substantial fraction of these "triple-positive" cells also produced IL-2, indicating the formation of memory T cells with high functional quality.

Figure 22E:
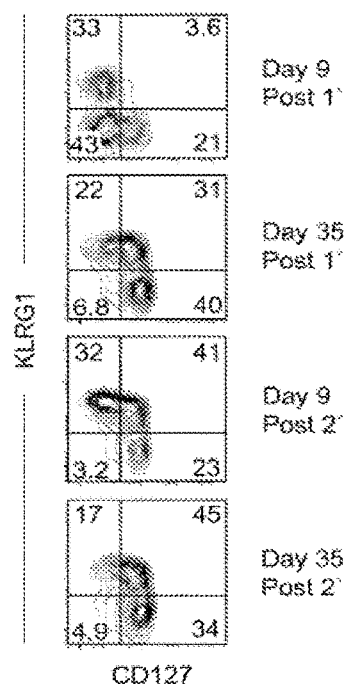

The markers KLRG1 and CD127, when measured around the peak of a virus-specific CD8 T cell response, have been associated with a short-lived effector cell (SLEC) and memory precursor cell (MPEC) fates, respectively. As observed during infection with LCMV, when the phenotype of antigen-specific H-2K$^b$-OVA$_{257}$ multimer-binding CD8 T cells was analyzed at day 9 post-immunization, a fraction of cells were polarized into either the KLRG1$^+$ CD127$^-$ SLEC or KLRG1$^-$ CD127$^+$ MPEC phenotype (FIG. 22E). Interestingly, 35 days after both the prime and boost immunizations, while the majority of cells had CD127$^+$ memory phenotype, they were roughly equally divided between KLRG1$^+$ and KLRG1$^-$ subsets, both of which are reported to increased recall potential over SLEC.

Example 23

Memory CD8 T Cells Induced by Sindbis Virus E2 Glycoprotein Pseudotyped Lentiviral Vector Particles Expand and Exhibit Anti-Viral Function To directly evaluate the function of memory CD8 T cells induced by SINVar1 immunization, an alternative antigen cassette termed LV1b, that encodes both the minimal OVA$_{257}$ and LCMV GP33 peptide sequences, two robust H-2Kb-restricted epitopes was employed.

Materials and Methods
MHC-I Multimer and Memory Phenotype Analysis

Splenocytes prepared as described above were stained with H-2K$^b$-OVA$_{257}$ MHC-I pentamers (ProImmune, Oxford, UK) in room temperature FACS buffer for 10 minutes in the presence of 2-4G2 antibody. Cells were washed once and stained with surface antibodies plus L/D NIR for 20 minutes on ice. Antibodies included CD127-FITC, CD44-PerCP-Cy5.5, KLRG1-APC, CD8-Alexa Fluor 700 (all from eBioscience), and B220-V500 (BD). Cells were washed, fixed with Cytofix®, and analyzed as above. Within the viable CD8 T cell population, CD44$^{hi}$ H-2K$^b$-OVA$_{257}$ pentamer$^+$ events, gated based on the 99.9$^{th}$ percentile in unimmunized mice, were analyzed for their expression of KLRG1 and CD127.

Vaccina Virus Challenge

C57BL/6 mice were immunized subcutaneously in the tail base on day 0 with a dose range of ID-VP02 encoding LV1b, a polyepitope construct containing the OVA$_{257}$ (SIINFEKL) (SEQ ID NO: 24) and LCMV GP33 (KAVYNFATM) (SEQ ID NO:66) H-2K$^b$-restricted epitopes, or HBSS vehicle. Five weeks later, mice were challenged intraperitoneally with 1×10$^7$ TCID$_{50}$ recombinant vaccinia virus expressing OVA (rVV-OVA), 1E7 TCID$_{50}$ wild-type vaccinia virus (VV-WT), or HBSS vehicle. Five days after challenge, spleens were harvested for OVA$_{257}$- and GP33-specific ICS as described above, and ovaries were harvested for quantitation of viral load by TCID$_{50}$ assay.

Results

Figure 23A:
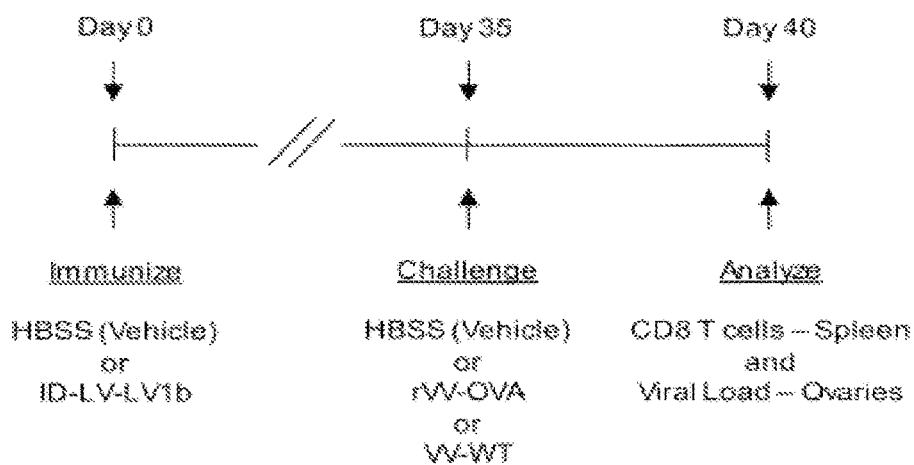
Figure 23B:
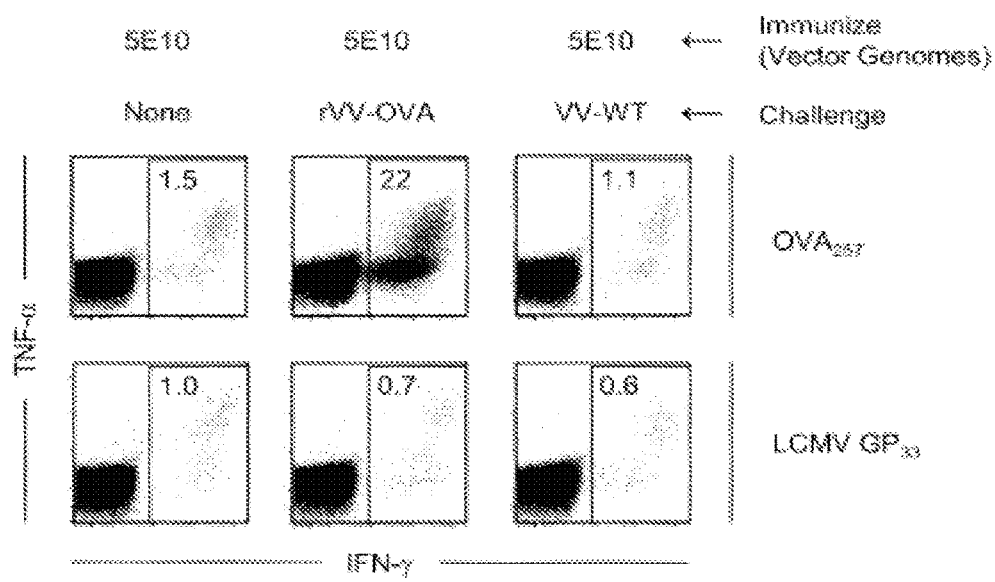
Figure 23C:
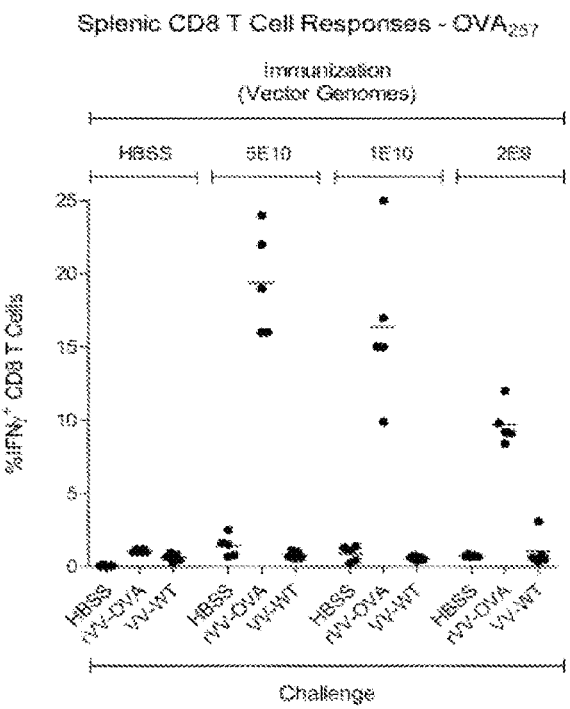
Figure 23D:
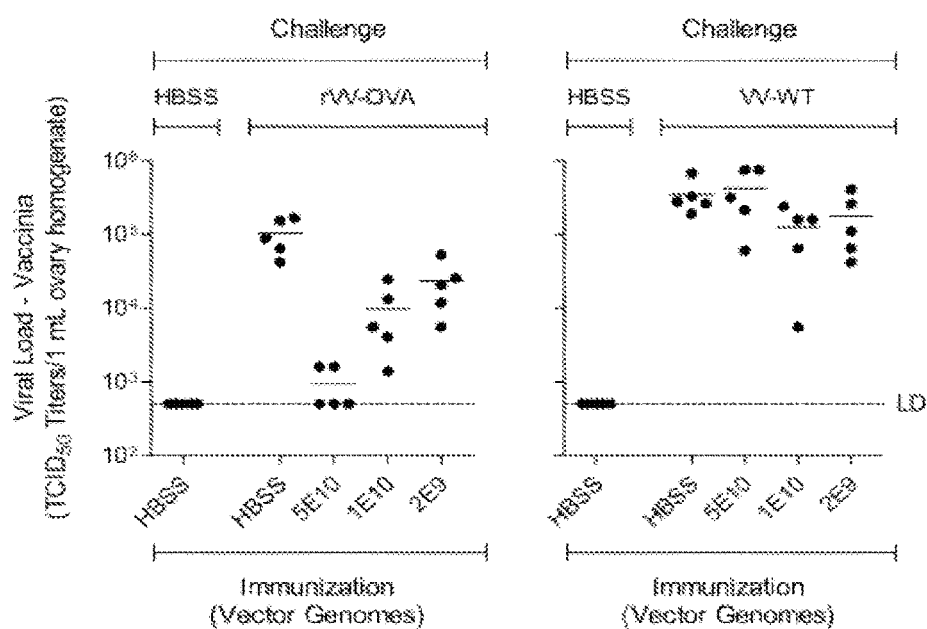

As depicted schematically in FIG. 23A, 35 days post-immunization with ID-VP02-LV1b, mice challenged with recombinant vaccinia virus expressing OVA (rVV-OVA), but not wild-type vaccinia virus (VV-WT), showed dramatic expansion of OVA25$_7$-specific CD8 T cells (FIG. 23B,C), indicating that these memory cells were recalled in an antigen-specific manner. Further, rVV-OVA did not expand GP33-specific memory cells (FIG. 23B), confirming the requirement for antigen-specificity within the same animal. Corresponding to the dose-dependent induction of CD8 T cells that responded to infection, there was a clear dose-dependent reduction in the viral load of rVV-OVA in the ovaries of infected mice (FIG. 23D). Importantly, the sole antigenic sequence shared between the LV1b antigen construct and the rVV-OVA challenge strain was the SIINFEKL MHC class I epitope, indicating that the protection was mediated by CD8 T cells. Confirming that protection was indeed antigen-specific, infection with VV-WT was not impacted by immunization.

Example 24

SINVar1 Immunization Provides Both Prophylactic and Therapeutic Anti-Tumor Efficacy The CT26 tumor cell line is derived from a spontaneous colon carcinoma in BALB/c mice. An endogenous epitope that can mediate rejection of implanted CT26 tumors is the AH1 peptide. While the MHC-TCR interaction is relatively weak with the AH1 epitope, the altered peptide ligand AH1A5 can stabilize this interaction, leading to greater CD8 T cell expansion and anti-tumor responses. To generate SINVar1 encoding this epitope, an antigen cassette was generated in which the AH1A5 sequence was inserted into full length OVA sequence (OVA-AH1A5), as previously reported. Brockstedt et al., Proc. Natl. Acad. Sci. U.S.A. 101(38), 13832 (2004).

Materials and Methods
In Vivo Cytotoxicity Assay

BALB/c mice (3 per group) were immunized subcutaneously at the tail base with ID-VP02 encoding OVA-AH1A5. Twelve days later, dye-labeled, peptide-pulsed target cells were transferred intravenously via the retroorbital sinus into immunized and untreated control mice. Target cells were prepared from naïve splenocytes by lysing red cells by hypotonic shock, then splitting the cells into three populations that were pulsed with 1 µg/mL of either AH1 (SPSYVYHQF) (SEQ ID NO: 67), AH1A5 (SPSYAYHQF) (SEQ ID NO: 25), or negative control NY-ESO-181-88 (RGPESRLL) (SEQ ID NO: 68) peptides. Cells were washed and then labeled with 2 µM CFSE (Invitrogen) plus one of three concentrations of Cell Trace Violet (Invitrogen): 2 µM, 0.2 µM, or 0.02 µM. Target cells were combined at a 1:1:1 ratio and 5×10$^6$ total cells were transferred to recipients. The following day, spleens were harvested and the relative recovery of each population was compared between naïve and immunized mice to calculate specific killing as previously described. Wonderlich et al., Curr. Protoc. Immunol. Chapter 3, Unit (2006).

CT26 Tumor Challenge

For prophylaxis experiments, BALB/c mice (10 per group) were immunized subcutaneously at the tail base with ID-VP02 encoding OVA-AH1A5, an antigen that contains a defined MHC-I-restricted rejection epitope for CT26 tumor cells. Four weeks later, immunized and untreated control mice were injected subcutaneously with $8 \times 10^4$ CT26 tumor cells on the right flank. Tumor growth was monitored three times per week and mice were euthanized when tumor area exceeded 100 $mm^2$. Experiments testing ID-VP02 in the therapeutic mode were performed the same way, with the exception that immunization with ID-VP02 was delayed until four days post tumor implantation.

Results

Figure 24A:
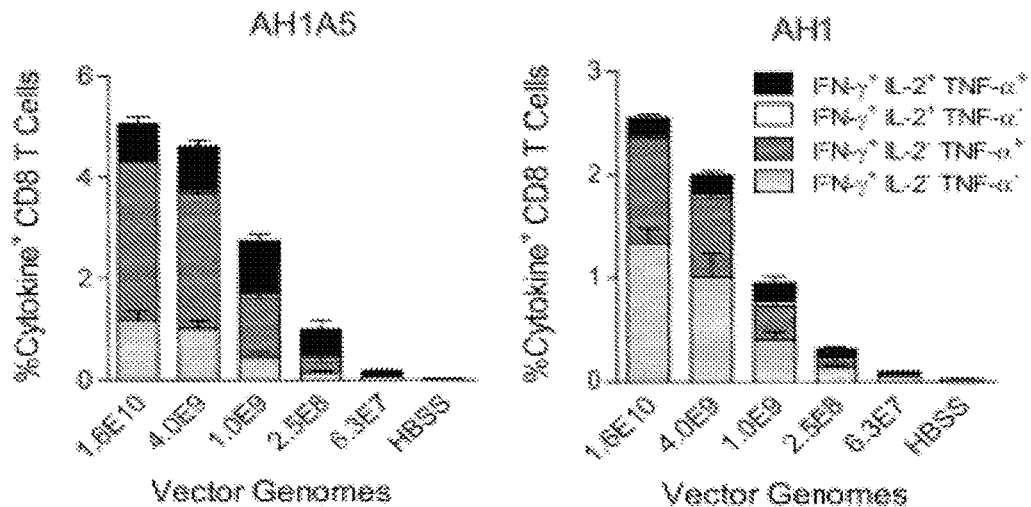
Figure 24B:
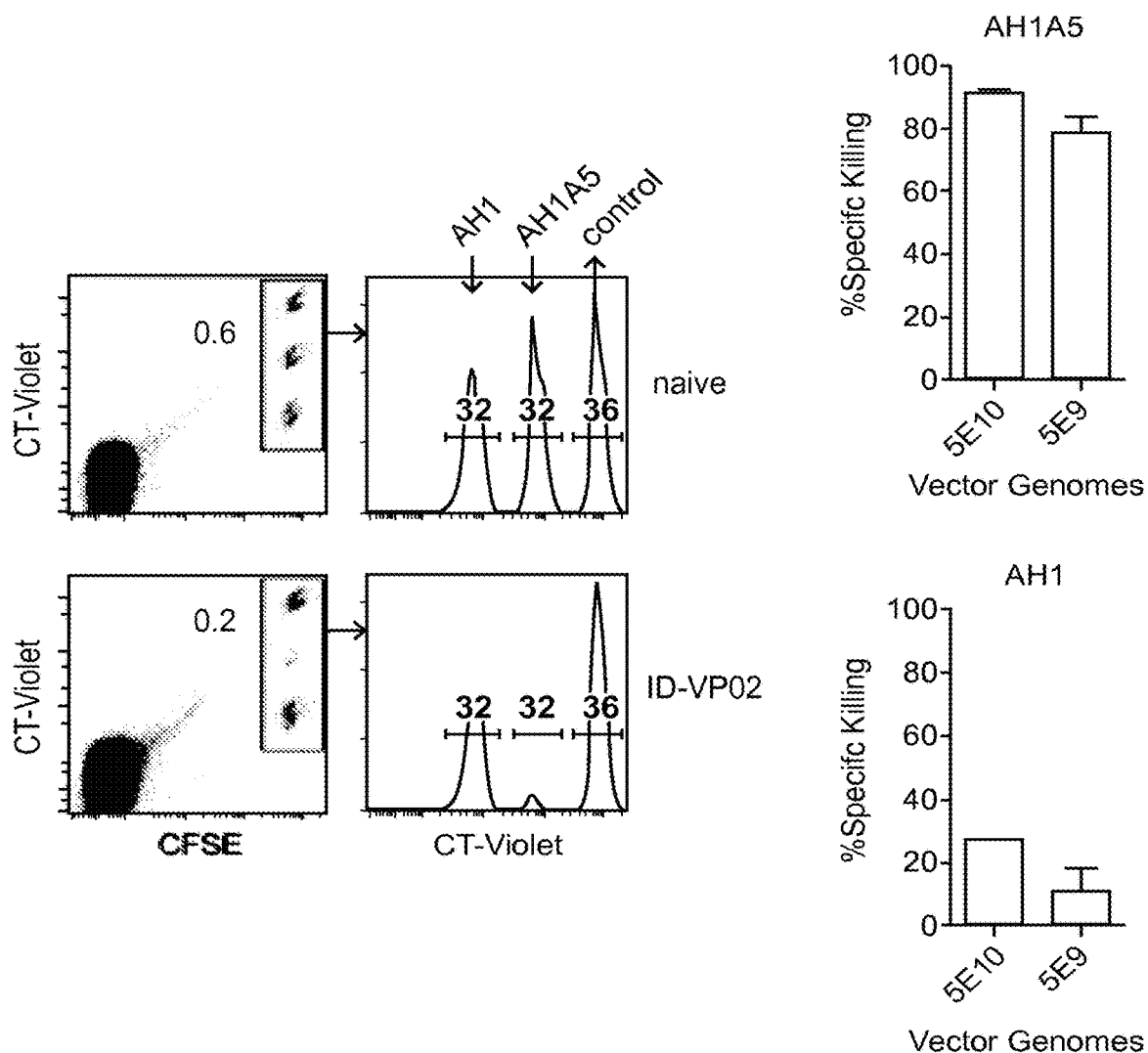

When BALB/c mice were immunized with ID-VP02 encoding OVA-AH1A5, we observed dose dependent induction of multifunctional AH1A5-specific CD8 T cells, approximately half of which cross-reacted with the endogenous AH1 sequence (FIG. 24A). The ability of ID-VP02 induced CD8 T cells to acquire cytolytic capacity was directly analyzed by in vivo cytotoxicity assay. Three splenocyte target cell populations were simultaneously labeled with CFSE plus varying concentrations of Cell Trace Violet, then pulsed with AH1, AH1A5, or a negative control peptide. Target cells were mixed at a 1:1:1 ratio, then co-transferred into recipient mice immunized 12 days earlier with ID-VP02 or left untreated. After 1 day, the relative recovery of AH1 and AH1A5 pulsed targets was reduced in ID-VP02 immunized mice, with specific killing rates over 90% against AH1A5 and about 25% against AH1 (FIG. 24B), indicating that ID-VP02 induces functional cytotoxic CD8 T cells against the immunizing antigen.

Figure 24C:
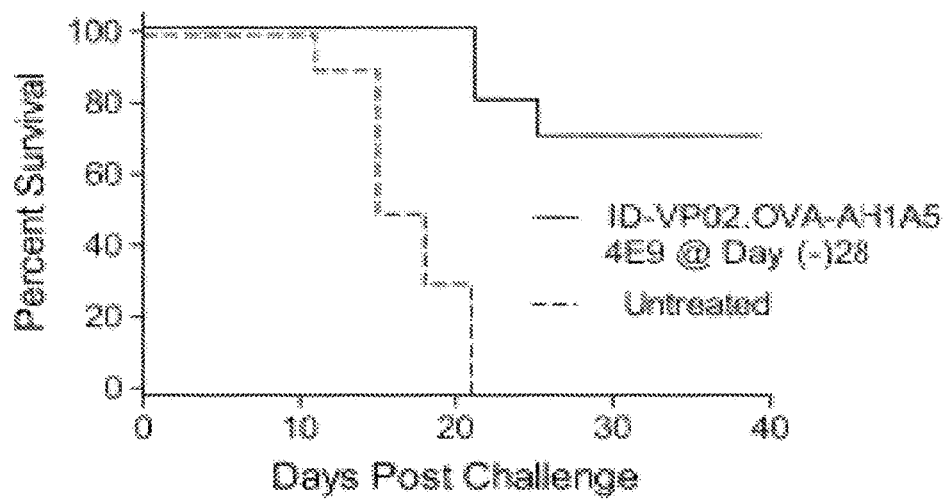
Figure 24D:
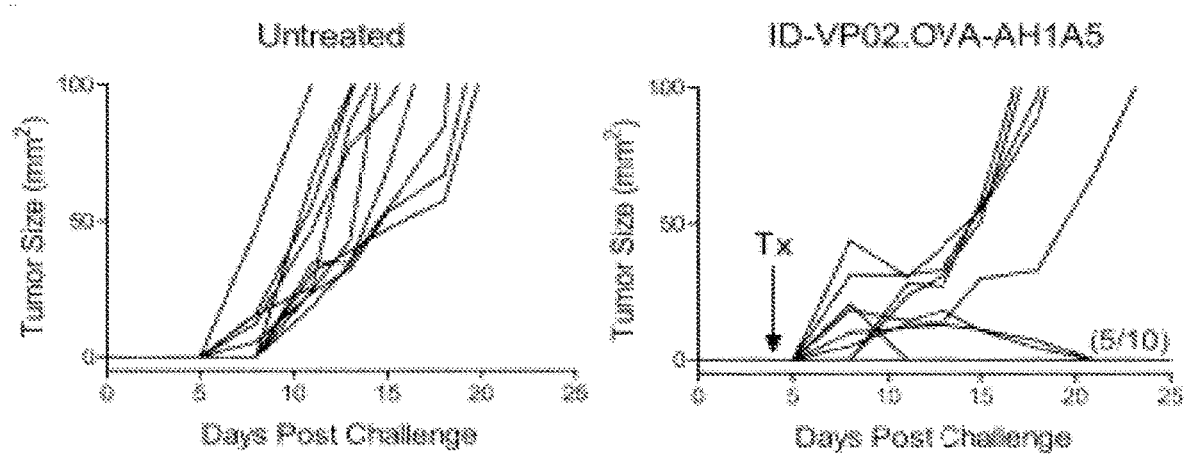

As a first test for anti-tumor efficacy, mice immunized subcutaneously with ID-VP02-OVA-AH1A5 or vehicle were challenged 28 days later with CT26 tumor cells implanted in the flank. Whereas all control mice had lethal tumor growth (>100 $mm^2$) by day 21, 70% of ID-VP02 immunized mice were able to reject the implanted tumors and these surviving mice were tumor-free for at least 60 days (FIG. 24C). These findings were extended by applying ID-VP02 as a therapy to previously implanted CT26 tumors. In this model, tumors were allowed to grow for 5 days, then animals were treated with ID-VP02-OVA-AH1A5 or vehicle control. As in the prophylactic experiments, all control animals succumbed to tumor growth within approximately three weeks (FIG. 24D). By contrast, all mice treated with ID-VP02 showed impacts on tumor progression, ranging from a delay in the growth kinetics to outright rejection. Tumors either failed to grow to a palpable size (2/10) or completely regressed (3/10) in the immunized group, leading to 50% of the mice being tumor-free out to at least day 60. These data show that ID-VP02 can exert anti-tumor cytotoxic activity in both the prophylactic and therapeutic settings, supporting the evaluation of ID-VP02 as a therapeutic for cancer in humans.

What is claimed:

1. A method of inducing an immune response comprising administering to a subject in need thereof a composition comprising pseudotyped lentiviral vector particles comprising (a) a Vpx protein or a Vpr protein that retains SAMHD1-inhibiting activity, (b) a lentiviral vector genome comprising an exogenous polynucleotide of interest, and (c) a plurality of envelope glycoproteins that preferentially bind cells expressing DC-SIGN, wherein said pseudotyped lentiviral vector particles are produced from a virus packaging cell cultured in a culture medium comprising kifunensine and said pseudotyped lentiviral vector particles are more highly mannosylated compared to control pseudotyped lentiviral vector particles prepared in the absence of kifunensine.

2. The method of claim 1, wherein the envelope glycoproteins are alphavirus glycoproteins.

3. The method of claim 2, wherein the envelope glycoproteins are Sindbis glycoproteins.

4. The method of claim 1, wherein high mannosylation is characterized by being more EndoH-sensitive than a control composition prepared in the absence of kifunensine.

5. The method of claim 4, wherein the EndoH sensitivity is determined by assessing the molecular weight of the envelope glycoproteins by sodium dodecyl sulfate-polyacrylamide gel electrophoresis (SDS-PAGE) after EndoH treatment.

6. The method of claim 5, wherein the molecular weight of the envelope glycoproteins after treatment with EndoH has shifted about 45% or more of the distance between (a) envelope glycoproteins not treated with an endoglycosidase, and (b) envelope glycoproteins treated with PNGase F.

7. The method of claim 6, wherein the molecular weight of the envelope glycoproteins after treatment with EndoH has shifted approximately 70% or more of the distance between (a) envelope glycoproteins not treated with endoglycosidase, and (b) envelope glycoproteins treated with PNGase F.

8. The method of claim 6, wherein the molecular weight of the envelope glycoproteins after treatment with EndoH has shifted approximately 90% or more of the distance between (a) envelope glycoproteins not treated with endoglycosidase, and (b) envelope glycoproteins treated with PNGase F.

9. The method of claim 1, wherein at least 30% of the envelope glycoproteins in said composition have an increased amount of EndoH-sensitive glycan as compared to control glycoproteins having the same amino acid sequence(s) in a control composition of pseudotyped retroviral vector particles prepared in the absence of a kifunensine.

10. The method of claim 1, wherein a majority of the envelope glycoproteins are highly mannosylated.

11. The method of claim 1, wherein the pseudotyped retroviral vector particles are integration deficient.

12. The method of claim 1, wherein the composition comprises a Sindbis E2 glycoprotein.

13. The method of claim 1, wherein the retroviral vector is a lentiviral vector.

14. The method of claim 12, wherein the retroviral vector is a lentiviral vector.

15. The method of claim 12, wherein the E2 glycoprotein is 90% identical to SEQ ID NO: 30 (SIN-Var1).

16. The method of claim 15, wherein (i) residue 160 of the E2 glycoprotein is absent or is an amino acid other than glutamic acid, (ii) one or more of residues 70, 76, or 159 of the E2 glycoprotein variant is a non-basic residue, and (iii) the E2 glycoprotein variant is not part of a fusion protein with Sindbis virus E3 glycoprotein.

17. The method of claim 16, wherein the E2 glycoprotein is SEQ ID NO: 30 (SIN-Var1).

18. The method of claim 1, wherein the Vpx protein comprises an amino acid sequence that is at least 80% identical to SIVmac Vpx (SEQ ID NO: 44).

19. The method of claim 1, wherein the Vpx protein comprises an amino acid sequence at least 90% identical to SIVmac Vpx (SEQ ID NO: 44), SIVsm Vpx (SEQ ID NO: 45), SIVrcm Vpx (SEQ ID NO: 46), or HIV-2 Vpx (SEQ ID NO: 47).

20. The method of claim 1, wherein the Vpr protein comprises an amino acid sequence at least 90% identical to SIVdeb Vpr (SEQ ID NO: 48) or SIVmus Vpr (SEQ ID NO: 49).

21. The method of claim 1, wherein the polynucleotide of interest encodes a tumor-specific antigen or a virus-specific antigen.

22. The method of claim 21, wherein the tumor-specific antigen is selected from the group consisting of NY-ESO-1, MAGE, MART-1/Melan-A, BAGE, RAGE, gp100, gp75, mda-7, tyrosinase, tyrosinase-related protein, renal cell carcinoma antigen, 5T4, SM22-alpha, carbonic anhydrase I, carbonic anhydrase IX (also known as G250), HIF-1alpha, HIF-2alpha, VEGF, prostate specific membrane antigen (PSMA), prostate-specific antigen (PSA), prostatic acid phosphates, six-transmembrane epithelial antigen of the prostate (STEAP), NKX3.1, telomerase enzyme, survivin, mesothelin, mutated ras, bcr/abl rearrangement, Her2/neu, mutated p53, wild-type p53, cytochrome P450 1B1, N-acetylglucosaminyltransferase-V, human papilloma virus protein E6, human papilloma virus protein E7, carcinoembryonic antigen, and alpha-fetoprotein.

23. The method of claim 21, wherein the virus-specific antigen is an HIV antigen, an SIV antigen, an adenovirus antigen, an enterovirus antigen, a coronavirus antigen, a calicivirus antigen, a distemper virus antigen, an Ebola virus antigen, a flavivirus antigen, a hepatitis virus antigen, a herpesvirus antigen, an infectious peritonitis virus antigen, an influenza virus antigen, a leukemia virus antigen, a Marburg virus antigen, an orthomyxovirus antigen, a papilloma virus antigen, a parainfluenza virus antigen, a paramyxovirus antigen, a parvovirus antigen, a pestivirus antigen, a picorna virus antigen, a poliovirus antigen, a pox virus antigen, a rabies virus antigen, a reovirus antigen, a retrovirus antigen, or a rotavirus antigen.

24. The method of claim 21, wherein the lentiviral vector genome further comprises a nucleotide sequence encoding a second antigen.

25. The method of claim 24 wherein the first and second antigen are expressed as a fusion protein that comprises a self-cleaving A2 peptide between the two antigens.

26. The method of claim 25, wherein self-cleaving A2 peptide comprises the amino acid sequence of SEQ ID NO: 56 or SEQ ID NO: 57.

27. The method of claim 26, wherein the first antigen is NY-ESO-1 and the second antigen is MAGE-A3.

28. The method of claim 24, wherein the first and second antigen are expressed from a bi-directional promoter.

29. The method of claim 1, wherein the envelope glycoproteins bind cells expressing mouse SIGNR1.

30. The method of claim 1, wherein the pseudotyped lentiviral vector particles more efficiently transduce cells expressing mouse SIGNR1 compared to cells not expressing mouse SIGNR1.

31. The method of claim 21, wherein the lentiviral vector genome further comprises a nucleotide sequence encoding a stimulatory molecule selected from the group consisting of GM-CSF, IL-2, IL-4, IL-6, IL-7, IL-15, IL-21, IL-23, TNFalpha, B7.1, B7.2, 4-1BB, CD40 ligand, and drug-inducible CD40.

32. The method of claim 1, wherein the polynucleotide of interest encodes a stimulatory molecule selected from the group consisting of GM-CSF, IL-2, IL-4, IL-6, IL-7, IL-15, IL-21, IL-23, TNFalpha, B7.1, B7.2, 4-1BB, CD40 ligand, and drug-inducible CD40.

* * * * *